(12) United States Patent
Li et al.

(10) Patent No.: US 10,297,768 B2
(45) Date of Patent: May 21, 2019

(54) MULTIDENTATE DINUCLEAR CYCLOMETALLATED COMPLEXES CONTAINING NCCN—NCCN LIGAND

(71) Applicants: Zhejiang University of Technology, Hangzhou (CN); AAC Microtech (Changzhou) Co., Ltd., Changzhou (CN)

(72) Inventors: Guijie Li, Hangzhou (CN); Yuanbin She, Hangzhou (CN); Xiangdong Zhao, Hangzhou (CN); Shaohai Chen, Saratoga, CA (US)

(73) Assignees: ZHEJIANG UNIVERSITY OF TECHNOLOGY, Hangzhou, Zhejiang Province (CN); AAC MICROTECH (CHANGZHOU) CO., LTD., Changzhou, Jiangsu Province (CN)

( * ) Notice: Subject to any disclaimer, the term of this patent is extended or adjusted under 35 U.S.C. 154(b) by 0 days.

(21) Appl. No.: 15/785,020

(22) Filed: Oct. 16, 2017

(65) Prior Publication Data

US 2019/0067598 A1 Feb. 28, 2019

(30) Foreign Application Priority Data

Aug. 31, 2017 (CN) .......................... 2017 1 0771918

(51) Int. Cl.
| | | |
|---|---|---|
| *C07D 239/02* | (2006.01) | |
| *C09K 11/06* | (2006.01) | |
| *C07F 15/00* | (2006.01) | |
| *H01L 51/50* | (2006.01) | |
| *H01L 51/00* | (2006.01) | |

(52) U.S. Cl.
CPC ........ *H01L 51/0084* (2013.01); *C07D 239/02* (2013.01); *C07F 15/006* (2013.01); *C09K 11/06* (2013.01); *C09K 2211/1044* (2013.01); *C09K 2211/185* (2013.01); *H01L 51/5016* (2013.01)

(58) Field of Classification Search
CPC ...... C07D 239/02; C09K 11/06; H05B 33/14; H01L 51/5032; H01L 51/5264; C07F 15/00
USPC .................. 544/225; 428/690, 917; 313/504; 257/40, E51.044, E51.014
See application file for complete search history.

(56) References Cited

U.S. PATENT DOCUMENTS 10,020,455 B2 * 7/2018 Li ....................... H01L 51/0087

* cited by examiner

*Primary Examiner* — Venkataraman Balasubramanian
(74) *Attorney, Agent, or Firm* — Na Xu; IPro, PLLC

(57) ABSTRACT

Disclosed herein are multidentate dinuclear cyclometallated complexes. The complexes are suitable as emitting materials or host materials in OLED devices.

Formula I

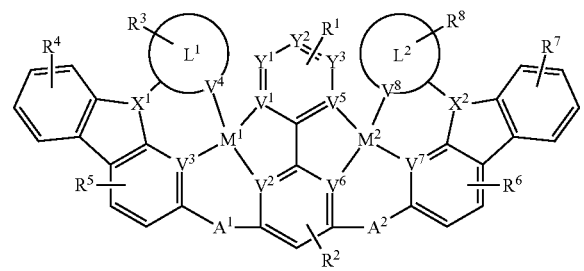

11 Claims, 3 Drawing Sheets

Up: experimental data;   Down: theoretical data $C_{44}H_{24}N_6O_2Pd_2$
Exact Mass: 880.003

Up: experimental data;     Down: theoretical data

Chemical Formula: $C_{44}H_{24}N_6O_2Pt_2$

MULTIDENTATE DINUCLEAR CYCLOMETALLATED COMPLEXES CONTAINING NCCN—NCCN LIGAND

TECHNICAL FIELD

The present disclosure relates to multidentate dinuclear cyclometallated complexes. The complexes are suitable as emitting materials or host materials in OLED devices.

BACKGROUND

Compounds capable of absorbing and/or emitting light can be ideally suited for use in a wide variety of optical and electroluminescent devices, including, for example, photo-absorbing devices such as solar- and photo-sensitive devices, organic light emitting diodes (OLEDs), photo-emitting devices, or devices capable of both photo-absorption and emission and as markers for bio-applications. Much research has been devoted to the discovery and optimization of organic and organometallic materials for using in optical and electroluminescent devices. Generally, research in this area aims to accomplish a number of goals, including improvements in absorption and emission efficiency, improvements in the stability of devices, as well as improvements in processing ability.

Despite significant advances in research devoted to optical and electro-optical materials, for example, red and green phosphorescent organometallic materials are commercial, and they have been used as phosphors in organic light emitting diodes (OLEDs), lighting and advanced displays. Many currently available materials exhibit a number of disadvantages, including poor processing ability, inefficient emission or absorption, and less than ideal stability, among others.

Especially, good blue emitters are very scarce. One big challenge is the stability of the blue devices. And the choice of the host materials has a great effect on the stability and the efficiency of the devices. The lowest triplet excited state energy of the blue phosphors is very high compared with that of the red and green phosphors, which means that the lowest triplet excited state energy of host materials for the blue devices should be even higher. So one of the problems is that there are very limited host materials to be used for the blue devices.

Generally, a chemical structural change will affect the electronic structure of the compounds, which thereby affects the optical properties of the compounds, for example, emission and absorption spectra. Thus, the compounds of this present invention can be tailored or tuned to a specific application that desires a particular emission or absorption characteristic. The optical properties of the metal compounds in this disclosure can be tuned by varying the structure of the ligand surrounding the metal center. For example, the metal compounds having a ligand with electron donating substituents or electron withdrawing substituents can be generally exhibit different optical properties, including emission and absorption spectra.

Owing to the potential of phosphorescent multidentate cyclometallated complexes for harvesting both electrogenerated singlet and triplet excitions to achieve 100% internal quantum efficiency, these complexes are good candidate for the emitting materials of OLEDs. Usually, there are "emitting portion" and "ancillary portion" in ligand of multidentate platinum complexes. If stabilizing substitution(s), such as conjugated group(s), aryl or heteroaromatic substitution(s) and so on, were introduced into the emitting portion. The "Highest Occupied Molecular Orbital" (HOMO) and/or "Lowest Unoccupied Molecular Orbital" (LUMO) energy level may be changed. So the energy gap between the HOMO and LUMO can be tuned. Thus the emission spectra of phosphorescent tetradentate platinum complexes can be modified to lesser or greater extents, such that the emission spectra can become narrower or broader, and/or such that the emission spectra can exhibit a blue shift or a red shift.

Thus, a need exists for new materials which exhibit improved performance in optical emitting and absorbing applications. Accordingly, such compounds, compositions, and devices comprising the same are disclosed herein.

SUMMARY

The present disclosure relates to multidentate dinuclear cyclometallated complexes. The complexes are suitable as emitting materials or host materials in OLED devices.

Disclosed herein are compounds of Formula I:

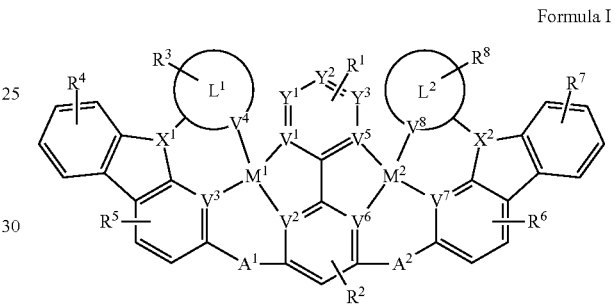

Formula I wherein each of $M^1$ and $M^2$ is independently a platinum or palladium.

wherein each of $L^1$ and $L^2$ is independently a six-membered carbocyclic, heterocyclic, heteroaryl ring.

wherein $V^1$, $V^2$, $V^3$, $V^4$, $V^5$, $V^6$, $V^7$ and $V^8$ are coordinated with Pt or Pd and are each independently comprise N and C; and at least two of $V^1$, $V^2$, $V^3$ and $V^4$ are N, at least two of $V^5$, $V^6$, $V^7$ and $V^8$ are N.

wherein each of $A^1$ and $A^2$ is independently selected from the group consisting O, S, $CH_2$, $CD_2$, $CR^aR^b$, C=O, $SiR^aR^b$, $GeH_2$, $GeR^aR^b$, NH, $NR^c$, PH, $PR^c$, $R^cP$=O, $AsR^c$, $R^cAs$=O, S=O, $SO_2$, Se, Se=O, $SeO_2$, BH, $BR^c$, $R^cBi$=O, BiH, or $BiR^c$.

wherein each of $X^1$ and $X^2$ is independently selected from the group consisting N, B, CH, $CD_2$, $CR^a$, SiH, SiD, $SiR^a$, $GeH_2$, GeD, $GeR^d$, P, P=O, As, As=O, Bi or Bi=O.

wherein $R^1$, $R^2$, $R^3$, $R^4$, $R^5$, $R^6$, $R^7$ and $R^8$ may represent mono-, di, tri, tetra-substitutions, or no substitution, and $R^1$, $R^2$, $R^3$, $R^4$, $R^5$, $R^6$, $R^7$, $R^8$, $R^a$, $R^b$, $R^c$ and $R^d$ are independently selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof. Two or more adjacent $R^1$, $R^2$, $R^3$, $R^4$, $R^5$, $R^6$, $R^7$ and $R^8$ are optionally joined to form a fused ring.

wherein $R^a$, $R^b$, $R^c$ and $R^d$ may represent mono-, di, tri, tetra-substitutions, or no substitution, and $R^a$, $R^b$, $R^c$ and $R^d$ are independently selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof.

In one aspect,

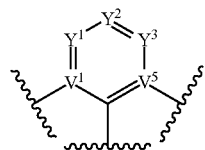

is selected from the group consisting

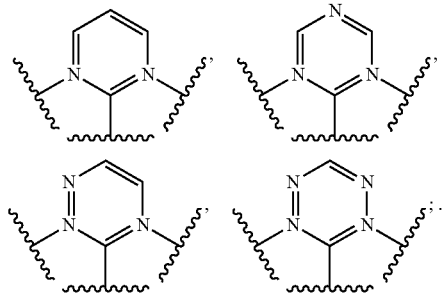

In one aspect, the compound has the structure of Formula II, Formula III, Formula IV and Formula V:

Formula II

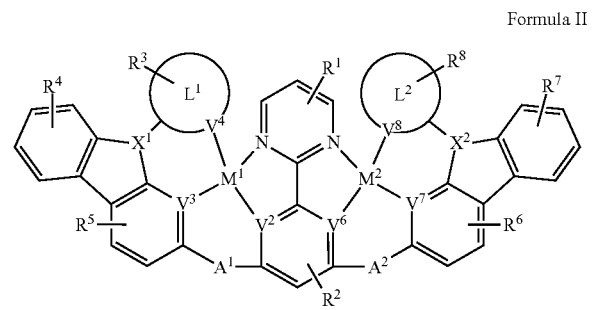

Formula III

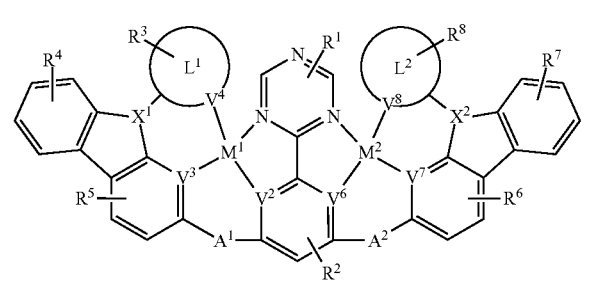

Formula IV

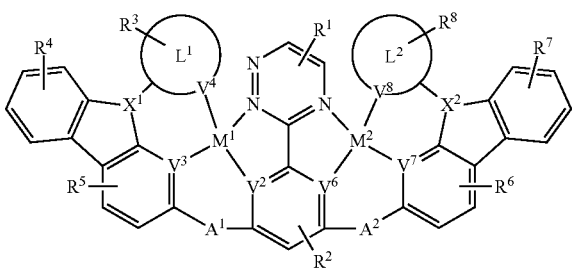

Formula V

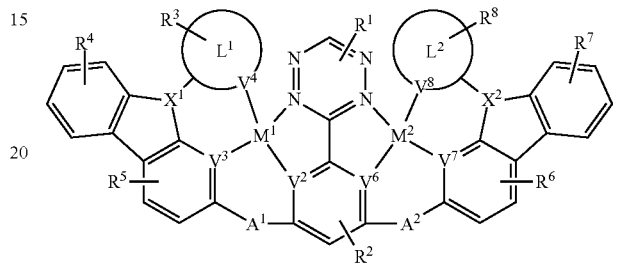

Also disclosed herein are compositions comprising one or more compounds disclosed herein.

Also disclosed herein are devices, such as OLEDs, comprising one or more compounds or compositions disclosed herein.

BRIEF DESCRIPTION OF THE FIGURES

The accompanying figures, which are incorporated in and constitute a part of this specification, illustrate several non-limiting aspects and together with the description serve to explain the principles of the invention.

Figure 1:
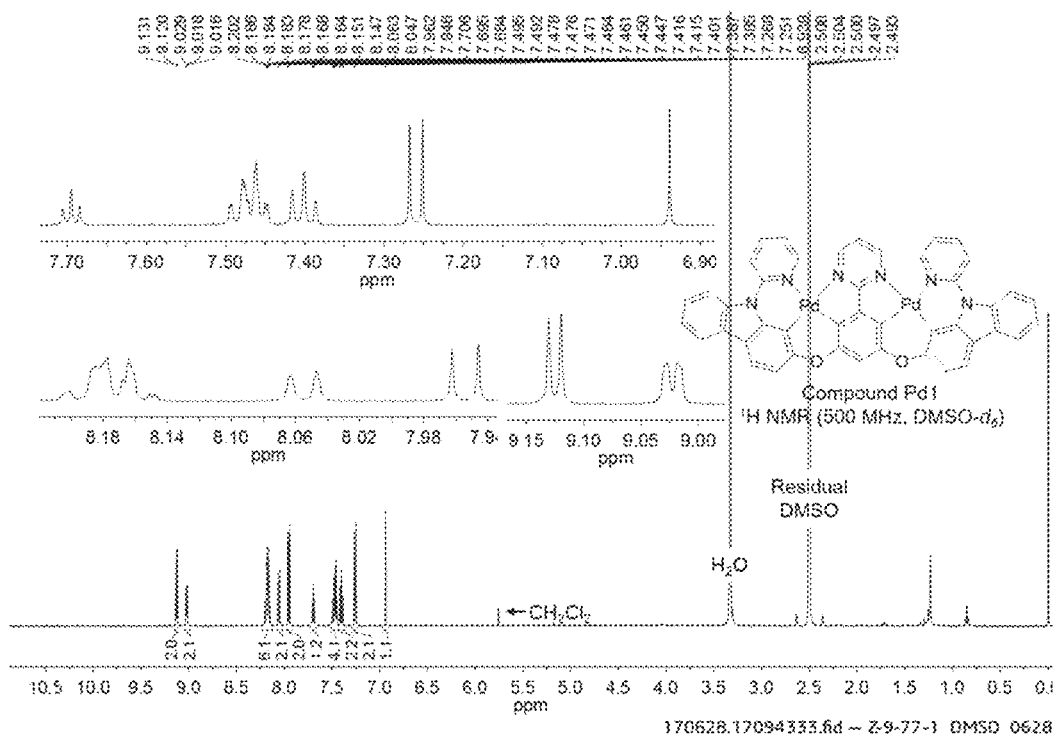
FIG. 1 shows the $^1$H NMR spectrum of Compound Pd1 in MDSO-$d_6$.

Additional aspects of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

As used in the specification and the appended claims, the singular forms "a", "an", and "the" include plural referents unless the context clearly dictates otherwise. Thus, for example, reference to "a component" includes mixtures of two or more components.

As used herein, the terms "optional" or "optionally" means that the subsequently described event or circumstance can or cannot occur, and that the description includes instances where said event or circumstance occurs and instances where it does not.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

As referred to herein, a linking atom can connect two groups such as, for example, an N and C group. A linking group is in one aspect disclosed as A, $A^1$, and/or $A^3$ herein. The linking atom can optionally, if valency permits, have other chemical moieties attached. For example, in one aspect, an oxygen would not have any other chemical groups attached as the valency is satisfied once it is bonded to two groups (e.g., N and/or C groups). In another aspect, when carbon is the linking atom, two additional chemical moieties can be attached to the carbon. Suitable chemical moieties includes, but are not limited to, hydrogen, hydroxyl, alkyl, alkoxy, =O, halogen, nitro, amine, amide, thiol, aryl, heteroaryl, cycloalkyl, and heterocyclyl.

The term "cyclic structure" or the like terms used herein refer to any cyclic chemical structure which includes, but is not limited to, aryl, heteroaryl, cycloalkyl, cycloalkenyl, heterocyclyl, carbene, and N-heterocyclic carbene.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$R^1$," "$R^2$," "$R^3$," and "$R^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $—(CH_2)_a—$, where "a" is an integer of from 2 to 500.

The terms "alkoxy" and "alkoxyl" as used herein to refer to an alkyl or cycloalkyl group bonded through an ether linkage, that is, an "alkoxy" group can be defined as $—OR^1$ where $R^1$ is alkyl or cycloalkyl as defined above. "Alkoxy" also includes polymers of alkoxy groups as just described; that is, an alkoxy can be a polyether such as $—OR^1—OR^2$ or $—OR^1—(OR^2)_a—OR^3$, where "a" is an integer of from 1 to 200 and $R^1$, $R^2$, and $R^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(R^1R^2)C=C(R^3R^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula $—NR^1R^2$, where $R^1$ and $R^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula $—N(-alkyl)_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$R^1$ or —C(O)O$R^1$, where $R^1$ can be alkyl, cycloalkyl, alkenyl, cycloalkenyl, alkynyl, cycloalkynyl, aryl, or heteroaryl group as described herein. The term "polyester" as used herein is represented by the formula —($R^1$O(O)C—$R^2$—C(O)O)$_a$— or —($R^1$O(O)C—$R^2$—OC(O))—, where $R^1$ and $R^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $R^1$O$R^2$, where $R^1$ and $R^2$ can be, independently, an alkyl, cycloalkyl, alkenyl, cycloalkenyl, alkynyl, cycloalkynyl, aryl, or heteroaryl group described herein. The term "polyether" as used herein is represented by the formula —($R^1$O—$R^2$O)$_a$—, where $R^1$ and $R^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocyclyl," as used herein refers to single and multi-cyclic non-aromatic ring systems and "heteroaryl as used herein refers to single and multi-cyclic aromatic ring systems: in which at least one of the ring members is other than carbon. The terms includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula $R^1$C(O)$R^2$, where $R^1$ and $R^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —Si$R^1R^2R^1$, where $R^1$, $R^2$, and $R^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)$R^1$, —S(O)$_2R^1$, —OS(O)$_2$R', or —OS(O)$_2$OR', where $R^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2R^1$, where $R^1$ can be hydrogen or an alkyl, cycloalkyl, alkenyl, cycloalkenyl, alkynyl, cycloalkynyl, aryl, or heteroaryl group as described herein. The term "sulfone" is represented by the formula $R^1$S(O)$_2R^2$, where $R^1$ and $R^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $R^1$S(O)$R^2$, where $R^1$ and $R^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted." whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

In some aspects, a structure of a compound can be represented by a formula:

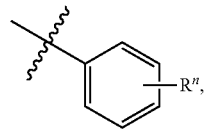

which is understood to be equivalent to a formula:

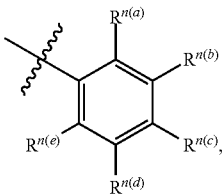

wherein n is typically an integer. That is, R″ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Several references to $R^1$, $R^2$, $R^3$, $R^4$, $R^5$, $R^6$, etc. are made in chemical structures and moieties disclosed and described herein. Any description of $R^1$, $R^2$, $R^3$, $R^4$, $R^5$, $R^6$, etc. in the specification is applicable to any structure or moiety reciting $R^1$, $R^2$, $R^3$, $R^4$, $R^5$, $R^6$, etc. respectively.

1. Compounds

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

Excitons decay from singlet excited states to ground state to yield prompt luminescence, which is fluorescence. If Excitons decay from triplet excited states to ground state to generate luminescence, which is phosphorescence. Because the strong spin-orbit coupling of the heavy metal atom enhances intersystem crossing (ISC) very efficiently between singlet and triplet excited state, phosphorescent metal complexes, such as platinum complexes, have demonstrated their potential to harvest both the singlet and triplet excitons to achieve 100% internal quantum efficiency. Thus phosphorescent metal complexes are good candidates as dopants in the emissive layer of organic light emitting devices (OLEDs) and a great deal of attention has been received both in the academic and industrial fields. And much achievement has been made in the past decade to led to the lucrative commercialization of the technology, for example, OLEDs have been used in advanced displays in smart phones, televisions and digital cameras.

However, to date, blue electroluminescent devices remain the most challenging area of this technology, one big problem is the stability of the blue devices. It has been proved that the choice of host materials is very important to the stability of the blue devices. But the lowest triplet excited state ($T_1$) energy of the blue phosphors is very high, which means that the lowest triplet excited state ($T_1$) energy of host materials for the blue devices should be even higher. This leads to much difficulty in the development of the host materials for the blue devices.

The metal complexes of this present invention can be tailored or tuned to a specific application that desires a particular emission or absorption characteristic. The optical properties of the metal complexes in this disclosure can be tuned by varying the structure of the ligand surrounding the metal center or varying the structure of fluorescent luminophore(s) on the ligands. For example, the metal complexes having a ligand with electron donating substituents or electron withdrawing substituents can be generally exhibit different optical properties, including emission and absorption spectra. The color of the metal complexes can be tuned by modifying the conjugated groups on the fluorescent luminophores and ligands.

The emission of such inventive complexes can be tuned, for example, from the ultraviolet to near-infrared, by, for example, modifying the ligand or fluorescent luminophore structure. A fluorescent luminophore is a group of atoms in an organic molecule, which can absorb energy to generate singlet excited state(s), the singlet exciton(s) produce(s) decay rapidly to yield prompt luminescence. In another aspect, the inventive complexes can provide emission over a majority of the visible spectrum. In a specific example, the inventive complexes can emit light over a range of from about 400 nm to about 700 nm. In another aspect, the inventive complexes have improved stability and efficiency over traditional emission complexes. In yet another aspect, the inventive complexes can be useful as luminescent labels in, for example, bio-applications, anti-cancer agents, emitters in organic light emitting diodes (OLED), or a combination thereof. In another aspect, the inventive complexes can be useful in light emitting devices, such as, for example, compact fluorescent lamps (CFL), light emitting diodes (LED), incandescent lamps, and combinations thereof.

Disclosed herein are compounds or compound complexes comprising platinum. The terms compound or compound complex are used interchangeably herein. In one aspect, the compounds discloses herein have a neutral charge.

The compounds disclosed herein, can exhibit desirable properties and have emission and/or absorption spectra that can be tuned via the selection of appropriate ligands. In another aspect, the present invention can exclude any one or more of the compounds, structures, or portions thereof, specifically recited herein.

The compounds disclosed herein are suited for use in a wide variety of optical and electro-optical devices, including, but not limited to, photo-absorbing devices such as solar- and photo-sensitive devices, organic light emitting diodes (OLEDs), photo-emitting devices, or devices capable of both photo-absorption and emission and as markers for bio-applications.

As briefly described above, the disclosed compounds are platinum complexes. In one aspect, the compounds disclosed herein can be used as host materials for OLED applications, such as full color displays.

The compounds disclosed herein are useful in a variety of applications. As light emitting materials, the compounds can be useful in organic light emitting diodes (OLED)s, luminescent devices and displays, and other light emitting devices.

In another aspect, the compounds can provide improved efficiency and/or operational lifetimes in lighting devices, such as, for example, organic light emitting devices, as compared to conventional materials.

The compounds of the invention can be made using a variety of methods, including, but not limited to those recited in the examples provided herein.

The compound disclosed herein can be a delayed fluorescent and/or phosphorescent emitter. In one aspect, the compounds disclosed herein can be a delayed fluorescent emitter. In another aspect, the compounds disclosed herein can be a phosphorescent emitter. In yet another aspect, the compounds disclosed herein can be a delayed fluorescent emitter and a phosphorescent emitter.

The present disclosure relates to multidentate dinuclear cyclometallated complexes. The complexes are suitable as emitting materials or host materials in OLED devices.

Disclosed herein are compounds of Formula I:

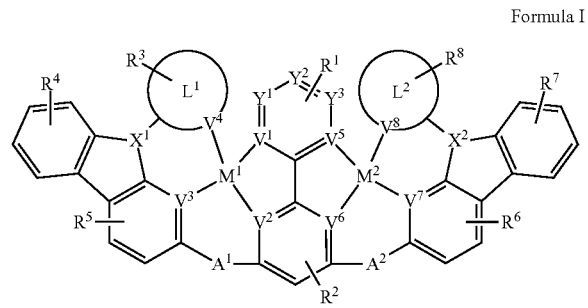

Formula I wherein each of $M^1$ and $M^2$ is independently a platinum or palladium.

wherein each of $L^1$ and $L^2$ is independently a six-membered carbocyclic, heterocyclic, heteroaryl ring.

wherein $V^1, V^2, V^3, V^4, V^5, V^6, V^7$ and $V^8$ are coordinated with Pt and are each independently comprise N and C; and at least two of $V^1, V^2, V^3$ and $V^7$ are N, at least two of $V^5, V^6, V^7$ and $V^8$ are N.

wherein each of $A^1$ and $A^2$ is independently selected from the group consisting O, S, $CH_2$, $CD_2$, $CR^aR^b$, C=O, $SiR^aR^b$, $GeH_2$, $GeR^aR^b$, NH, $NR^c$, PH, $PR^c$, $R^cP$=O, $AsR^c$, $R^cAs$=O, S=O, $SO_2$, Se, Se=O, $SeO_2$, BH, $BR^c$, $R^cBi$=O, BiH, or $BiR^c$.

wherein each of $X^1$ and $X^2$ is independently selected from the group consisting N, B, CH, $CD_2$, $CR^a$, SiH, SiD, $SiR^a$, $GeH_2$, GeD, $GeR^d$, P, P=O, As, As=O, Bi or Bi=O.

wherein $R^1, R^2, R^3, R^4, R^5, R^6, R^7$ and $R^8$ may represent mono-, di, tri, tetra-substitutions, or no substitution, and $R^1, R^2, R^3, R^4, R^5, R^6, R^7, R^8, R^a, R^b, R^c$ and $R^d$ are independently selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof. Two or more adjacent $R^1, R^2, R^3, R^4, R^5, R^6, R^7$ and $R^8$ are optionally joined to form a fused ring.

wherein $R^a, R^b, R^c$ and $R^d$ may represent mono-, di, tri, tetra-substitutions, or no substitution, and $R^a, R^b, R^c$ and $R^d$ are independently selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof.

In one aspect,

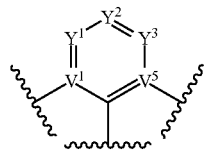

is selected from the group consisting

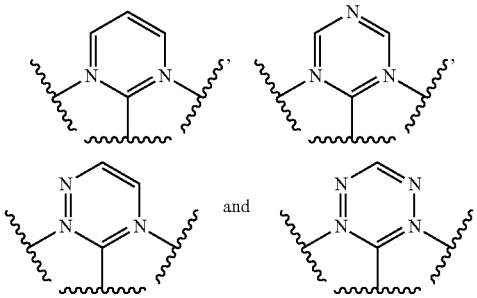

In one aspect, the compound has one of the structure of Formula II, Formula III, Formula IV and Formula V:

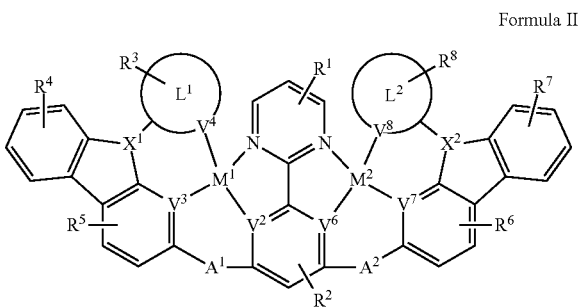

Formula II

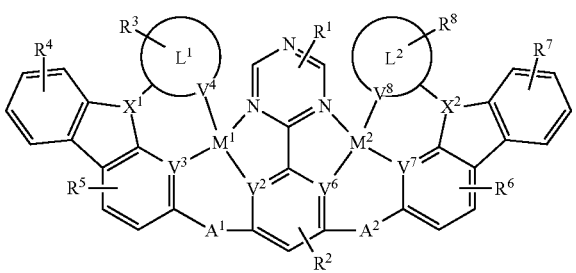

Formula III

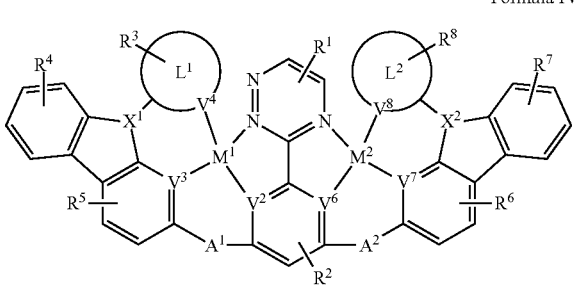

Formula IV

-continued

Formula V

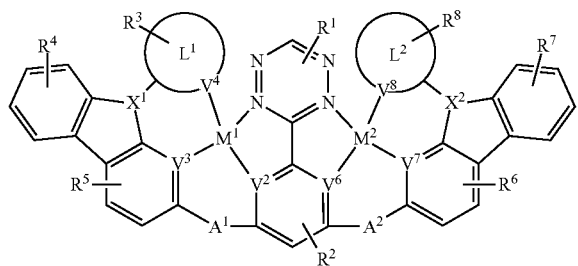

A. M Groups

In one aspect, each of $M^1$ and $M^2$ is independently a platinum or palladium.

In another aspect, $M^1$ is a platinum, $M^2$ is a palladium.
In another aspect, $M^1$ is a palladium, $M^2$ is a platinum.
In another aspect, $M^1$ is a platinum, $M^2$ is also a platinum.
In another aspect, $M^1$ is a palladium, $M^2$ is also a palladium.

B. L Groups

In one aspect, $L^1$ is a six-membered carbocyclic, heterocyclic, heteroaryl ring.

In another aspect, $L^2$ is a six-membered carbocyclic, heterocyclic, heteroaryl ring.

C. V Groups

In one aspect, $V^1$, $V^2$, $V^3$, $V^4$, $V^5$, $V^6$, $V^7$ and $V^8$ are coordinated with $M^1$ or $M^2$ and are each independently comprise N and C; and at least two of $V^1$, $V^2$, $V^3$ and $V^4$ are N, at least two of $V^5$, $V^6$, $V^7$ and $V^8$ are N.

In another aspect, $V^1$ and $V^4$ are N, $V^2$ and $V^3$ are C, $V^5$ and $V^8$ are N, $V^6$ and $V^7$ are C.

In yet another aspect, $V^1$, $V^2$ and $V^3$ are C, and $V^4$ is N, $V^5$ and $V^8$ are N, $V^6$ and $V^7$ are C.

In yet another aspect, $V^1$ and $V^3$ are C, $V^2$ and $V^4$ are N, $V^5$ and $V^7$ are C, $V^6$ and $V^8$ are N.

D. A Groups

In one aspect, each of $A^1$ and $A^2$ is independently selected from the group consisting O, S, $CH_2$, $CD_2$, $CR^aR^b$, C=O, $SiR^aR^b$, $GeH_2$, $GeR^aR^b$, NH, $NR^c$, PH, $PR^c$, $R^cP$=O, $AsR^c$, $R^cAs$=O, S=O, $SO_2$, Se, Se=O, $SeO_2$, BH, $BR^c$, $R^cBi$=O, BiH, or $BiR^c$.

In another aspect, $A^1$ is O, $A^2$ is O.
In another aspect, $A^1$ is O, $A^2$ is S.
In another aspect, $A^1$ is $CR^aR^b$, $A^2$ is $CR^aR^b$.
In another aspect, $A^1$ is $NR^c$, $A^2$ is $NR^c$.
In another aspect, $A^1$ is O, $A^2$ is $NR^c$.
In another aspect, $A^1$ is $CR^aR^b$, $A^2$ is $NR^c$.
In yet another aspect, $A^1$ is $BR^c$, $A^2$ is $BR^c$.

E. X Groups

In one aspect, each of $X^1$ and $X^2$ is independently selected from the group consisting N, B, CH, CD, $CR^a$, SiH, SiD, $SiR^a$, GeH, GeD, $GeR^d$, P, P=O, As, As=O, Bi or Bi=O.

In another aspect, $X^1$ is N, $X^2$ is N.
In another aspect, $X^1$ is B, $X^2$ is B.
In another aspect, $X^1$ is B, $X^2$ is N.
In another aspect, $X^1$ is N, $X^2$ is B.
In another aspect, $X^1$ is P=O, $X^2$ is N.
In another aspect, $X^1$ is N, $X^2$ is P=O.
In another aspect, is N $X^2$ is P=O.
In another aspect, $X^1$ is $CR^a$, $X^2$ is $CR^a$.
1 In another aspect, $X^1$ is $CR^a$, $X^2$ is N.
In another aspect, $X^1$ is N, $X^2$ is $CR^a$.
In another aspect, $X^1$ is $CR^a$, $X^2$ is $CR^a$.
In another aspect, $X^1$ is $SiR^a$, $X^2$ is N.

In another aspect. $X^1$ is N, $X^2$ is $SiR^a$.
In another aspect, $X^1$ is $SiR^a$, $X^2$ is $SiR^a$.
In yet another aspect, $X^1$ is $SiR^a$, $X^2$ is N.

F. R Groups

In one aspect, $R^1$ is present. In another aspect, $R^1$ is absent.

In one aspect, $R^1$ is a mono-substitution. In another aspect, $R^1$ is a di-substitution. In another aspect, $R^1$ is a tri-substitution. In yet another aspect, $R^1$ is a tetra-substitution.

In another aspect, $R^1$ is selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof.

In one aspect, $R^2$ is present. In another aspect, $R^2$ is absent.

In one aspect. $R^2$ is a mono-substitution. In another aspect, $R^2$ is a di-substitution. In another aspect, $R^2$ is a tri-substitution. In yet another aspect, $R^2$ is a tetra-substitution.

In another aspect, $R^2$ is selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof.

In one aspect. $R^3$ is present. In another aspect, $R^3$ is absent.

In one aspect, $R^3$ is a mono-substitution. In another aspect. $R^3$ is a di-substitution. In another aspect. $R^3$ is a tri-substitution. In yet another aspect, $R^3$ is a tetra-substitution.

In another aspect, $R^3$ is selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof.

In one aspect, $R^4$ is present. In another aspect, $R^4$ is absent.

In one aspect, $R^4$ is a mono-substitution. In another aspect, $R^4$ is a di-substitution.

In another aspect, $R^4$ is selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof.

In one aspect, $R^5$ is present. In another aspect, $R^5$ is absent.

In one aspect, $R^5$ is a mono-substitution. In another aspect, $R^5$ is a di-substitution.

In another aspect, $R^5$ is selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof.

In one aspect, $R^6$ is present. In another aspect, $R^6$ is absent.

In one aspect, $R^6$ is a mono-substitution. In another aspect, $R^6$ is a di-substitution.

In another aspect, $R^6$ is selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof.

In one aspect, $R^7$ is present. In another aspect, $R^7$ is absent.

In one aspect, $R^7$ is a mono-substitution. In another aspect, $R^7$ is a di-substitution.

In another aspect, $R^7$ is selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof.

In one aspect, $R^8$ is present. In another aspect, $R^8$ is absent.

In one aspect, $R^8$ is a mono-substitution. In another aspect. $R^8$ is a di-substitution. In another aspect, $R^8$ is a tri-substitution. In yet another aspect, $R^8$ is a tetra-substitution.

In another aspect, $R^8$ is selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof.

In one aspect, $R^a$ is selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof.

In another aspect, $R^b$ is selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof.

In one aspect, $R^c$ is selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof.

In another aspect, $R^d$ is selected from the group consisting hydrogen, deuterium, aryl, cycloalkyl, cycloalkenyl, heterocyclyl, heteroaryl, alkyl, alkenyl, alkynyl, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof.

In one aspect, for any of the platinum complexes illustrated in this disclosure, can comprise one or more of the following structures. In another aspect, they can also comprise other structures or portions thereof not specifically recited herein, and the present invention is not intended to be limited to those structures or portions thereof specifically recited.

G. Exemplary Compounds

Compound Pt1

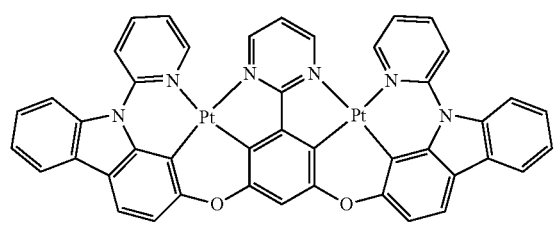

Compound Pt2

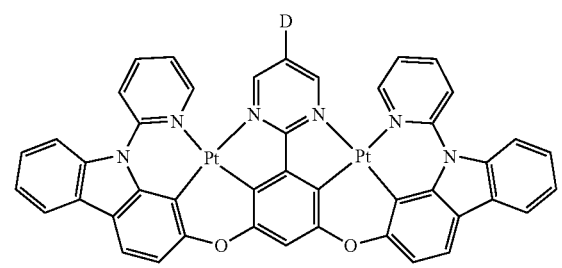

-continued
Compound Pt3
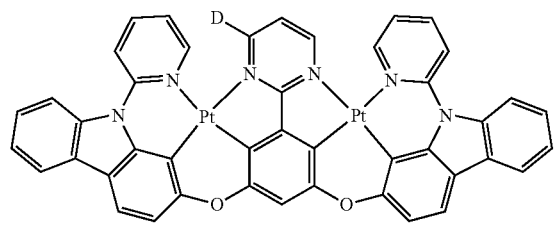
Compound Pt4
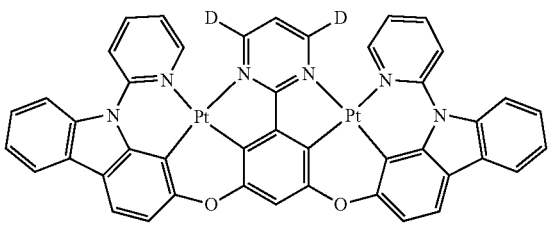
Compound Pt5
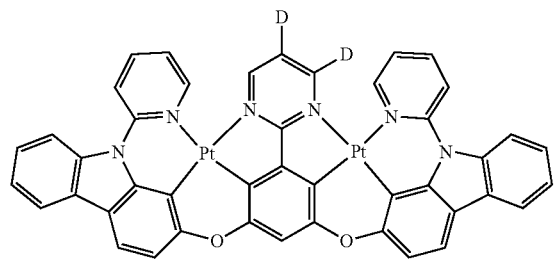
Compound Pt6
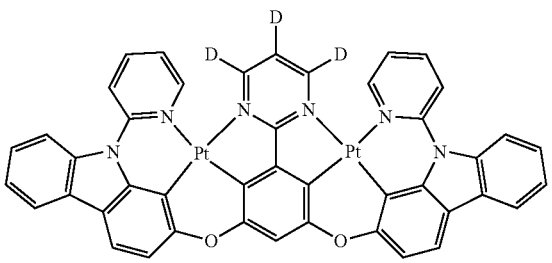
Compound Pt7
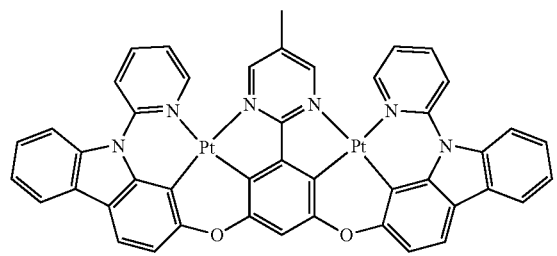
Compound Pt8
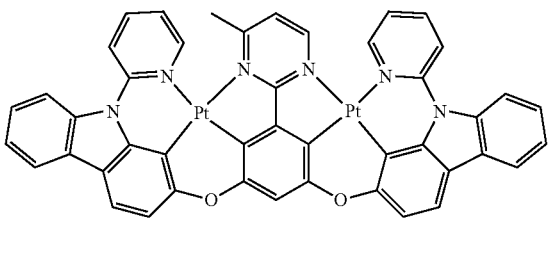
Compound Pt9
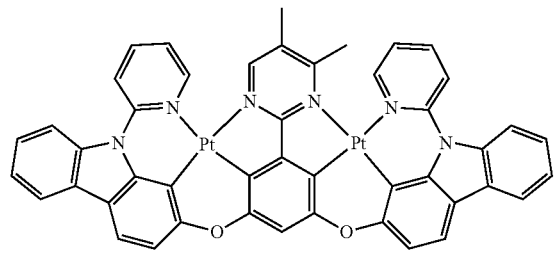
Compound Pt10
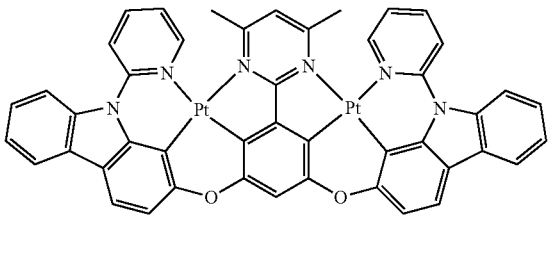
Compound Pt11
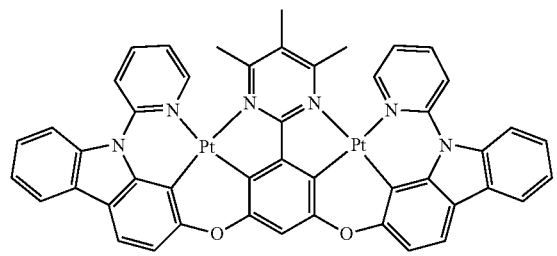
Compound Pt12
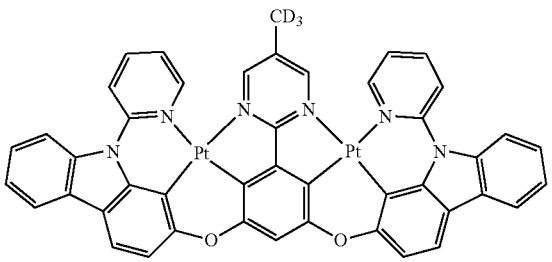

-continued
Compound Pt13
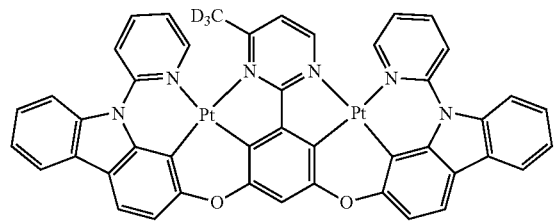
Compound Pt14
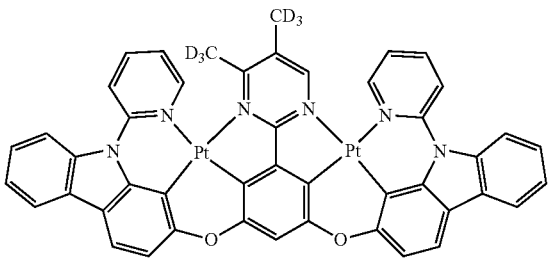
Compound Pt15
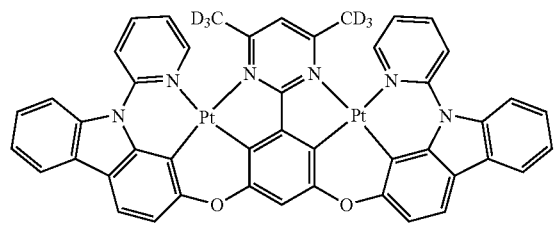
Compound Pt16
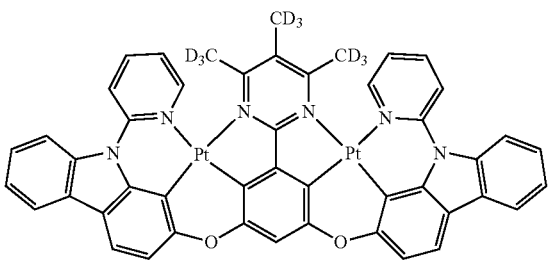
Compound Pt17
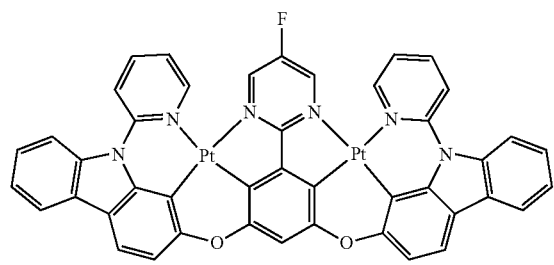
Compound Pt18
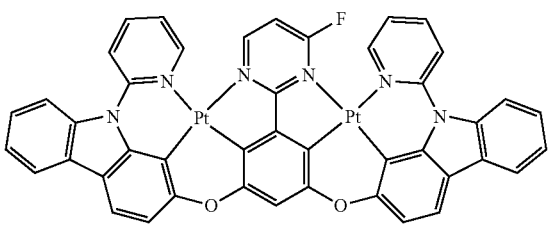
Compound Pt19
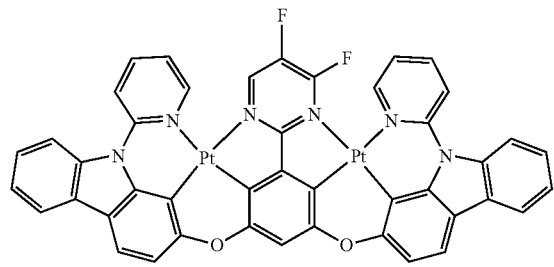
Compound Pt20
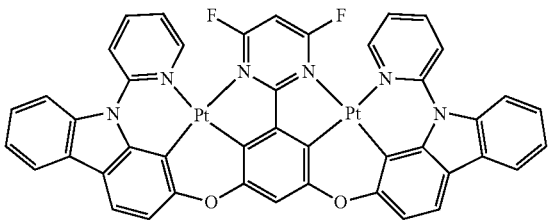
Compound Pt21
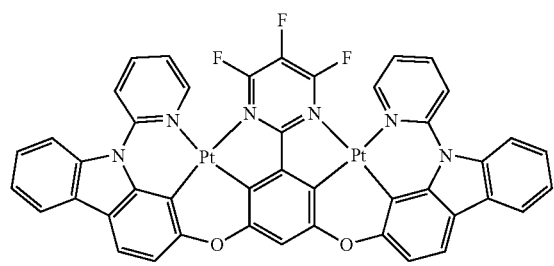
Compound Pt22
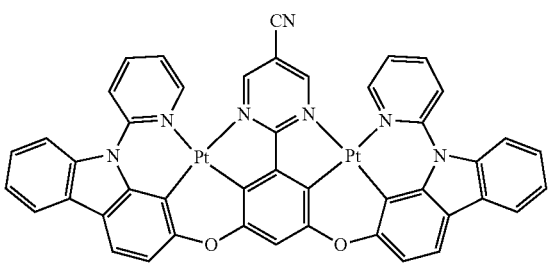

-continued
Compound Pt23
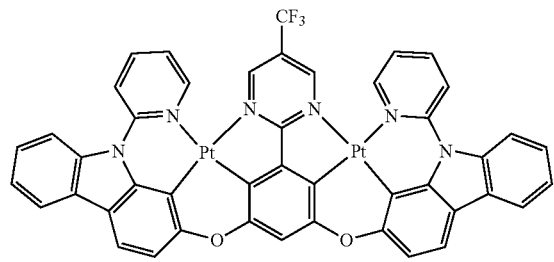
Compound Pt24
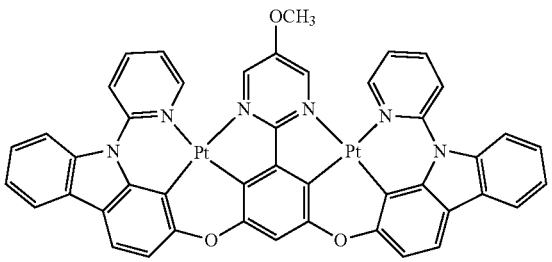
Compound Pt25
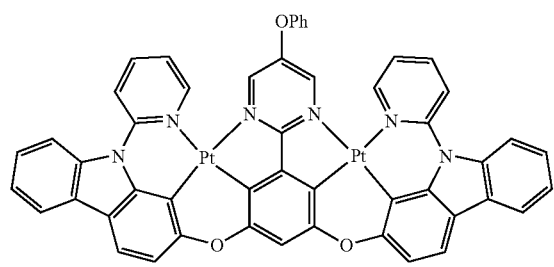
Compound Pt26
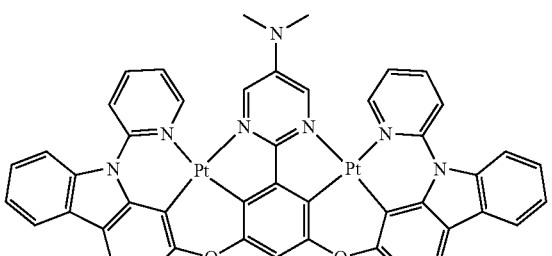
Compound Pt27
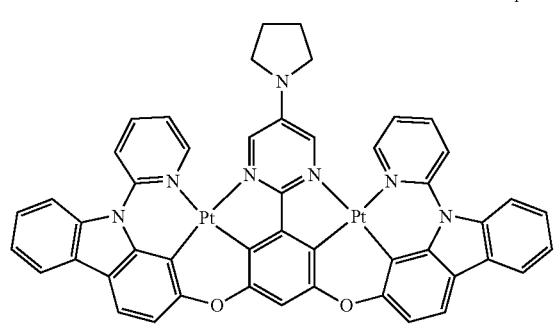
Compound Pt28
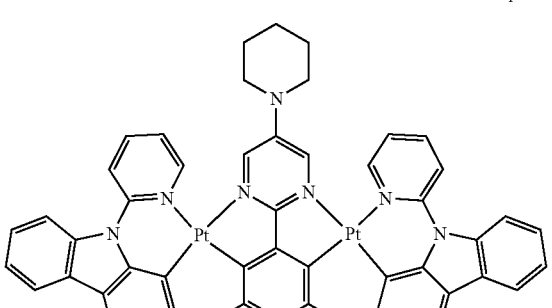
Compound Pt29
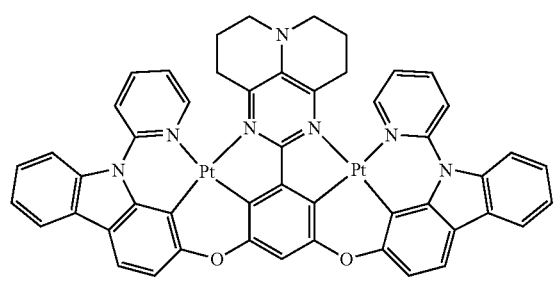
Compound Pt30
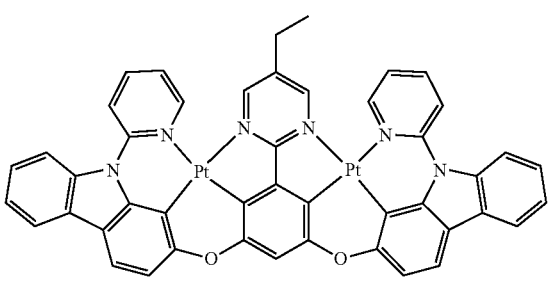
Compound Pt31
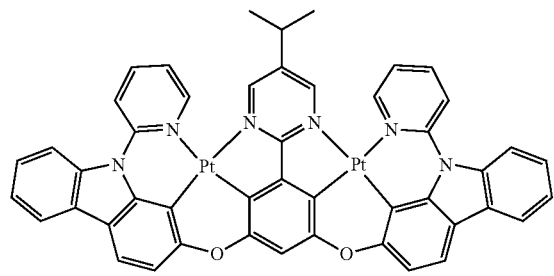
Compound Pt32
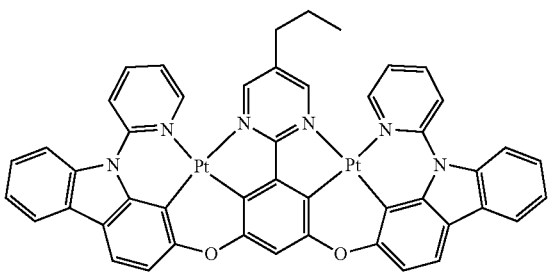

-continued
Compound Pt33
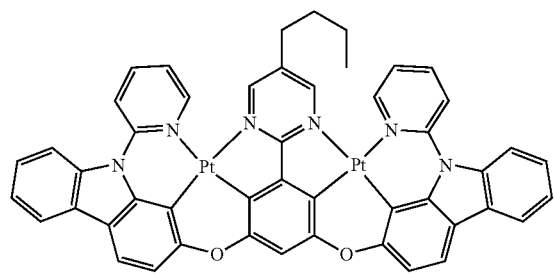
Compound Pt34
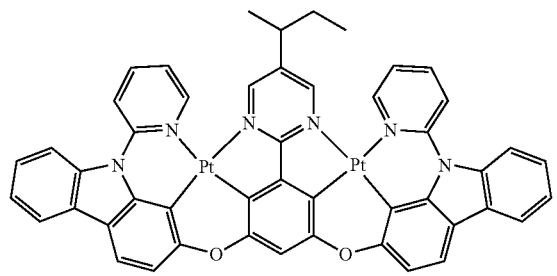
Compound Pt35
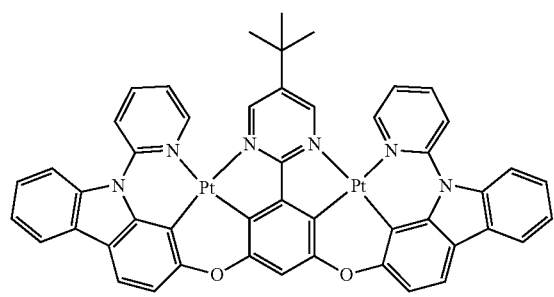
Compound Pt36
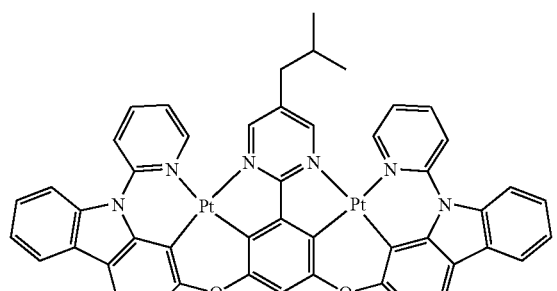
Compound Pt37
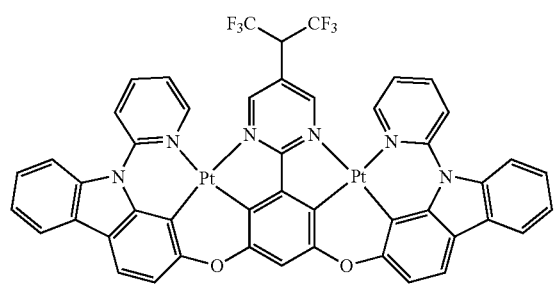
Compound Pt38
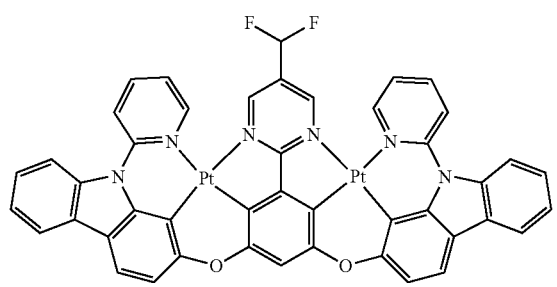
Compound Pt39
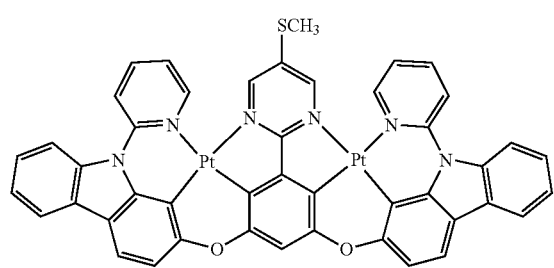
Compound Pt40
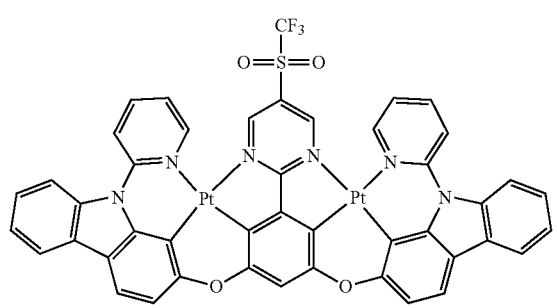
Compound Pt41
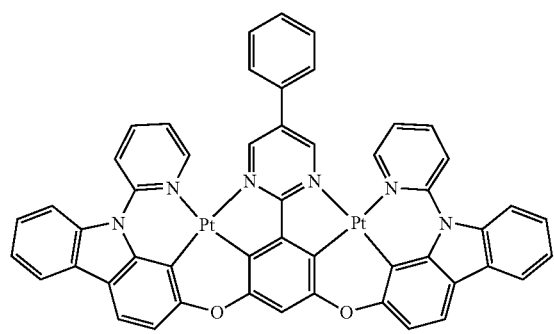
Compound Pt42
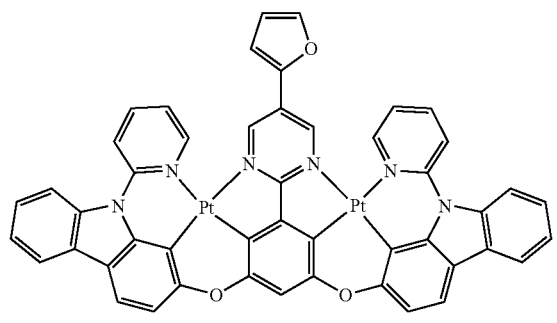

-continued
Compound Pt43
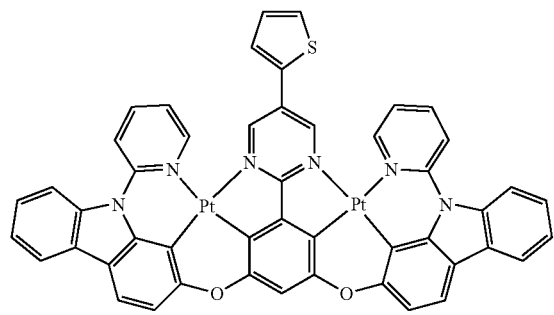
Compound Pt44
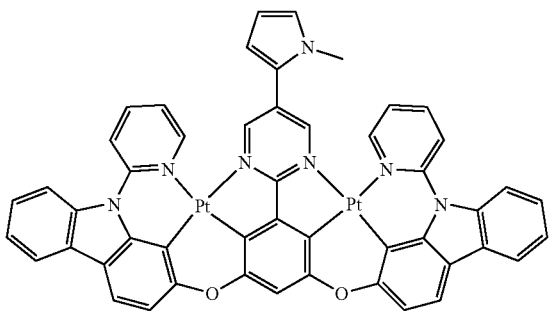
Compound Pt45
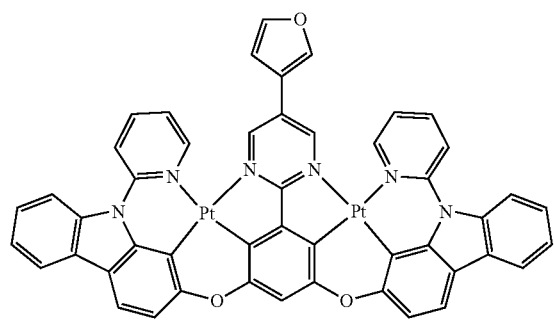
Compound Pt46
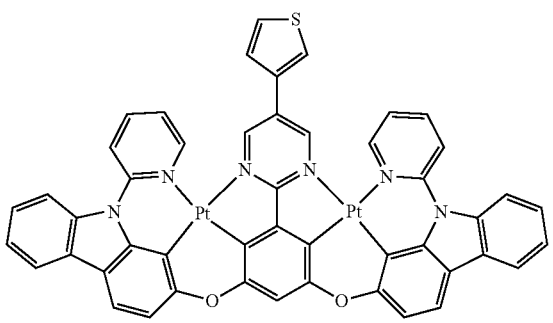
Compound Pt47
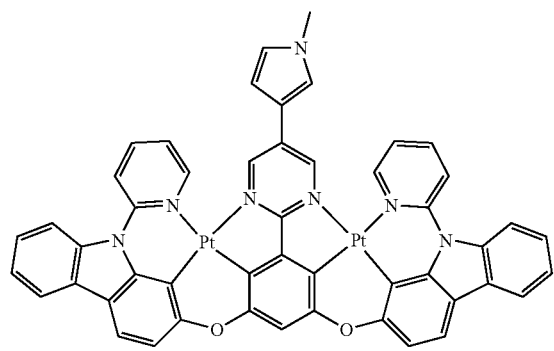
Compound Pt48
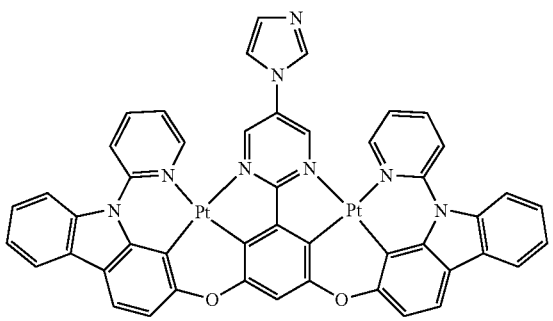
Compound Pt49
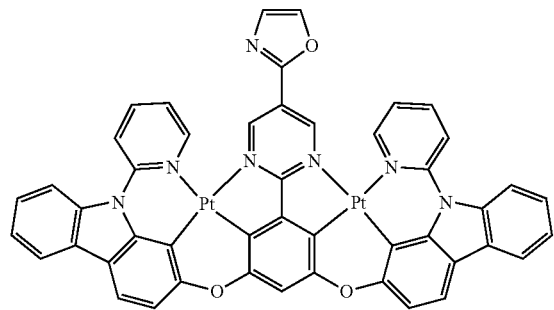
Compound Pt50
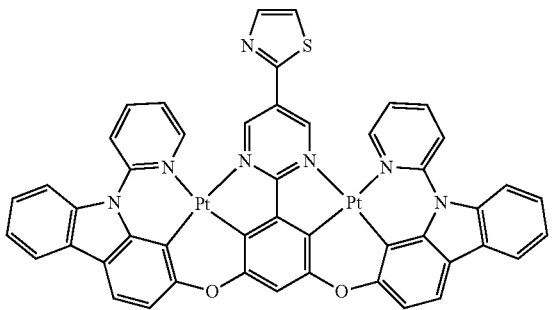

-continued
Compound Pt51
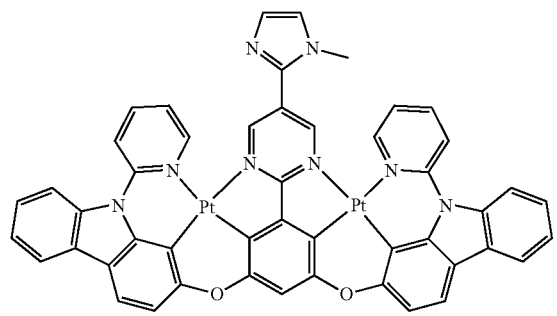
Compound Pt52
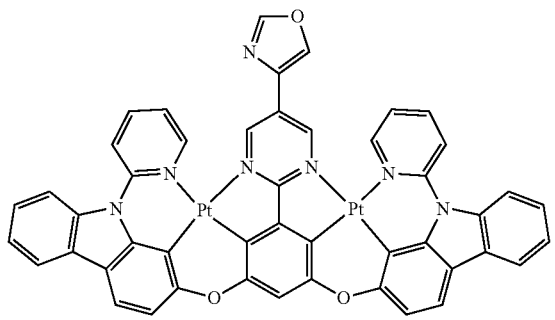
Compound Pt53
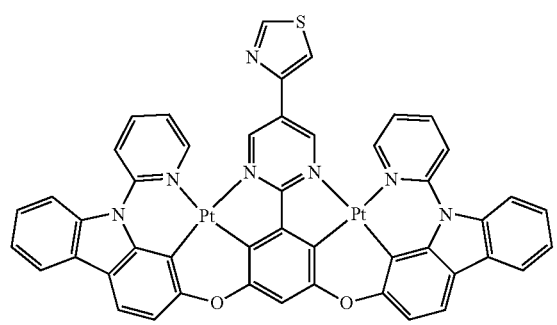
Compound Pt54
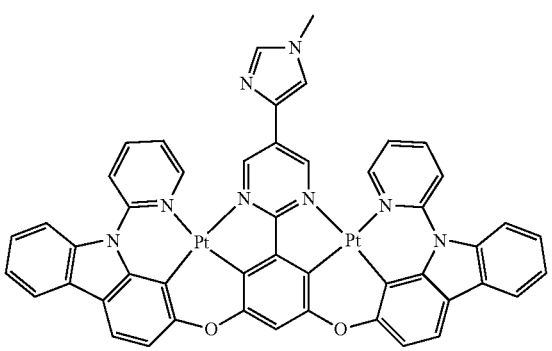
Compound Pt55
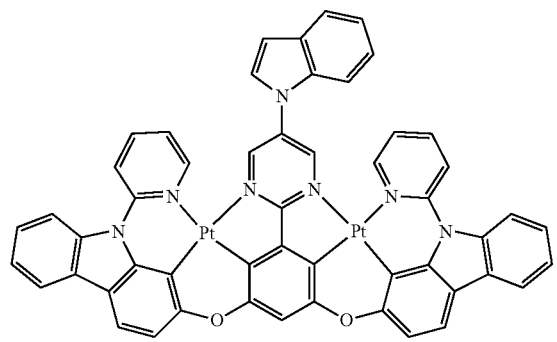
Compound Pt56
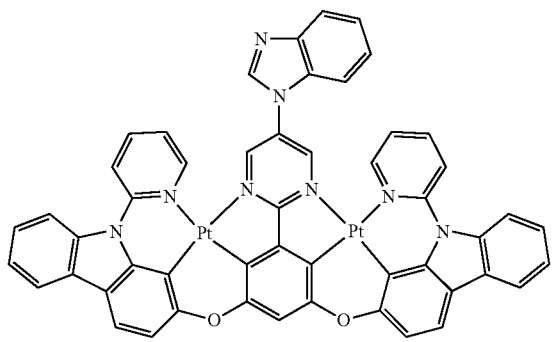
Compound Pt57
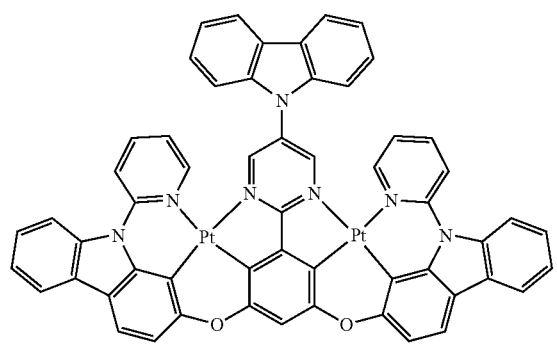
Compound Pt58
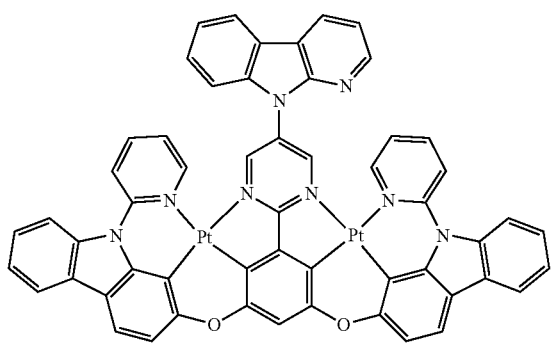

-continued
Compound Pt59
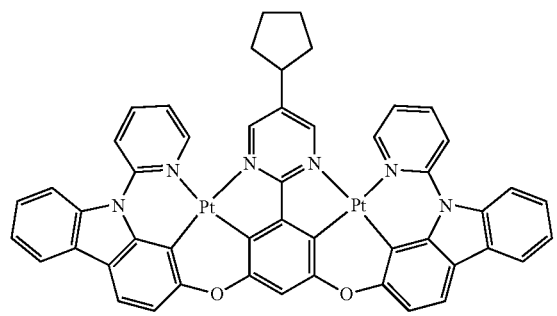
Compound Pt60
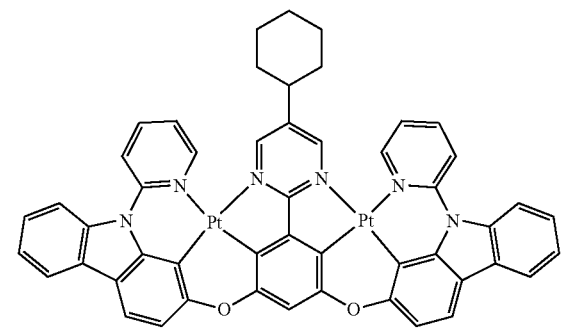
Compound Pt61
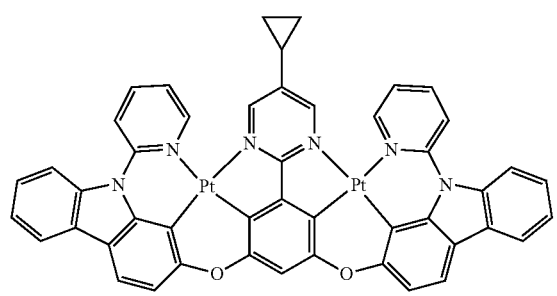
Compound Pt62
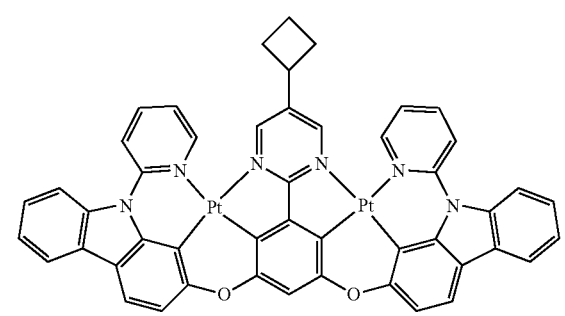
Compound Pt63
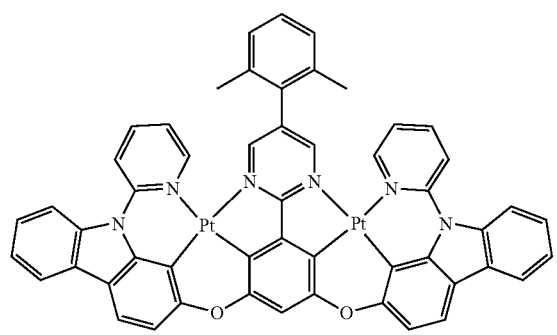
Compound Pt64
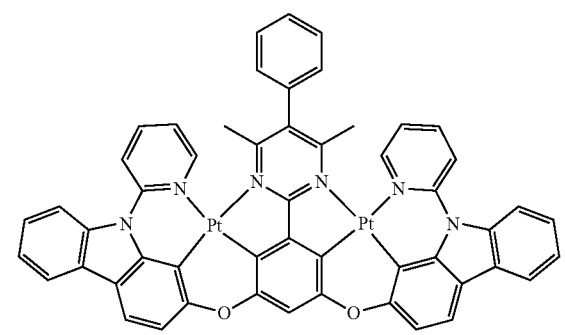
Compound Pt65
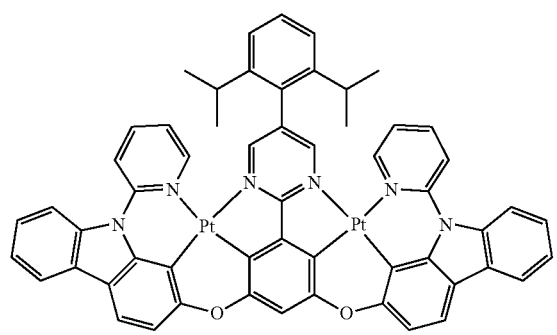
Compound Pt66
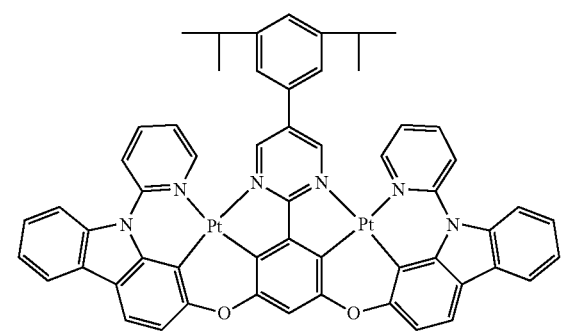

-continued
Compound Pt67
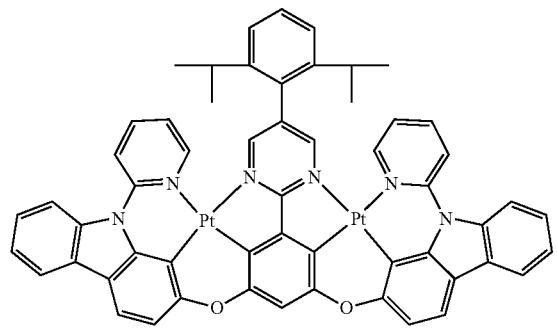
Compound Pt68
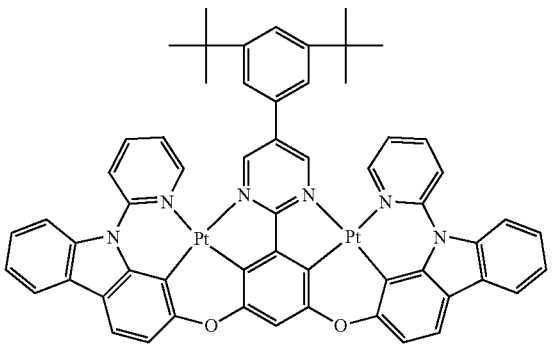
Compound Pt69
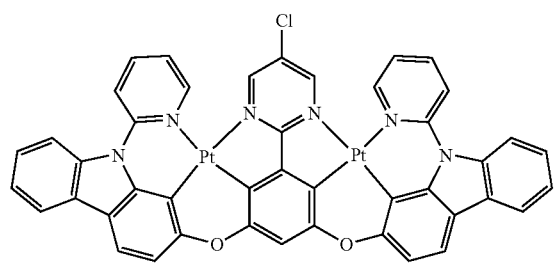
Compound Pt70
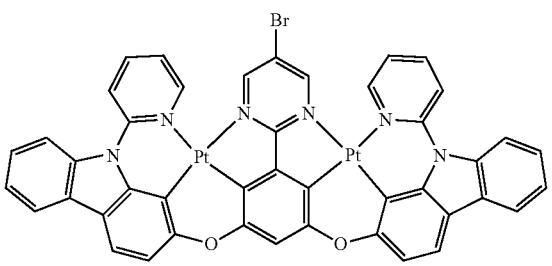
Compound Pt71
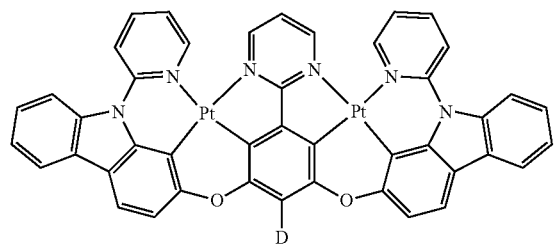
Compound Pt72
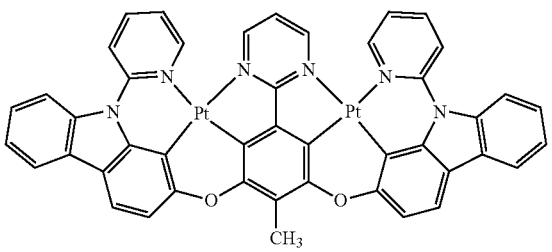
Compound Pt73
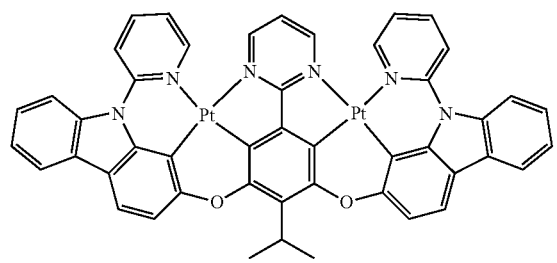
Compound Pt74
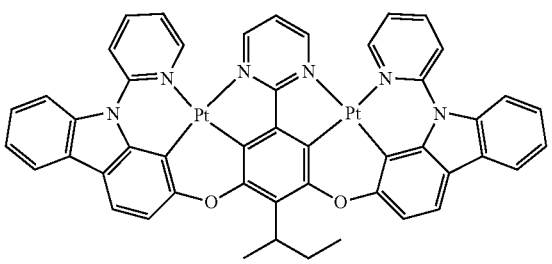
Compound Pt75
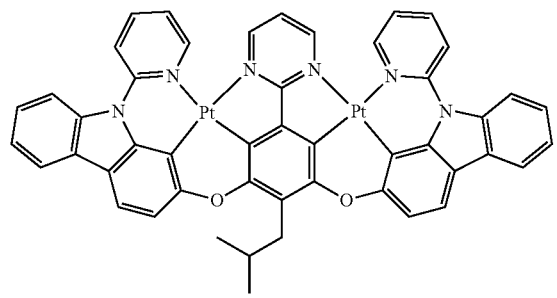
Compound Pt76

-continued
Compound Pt77
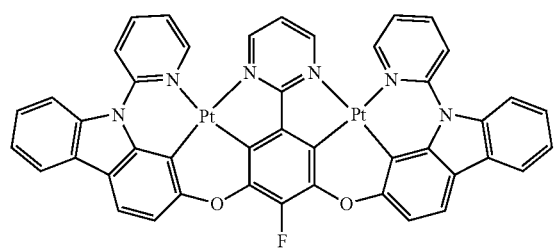
Compound Pt78
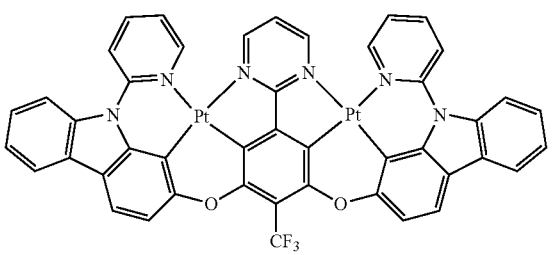
Compound Pt79
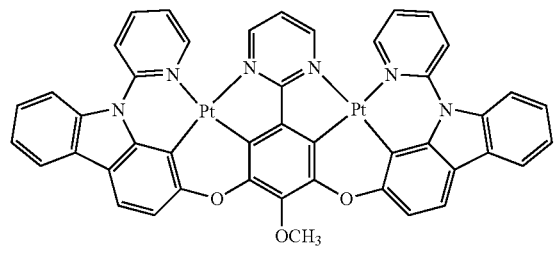
Compound Pt80
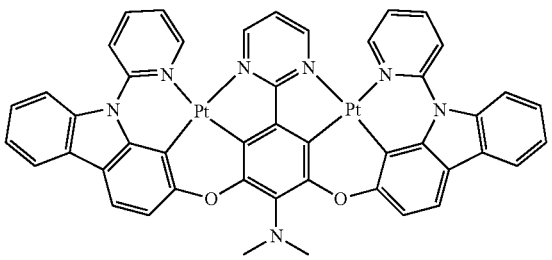
Compound Pt81
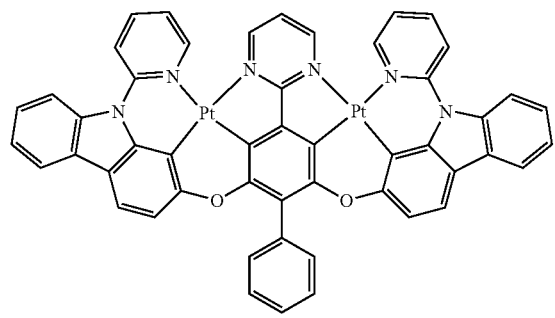
Compound Pt82
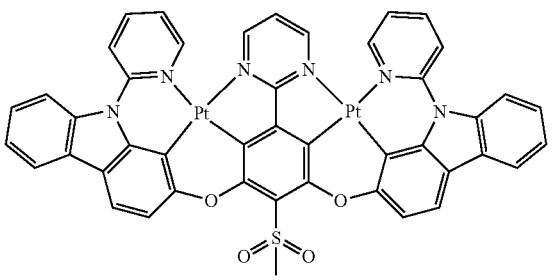
Compound Pt83
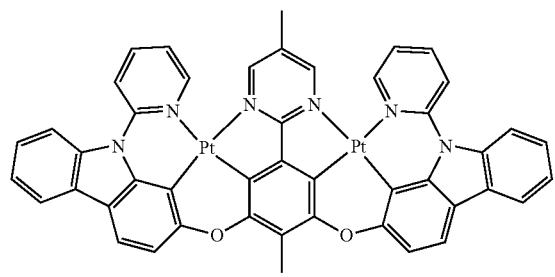
Compound Pt84
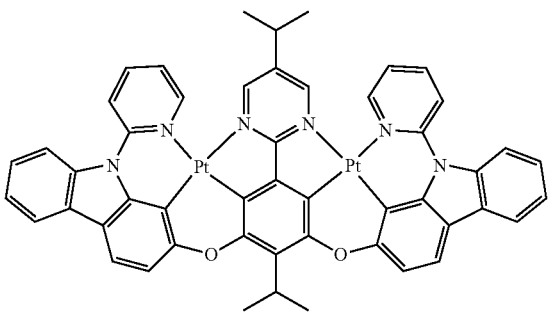
Compound Pt85
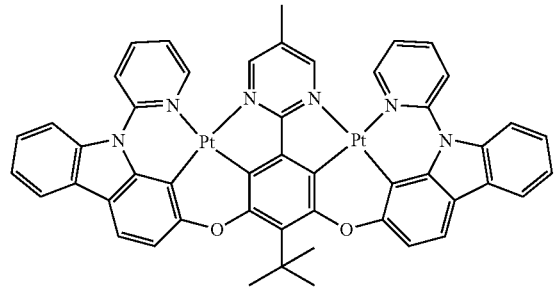
Compound Pt86
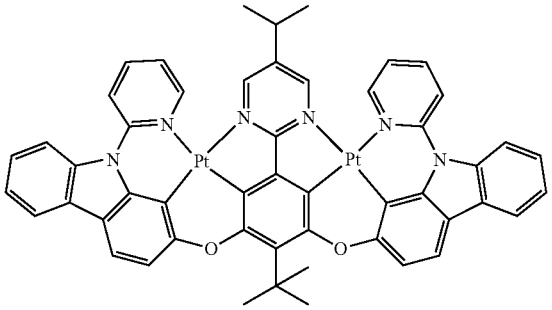

-continued
Compound Pt87
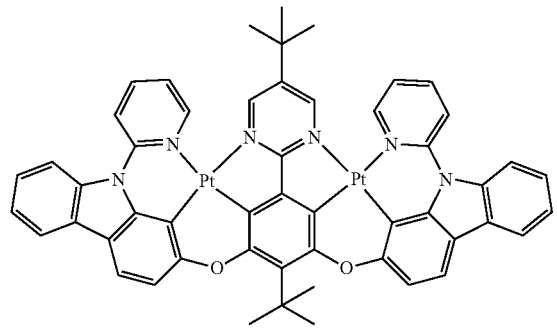
Compound Pt88
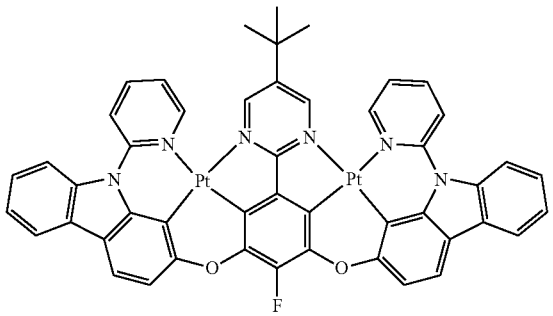
Compound Pt89
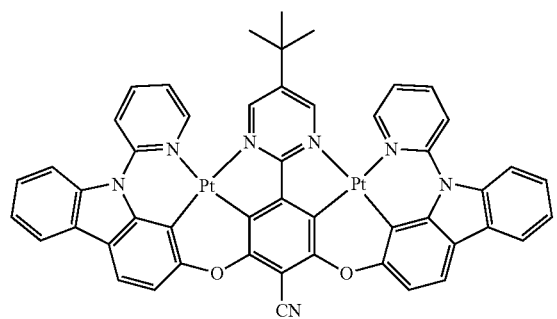
Compound Pt90
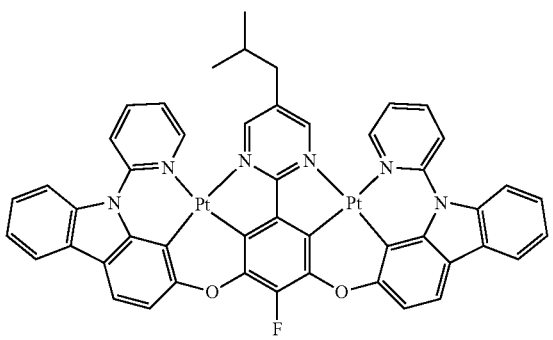
Compound Pt91
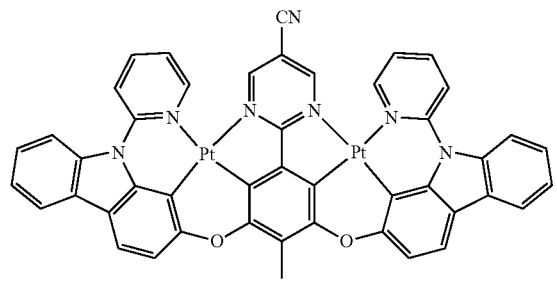
Compound Pt92
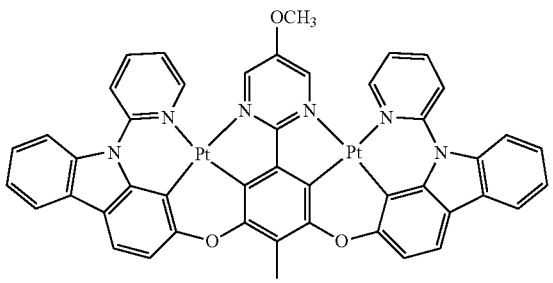
Compound Pt93
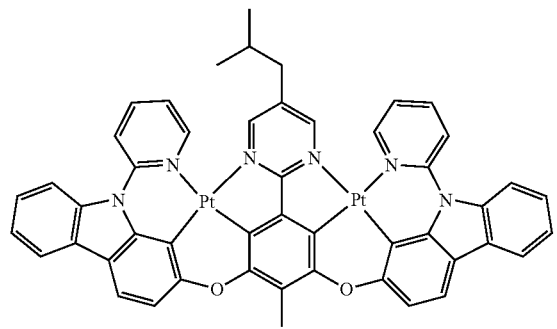
Compound Pt94
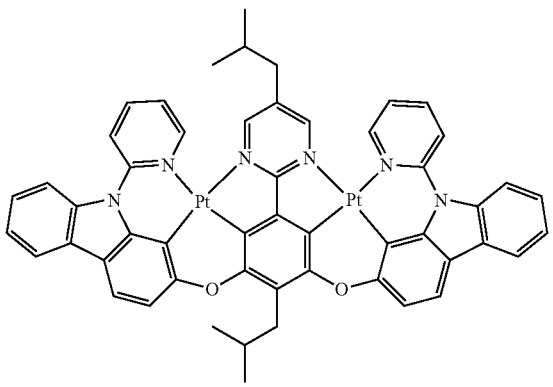

Compound Pt95
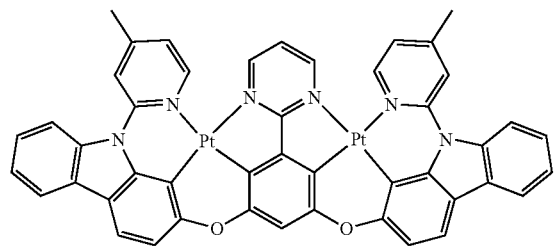
Compound Pt96
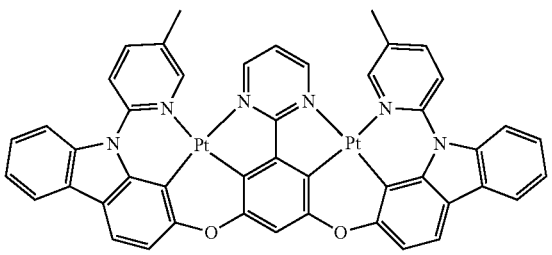
Compound Pt97
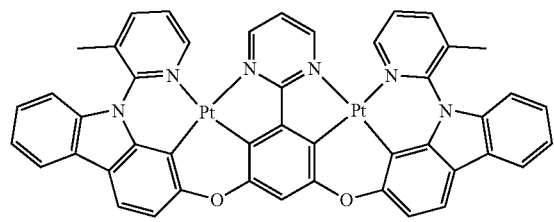
Compound Pt98
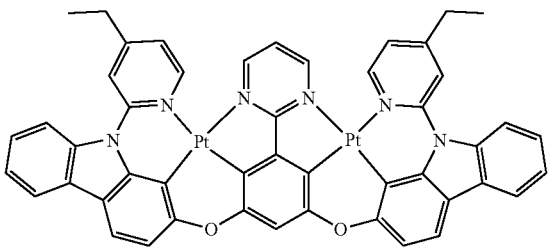
Compound Pt99
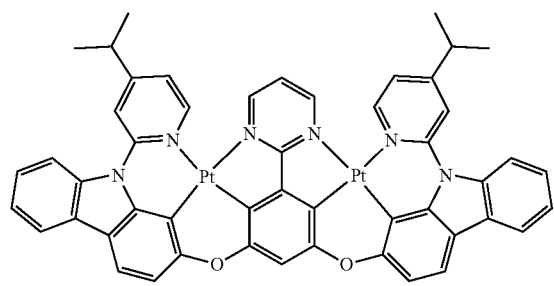
Compound Pt100
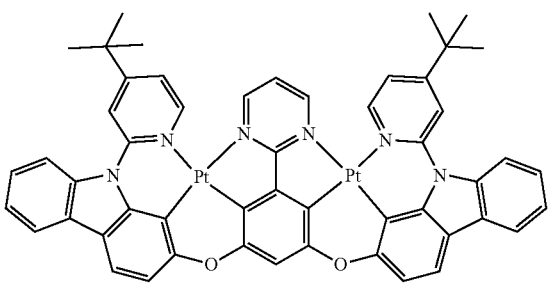
Compound Pt101
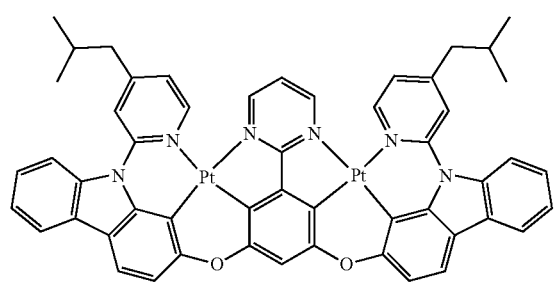
Compound Pt102
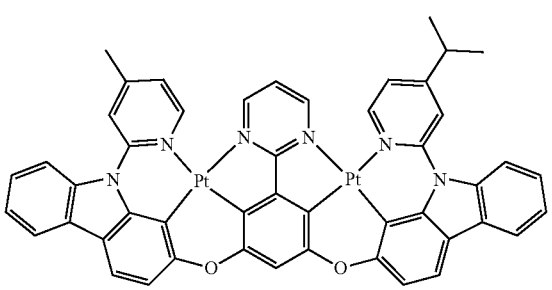
Compound Pt103
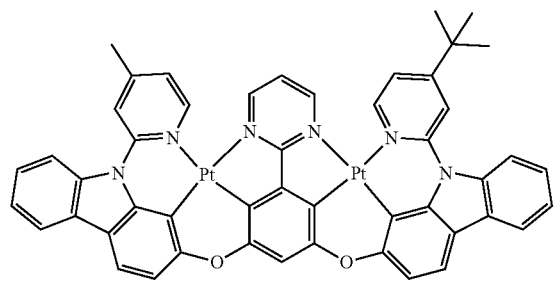
Compound Pt104

-continued
Compound Pt105
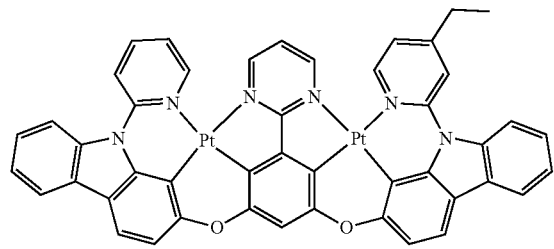
Compound Pt106
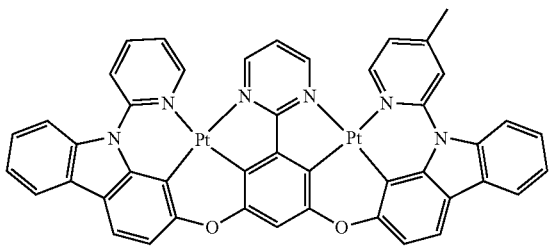
Compound Pt107
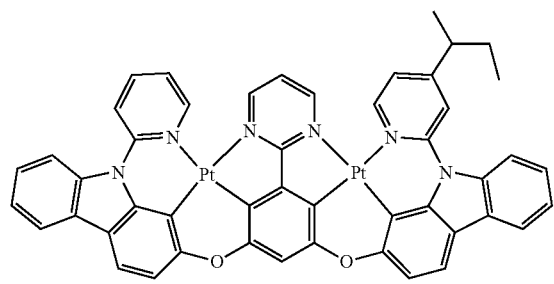
Compound Pt108
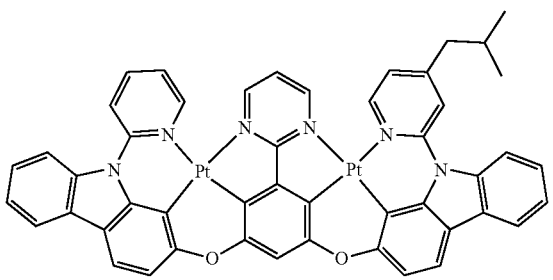
Compound Pt109
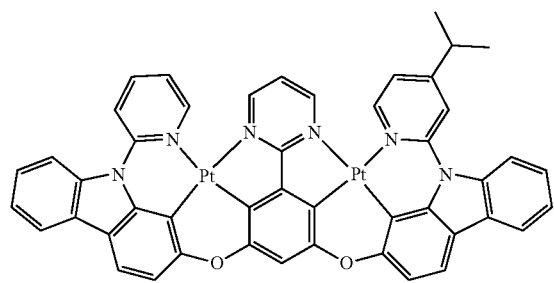
Compound Pt110
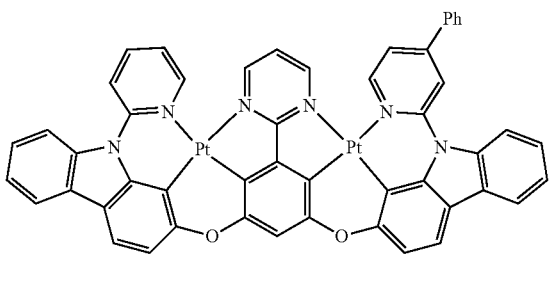
Compound Pt111
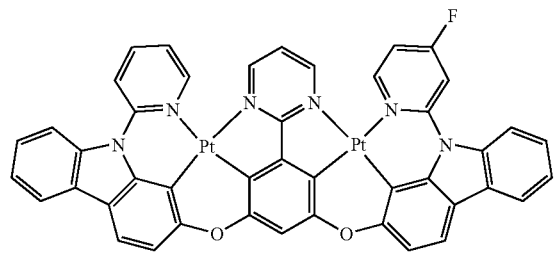
Compound Pt112
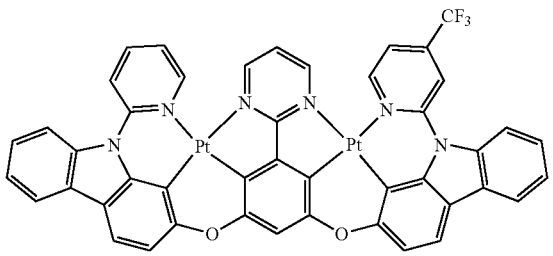
Compound Pt113
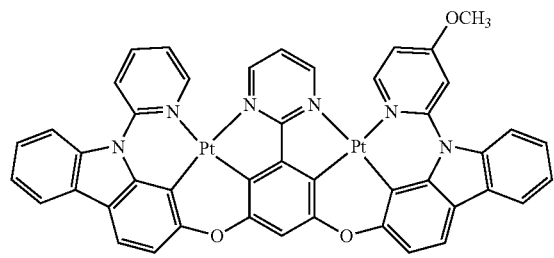
Compound Pt114

-continued
Compound Pt115
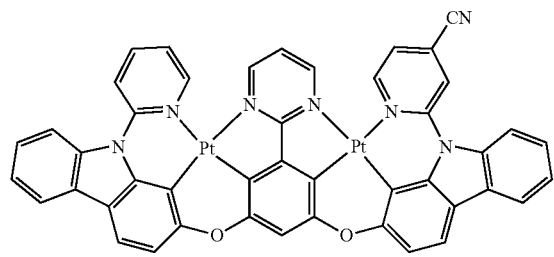
Compound Pt116
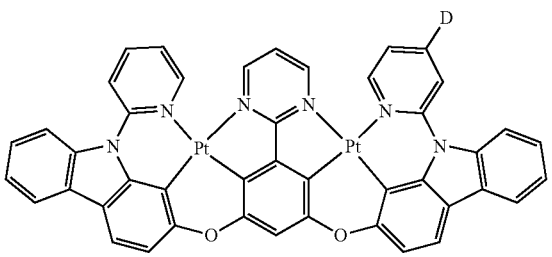
Compound Pt117
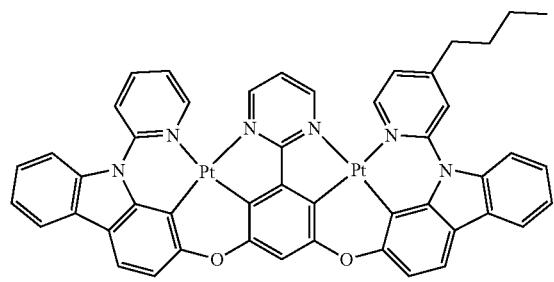
Compound Pt118
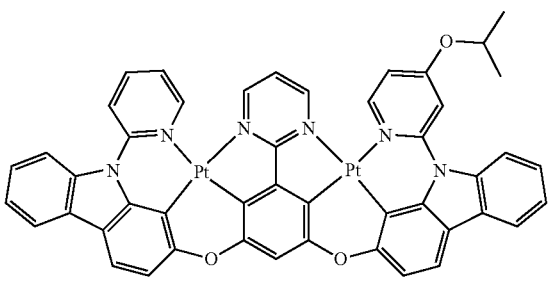
Compound Pt119
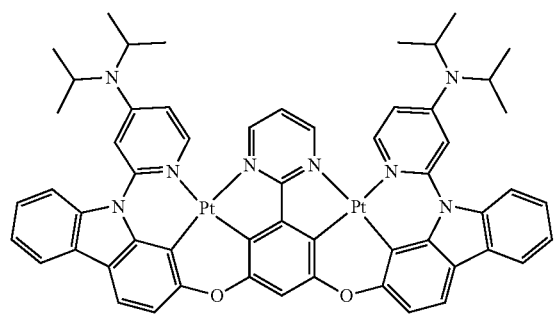
Compound Pt120
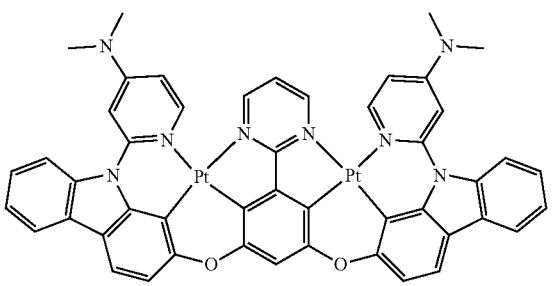
Compound Pt121
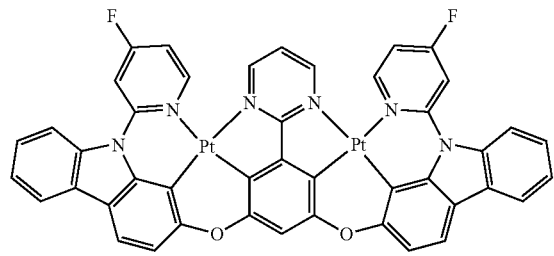
Compound Pt122
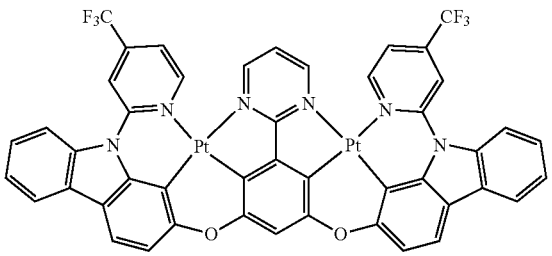
Compound Pt123
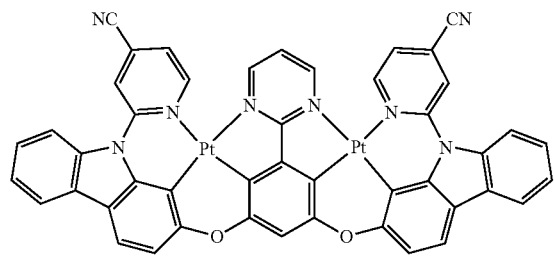
Compound Pt124
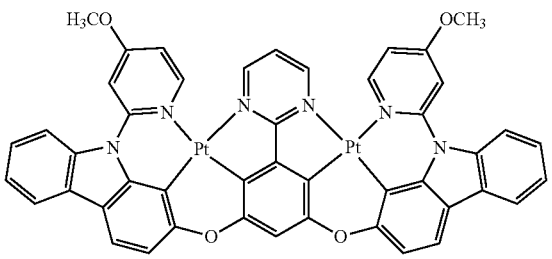

-continued
Compound Pt125
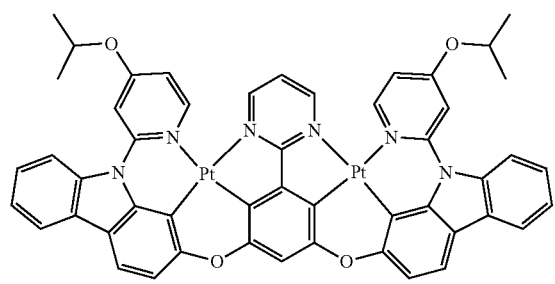
Compound Pt126
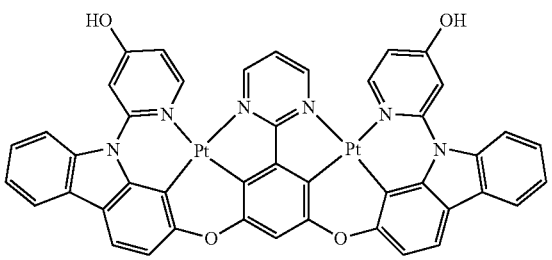
Compound Pt127
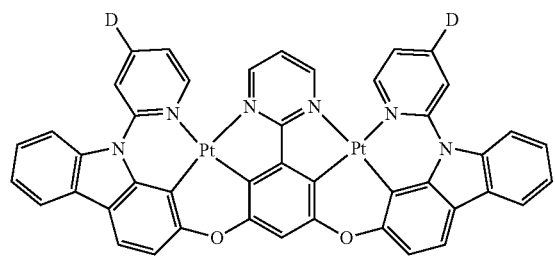
Compound Pt128
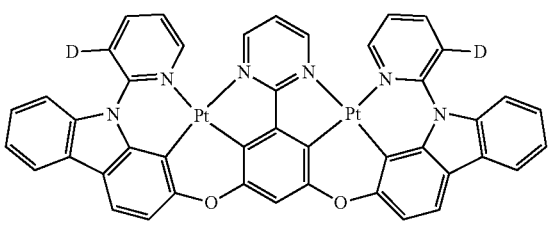
Compound Pt129
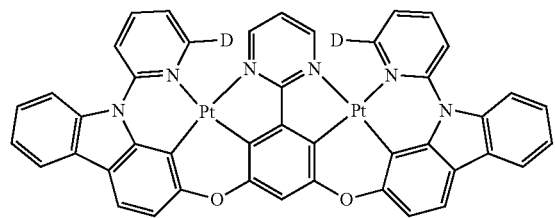
Compound Pt130
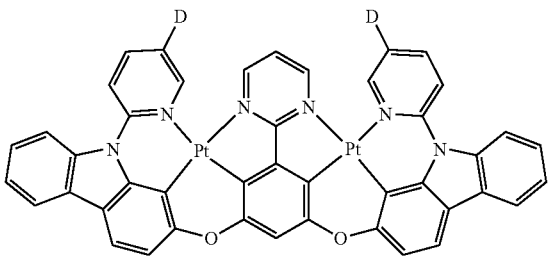
Compound Pt131
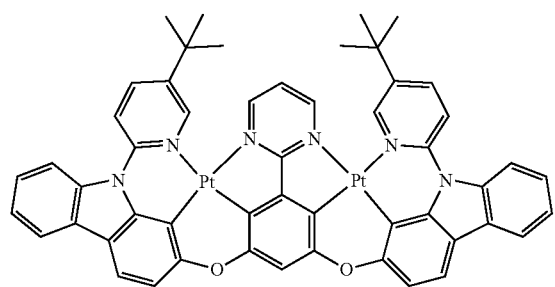
Compound Pt132
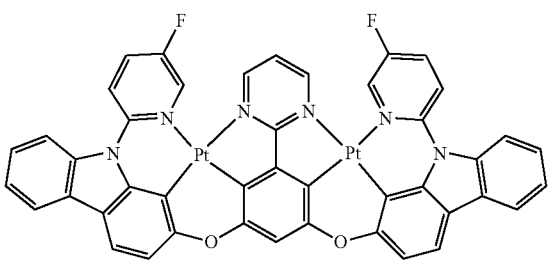
Compound Pt133
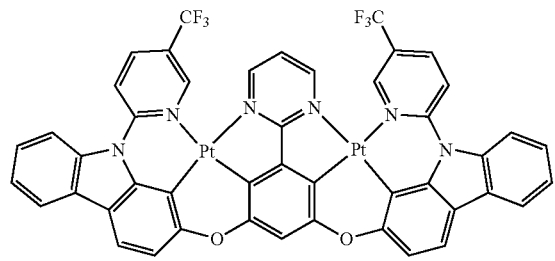
Compound Pt134
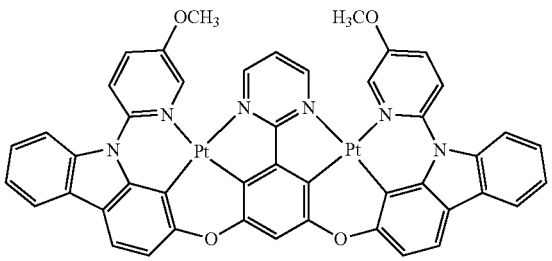

-continued
Compound Pt135
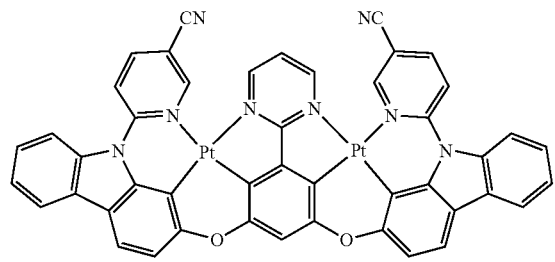
Compound Pt136
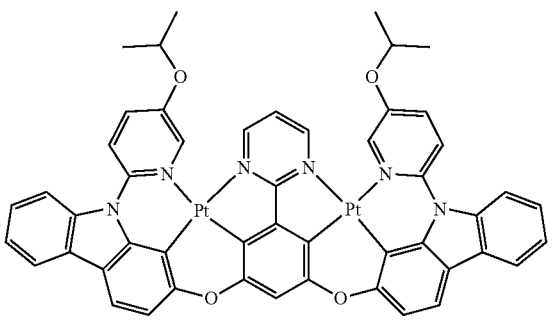
Compound Pt137
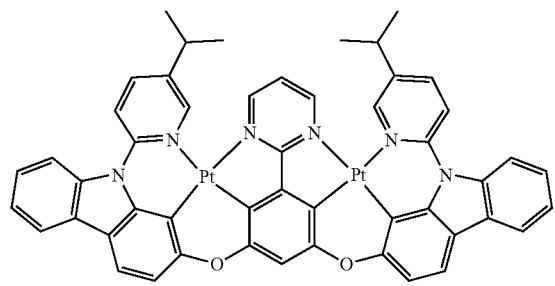
Compound Pt138
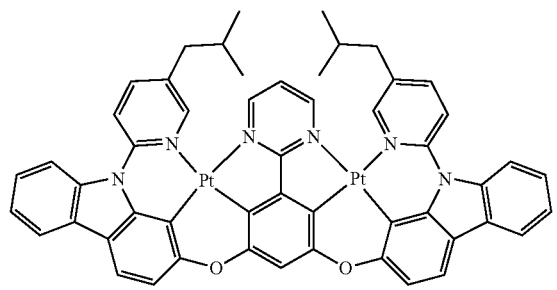
Compound Pt139
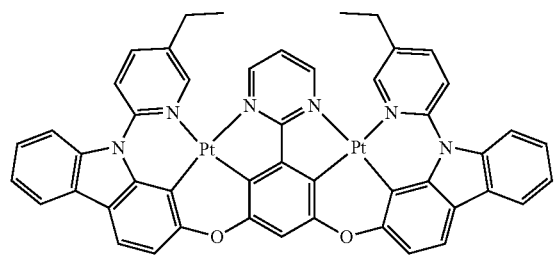
Compound Pt140
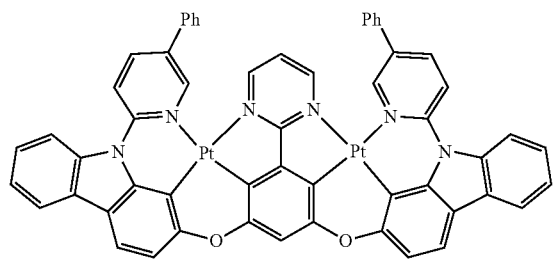
Compound Pt141
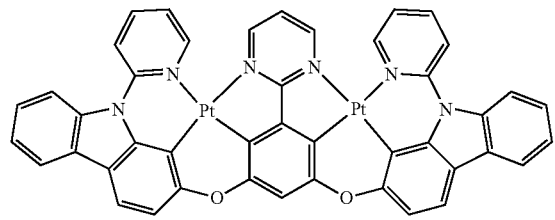
Compound Pt142
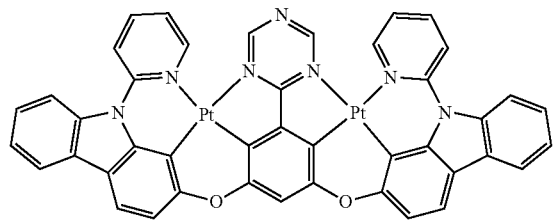
Compound Pt143
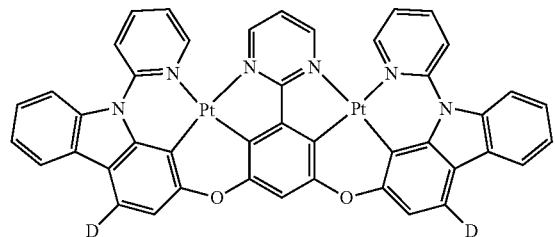
Compound Pt144
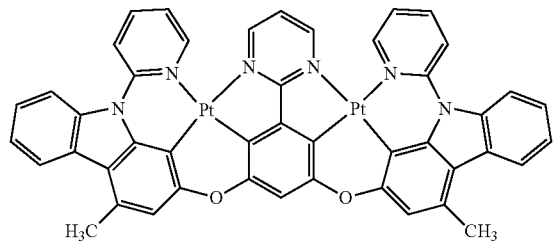

-continued
Compound Pt145
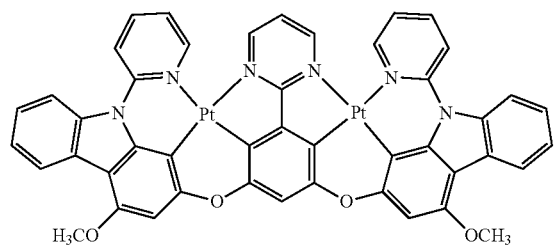
Compound Pt146
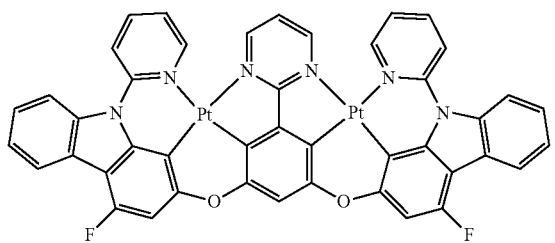
Compound Pt147
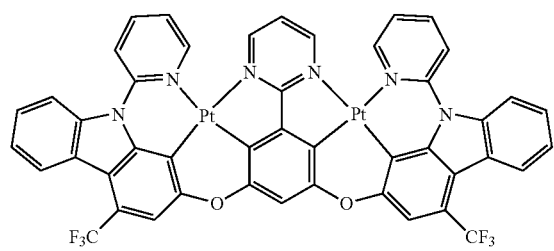
Compound Pt148
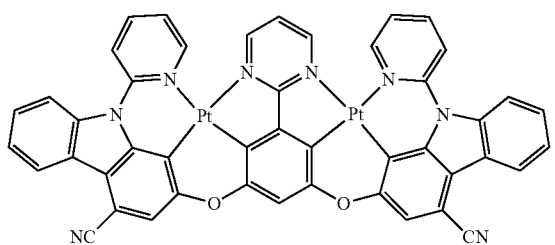
Compound Pt149
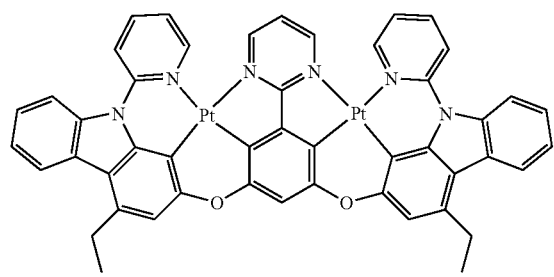
Compound Pt150
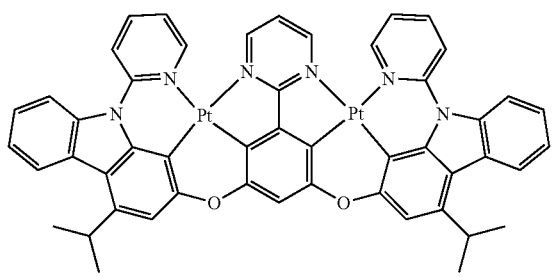
Compound Pt151
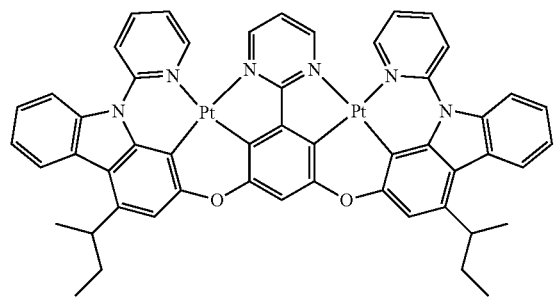
Compound Pt152
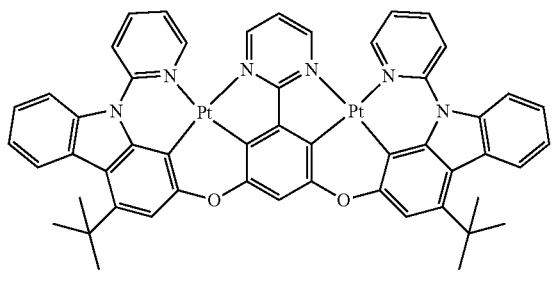
Compound Pt153
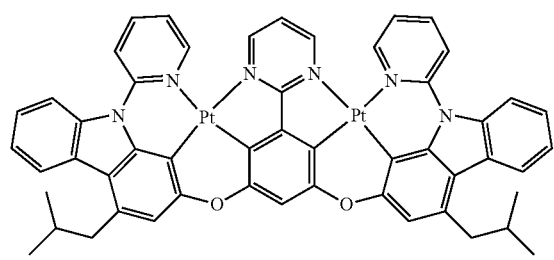
Compound Pt154
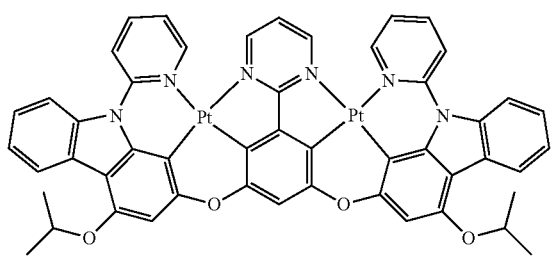

-continued
Compound Pt155
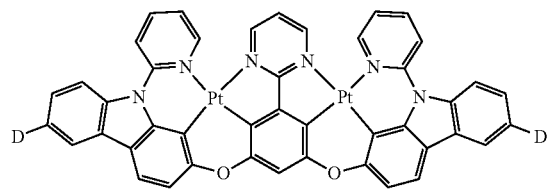
Compound Pt156
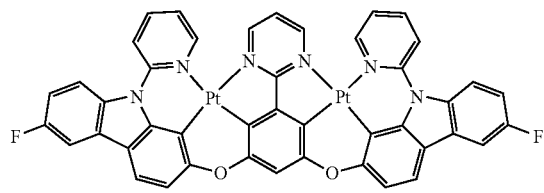
Compound Pt157
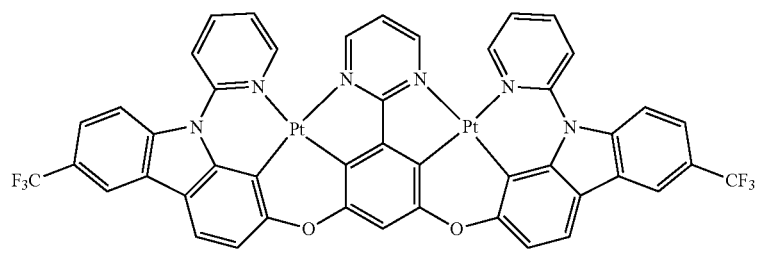
Compound Pt158
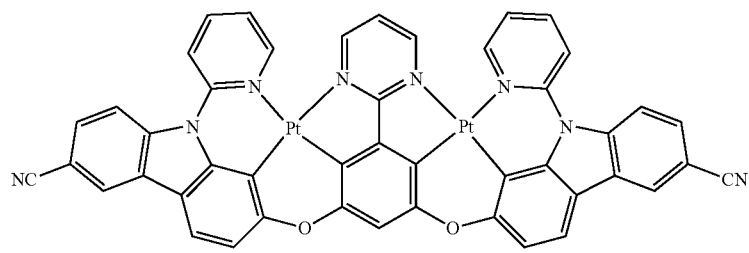
Compound Pt159
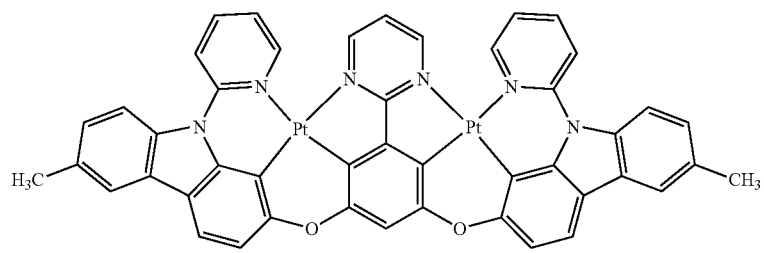
Compound Pt160
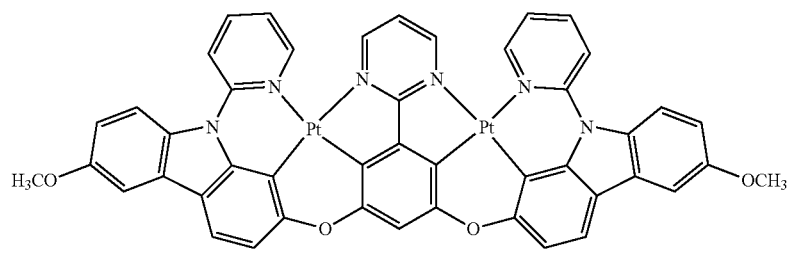
Compound Pt161
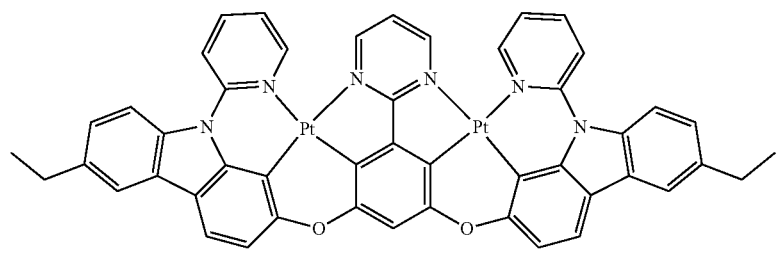

-continued
Compound Pd162
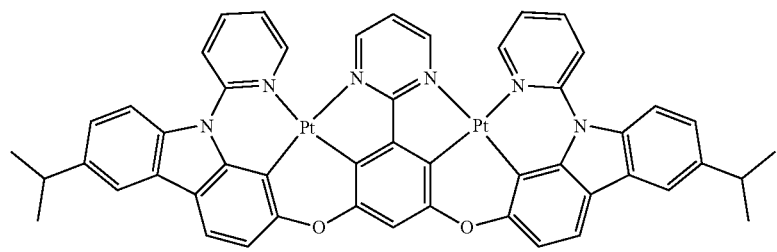
Compound Pt163
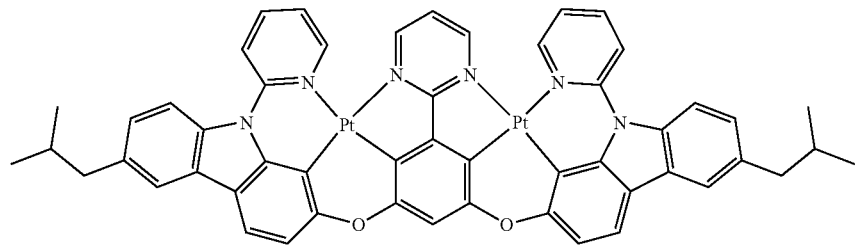
Compound Pt164
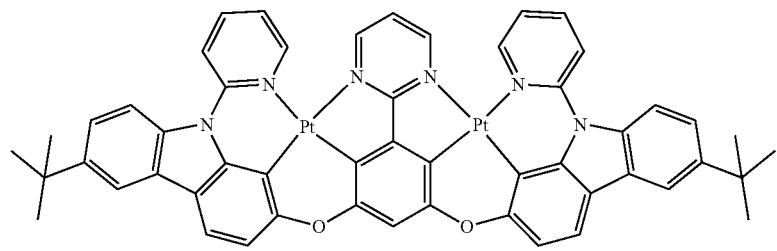
Compound Pt165
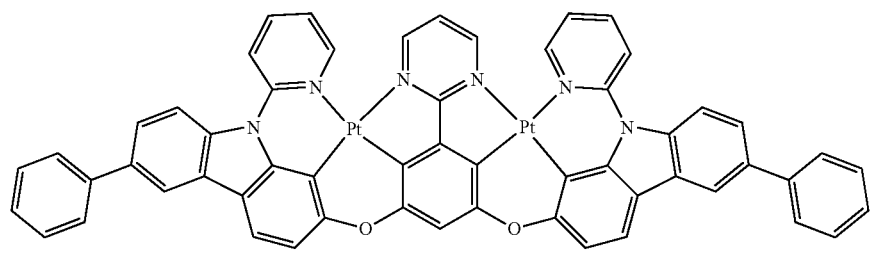
Compound Pt166
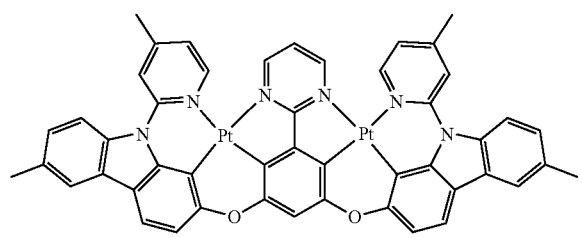
Compound Pt167
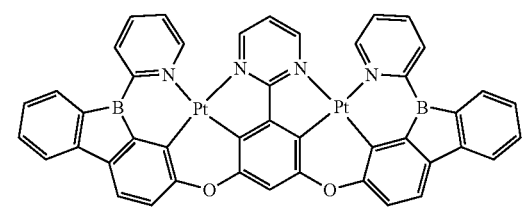
Compound Pt168
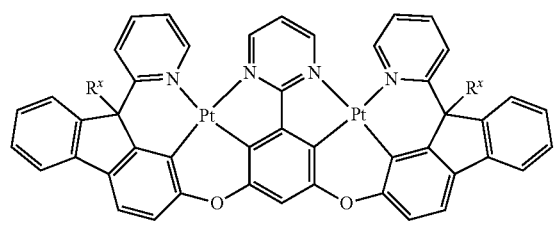
Compound Pt169
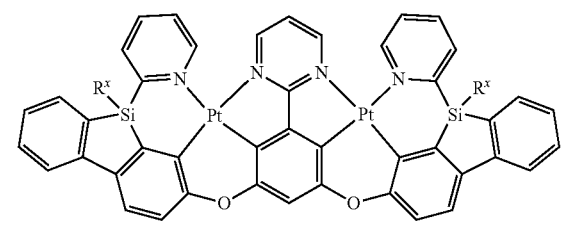

-continued
Compound Pt170
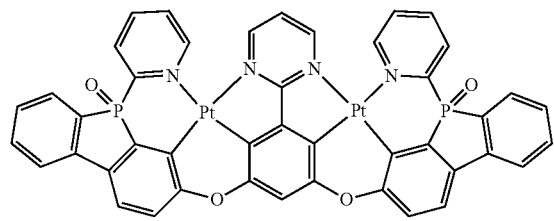
Compound Pt171
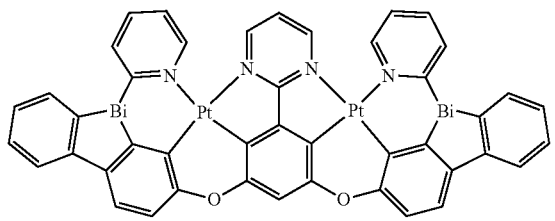
Compound Pt172
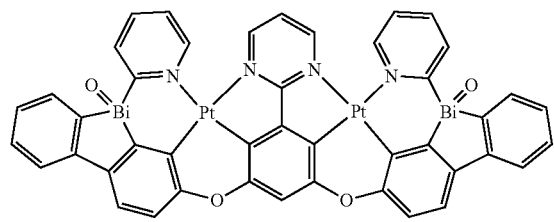
Compound Pt173
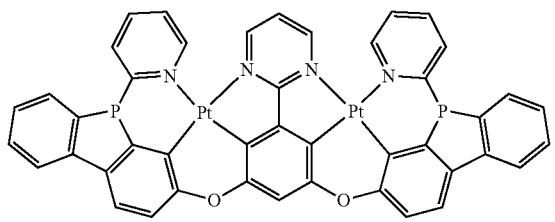
Compound Pt174
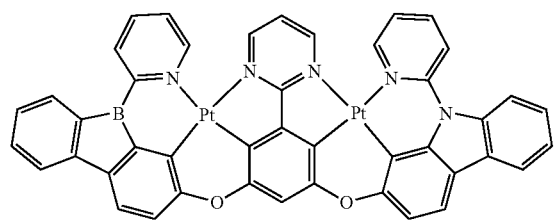
Compound Pt175
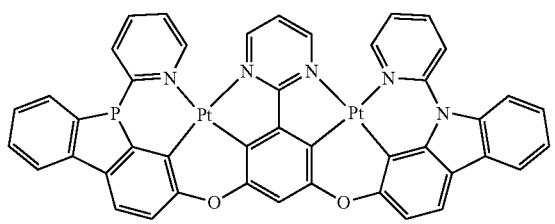
Compound Pt176
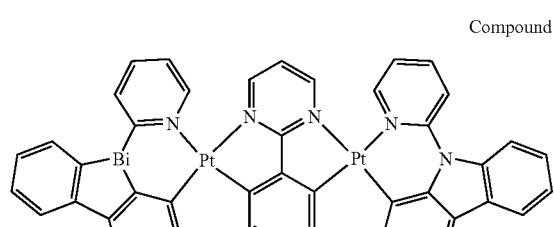
Compound Pt177
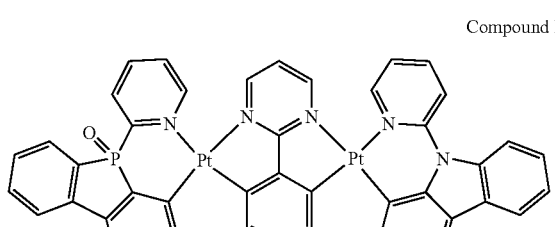
Compound Pt178
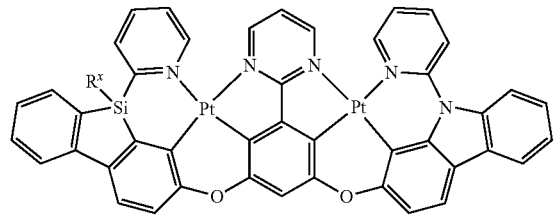
Compound Pt179
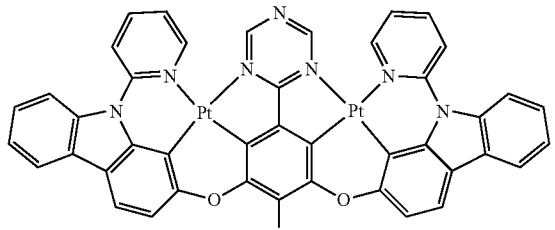
Compound Pt180
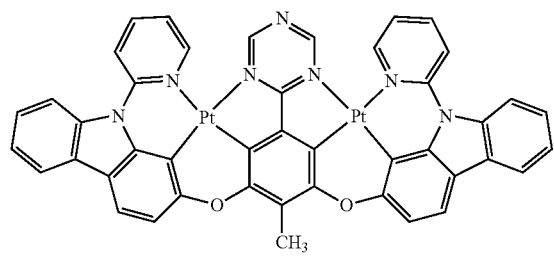

-continued
Compound Pt182
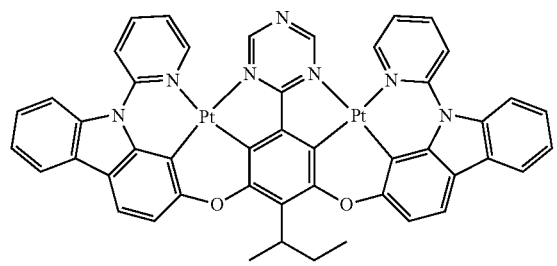
Compound Pt183
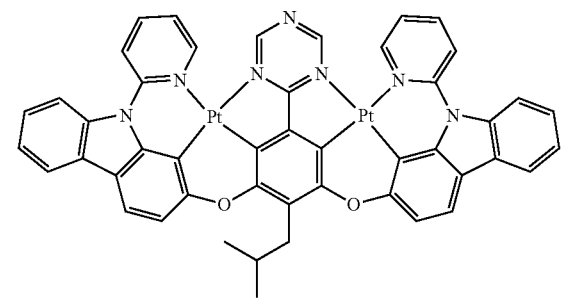
Compound Pt184
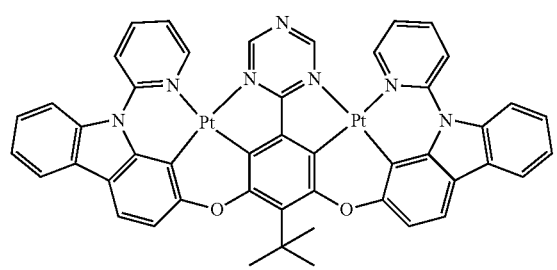
Compound Pt185
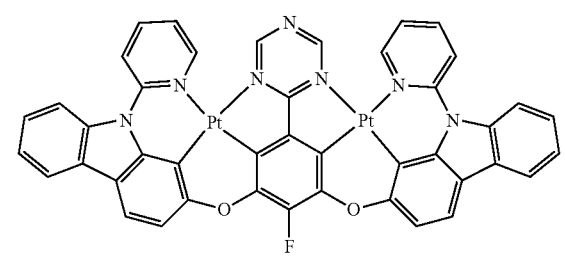
Compound Pt186
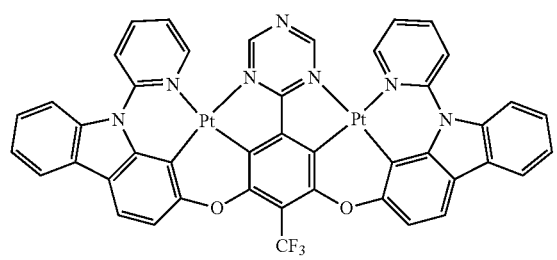
Compound Pt187
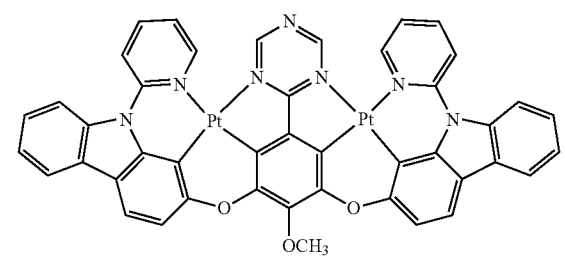
Compound Pt188
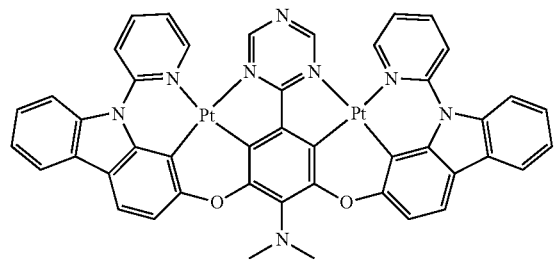
Compound Pt189
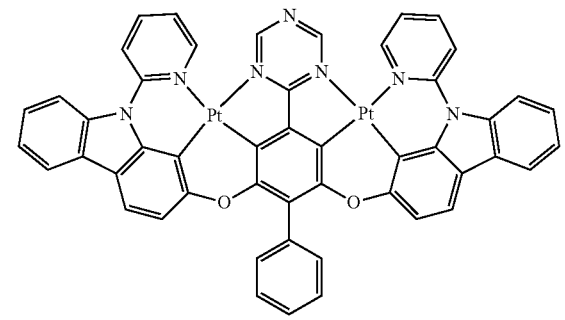
Compound Pt190
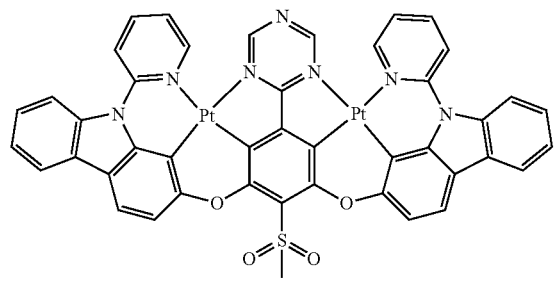
Compound Pt191
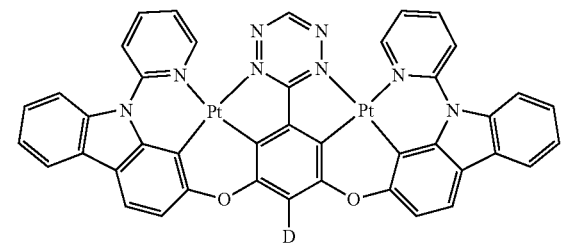

-continued
Compound Pt192
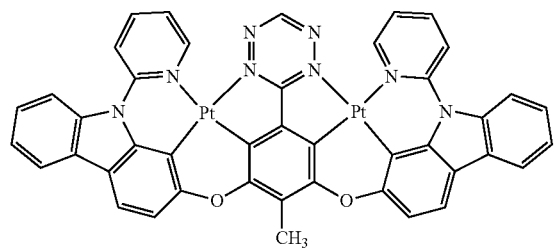
Compound Pt193
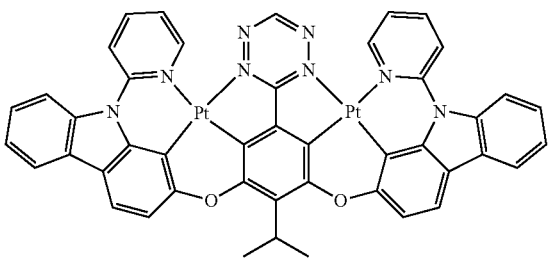
Compound Pt194
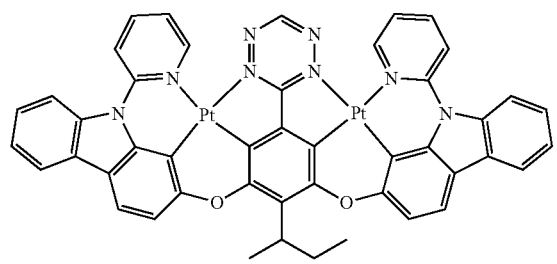
Compound Pt195
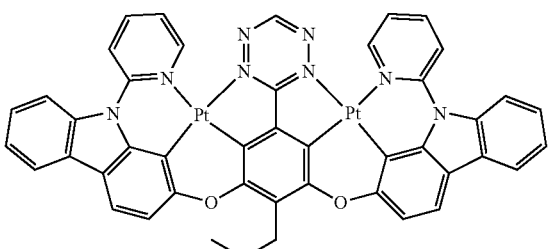
Compound Pt196
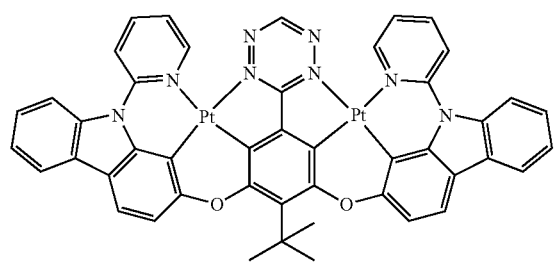
Compound Pt197
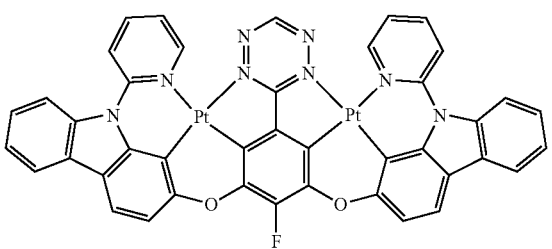
Compound Pt198
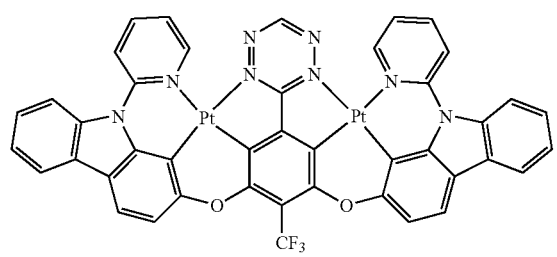
Compound Pt199
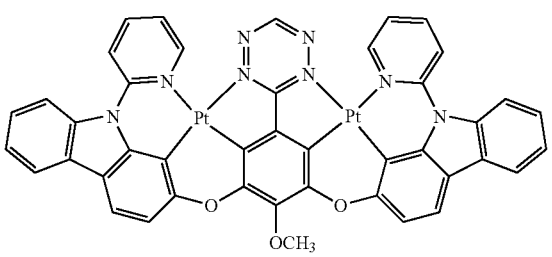
Compound Pt200
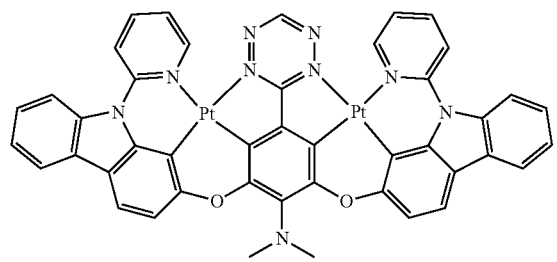
Compound Pt201
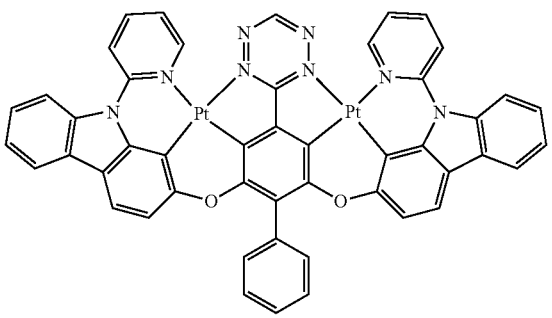

-continued
Compound Pt202
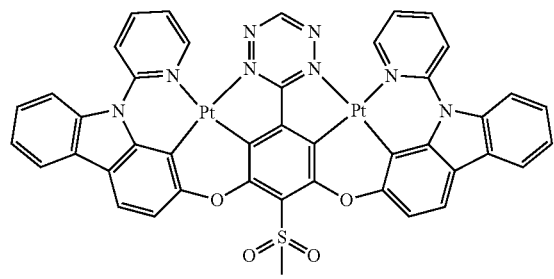
Compound Pt203
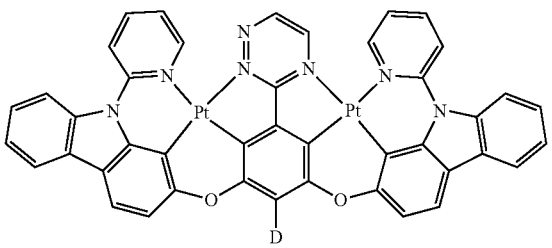
Compound Pt204
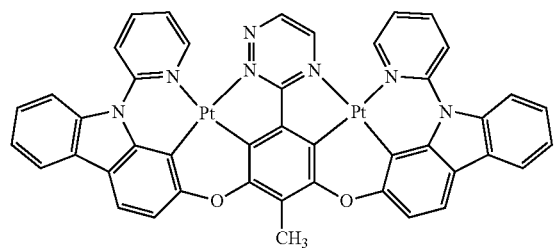
Compound Pt205
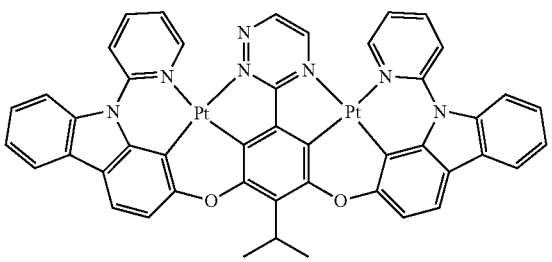
Compound Pt206
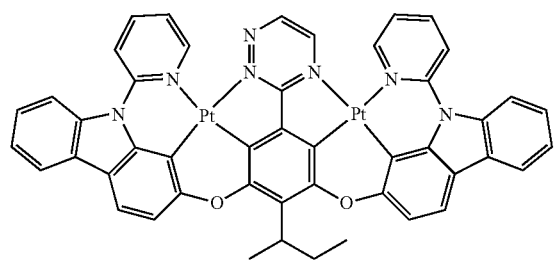
Compound Pt207
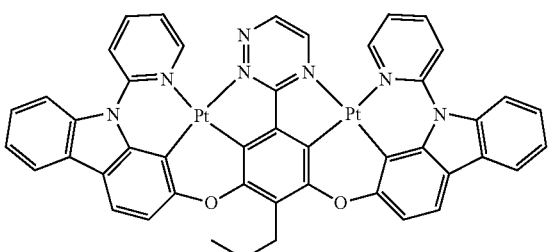
Compound Pt208
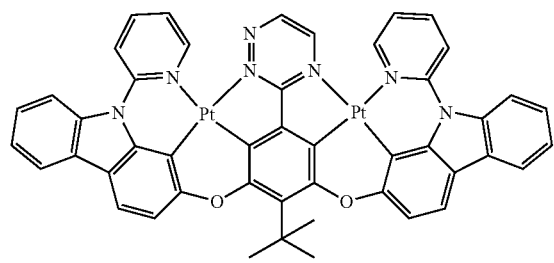
Compound Pt209
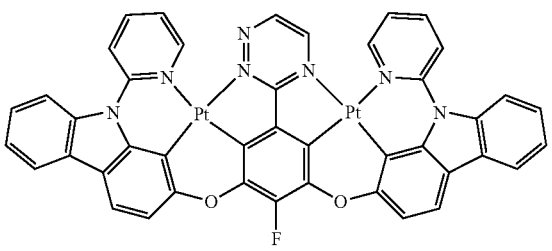
Compound Pt210
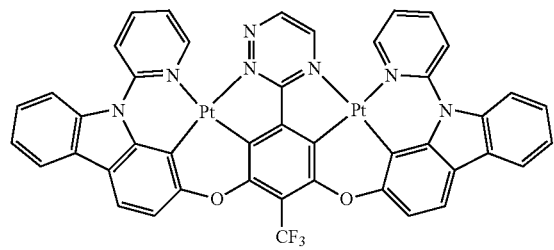
Compound Pt211
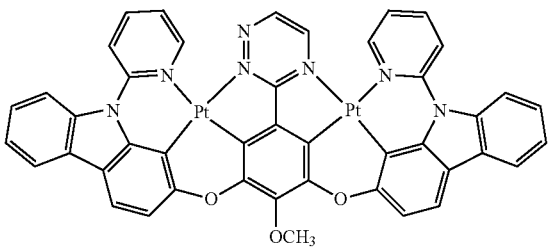

Compound Pt212
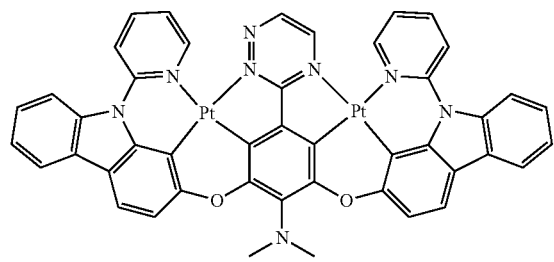
Compound Pt213
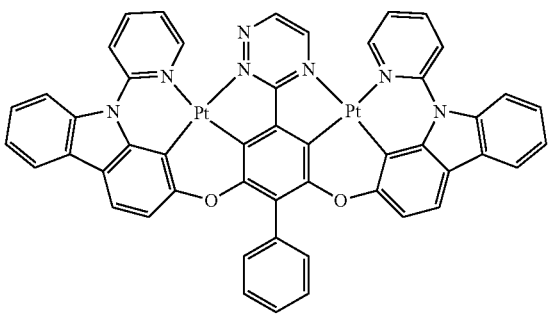
Compound Pt214
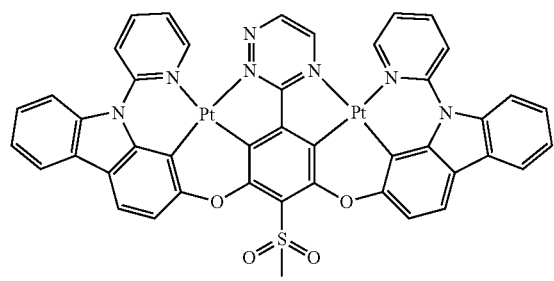
Compound Pt215
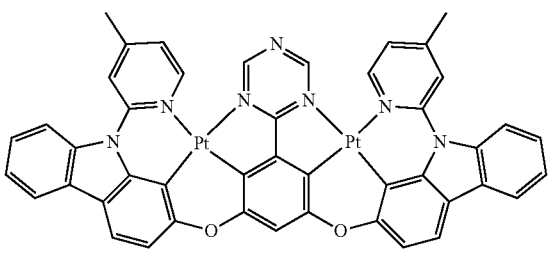
Compound Pt216
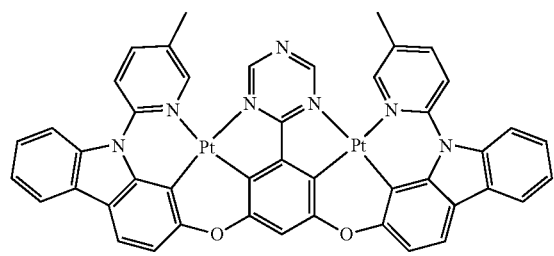
Compound Pt217
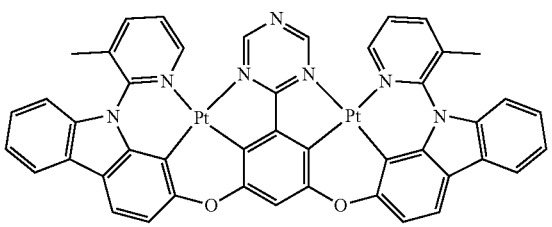
Compound Pt218
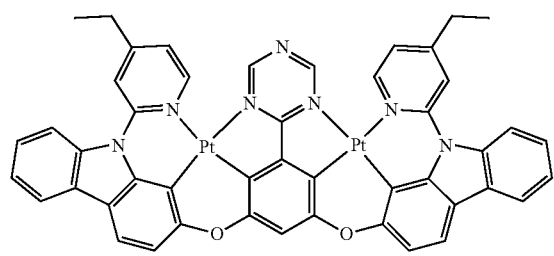
Compound Pt219
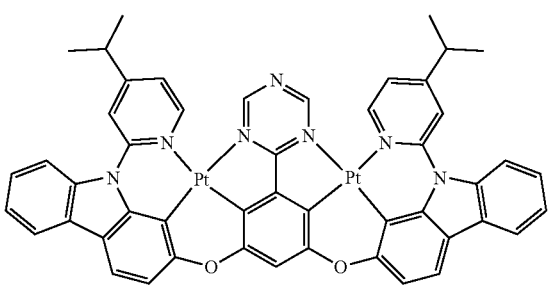
Compound Pt220
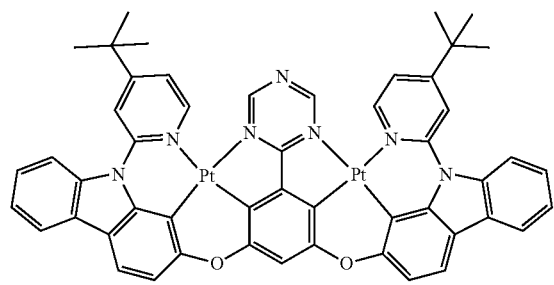
Compound Pt221
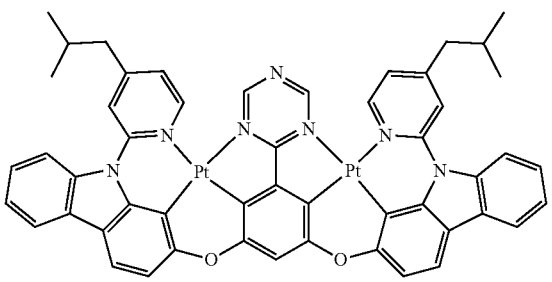

Compound Pt222
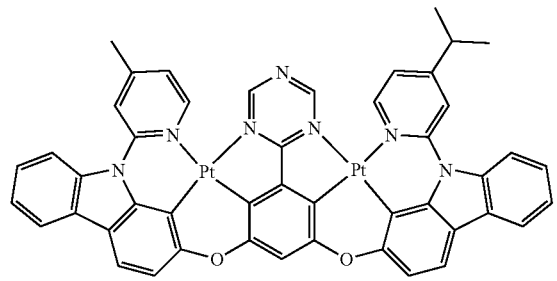
Compound Pt223
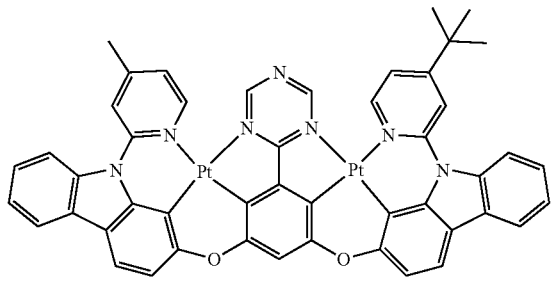
Compound Pt224
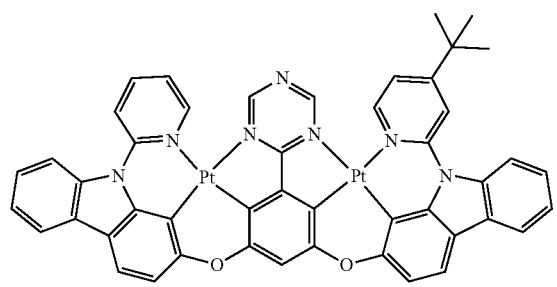
Compound Pt225
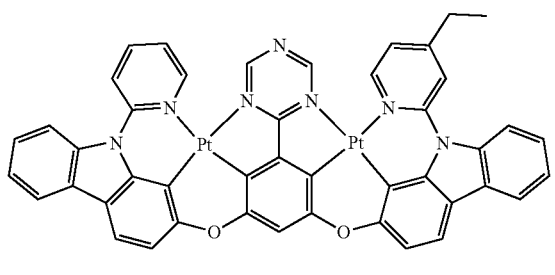
Compound Pt226
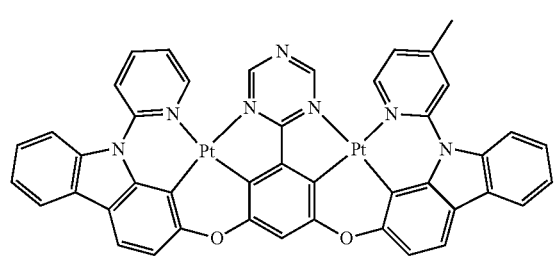
Compound Pt227
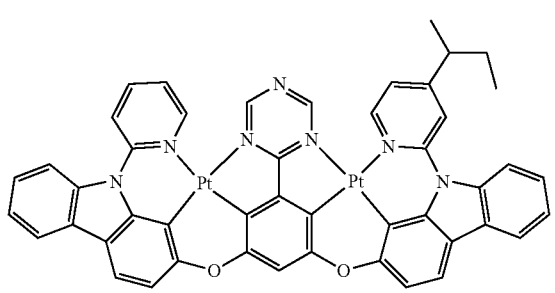
Compound Pt228
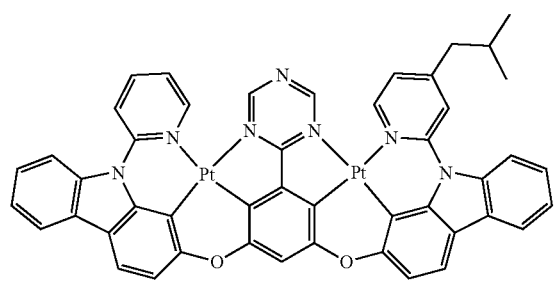
Compound Pt229
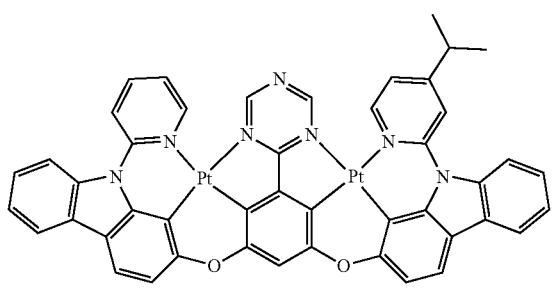
Compound Pt230
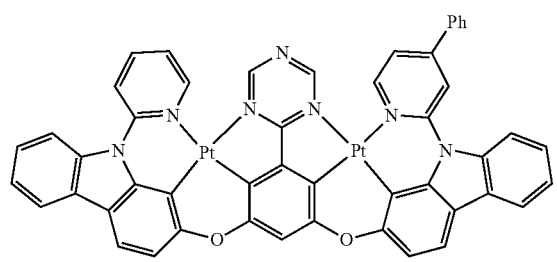
Compound Pt231
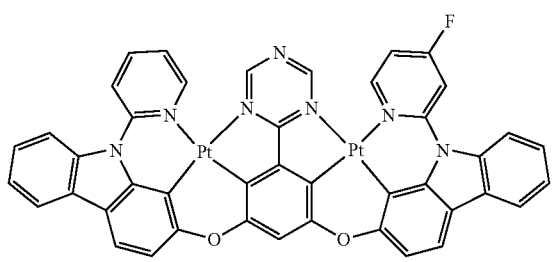

-continued
Compound Pt232
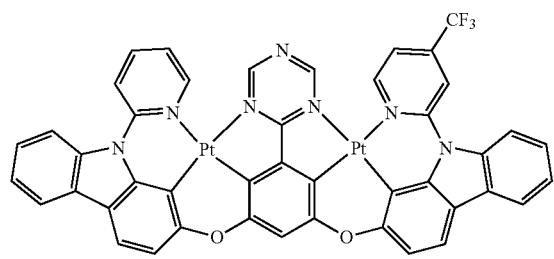
Compound Pt233
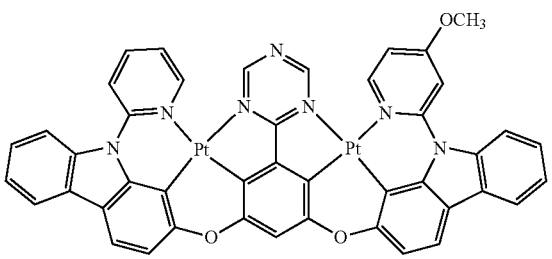
Compound Pt234
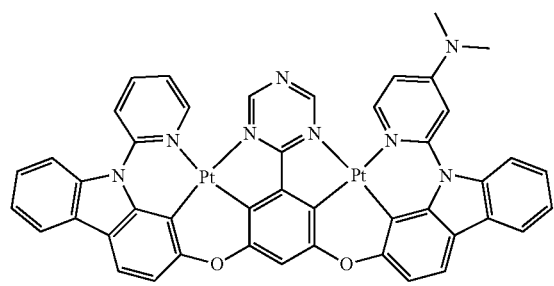
Compound Pt235
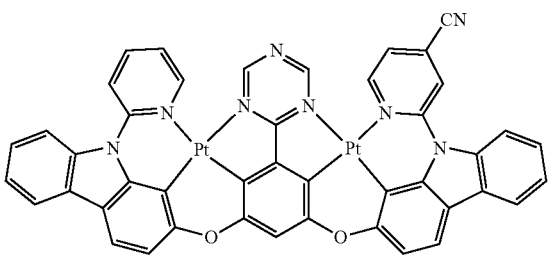
Compound Pt236
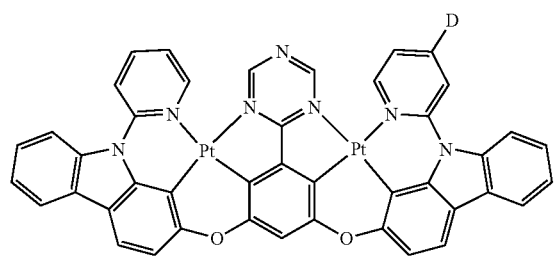
Compound Pt237
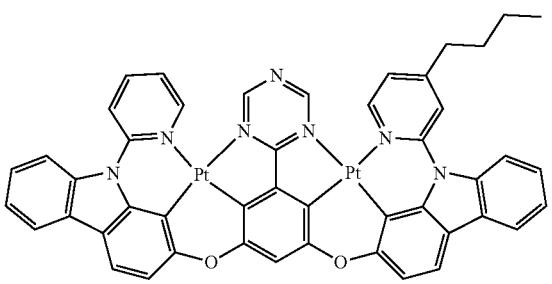
Compound Pt238
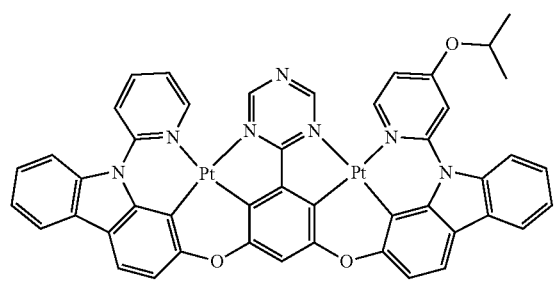
Compound Pt239
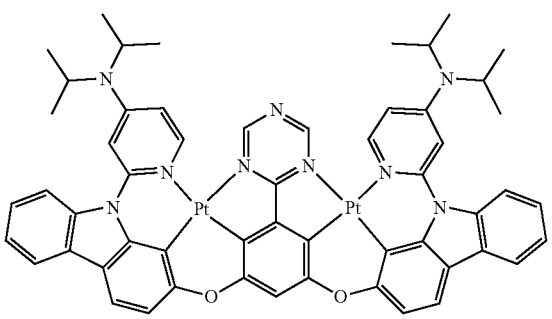
Compound Pt240
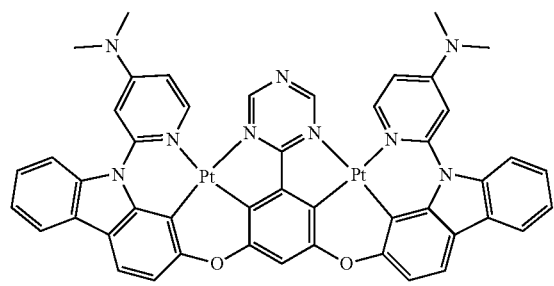
Compound Pt241
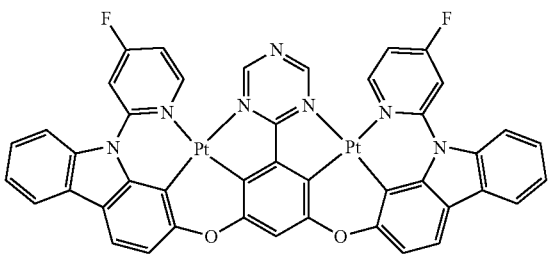

Compound Pt242
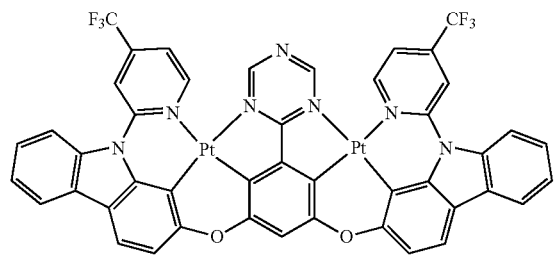
Compound Pt243
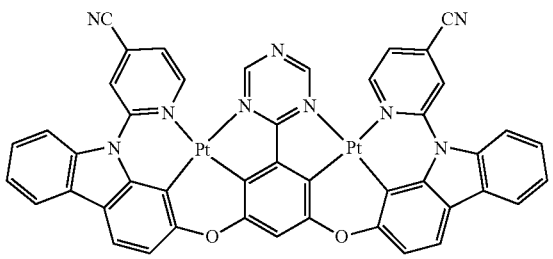
Compound Pt244
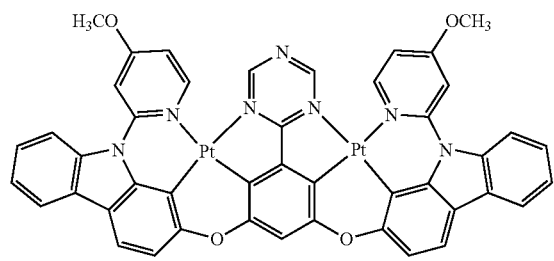
Compound Pt245
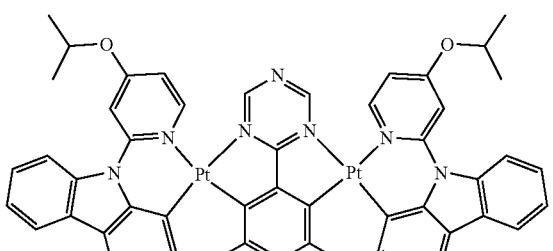
Compound Pt246
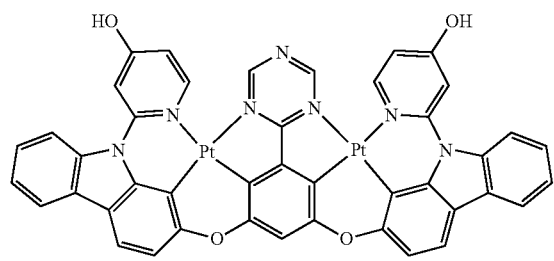
Compound Pt247
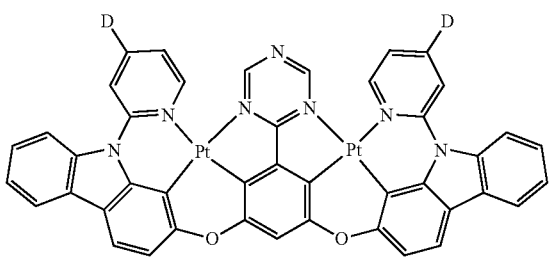
Compound Pt248
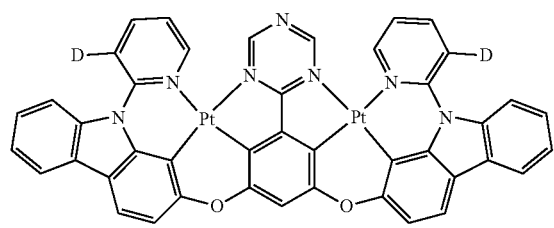
Compound Pt249
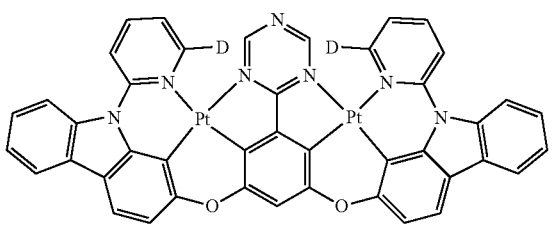
Compound Pt250
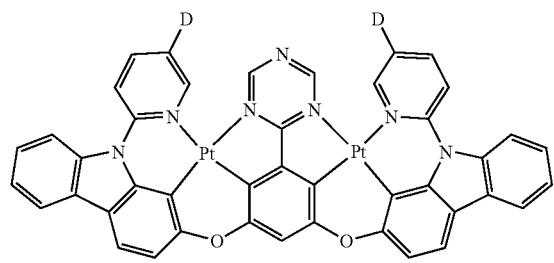
Compound Pt251
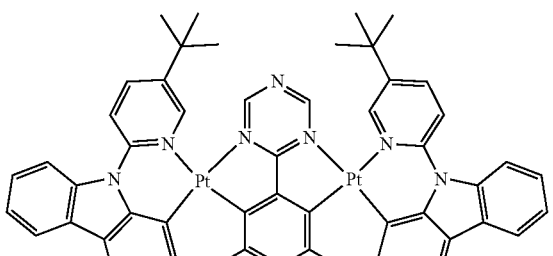

-continued
Compound Pt252
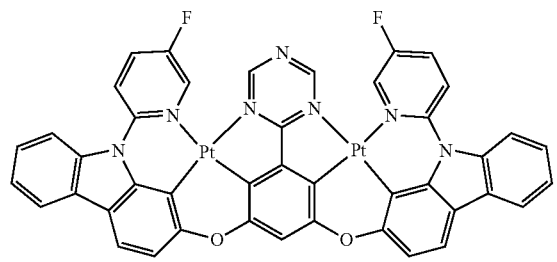
Compound Pt253
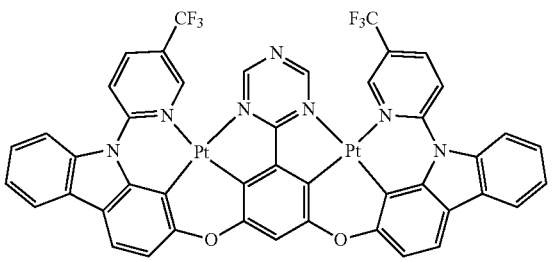
Compound Pt254
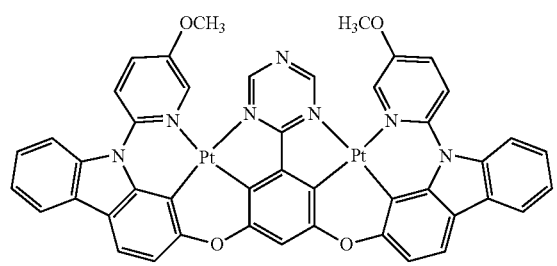
Compound Pt255
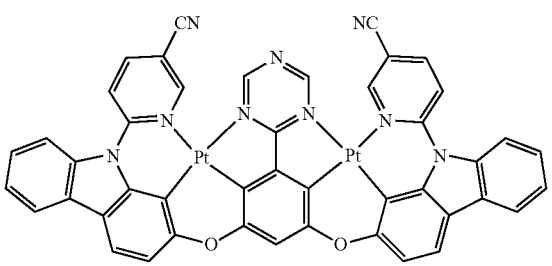
Compound Pt256
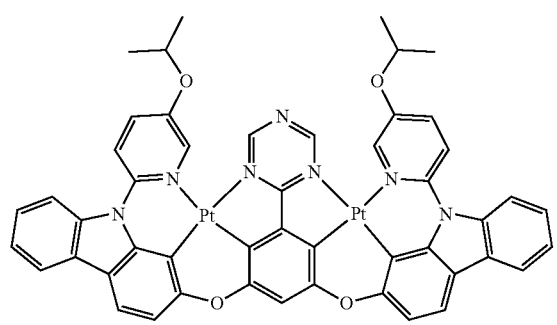
Compound Pt257
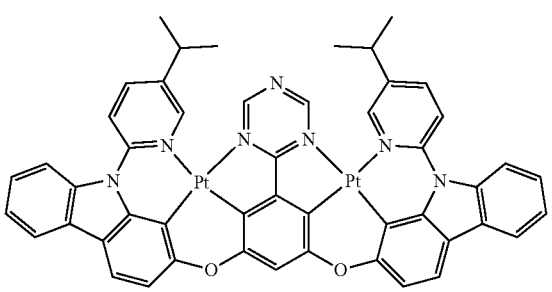
Compound Pt258
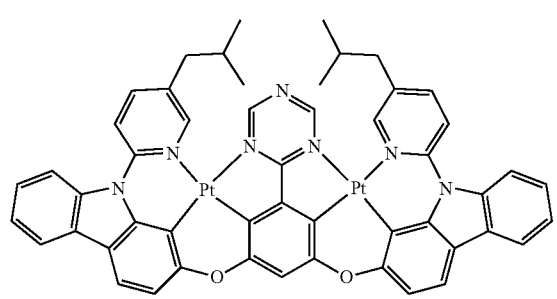
Compound Pt259
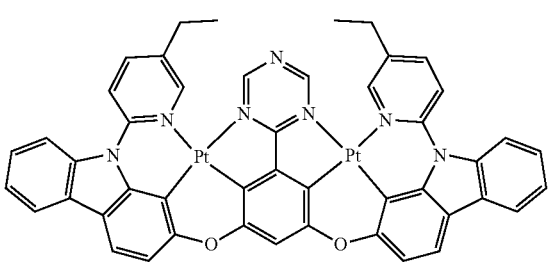
Compound Pt260
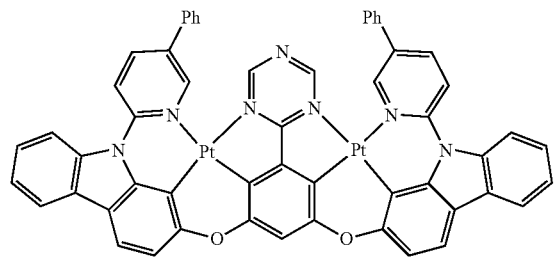
Compound Pt261
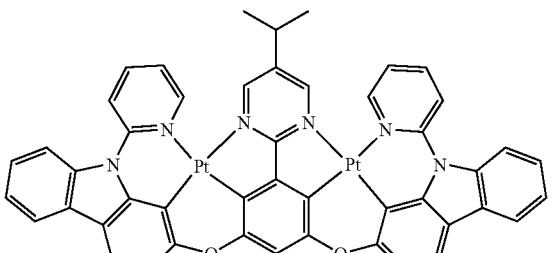

-continued
Compound Pt262
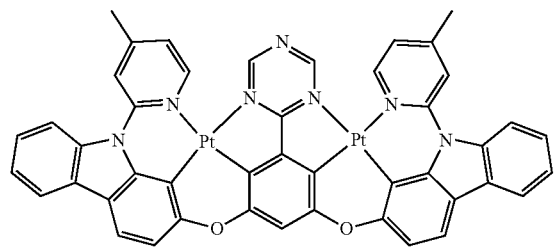
Compound Pd1
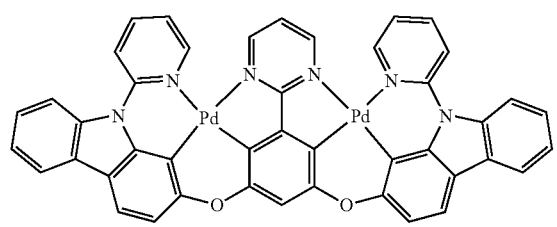
Compound Pd2
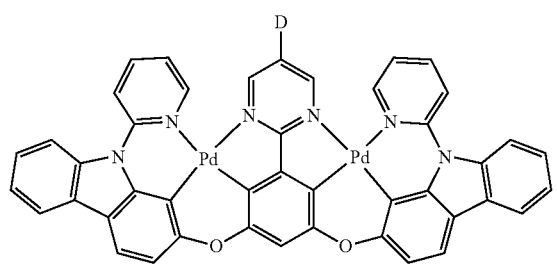
Compound Pd3
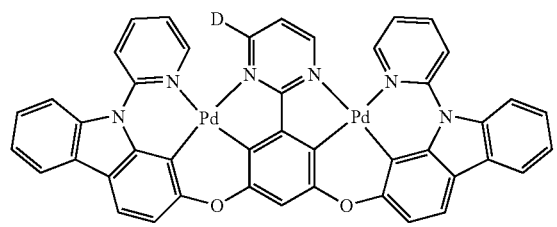
Compound Pd4
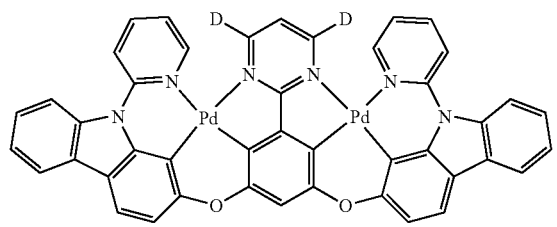
Compound Pd5
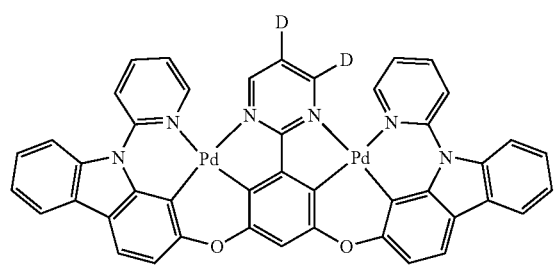
Compound Pd6
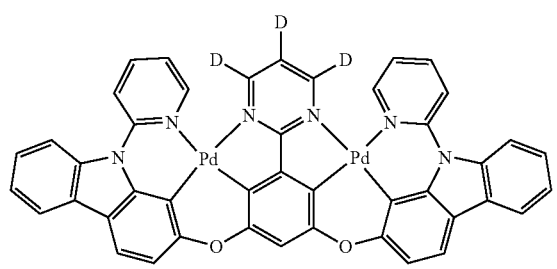
Compound Pd7
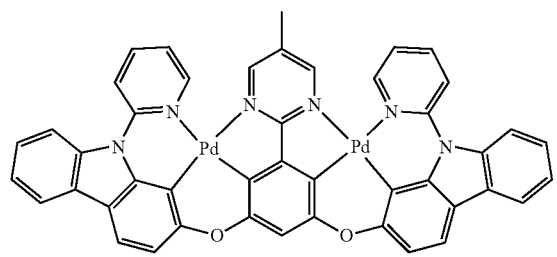
Compound Pd8
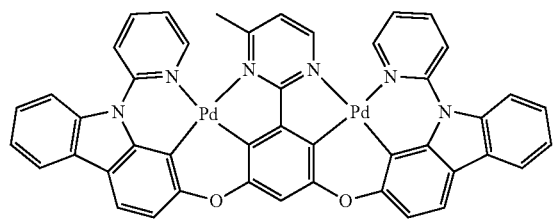

-continued
Compound Pd 9
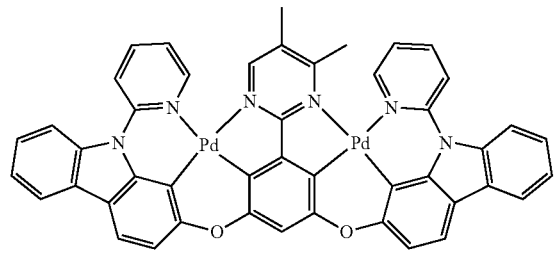
Compound Pd10
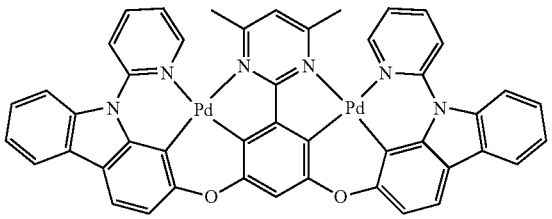
Compound Pd11
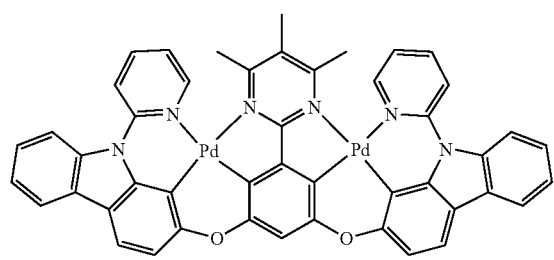
Compound Pd12
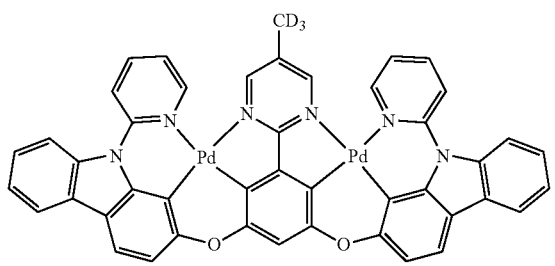
Compound Pd13
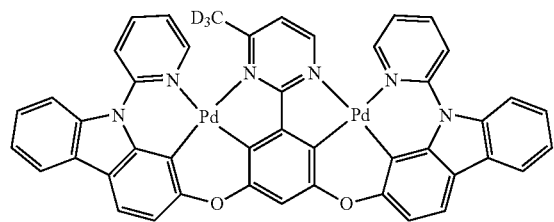
Compound Pd14
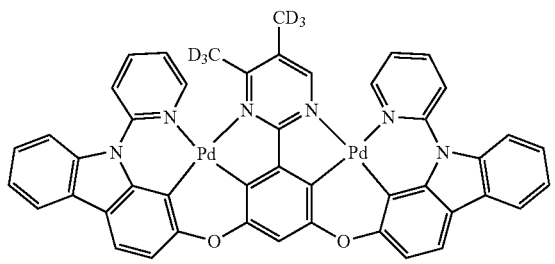
Compound Pd15
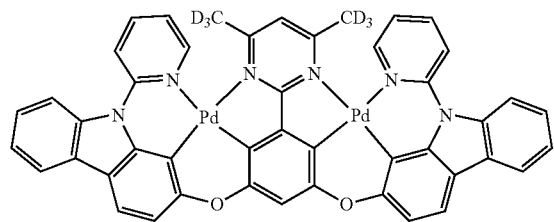
Compound Pd16
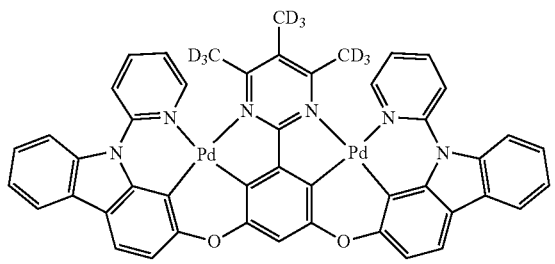
Compound Pd17
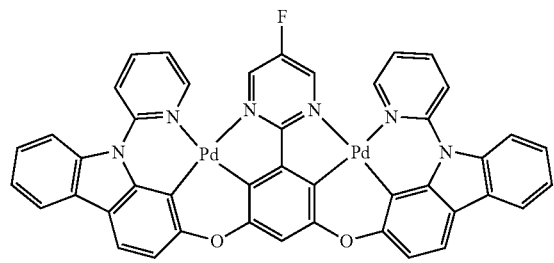
Compound Pd18
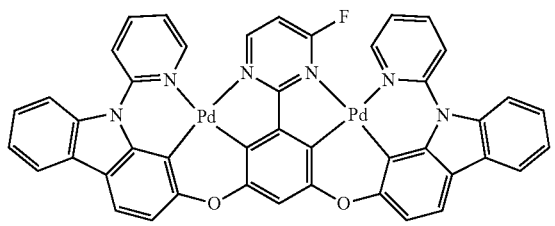

-continued
Compound Pd19
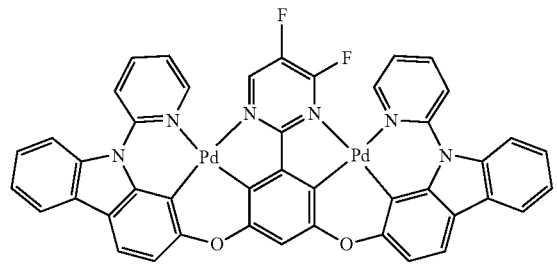
Cmpound Pd20
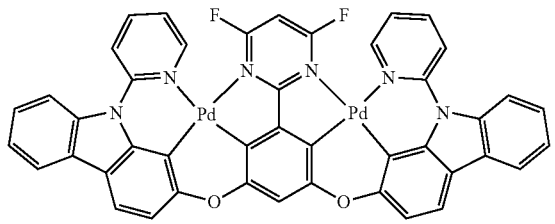
Compound Pd21
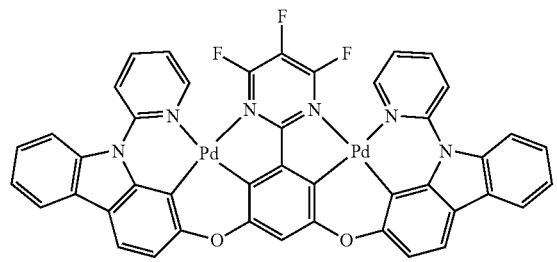
Compound Pd22
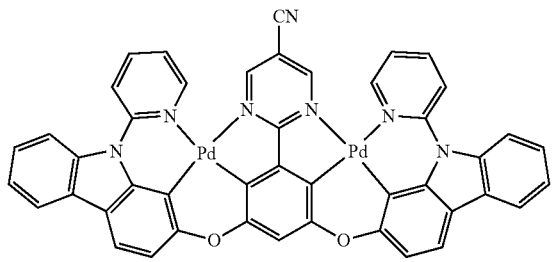
Compound Pd23
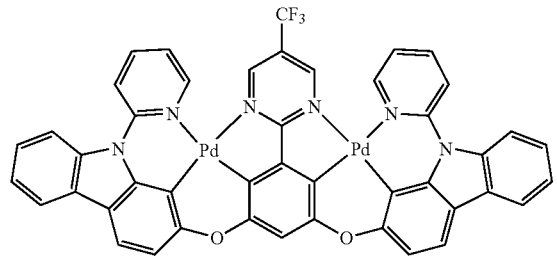
Compound Pd24
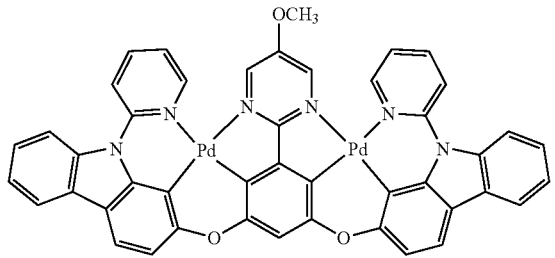
Compound Pd25
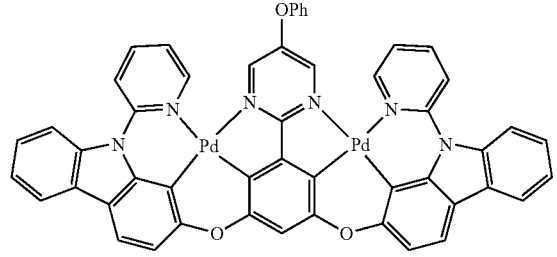
Compound Pd26
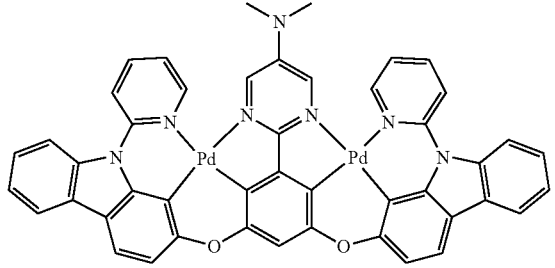
Compound Pd27
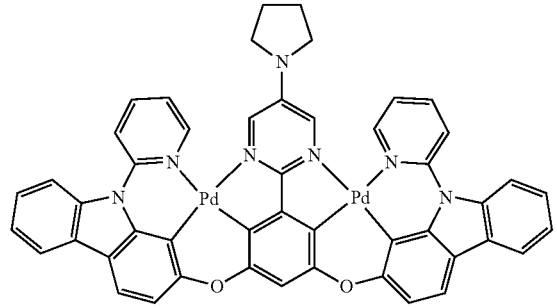
Compound Pd28
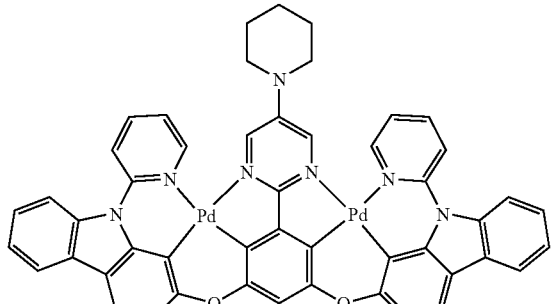

-continued
Compound Pd29
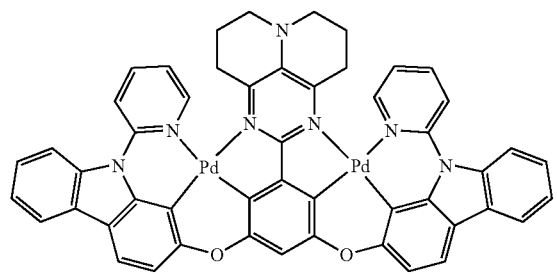
Compound Pd30
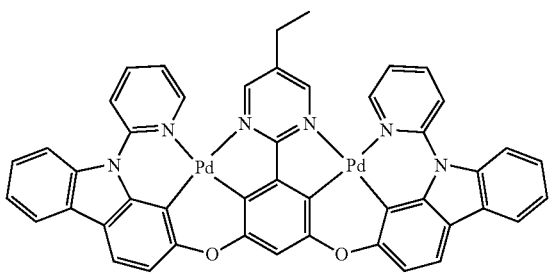
Compound Pd31
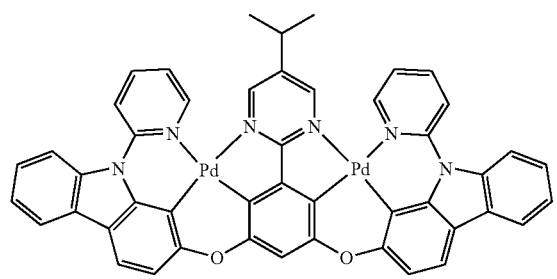
Compound Pd32
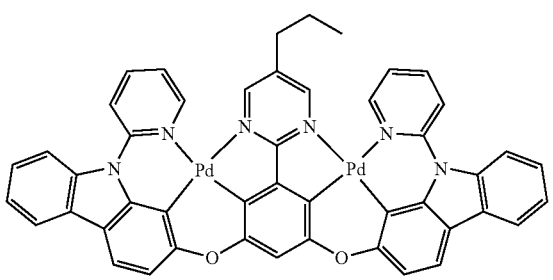
Compound Pd33
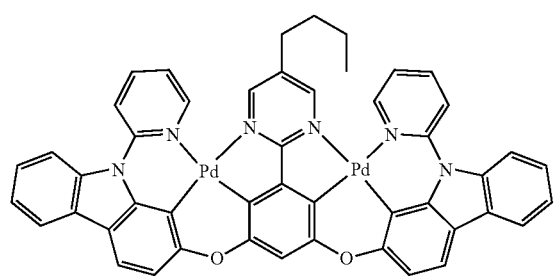
Compound Pd34
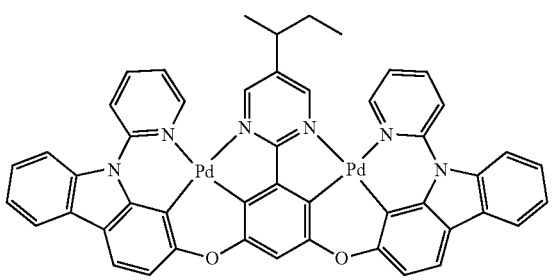
Compound Pd35
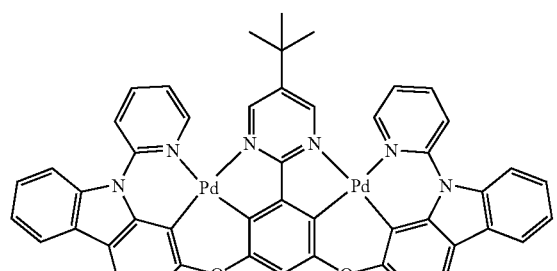
Compound Pd36
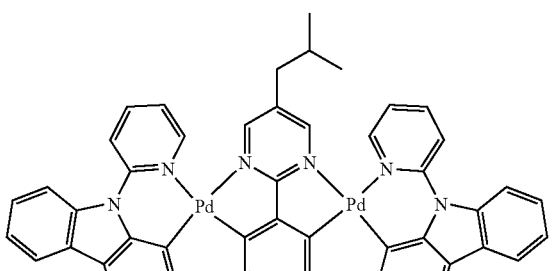
Compound Pd37
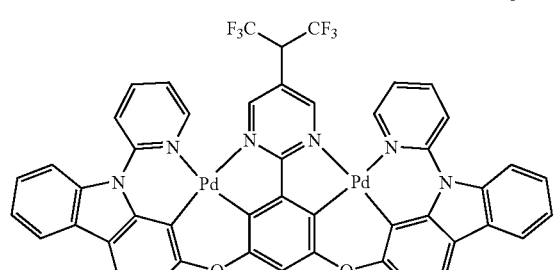
Compound Pd38
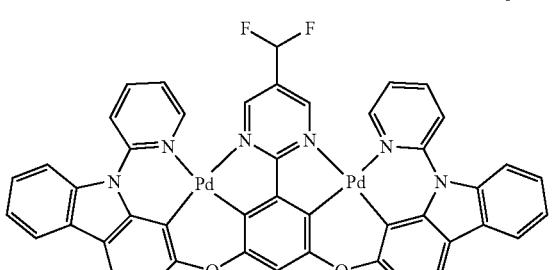

-continued
Compound Pd39
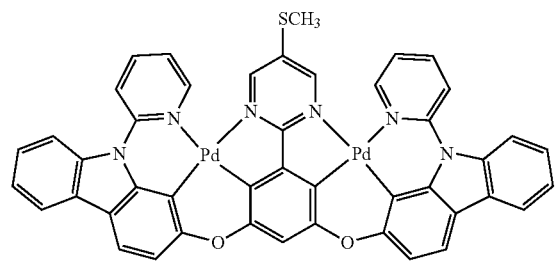
Compound Pd40
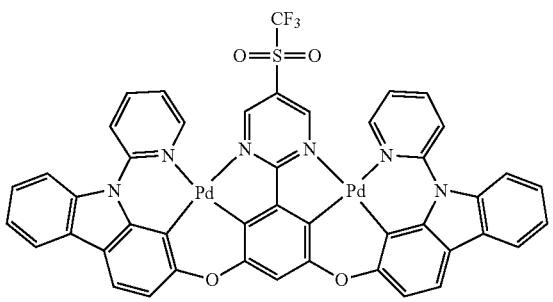
Compound Pd41
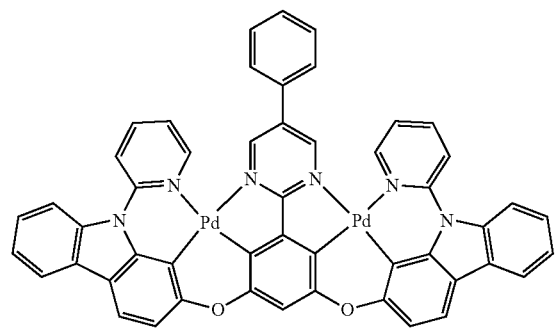
Compound Pd42
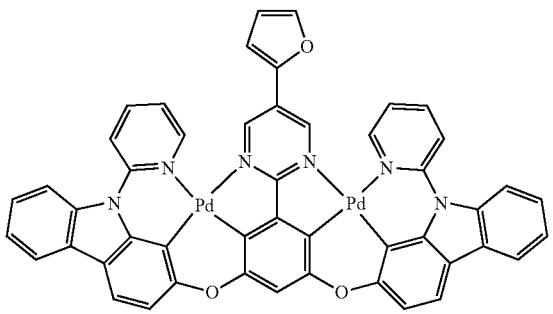
Compound Pd43
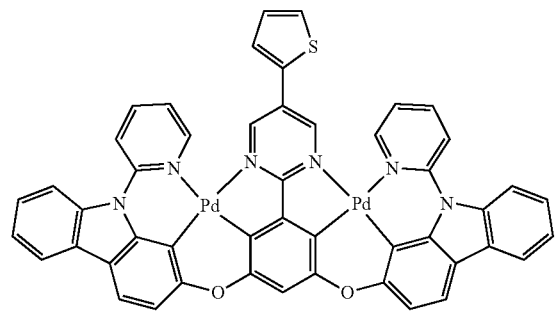
Compound Pd44
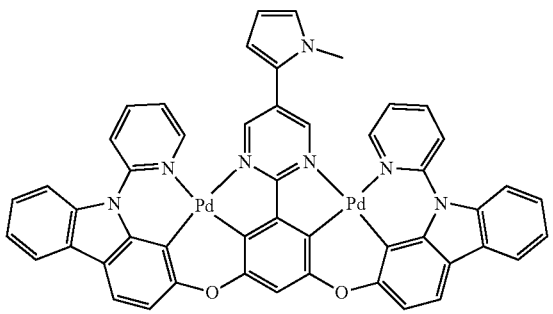
Compound Pd45
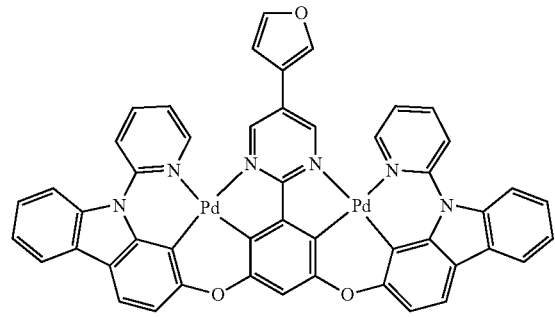
Compound Pd46
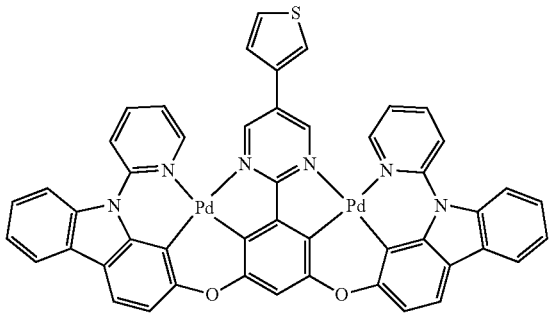

Compound Pd47
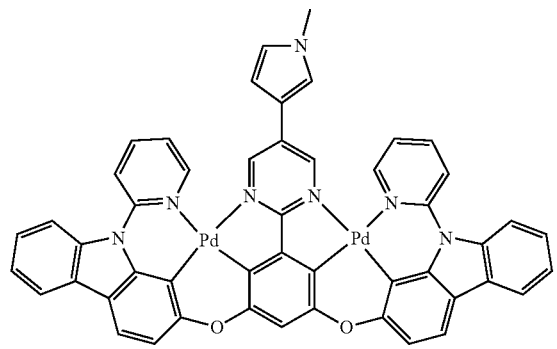
Compound Pd48
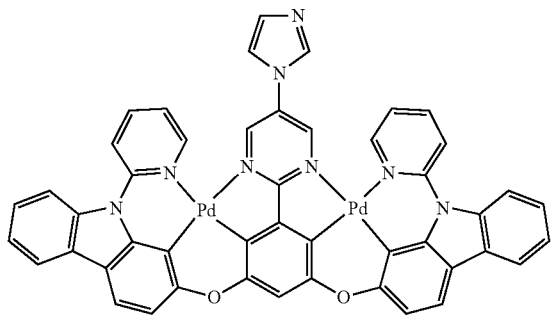
Compound Pd49
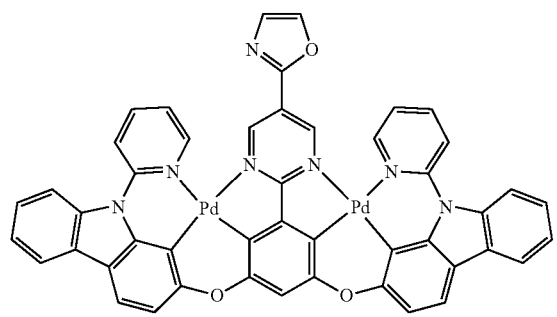
Compound Pd50
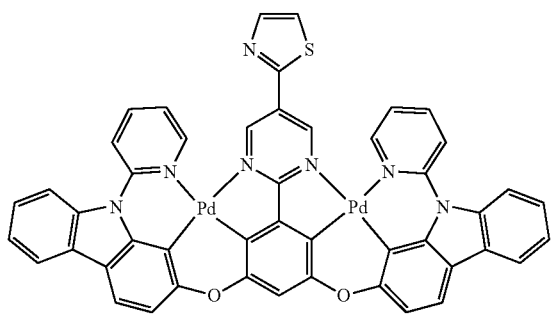
Compound Pd51
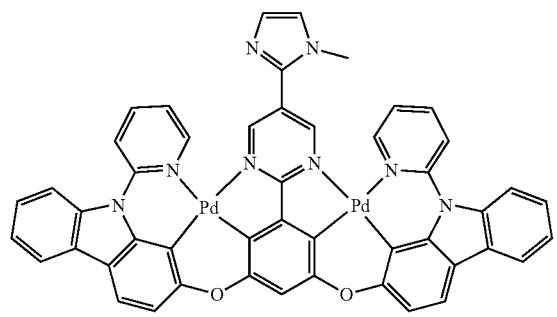
Compound Pd52
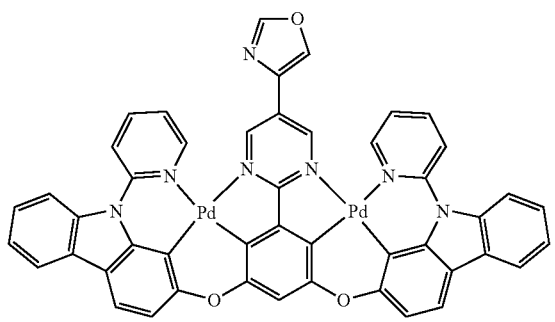
Compound Pd53
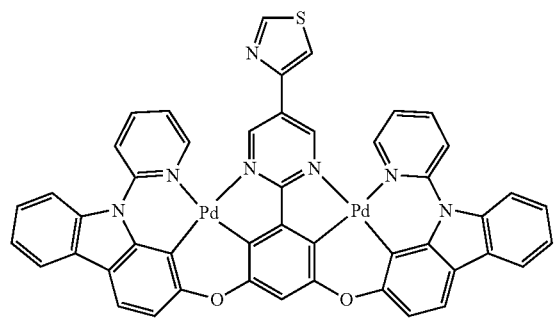
Compound Pd54
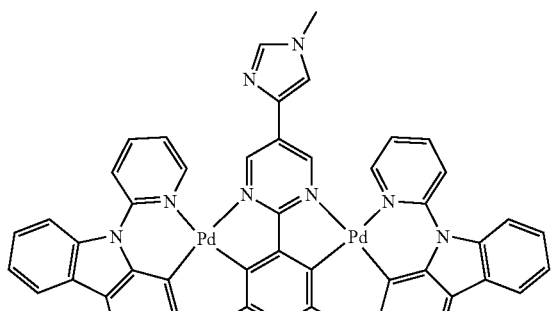

-continued
Compound Pd55
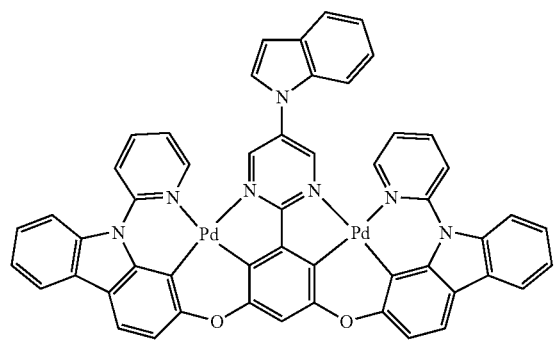
Compound Pd56
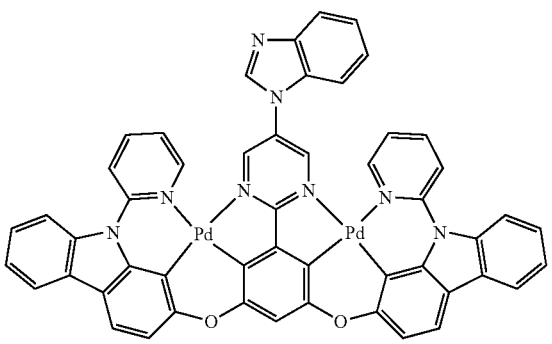
Compound Pd57
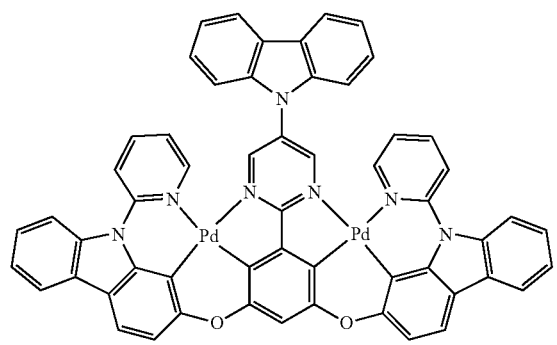
Compound Pd58
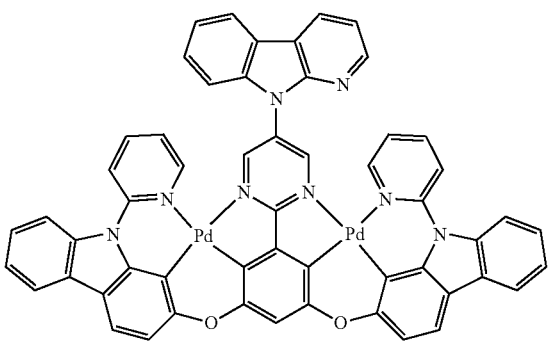
Compound Pd59
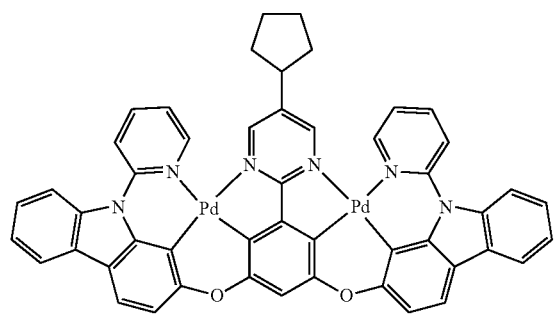
Compound Pd60
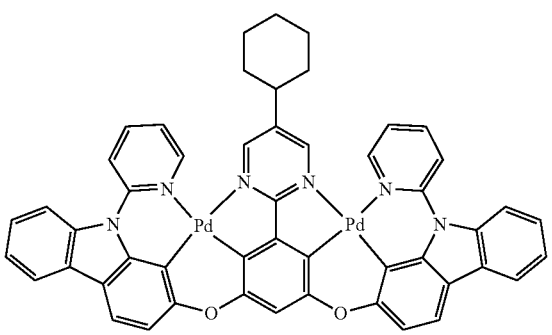
Compound Pd61
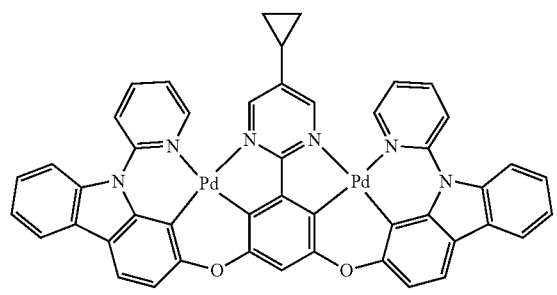
Compound Pd62
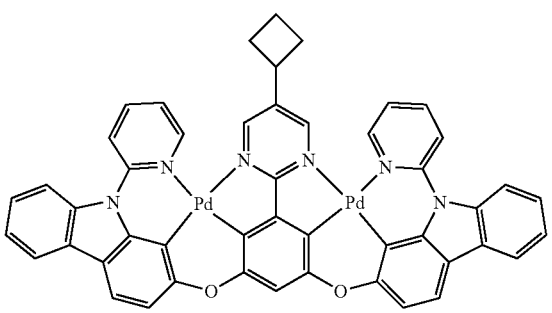

-continued
Compound Pd63
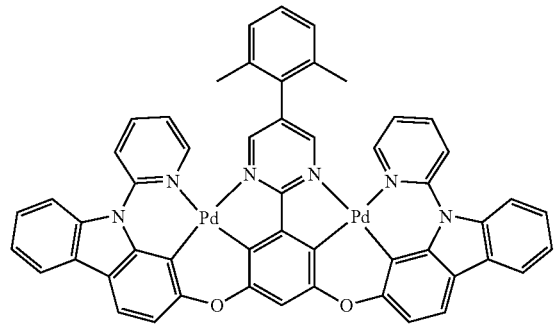
Compound Pd64
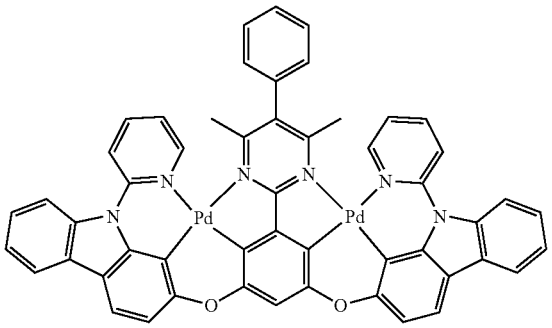
Compound Pd65
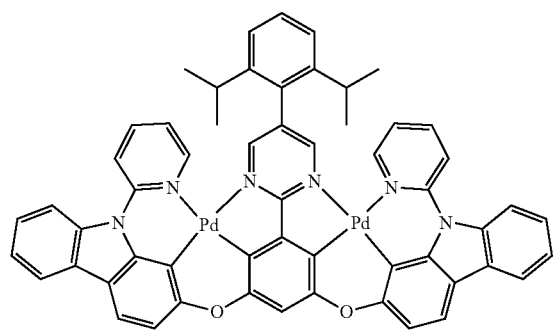
Compound Pd66
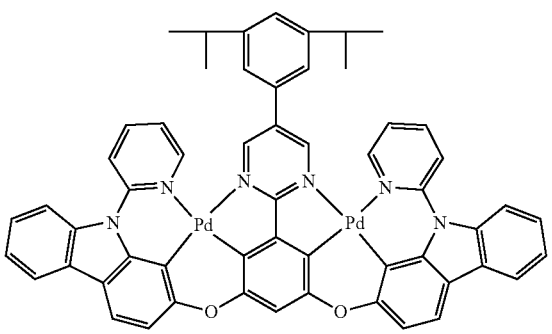
Compound Pd67
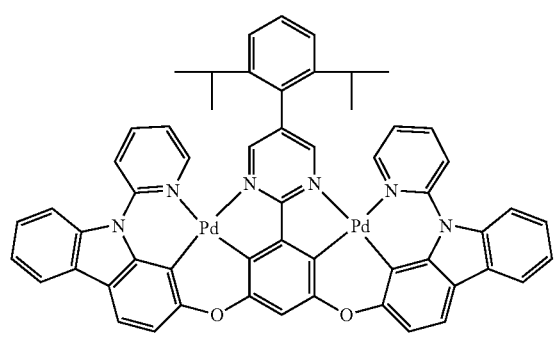
Compound Pd68
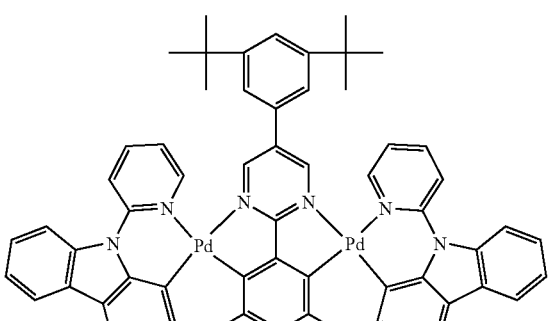
Compound Pd69
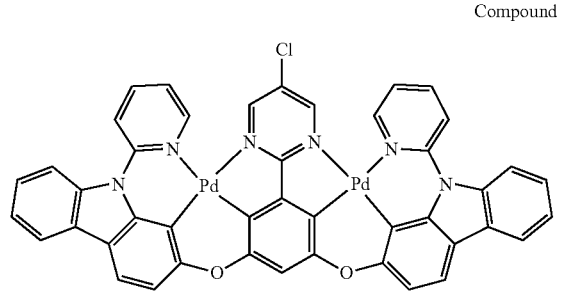
Compound Pd70
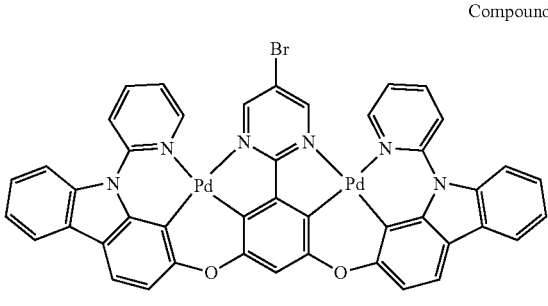
Compound Pd71
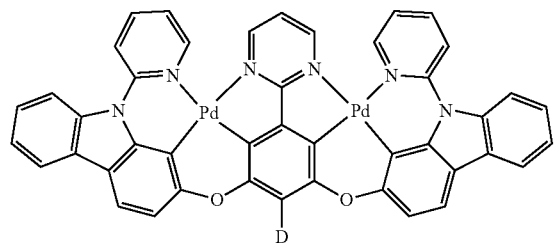
Compound Pd72
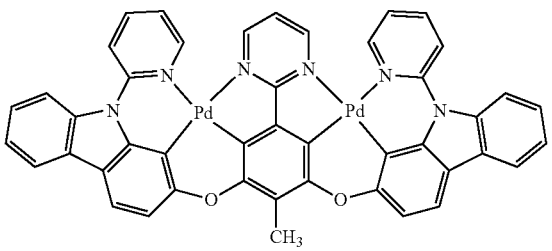

-continued
Compound Pd73
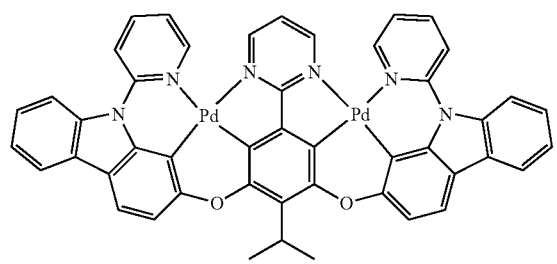
Compound Pd74
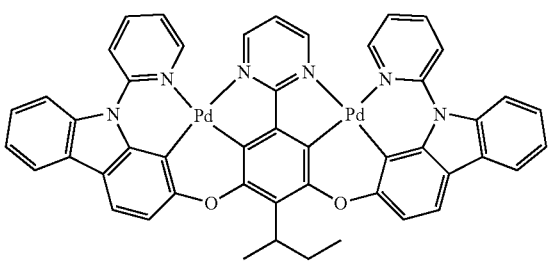
Compound Pd75
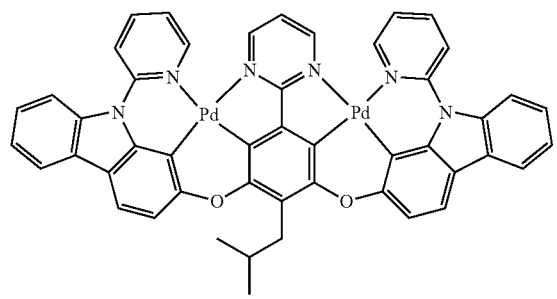
Compound Pd76
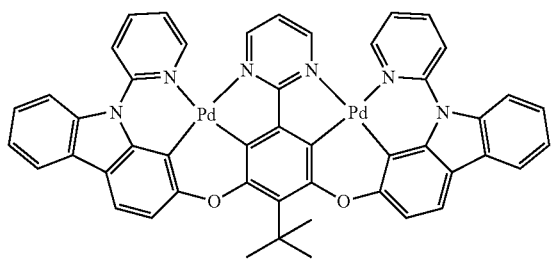
Compound Pd77
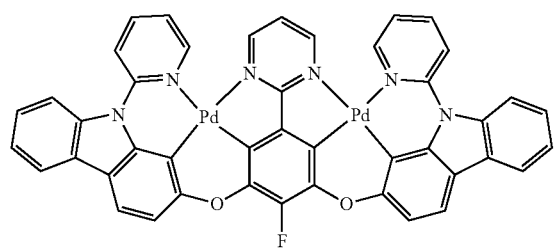
Compound Pd78
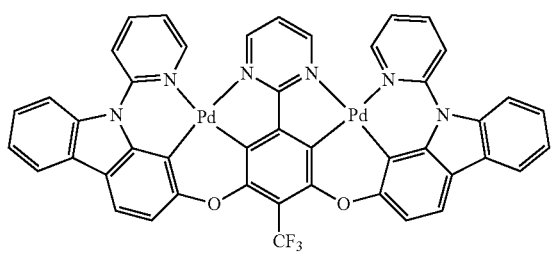
Compound Pd79
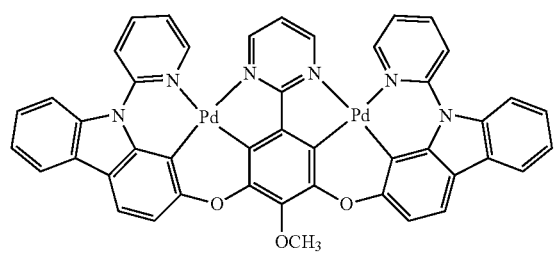
Compound Pd80
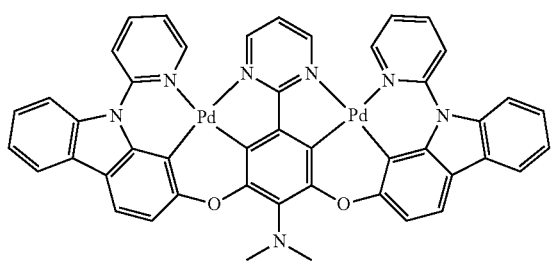
Compound Pd81
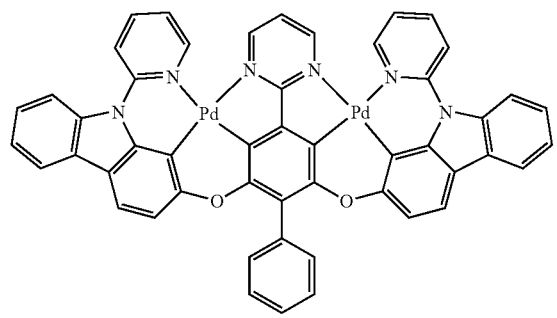
Compound Pd82
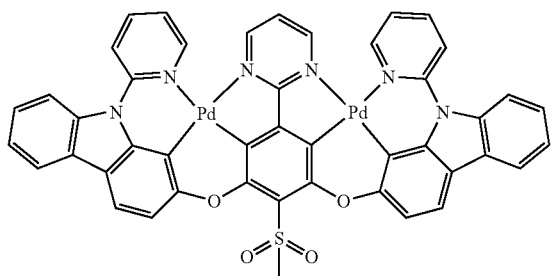

-continued
Compound Pd83
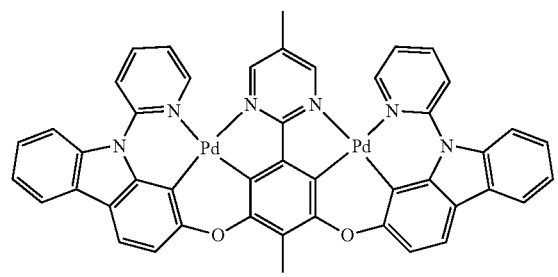
Compound Pd84
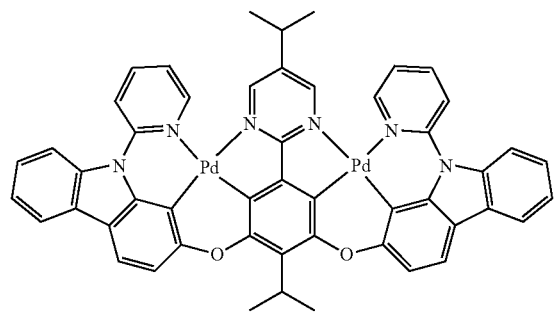
Compound Pd85
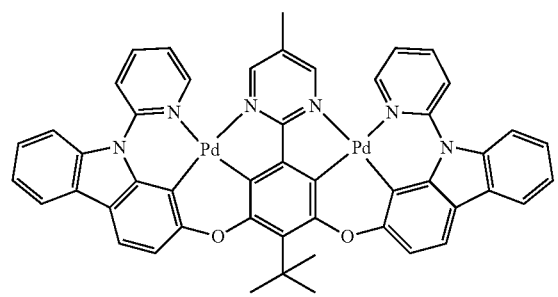
Compound Pd86
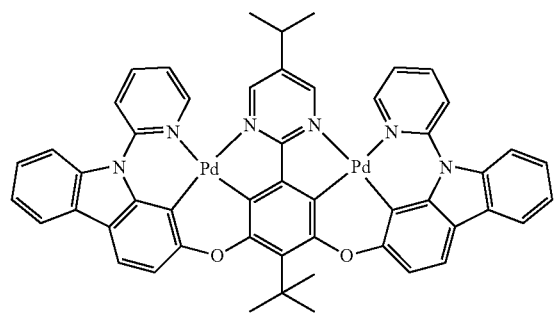
Compound Pd87
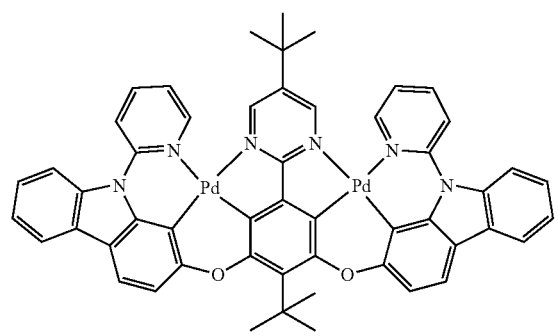
Compound Pd88
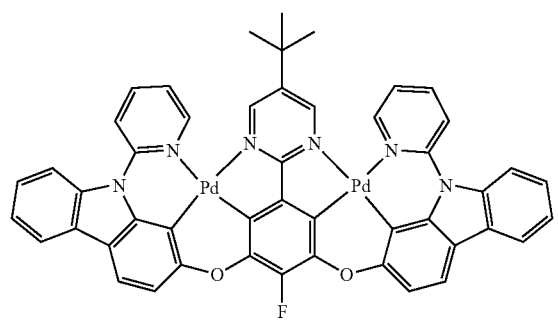
Compound Pd89
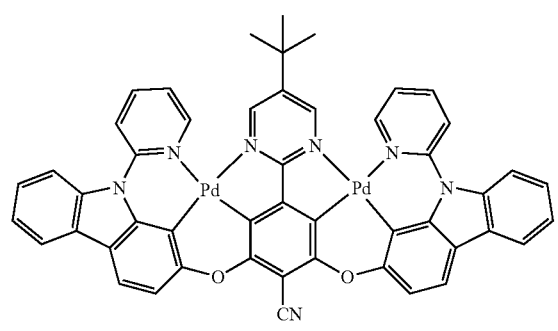
Compound Pd90
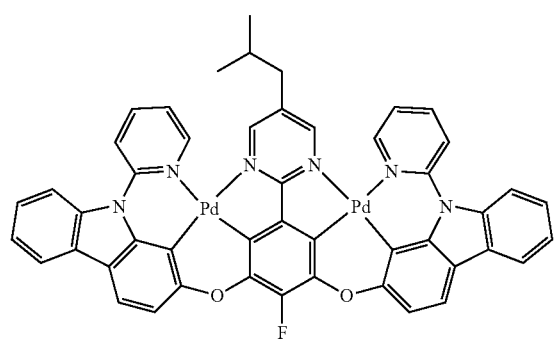

-continued
Compound Pd91
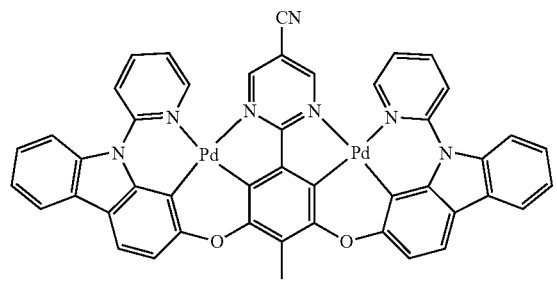
Compound Pd92
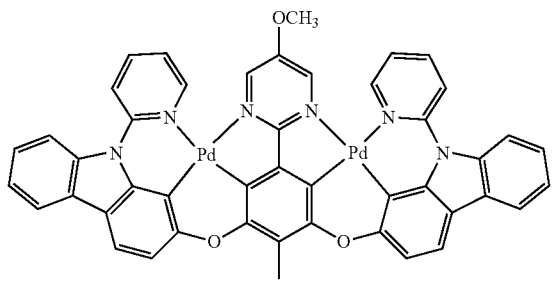
Compound Pd93
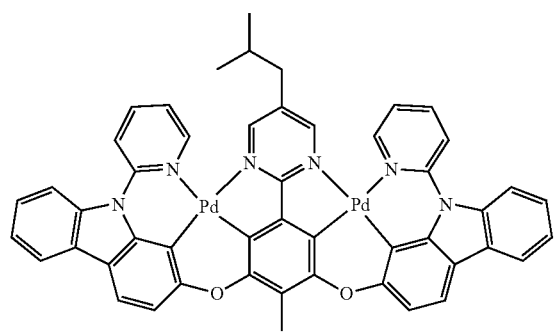
Compound Pd94
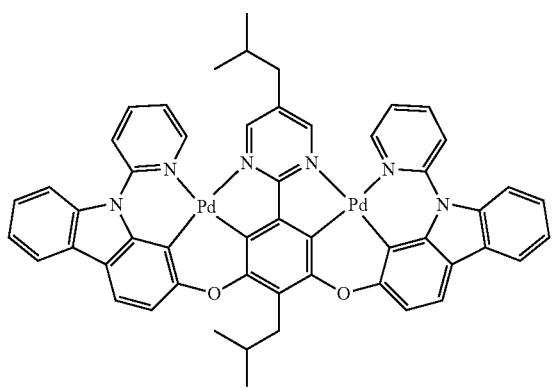
Compound Pd95
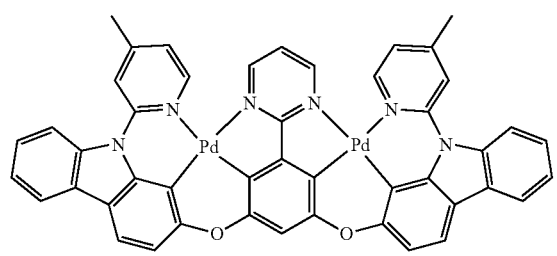
Compound Pd96
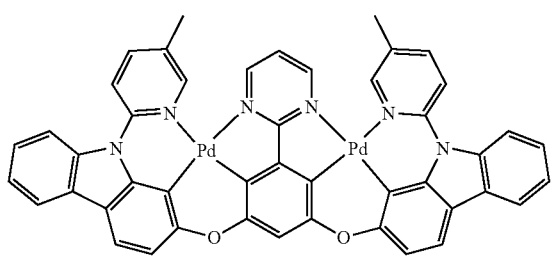
Compound Pd97
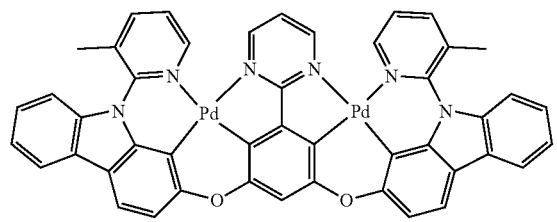
Compound Pd98
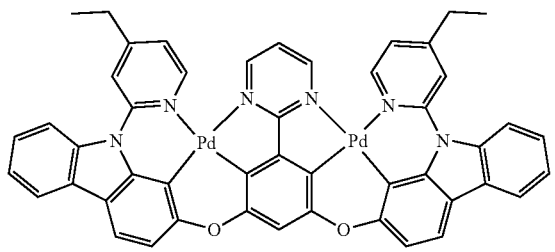
Compound Pd99
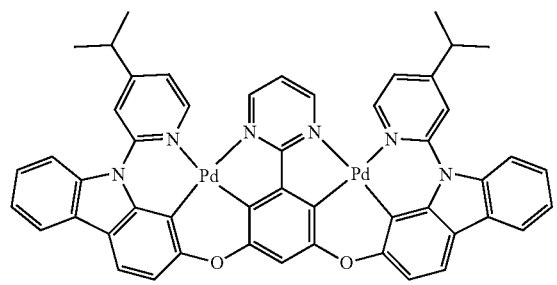
Compound Pd100
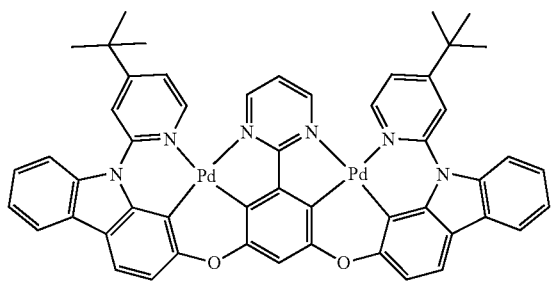

-continued
Compound Pd101
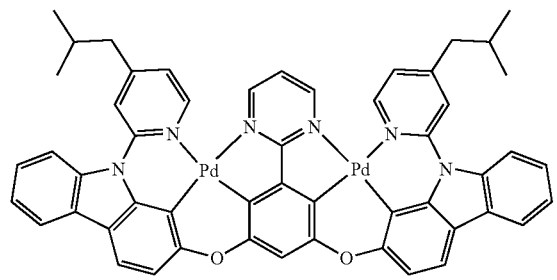
Compound Pd102
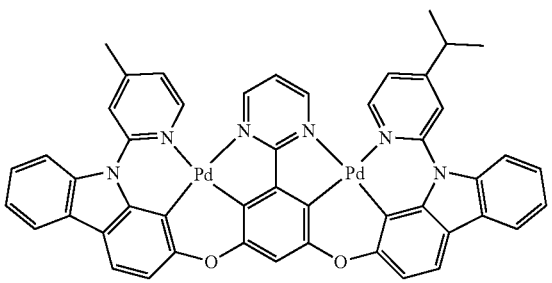
Compound Pd103
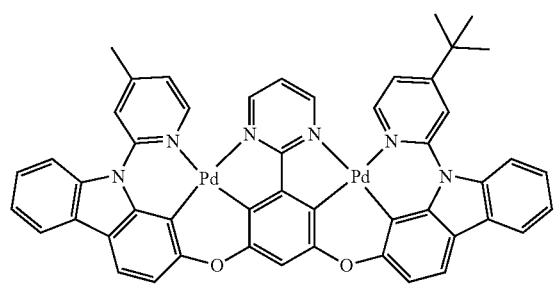
Compound Pd104
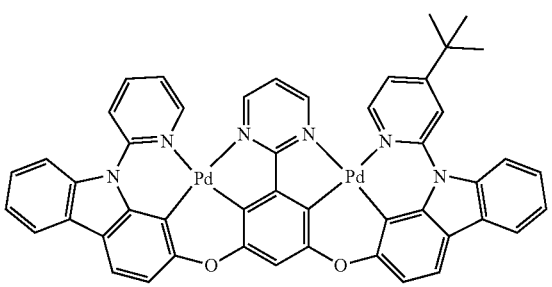
Compound Pd105
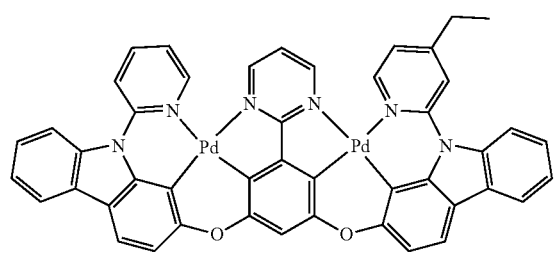
Compound Pd106
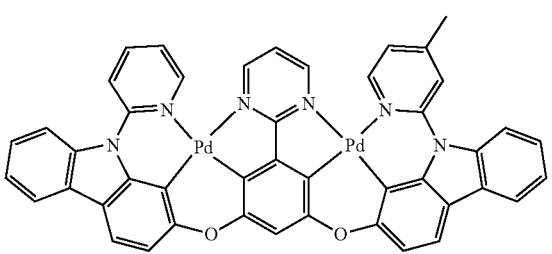
Compound Pd107
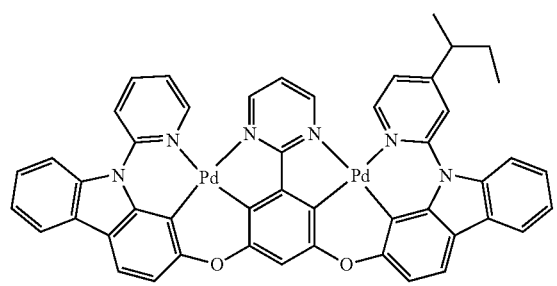
Compound Pd108
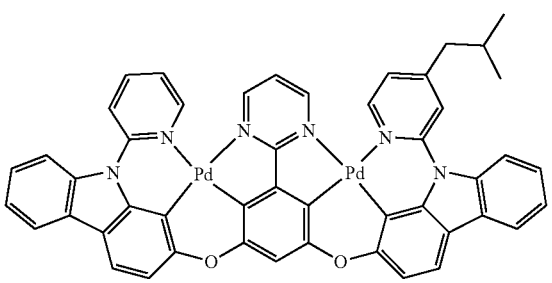
Compound Pd109
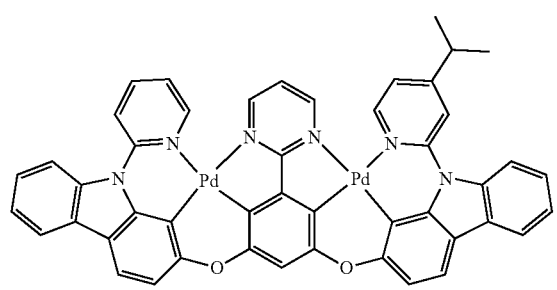
Compound Pd110

-continued
Compound Pd111
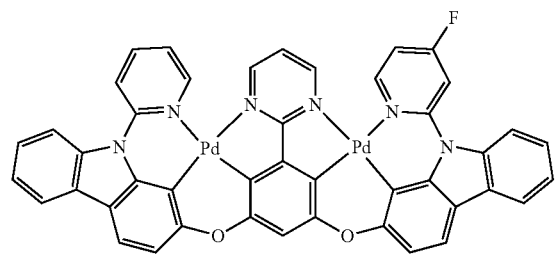
Compound Pd112
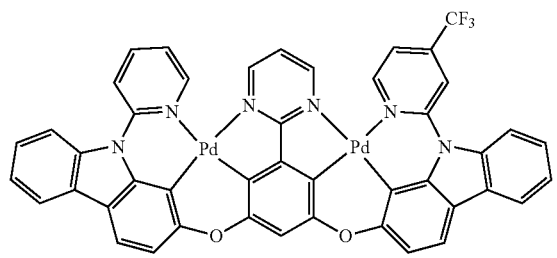
Compound Pd113
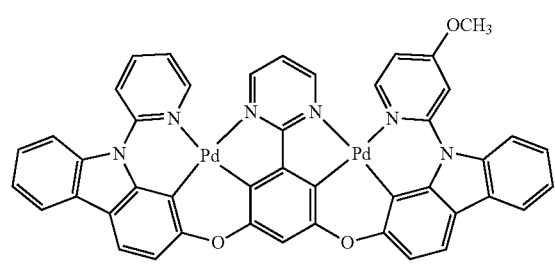
Compound Pd114
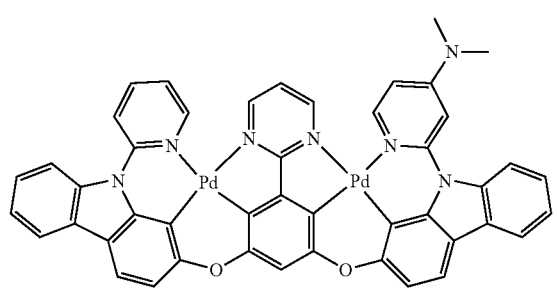
Compound Pd115
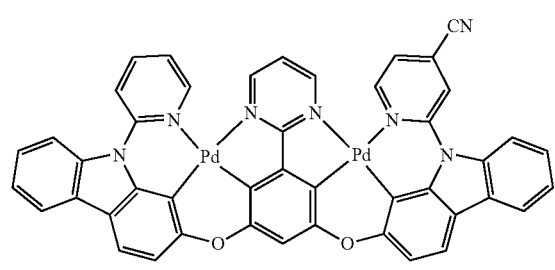
Compound Pd116
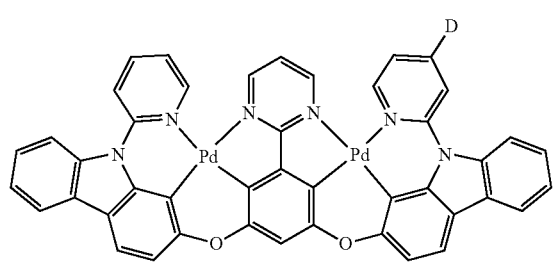
Compound Pd117
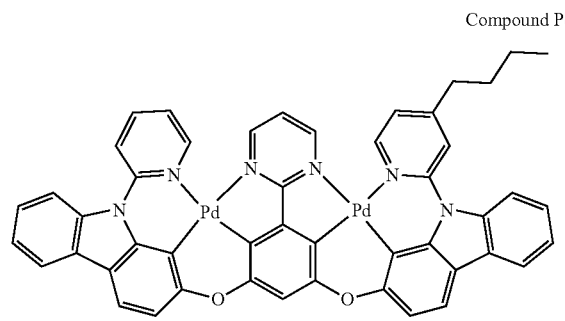
Compound Pd118
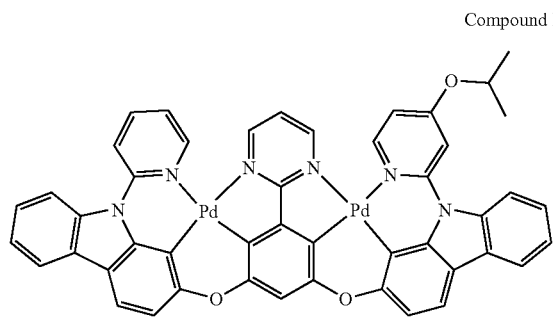
Compound Pd119
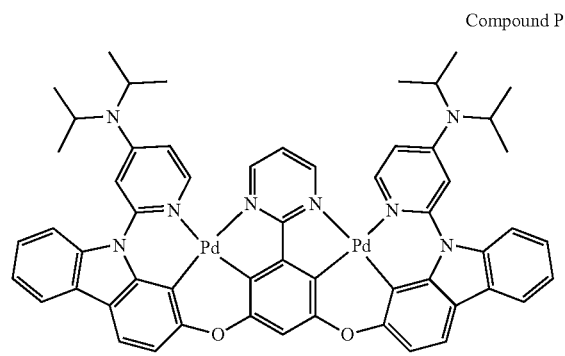
Compound Pd120
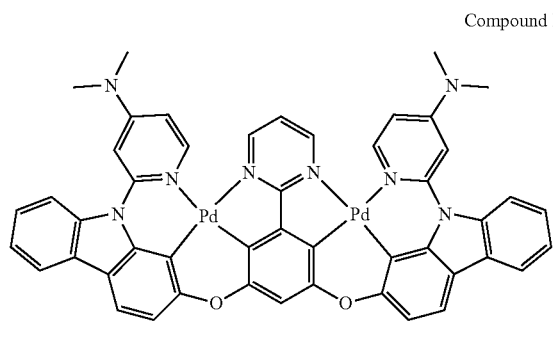

-continued
Compound Pd121
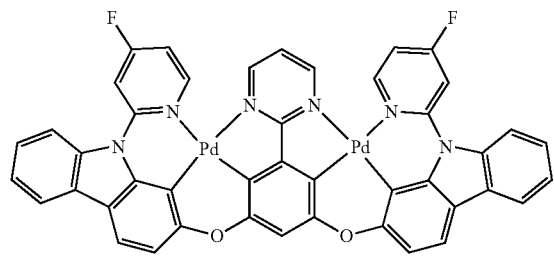
Compound Pd122
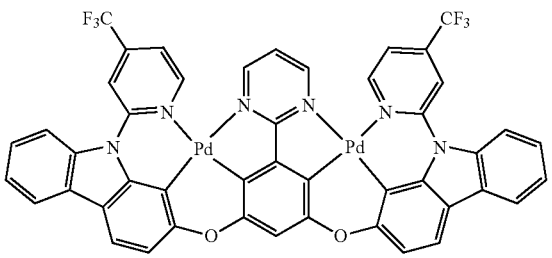
Compound Pd123
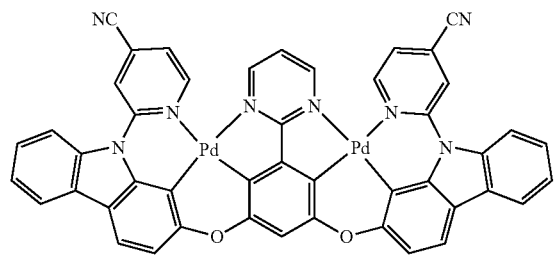
Compound Pd124
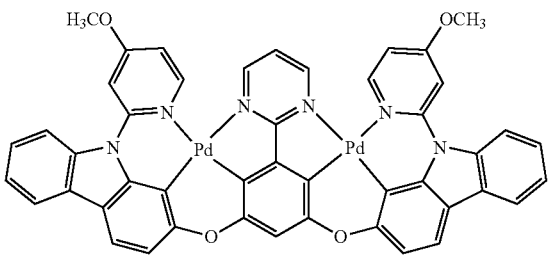
Compound Pd125
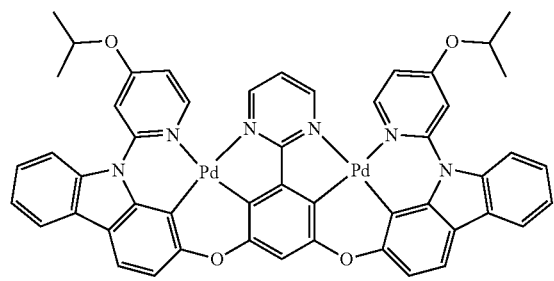
Compound Pd126
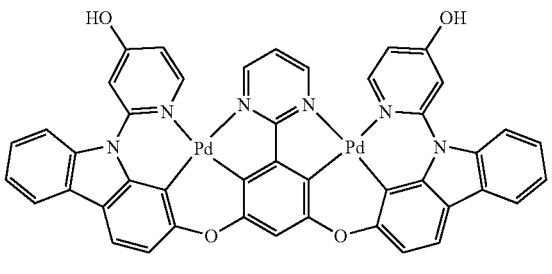
Compound Pd127
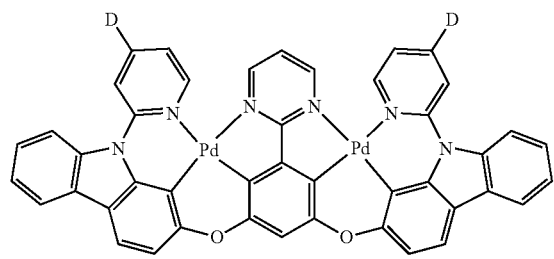
Compound Pd128
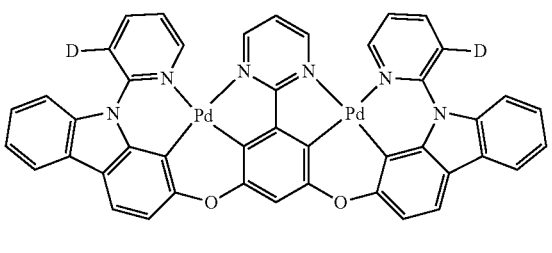
Compound Pd129
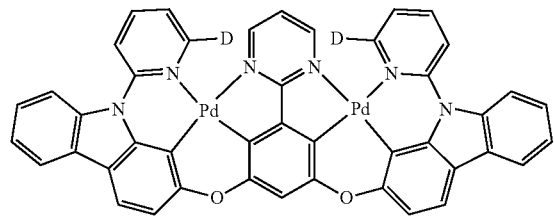
Compound Pd130
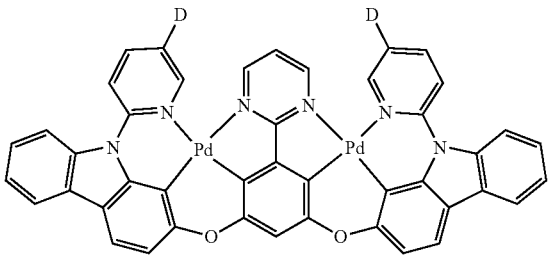

-continued
Compound Pd131
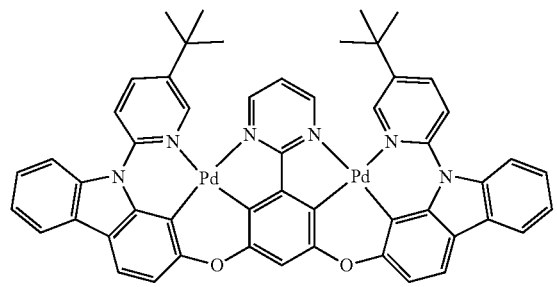
Compound Pd133
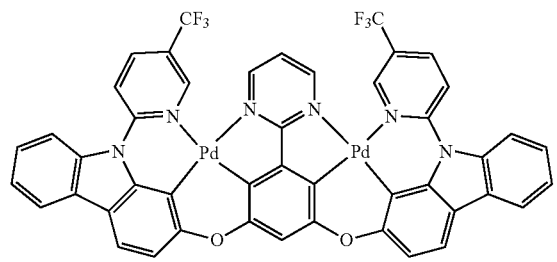
Compound Pd135
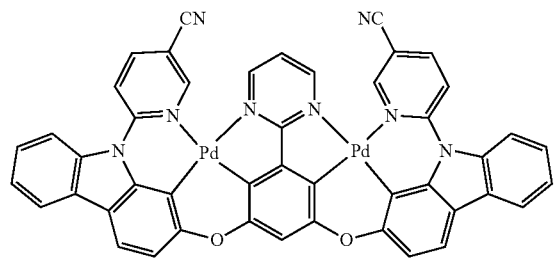
Compound Pd137
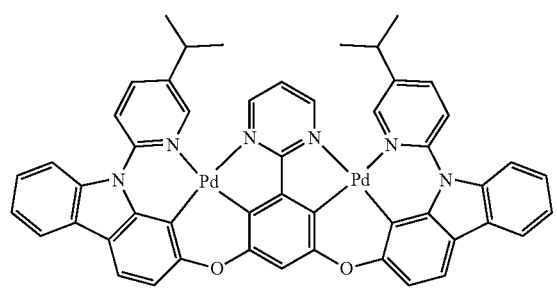
Compound Pd139
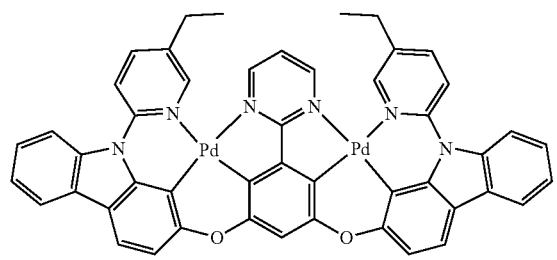
Compound Pd132
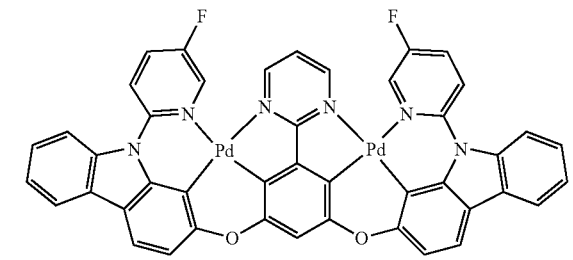
Compound Pd134
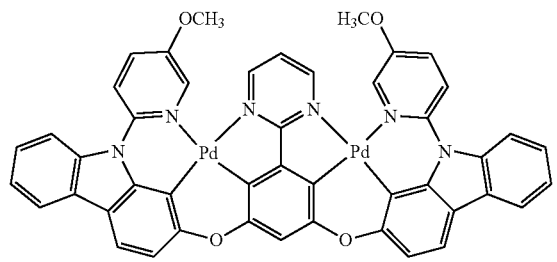
Compound Pd136
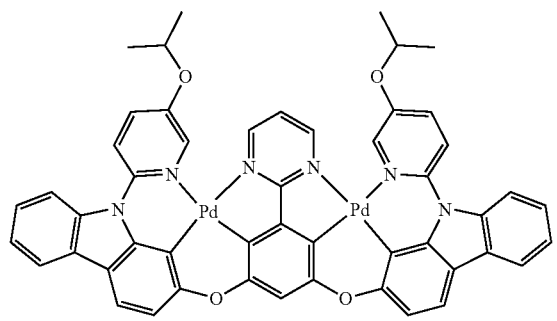
Compound Pd138
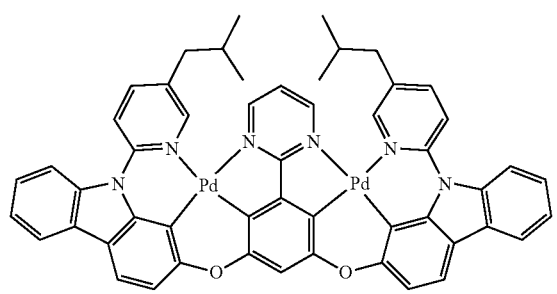
Compound Pd140
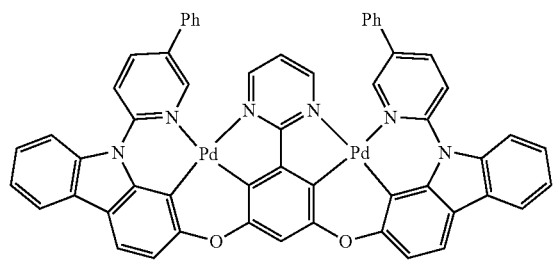

-continued
Compound Pd141
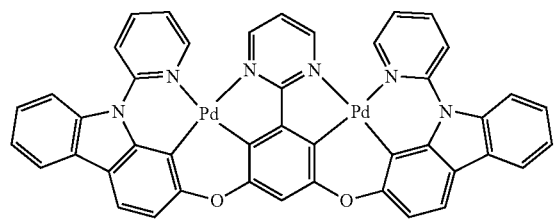
Compound Pd143
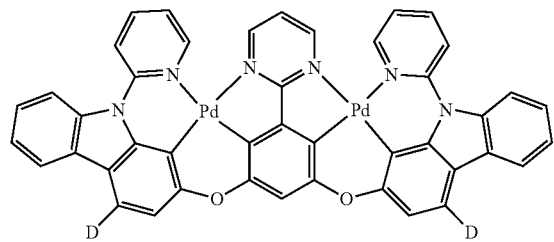
Compound Pd145
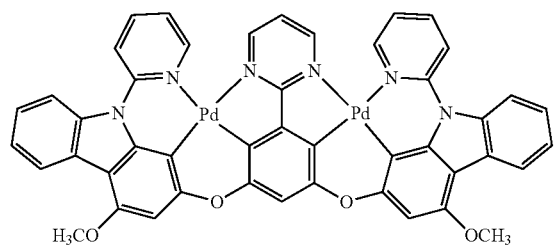
Compound Pd142
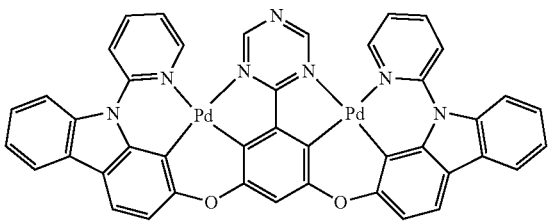
Compound Pd144
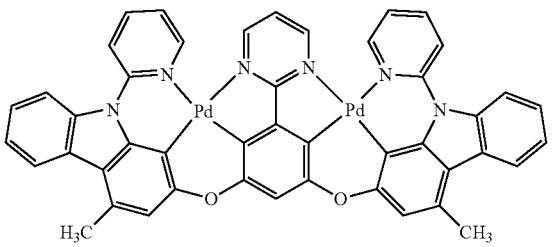
Compound Pd146
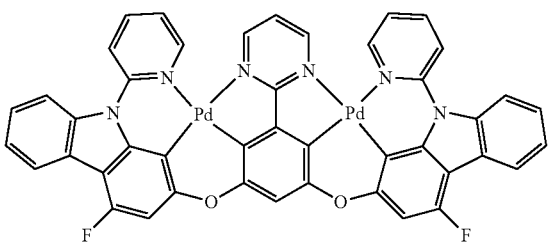
Compound Pd147
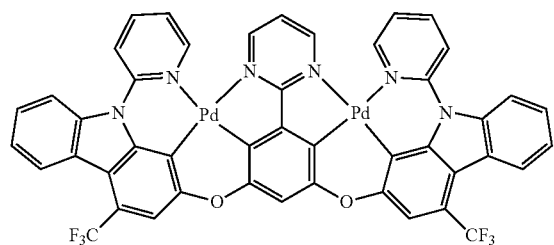
Compound Pd148
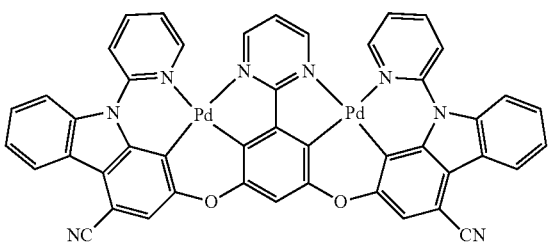
Compound Pd149
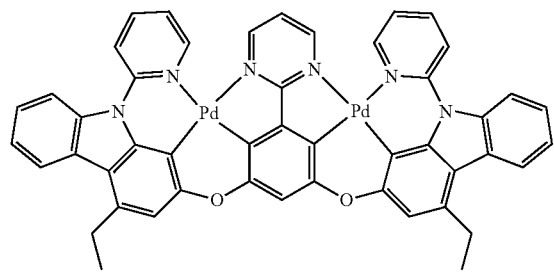
Compound Pd150
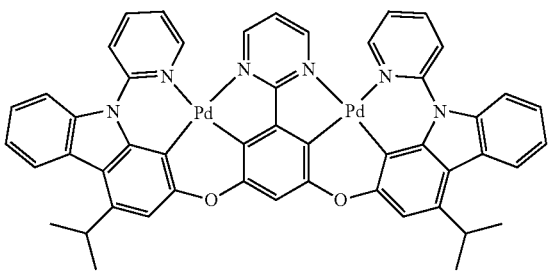

-continued
Compound Pd151
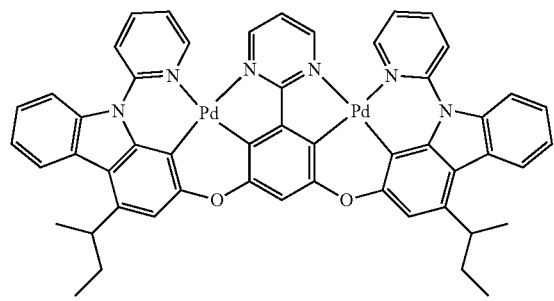
Compound Pd152
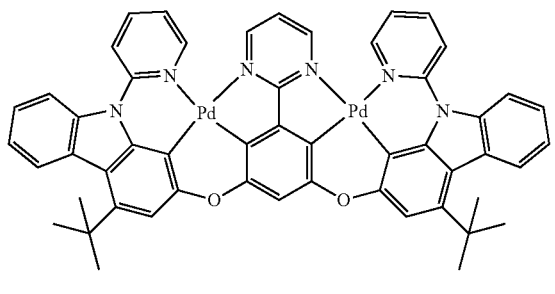
Compound Pd153
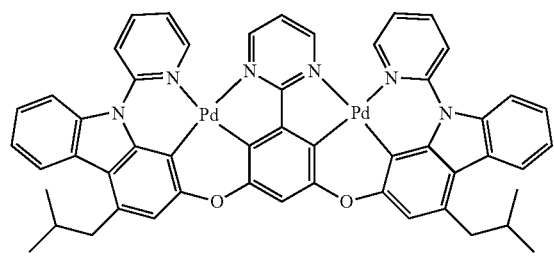
Compound Pd154
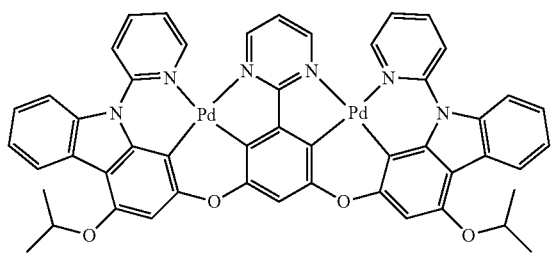
Compound Pd155
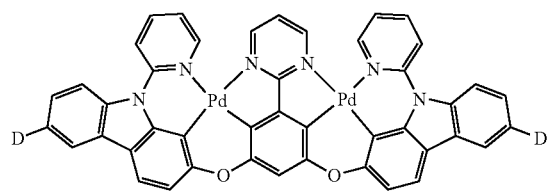
Compound Pd156
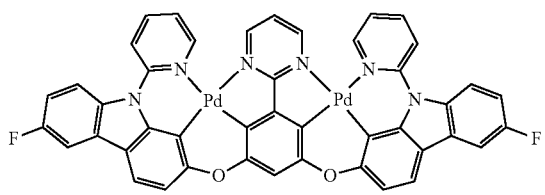
Compound Pd157
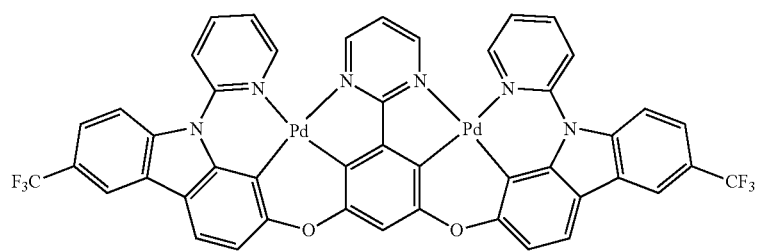
Compound Pd158
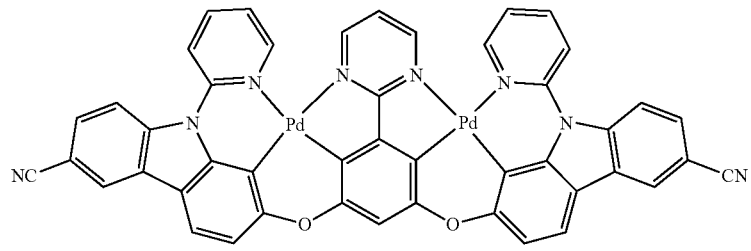
Compound Pd159
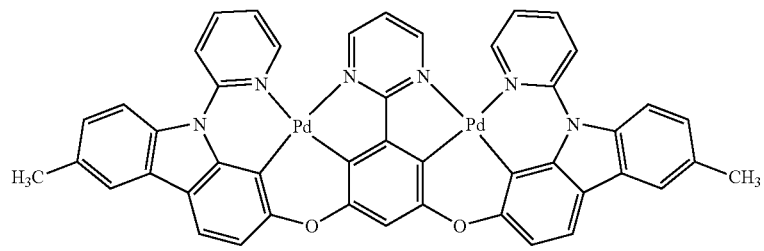

-continued
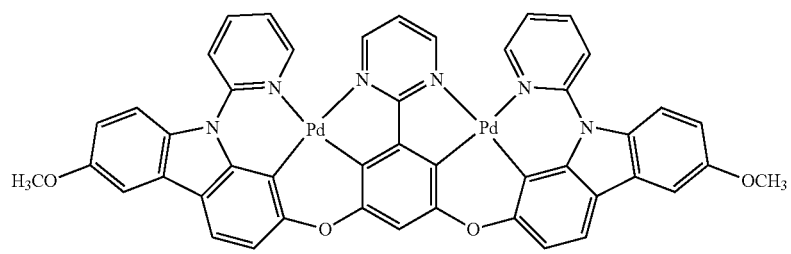
Compound Pd160
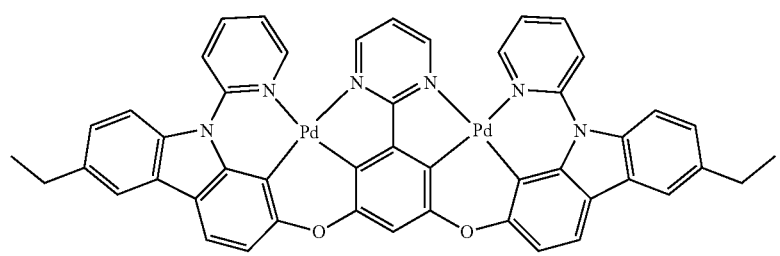
Compound Pd161
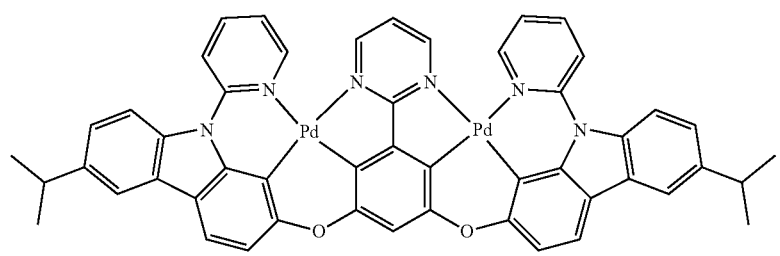
Compound Pd162
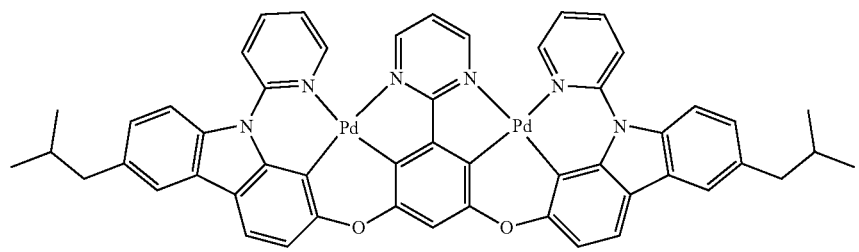
Compound Pd163
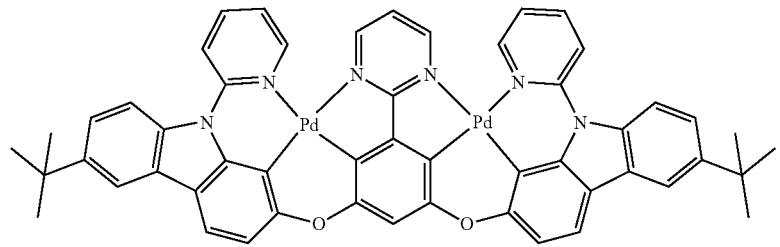
Compound Pd164
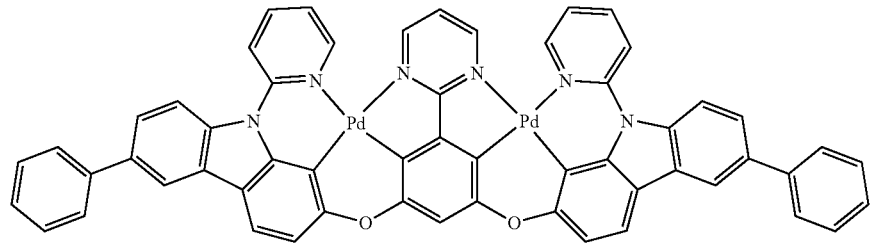
Compound Pd165

-continued
Compound Pd166
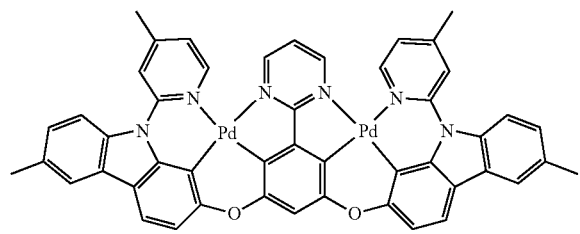
Compound Pd167
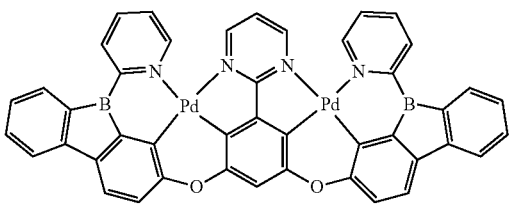
Compound Pd168
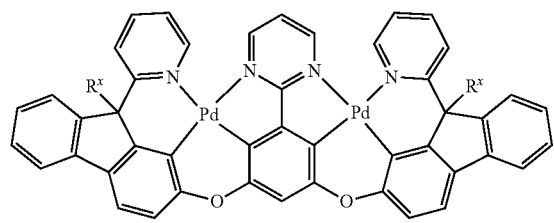
Compound Pd169
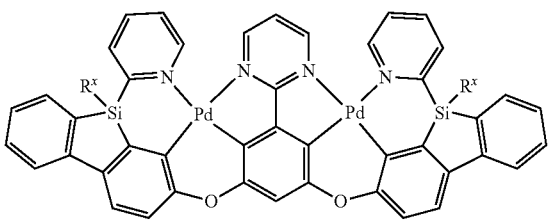
Compound Pd170
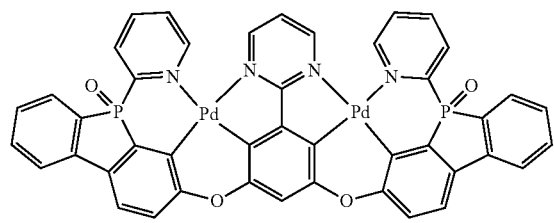
Compound Pd171
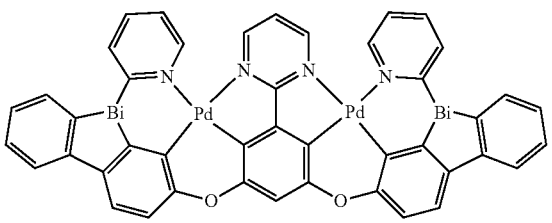
Compound Pd172
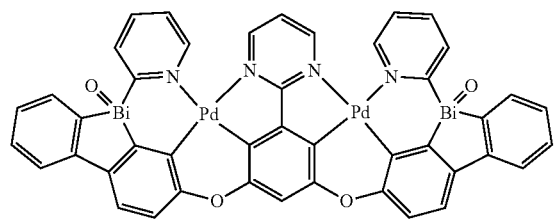
Compound Pd173
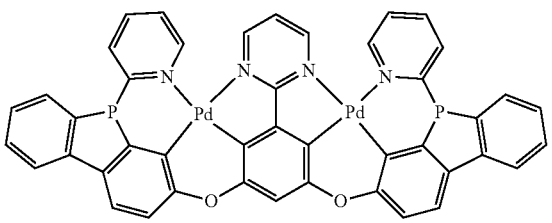
Compound Pd174
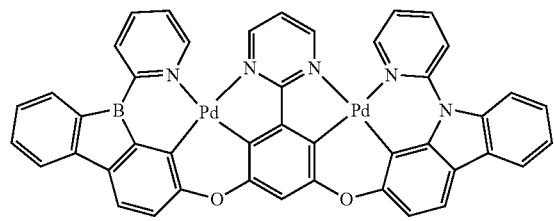
Compound Pd175
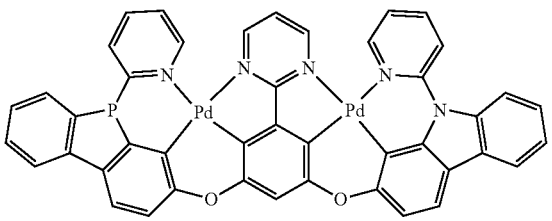
Compound Pd176
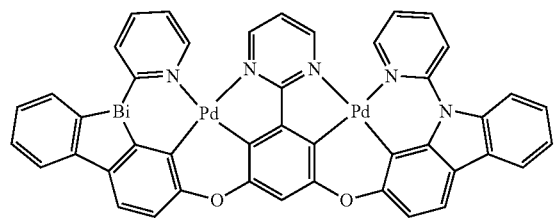
Compound Pd177
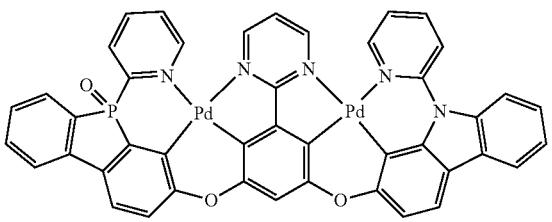

-continued
Compound Pd179
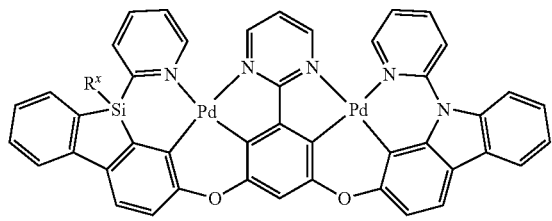
Compound Pd178
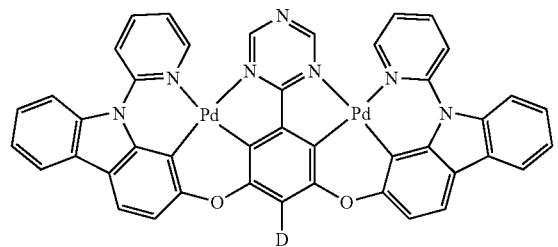
Compound Pd180
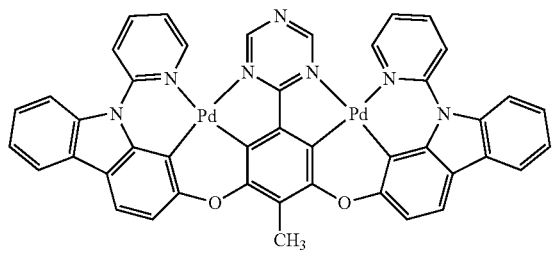
Compound Pd181
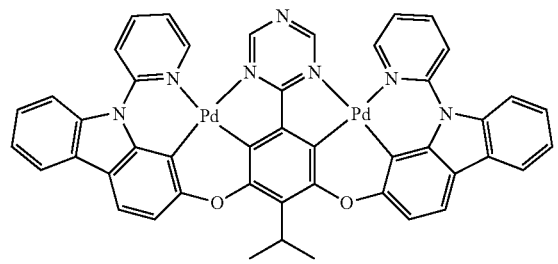
Compound Pd182
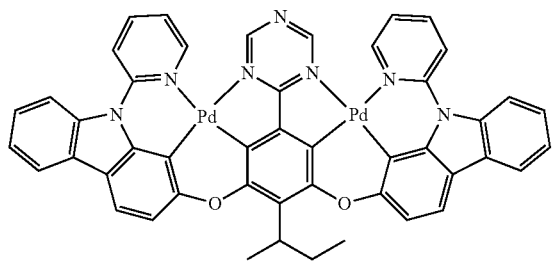
Compound Pd183
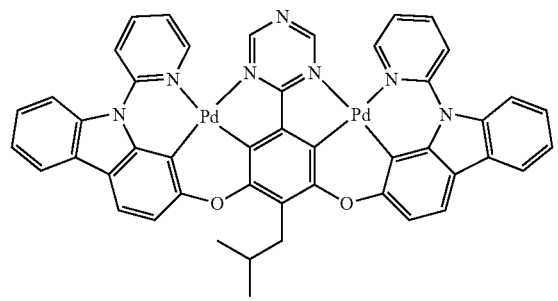
Compound Pd184
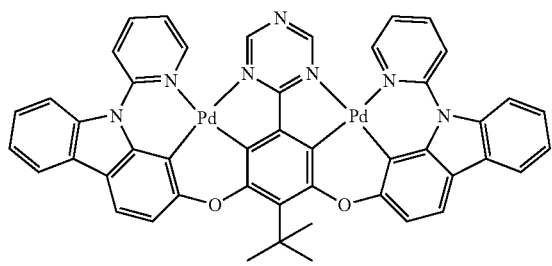
Compound Pd185
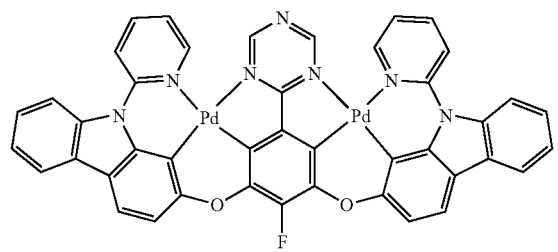
Compound Pd186
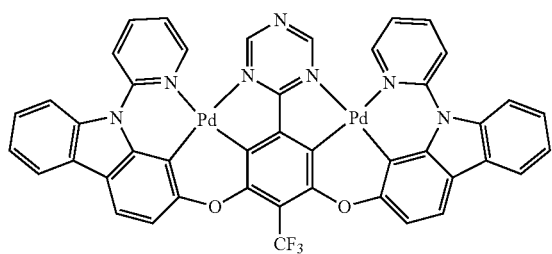
Compound Pd187
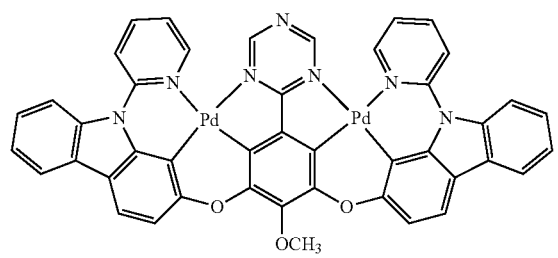

-continued
Compound Pd188
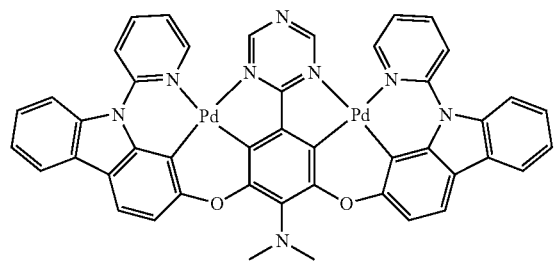
Compound Pd189
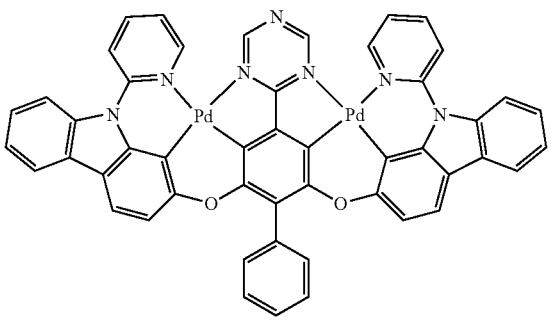
Compound Pd190
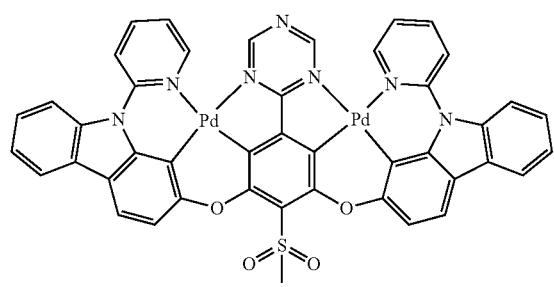
Compound Pd191
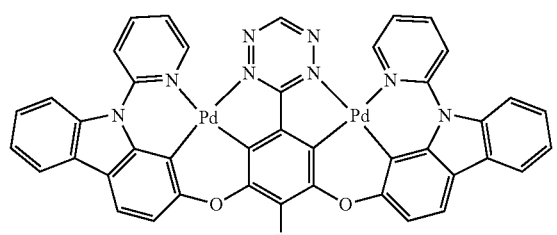
Compound Pd192
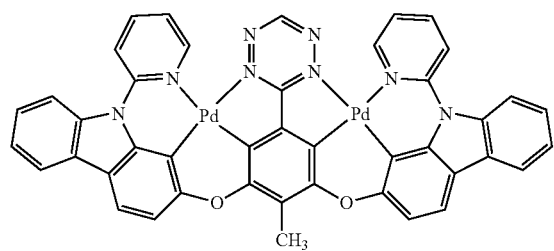
Compound Pd193
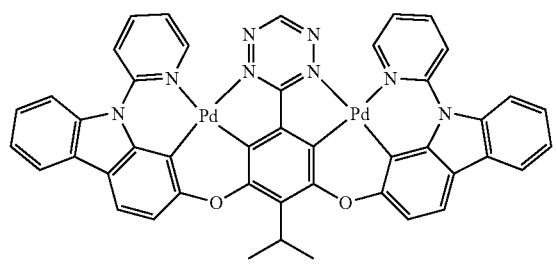
Compound Pd194
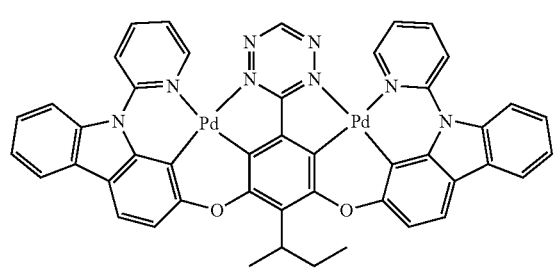
Compound Pd195
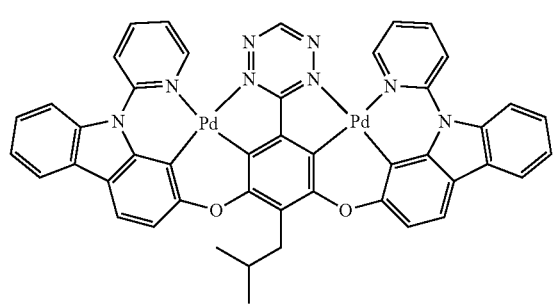
Compound Pd196
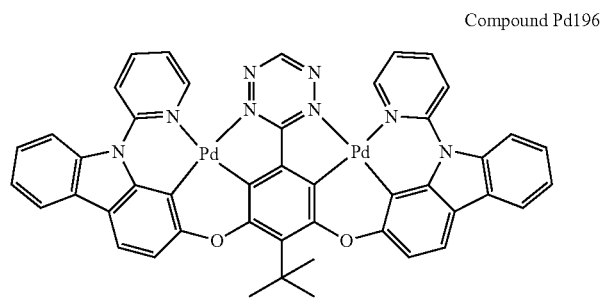
Compound Pd197
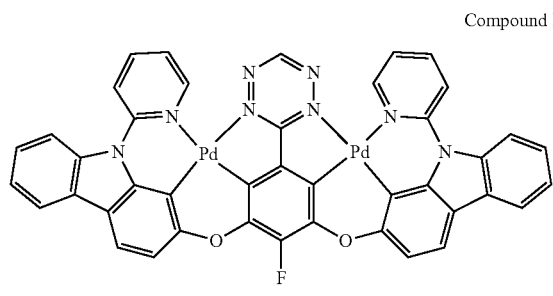

-continued
Compound Pd198
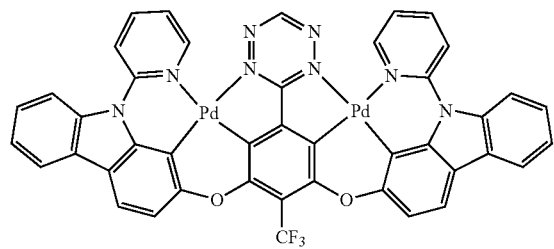
Compound Pd199
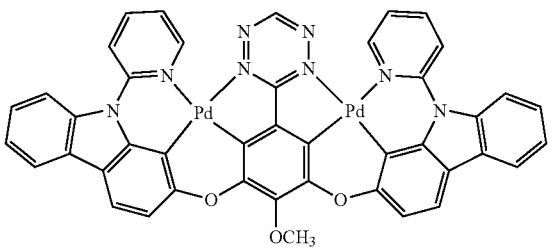
Compound Pd200
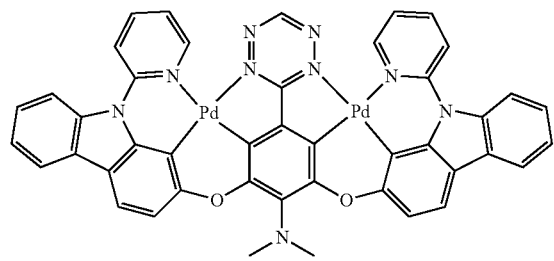
Compound Pd201
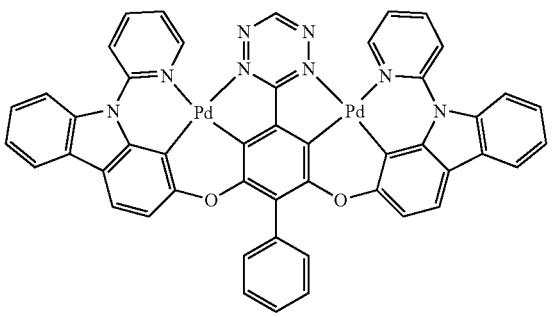
Compound Pd202
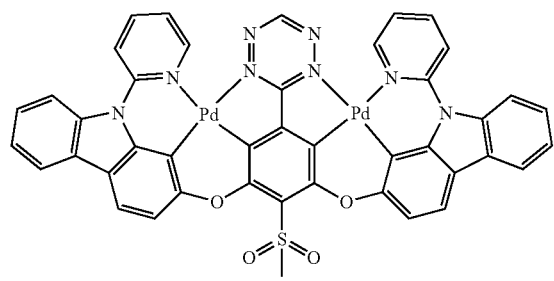
Compound Pd203
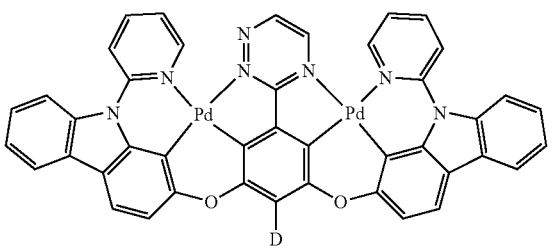
Compound Pd204
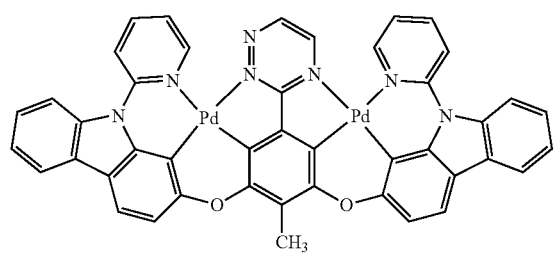
Compound Pd205
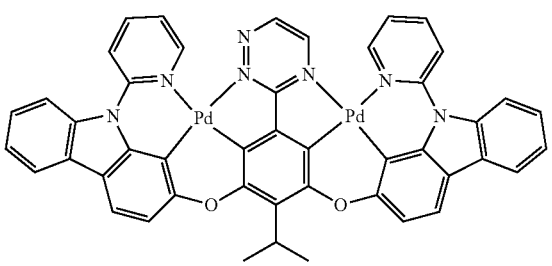
Compound Pd206
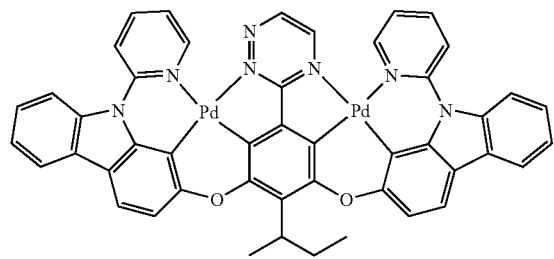
Compound Pd207
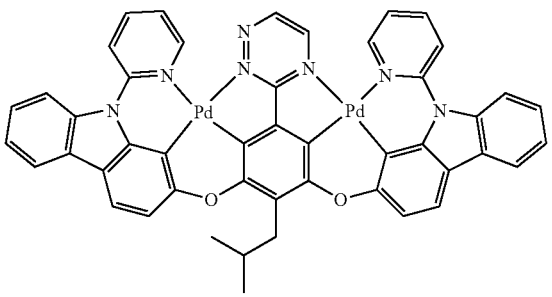

-continued
Compound Pd208
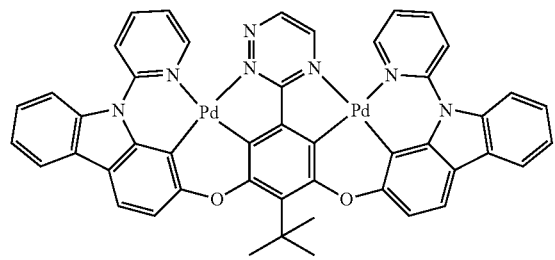
Compound Pd209
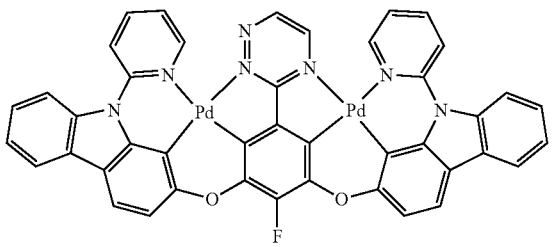
Compound Pd210
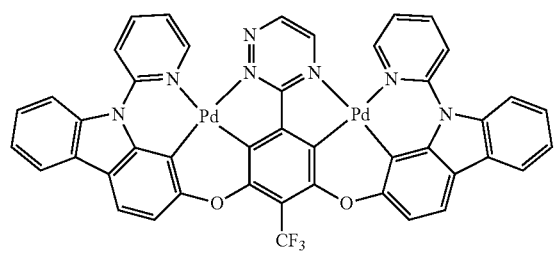
Compound Pd211
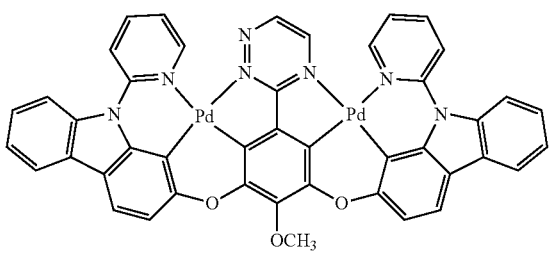
Compound Pd212
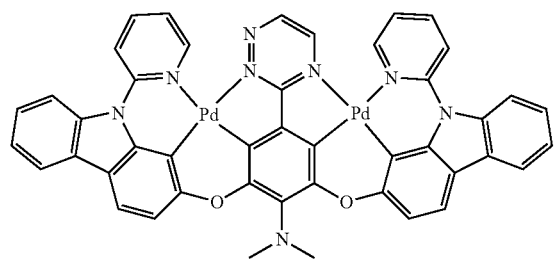
Compound Pd213
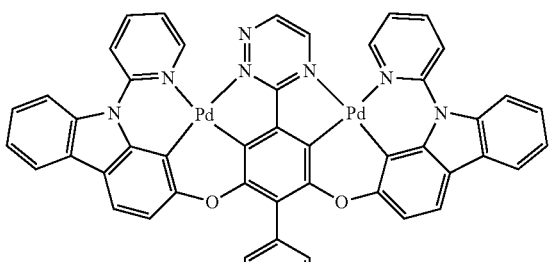
Compound Pd214
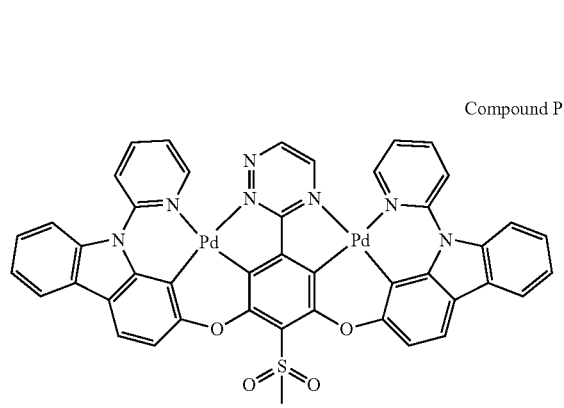
Compound Pd215
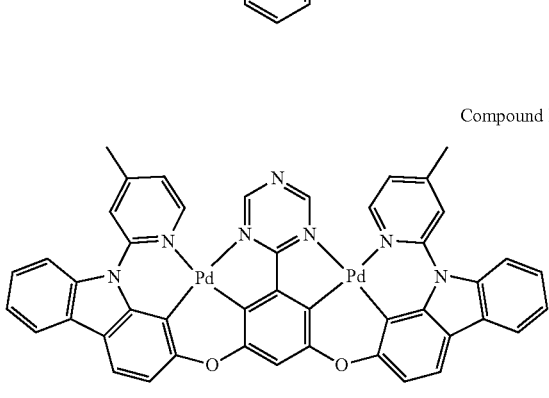
Compound Pd216
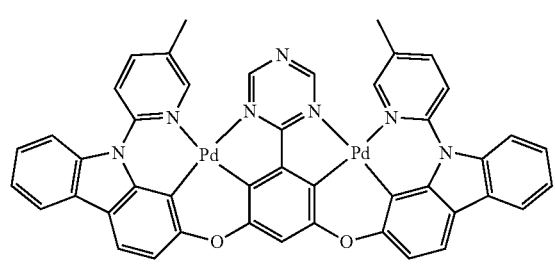
Compound Pd217
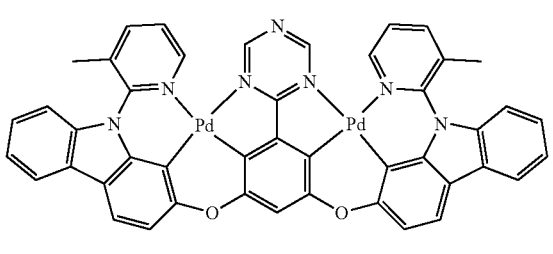

Compound Pd218
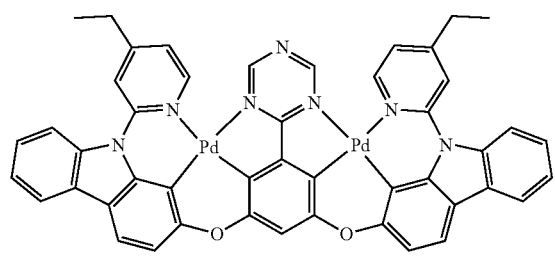
Compound Pd219
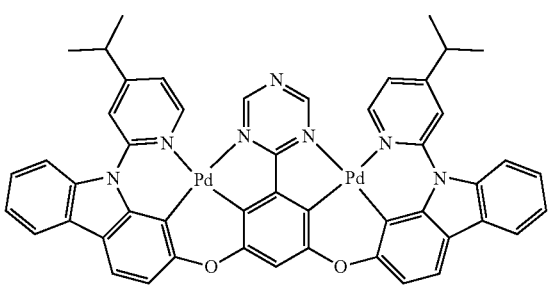
Compound Pd220
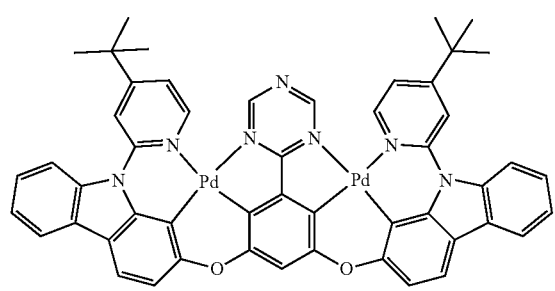
Compound Pd221
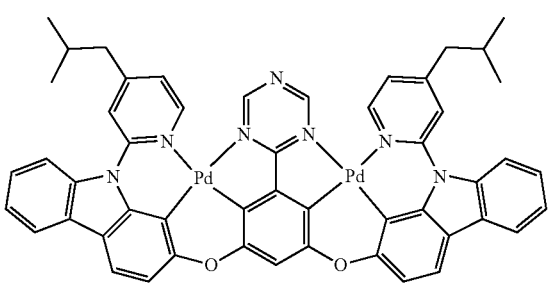
Compound Pd222
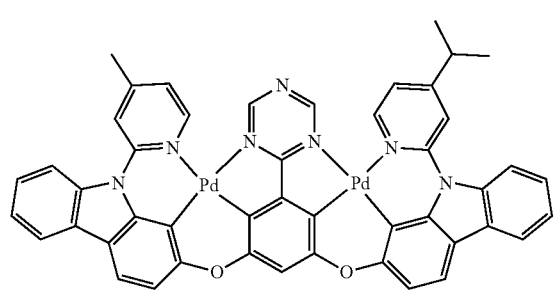
Compound Pd223
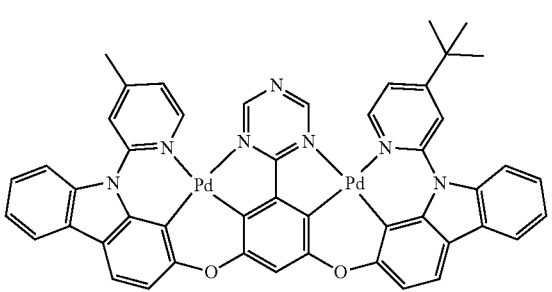
Compound Pd224
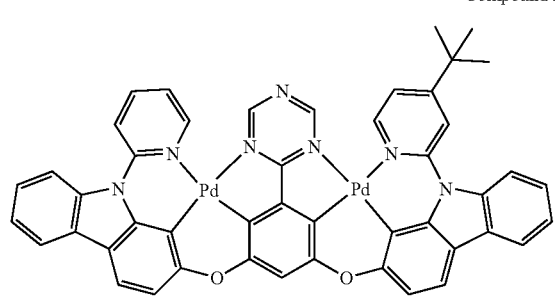
Compound Pd225
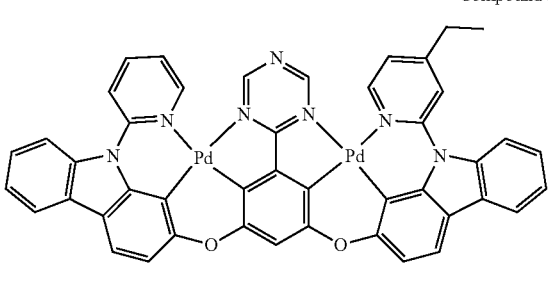
Compound Pd226
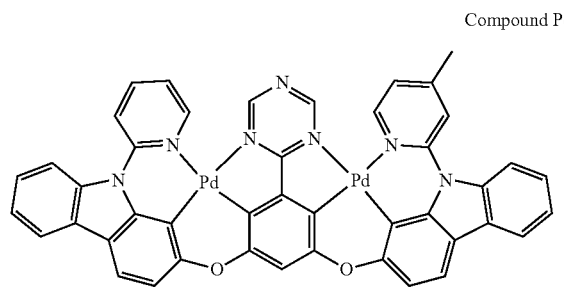
Compound Pd227
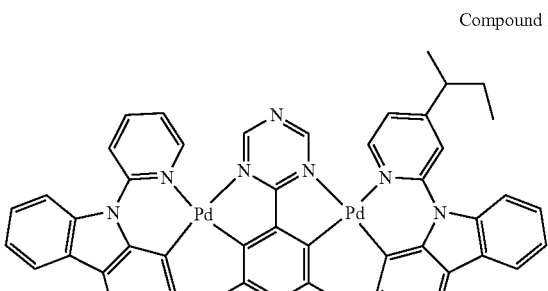

-continued
Compound Pd228
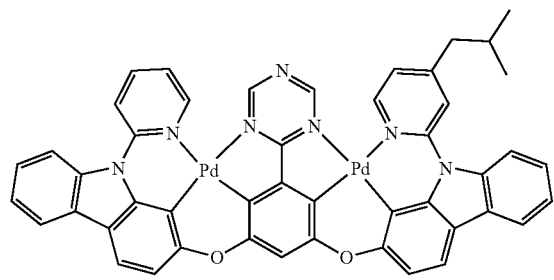
Compound Pd229
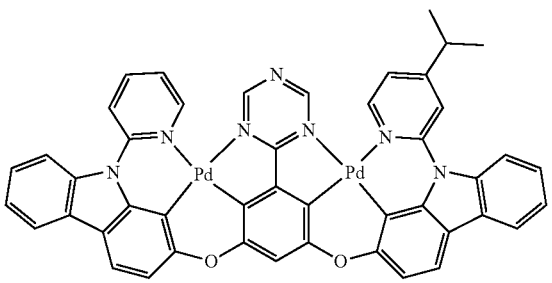
Compound Pd230
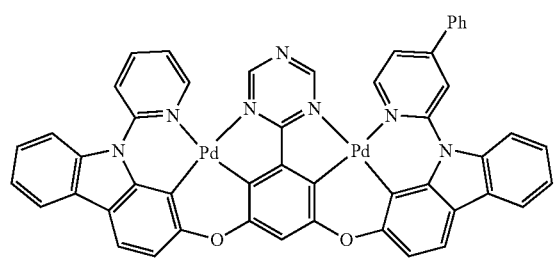
Compound Pd231
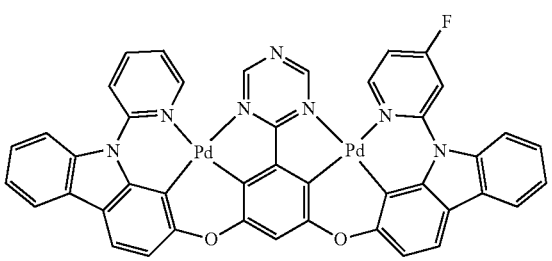
Compound Pd232
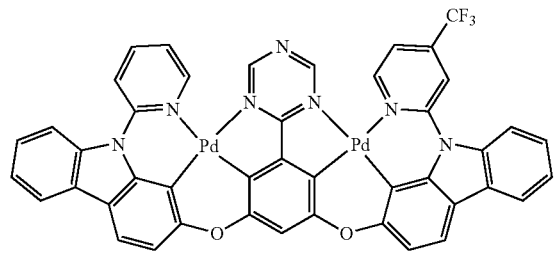
Compound Pd233
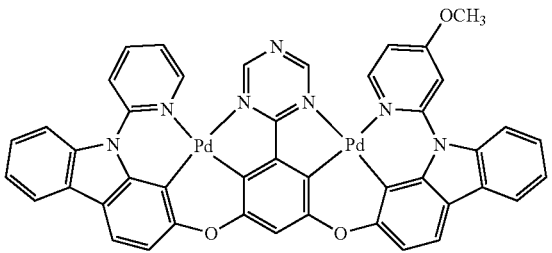
Compound Pd234
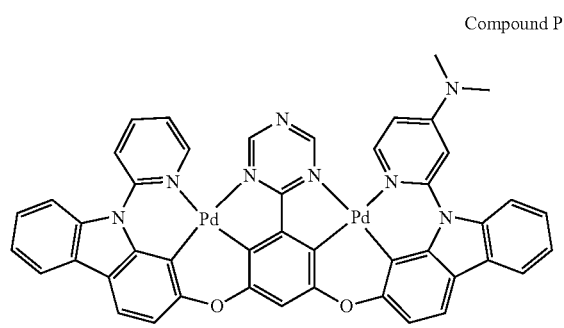
Compound Pd235
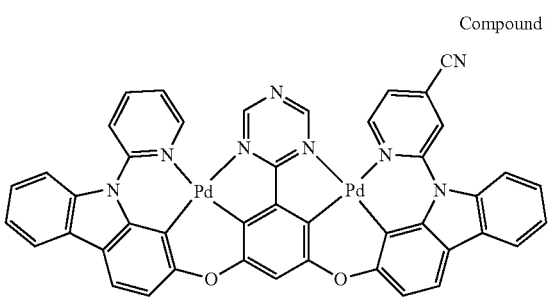
Compound Pd236
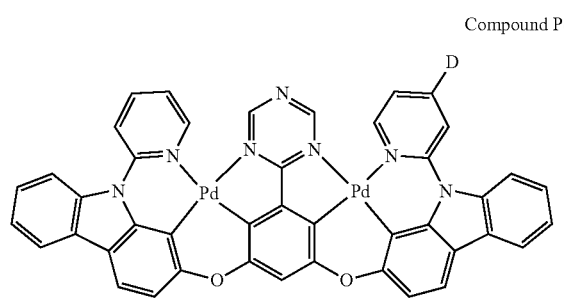
Compound Pd237
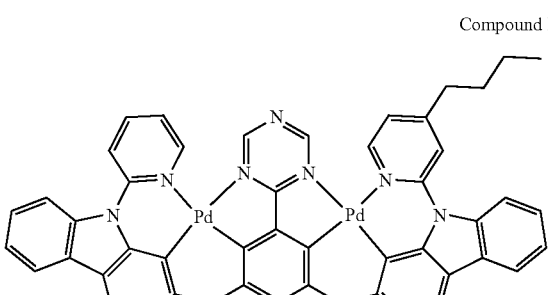

-continued
Compound Pd238
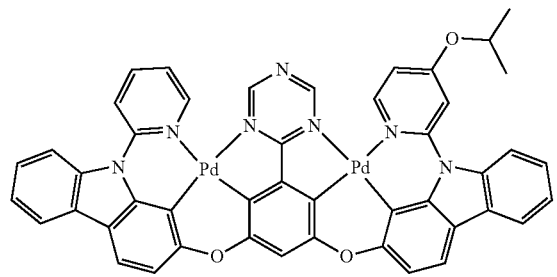
Compound Pd239
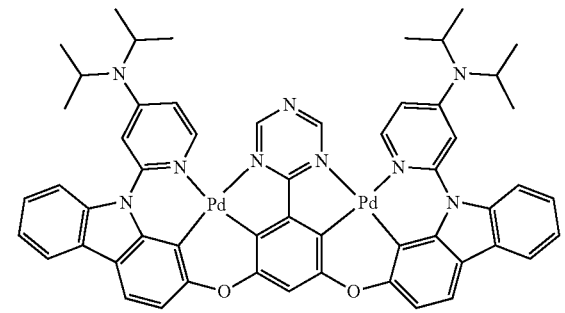
Compound Pd240
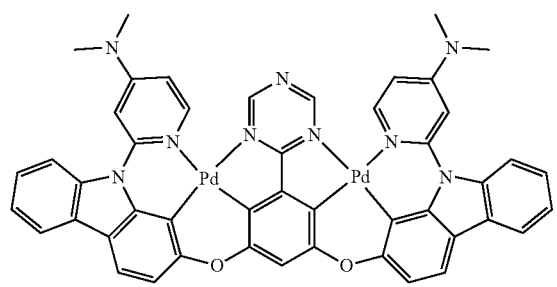
Compound Pd241
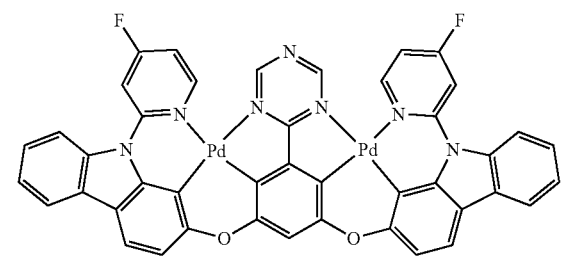
Compound Pd242
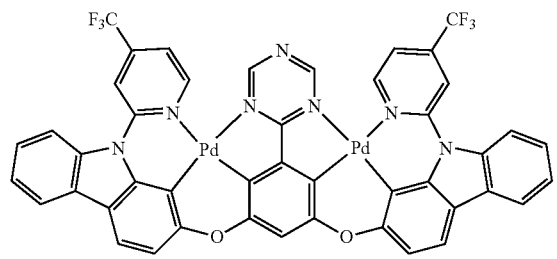
Compound Pd243
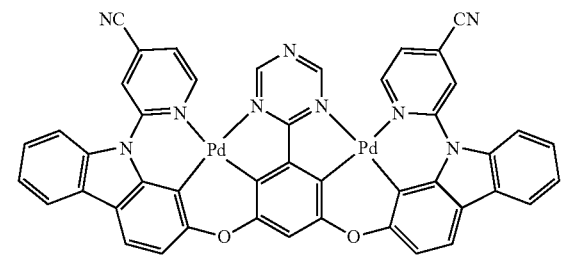
Compound Pd244
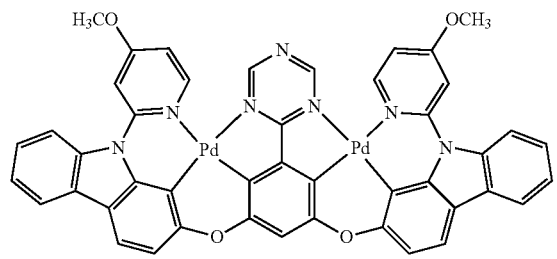
Compound Pd245
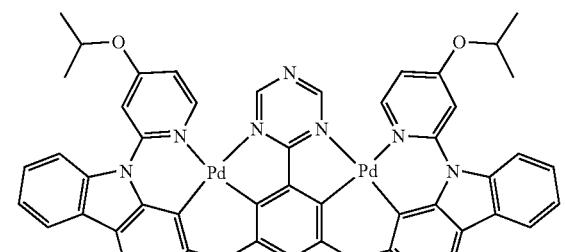
Compound Pd246
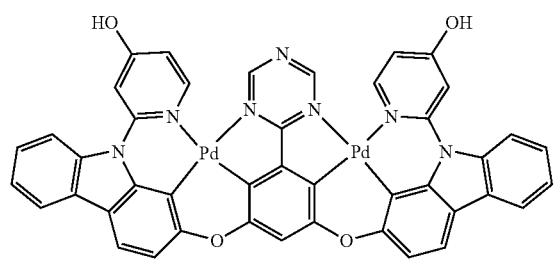
Compound Pd247
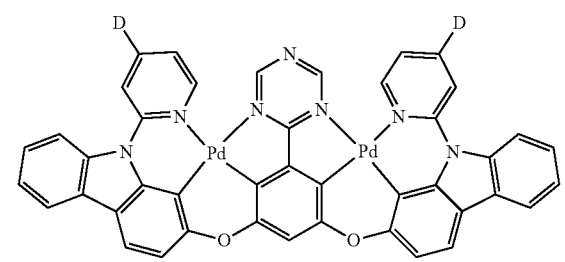

-continued
Compound Pd248
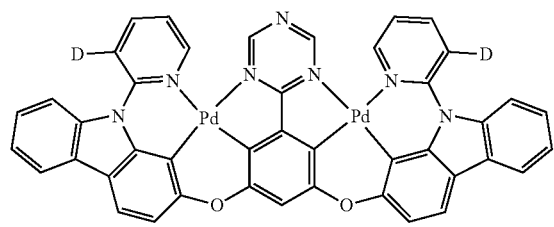
Compound Pd250
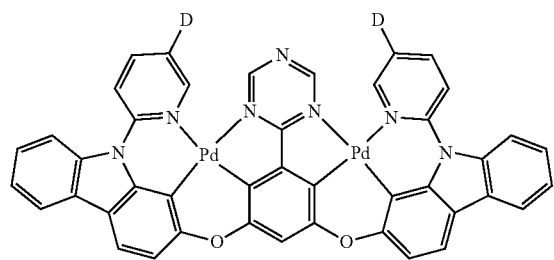
Compound Pd252
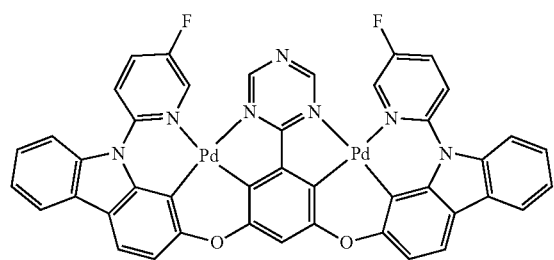
Compound Pd254
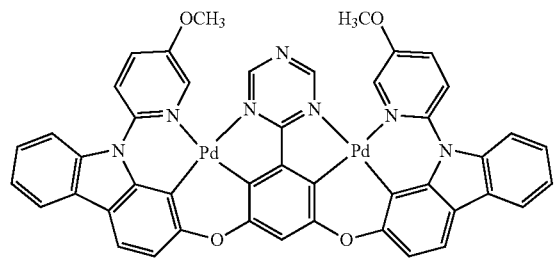
Compound Pd256
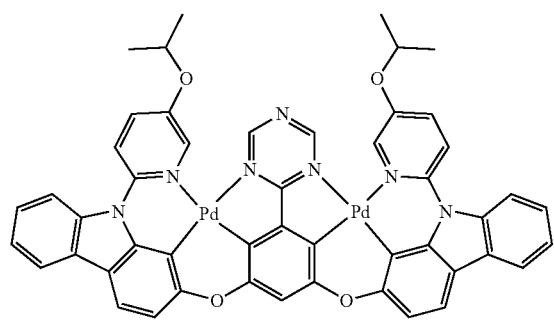
Compound Pd249
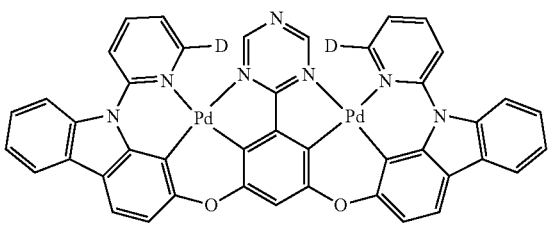
Compound Pd251
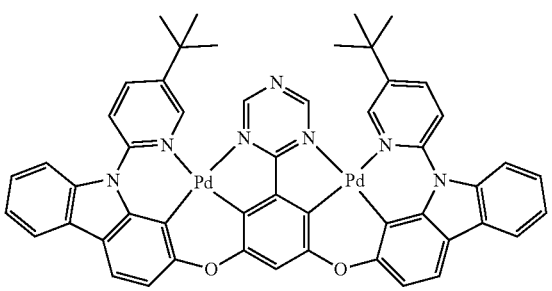
Compound Pd253
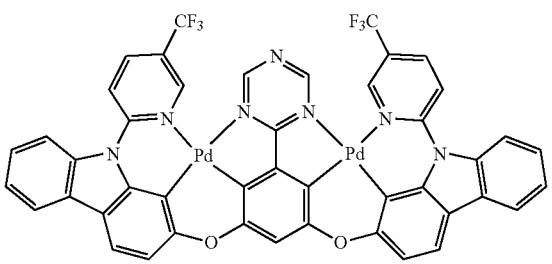
Compound Pd255
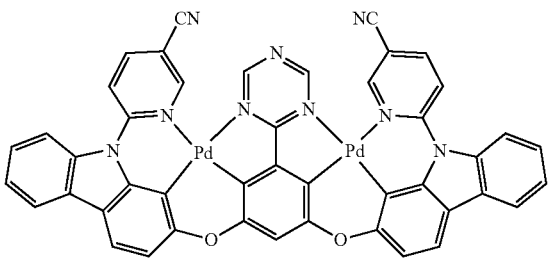
Compound Pd257
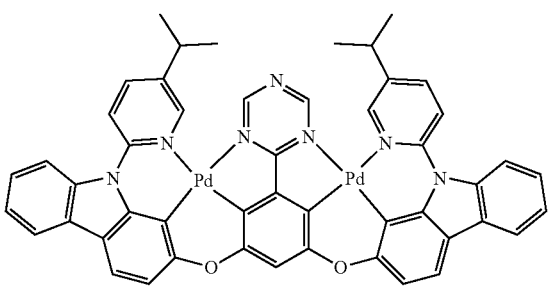

Compound Pd258
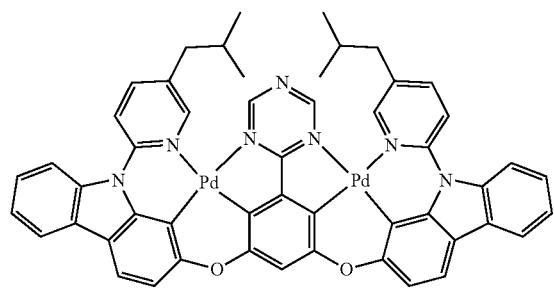
Compound Pd259
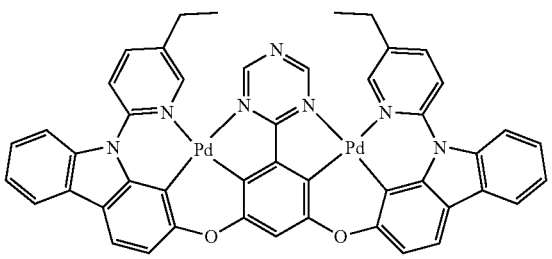
Compound Pd260
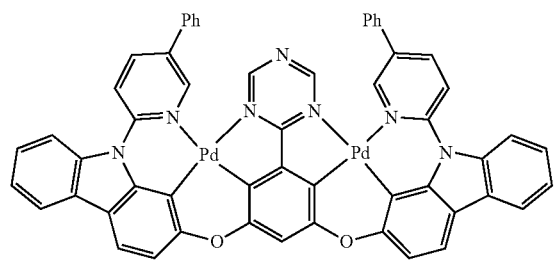
Compound Pd261
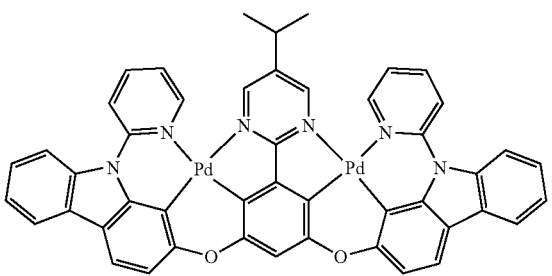
Compound Pd262
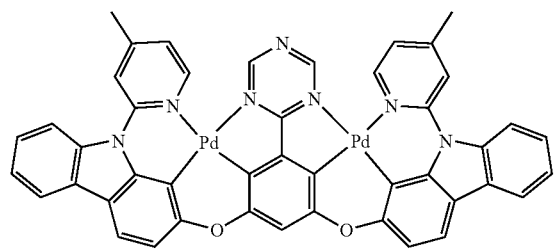
Compound PtPd1
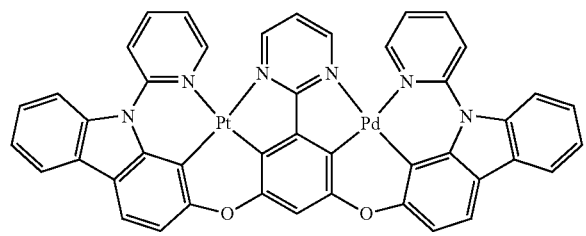
Compound PtPd2
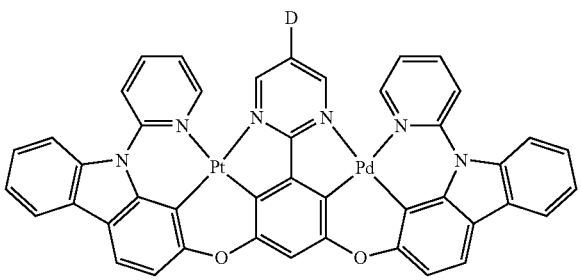
Compound PtPd3
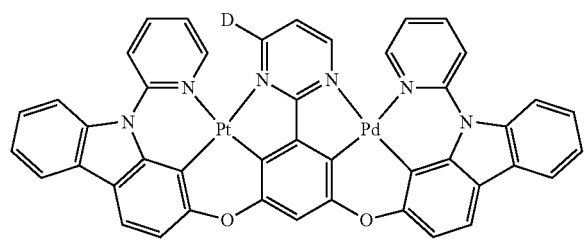
Compound PtPd4
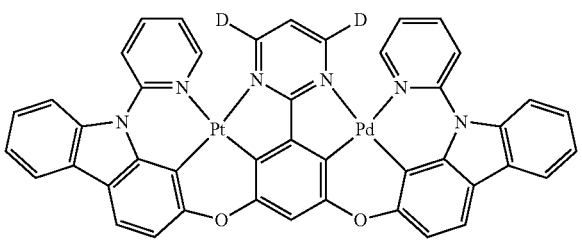

-continued
Compound PtPd5
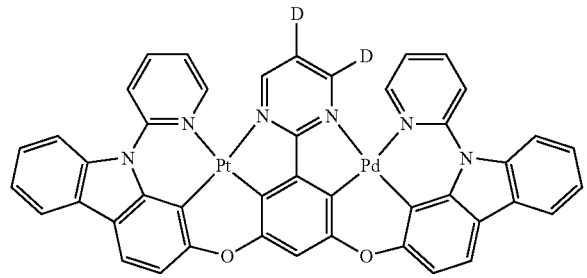
Compound PtPd6
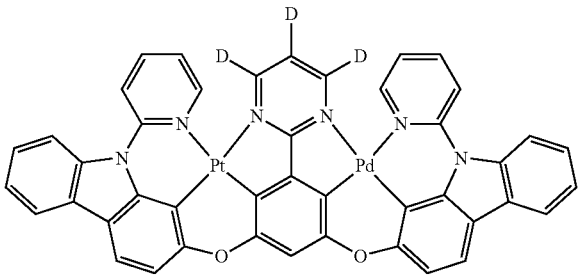
Compound PtPd7
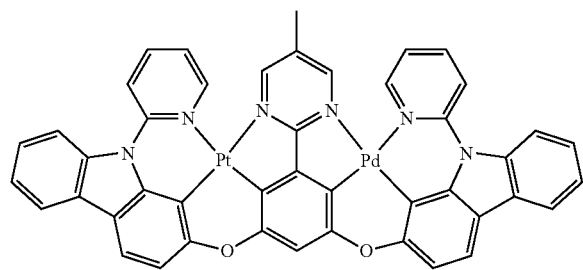
Compound PtPd8
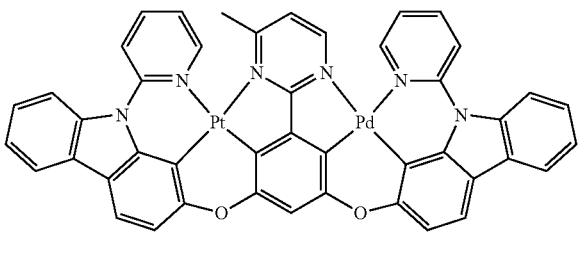
Compound PtPd9
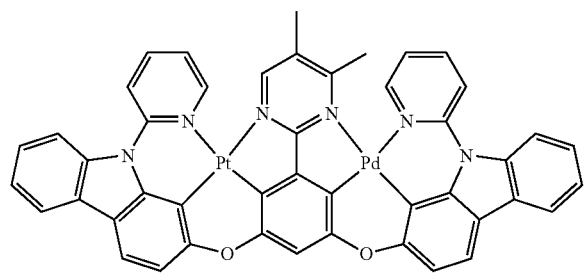
Compound PtPd10
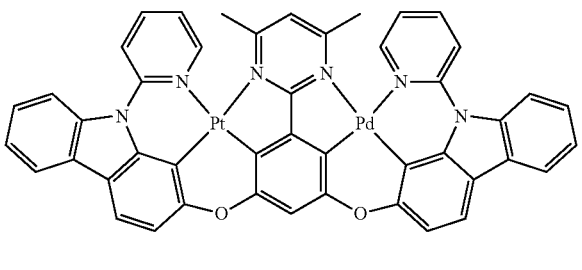
Compound PtPd11
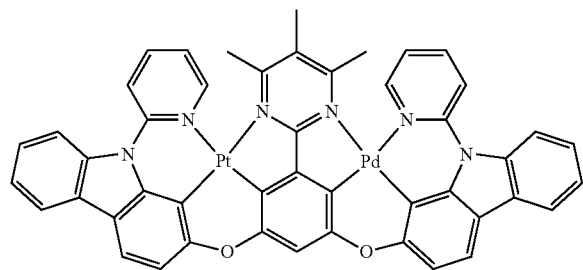
Compound PtPd12
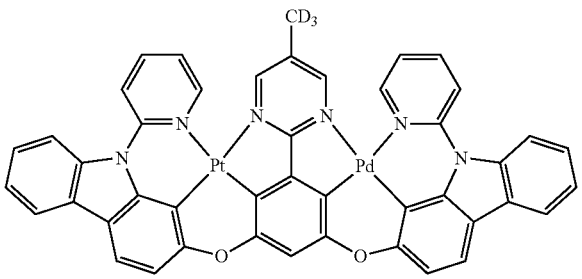
Compound PdPt13
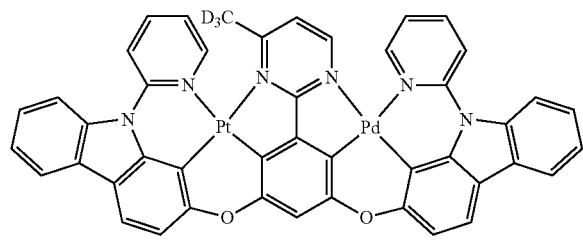
Compound PtPd14
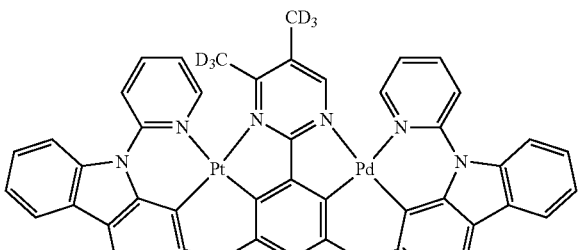

-continued
Compound PdPt15
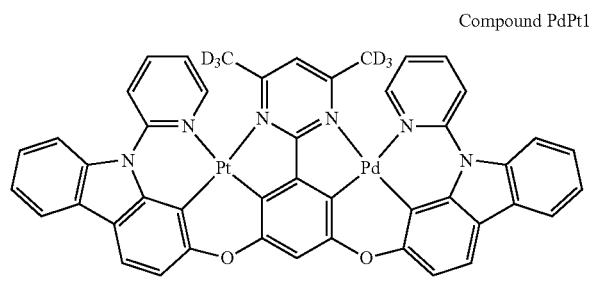
Compound PtPd16
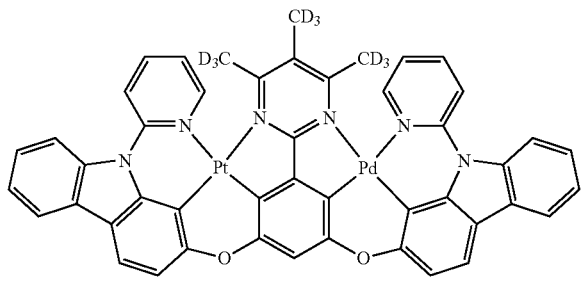
Compound PtPd17
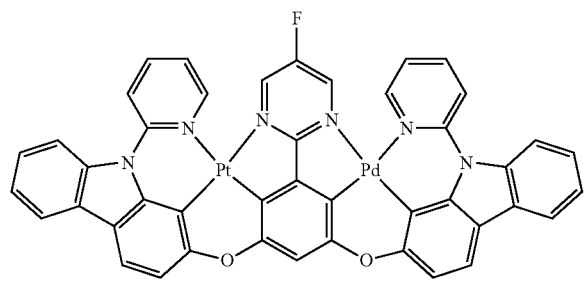
Compound PtPd18
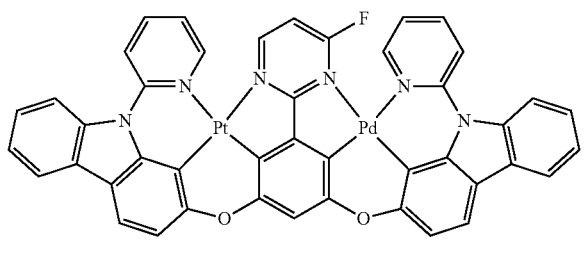
Compound PtPd19
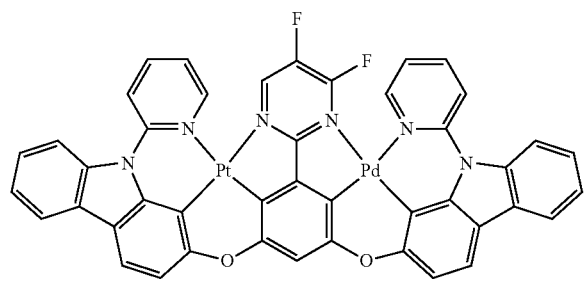
Compound PdPt20
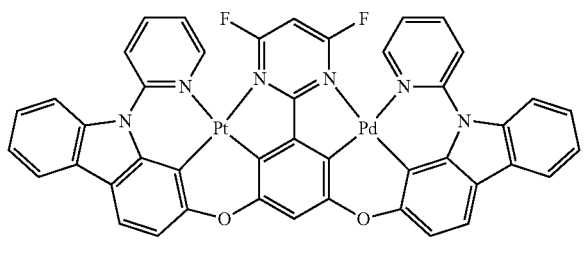
Compound PtPd21
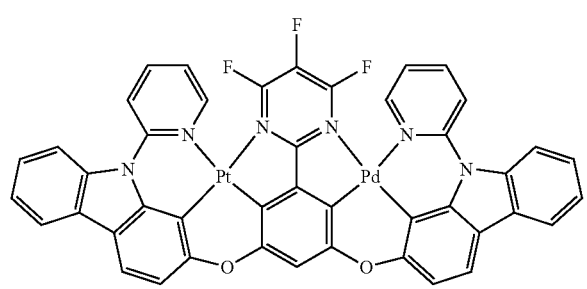
Compound PtPd22
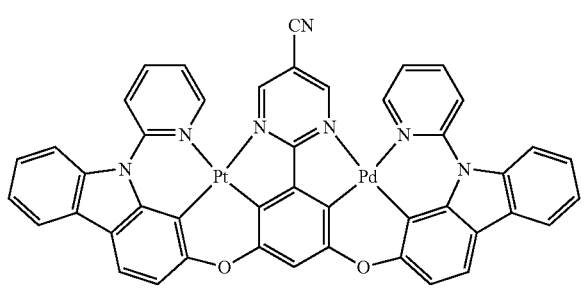
Compound PtPd23
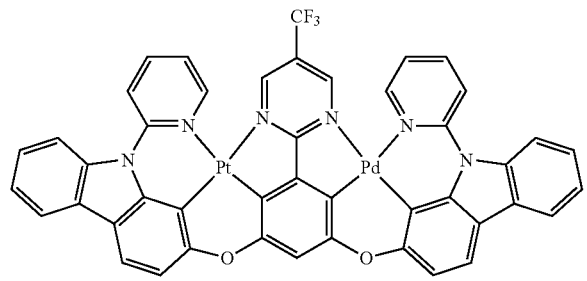
Compound PtPd24
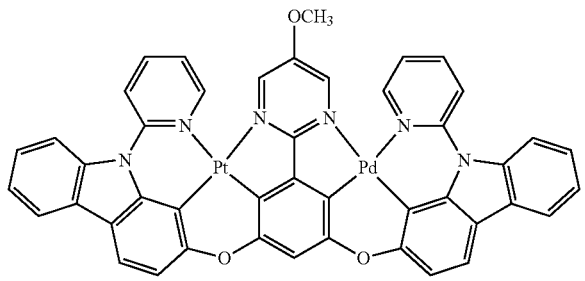

-continued
Compound PtPd25
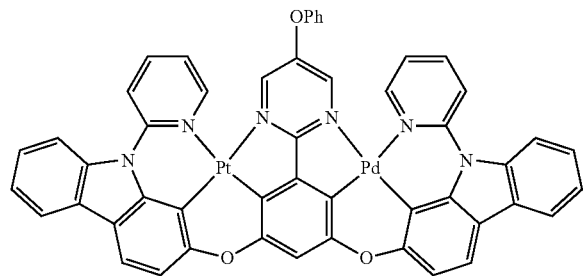
Compound PtPd26
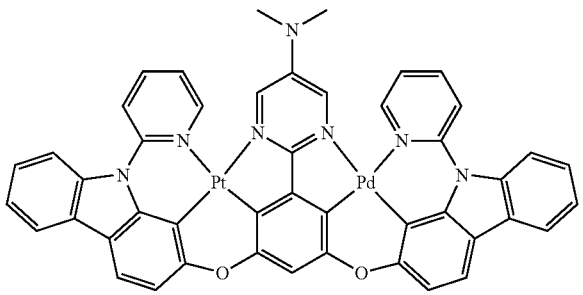
Compound PtPd27
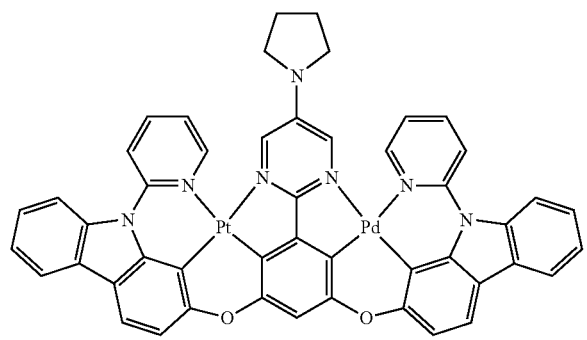
Compound PtPd28
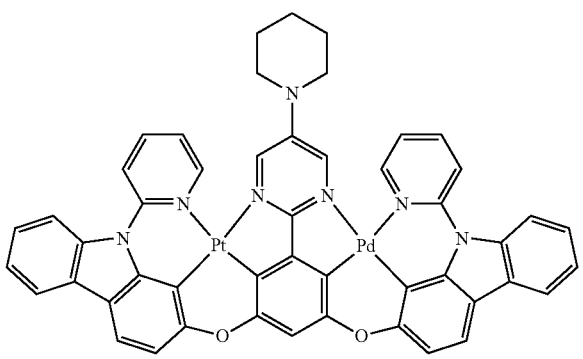
Compound PtPd29
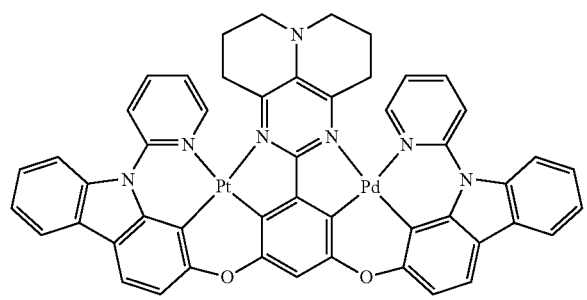
Compound PtPd30
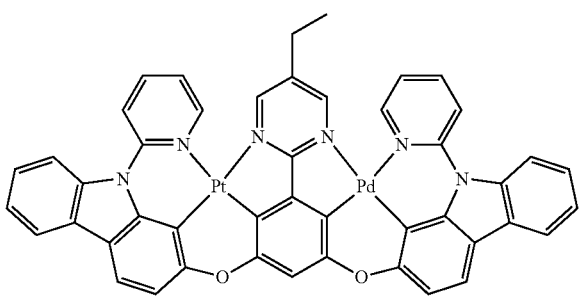
Compound PtPd31
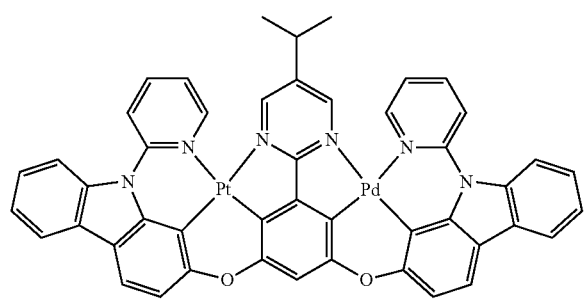
Compound PtPd32
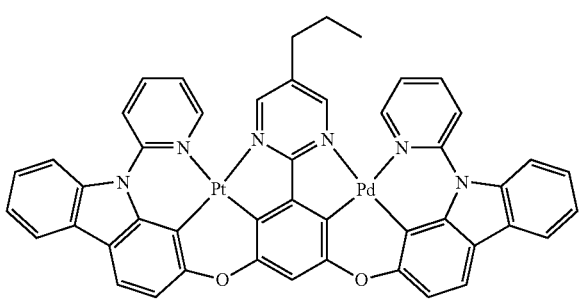
Compound PtPd33
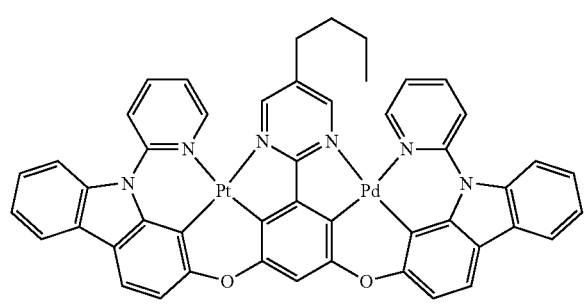
Compound PtPd34
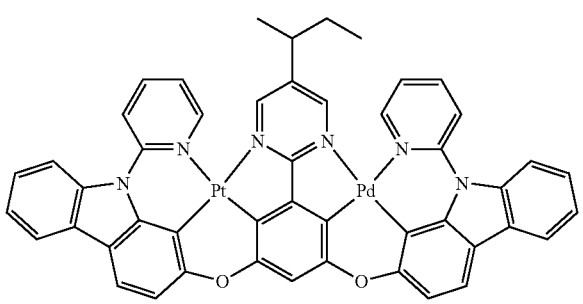

-continued
Compound PtPd35
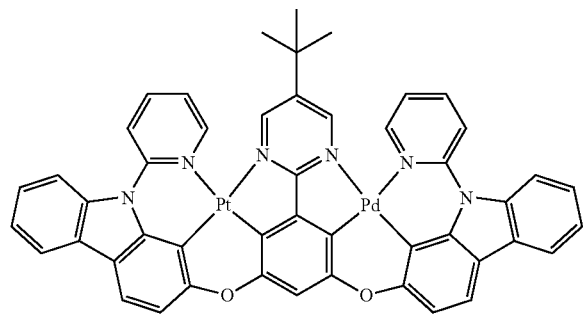
Compound PtPd36
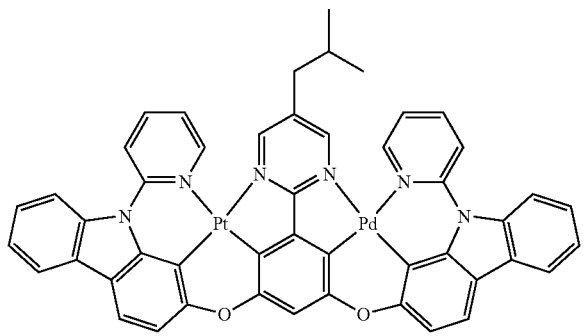
Compound PtPd37
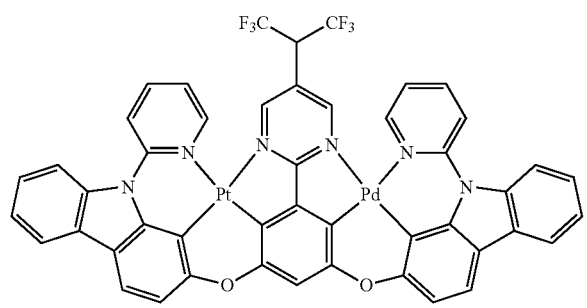
Compound PtPd38
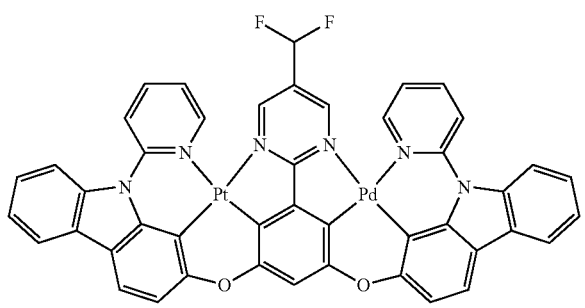
Compound PtPd39
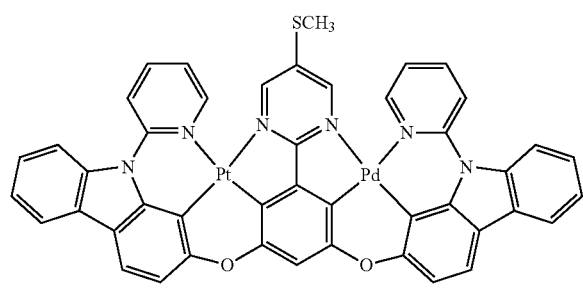
Compound PtPd40
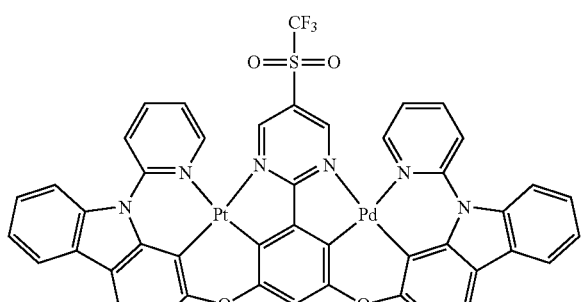
Compound PtPd41
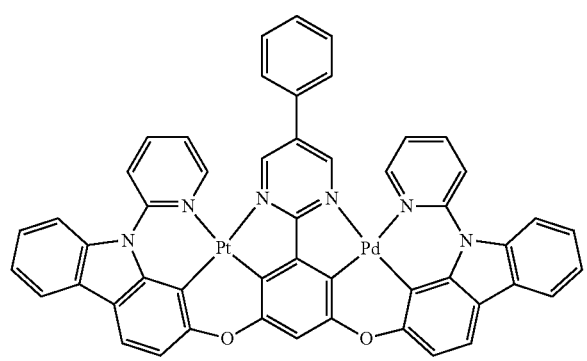
Compound PtPd42
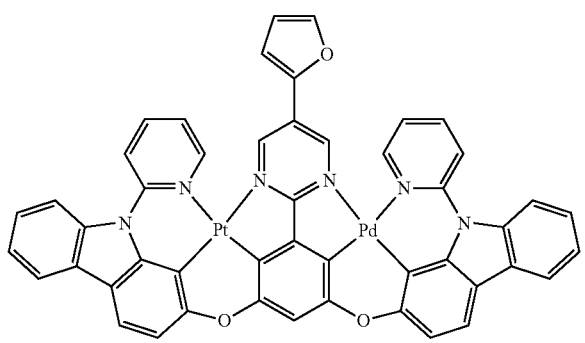

-continued
Compound PtPd43
Compound PtPd44
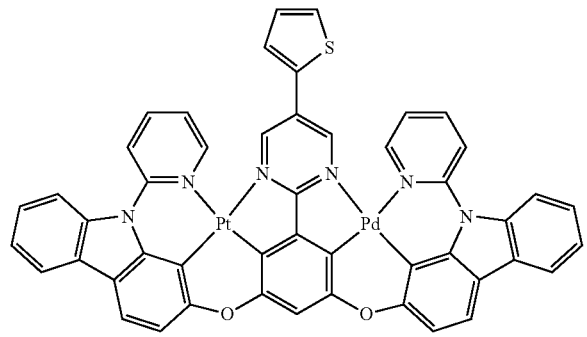 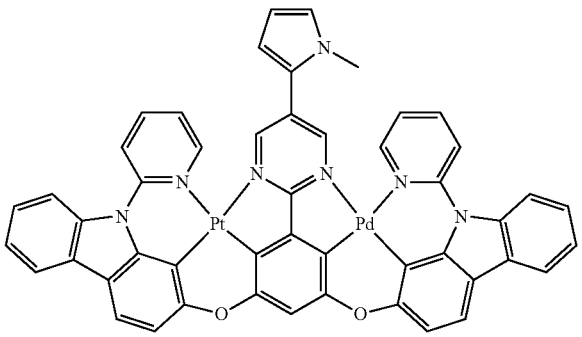
Compound PtPd45
Compound PtPd46
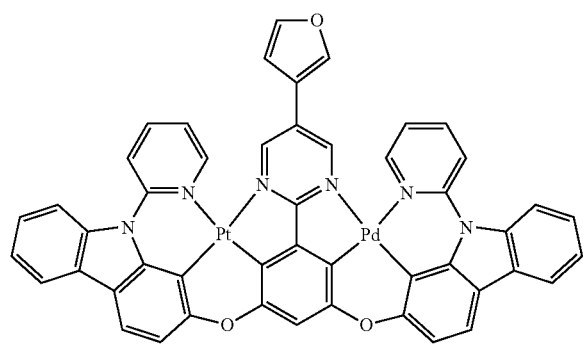 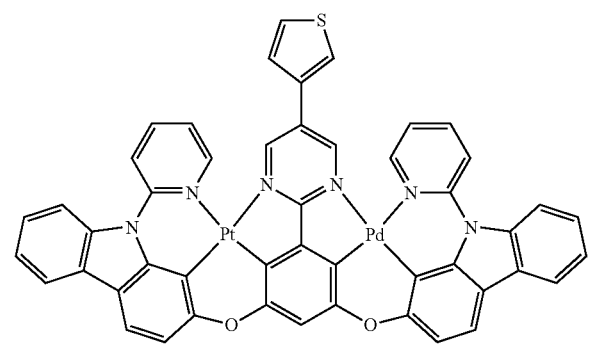
Compound PtPd47
Compound PtPd48
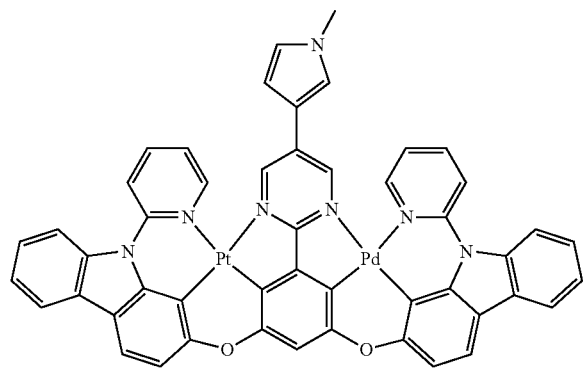 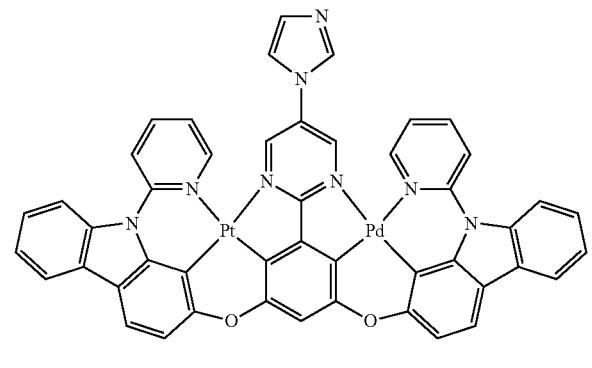
Compound PtPd49
Compound PtPd50
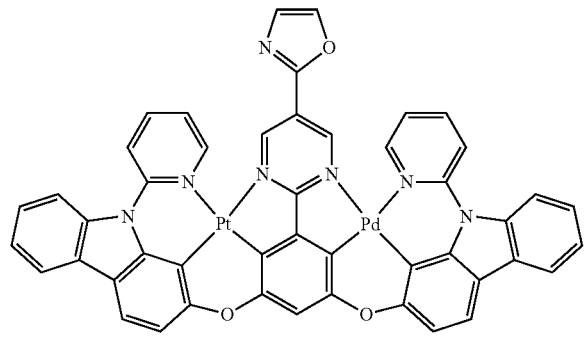

-continued
Compound PtPd51
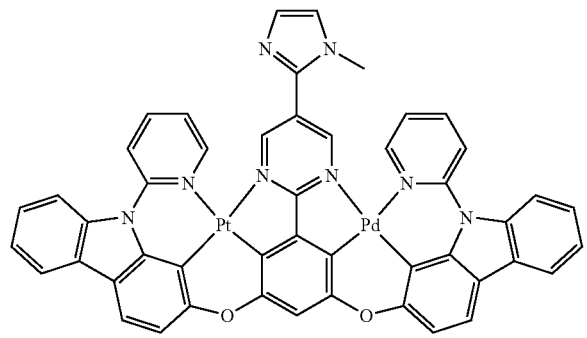
Compound PtPd52
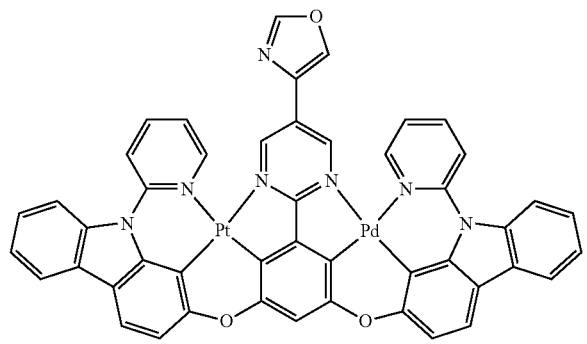
Compound PtPd53
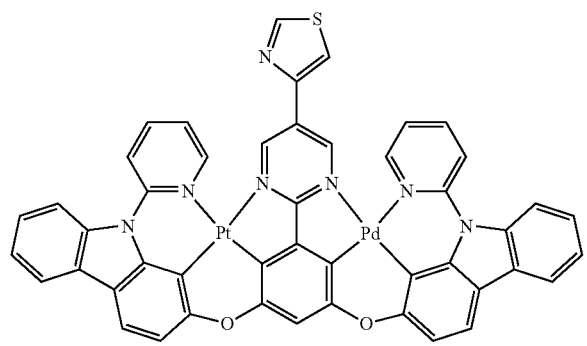
Compound PtPd54
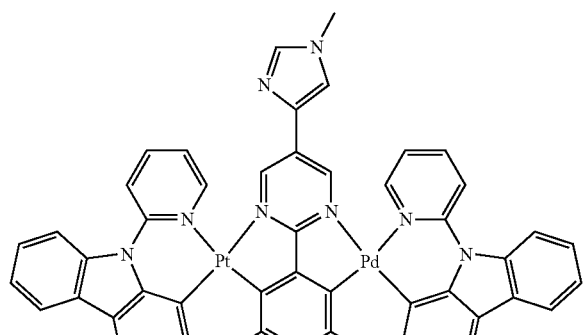
Compound PtPd55
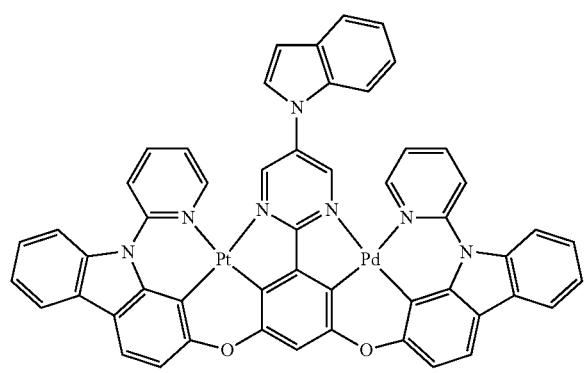
Compound PtPd56
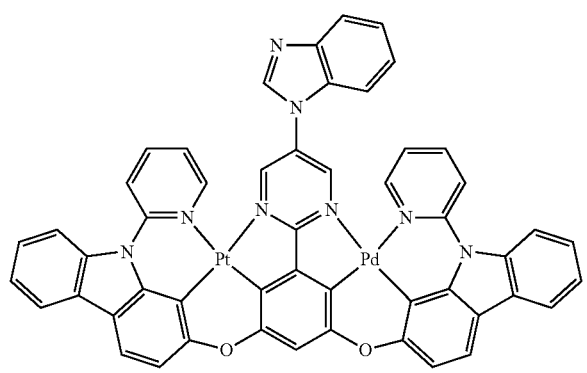
Compound PtPd57
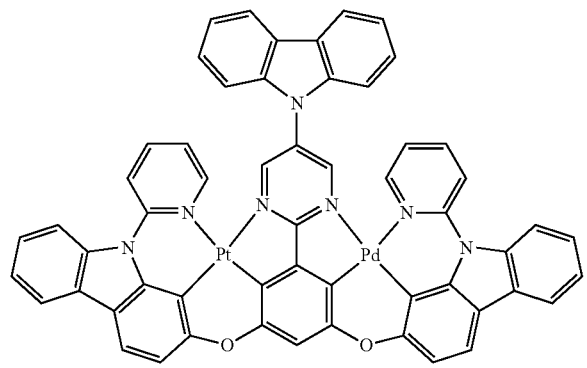
Compound PtPd58
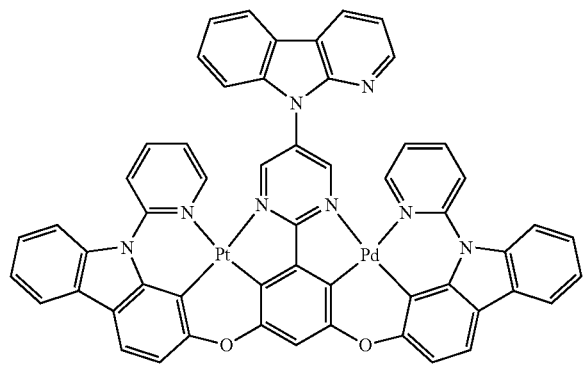

Compound PtPd59
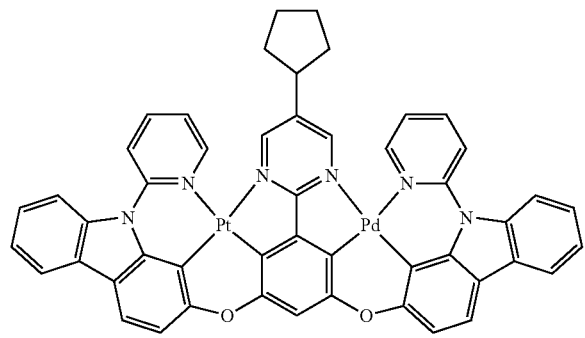
Compound PtPd60
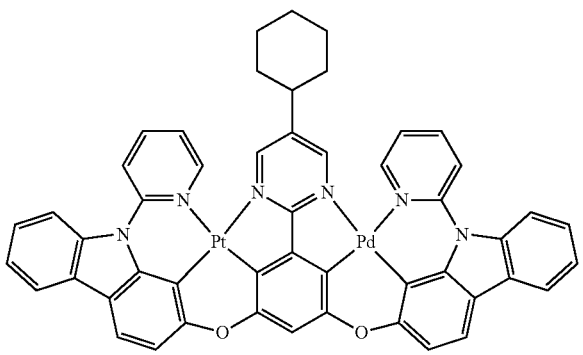
Compound PtPd61
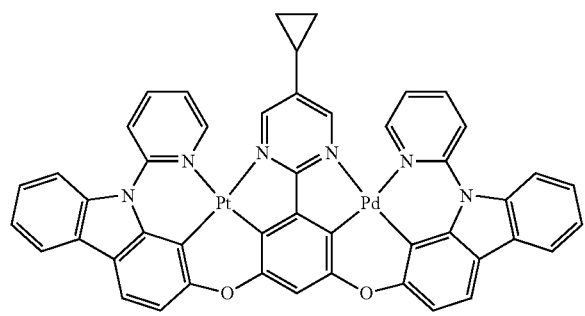
Compound PtPd62
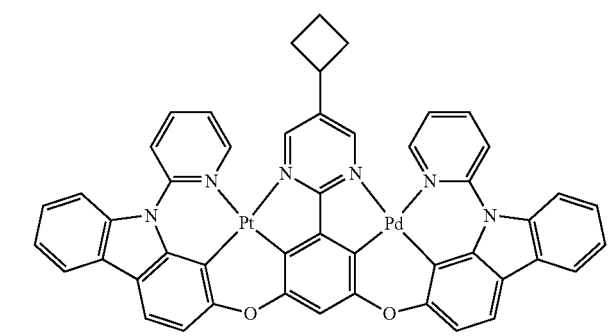
Compound PtPd63
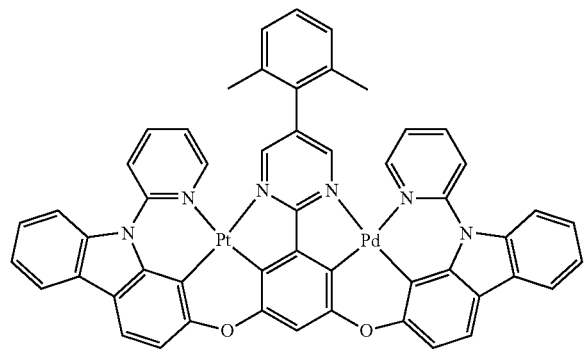
Compound PtPd64
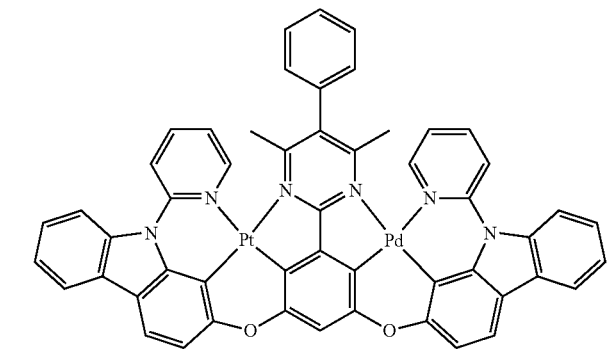
Compound PtPd65
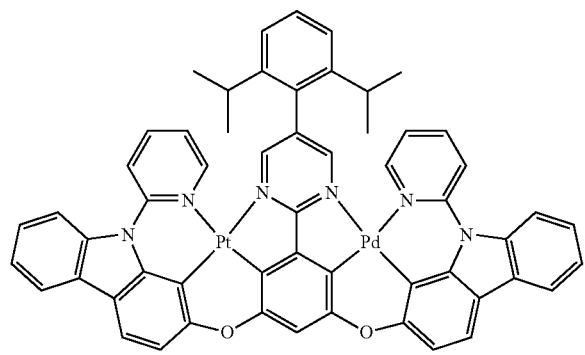
Compound PtPd66
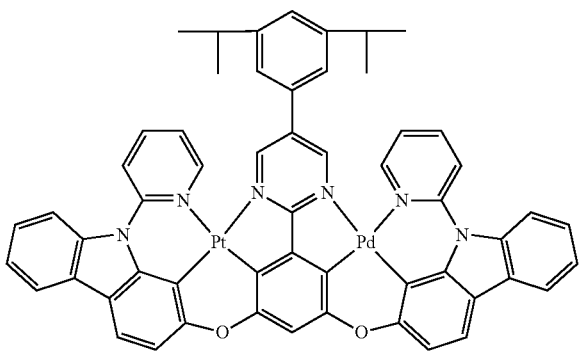

-continued
Compound PtPd67
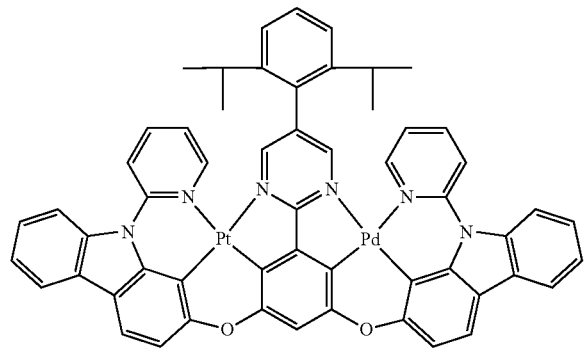
Compound PtPd68
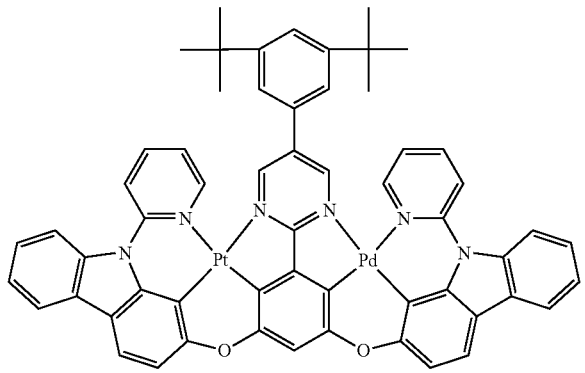
Compound PtPd69
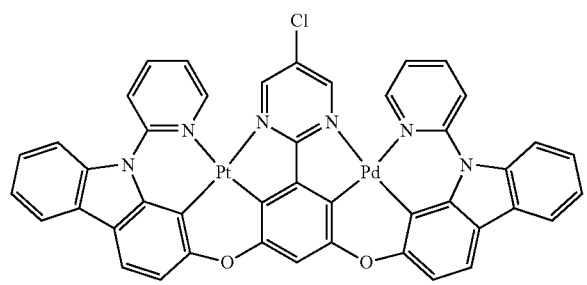
Compound PtPd70
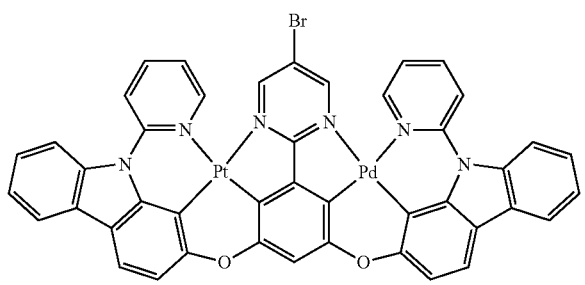
Compound PtPd71
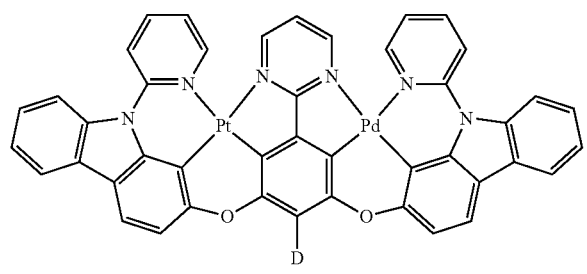
Compound PtPd72
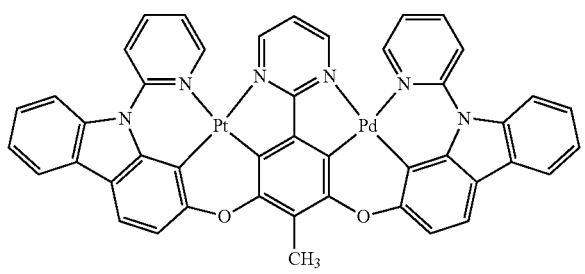
Compound PtPd73
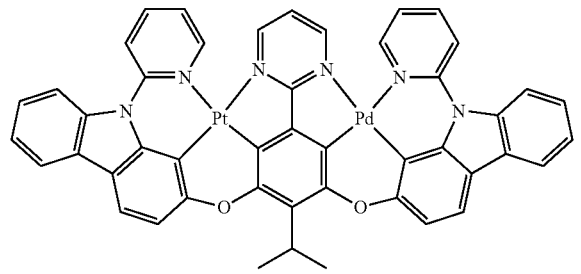
Compound PtPd74
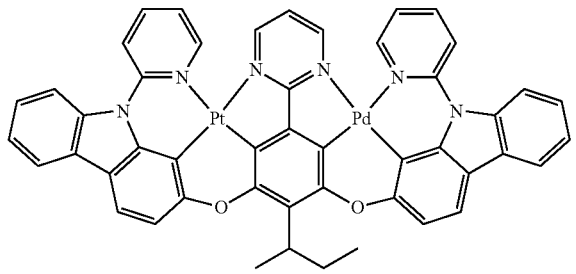
Compound PtPd75
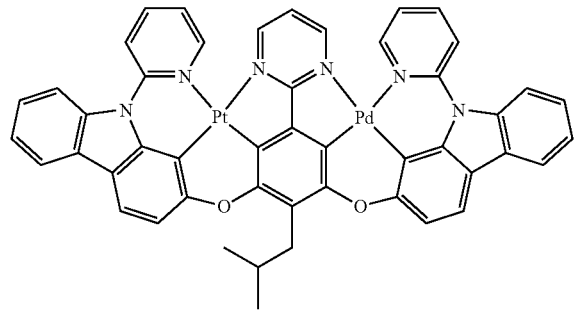
Compound PtPd76
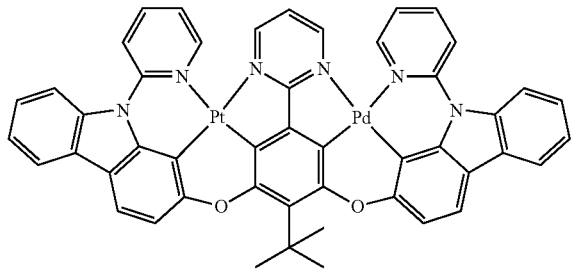

-continued
Compound PtPd77
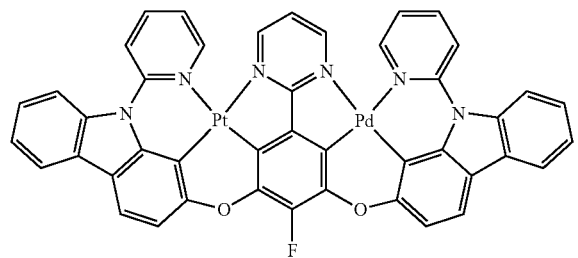
Compound PtPd78
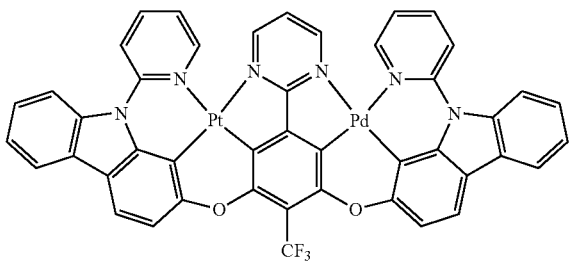
Compound PtPd79
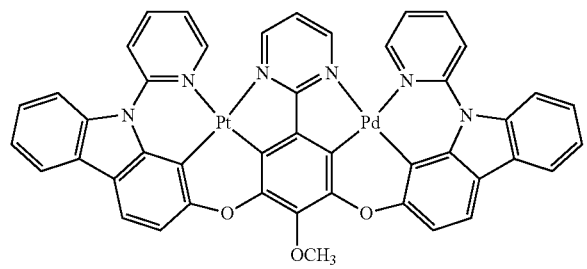
Compound PtPd80
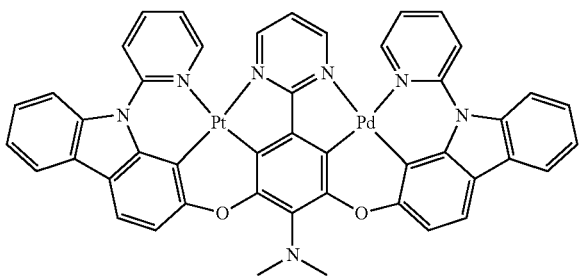
Compound PtPd81
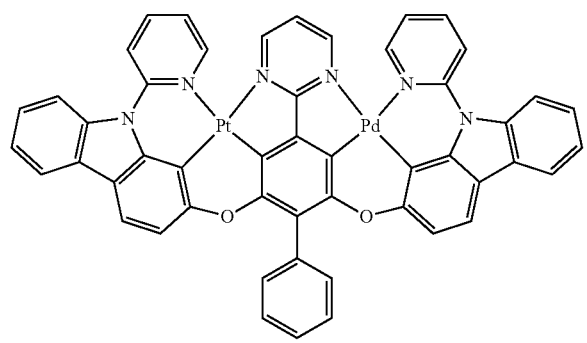
Compound PtPd82
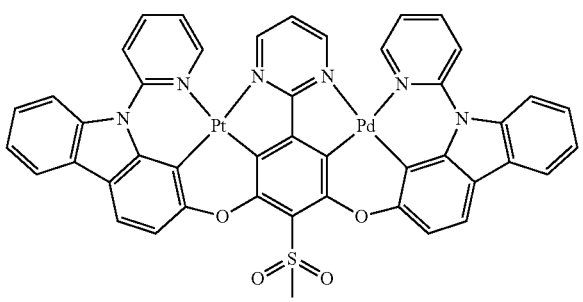
Compound PtPd83
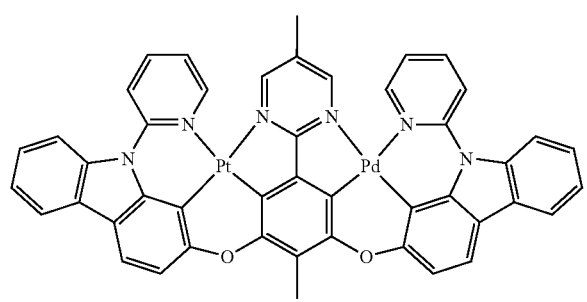
Compound PtPd84
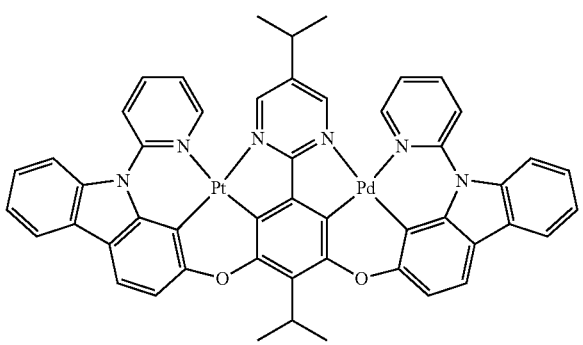

-continued
Compound PtPd85
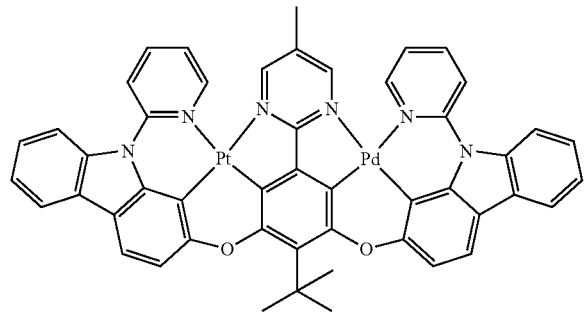
Compound PtPd86
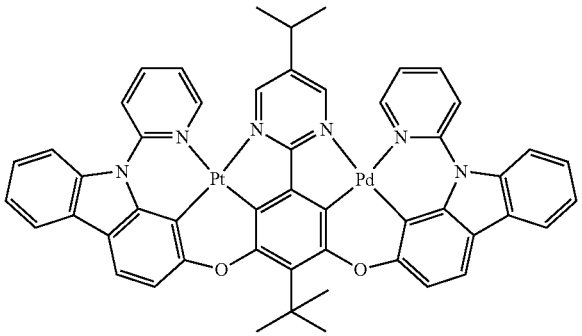
Compound PtPd87
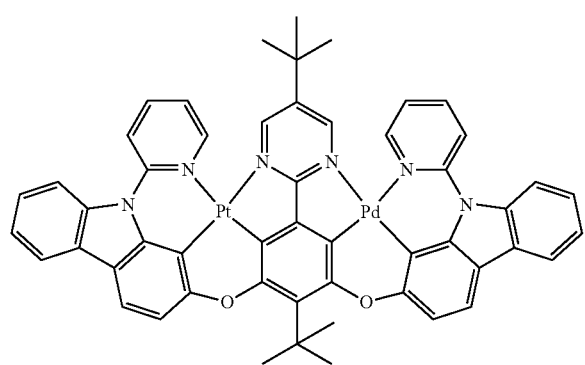
Compound PtPd88
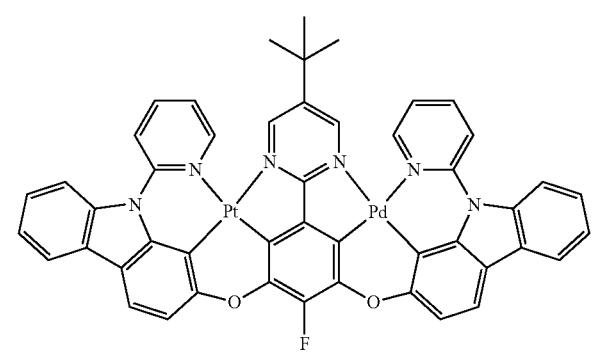
Compound PtPd89
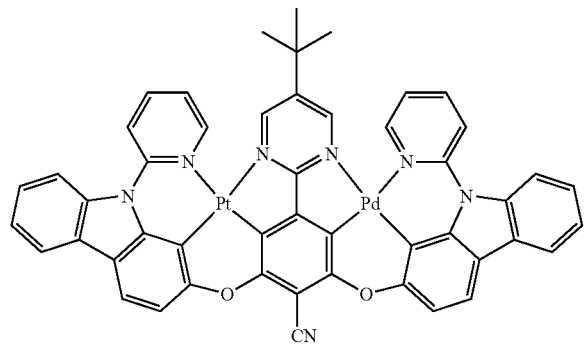
Compound PtPd90
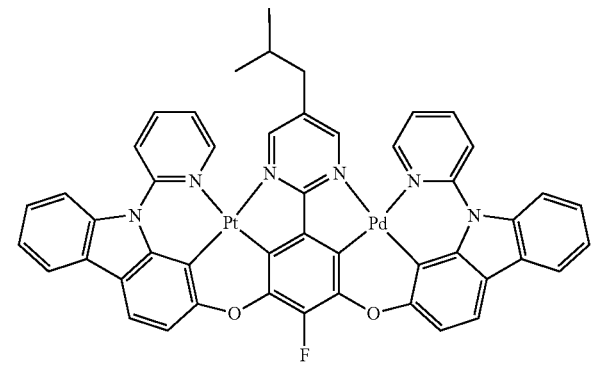
Compound PtPd91
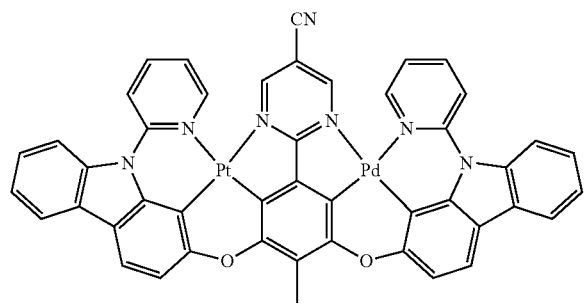
Compound PtPd92
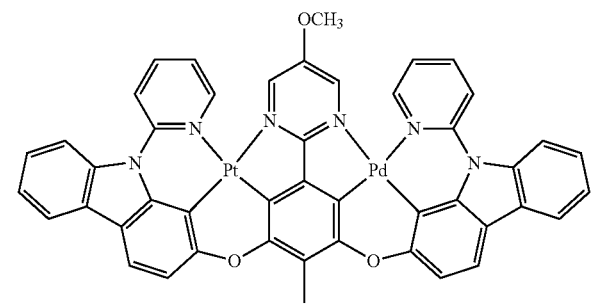

-continued
Compound PtPd93
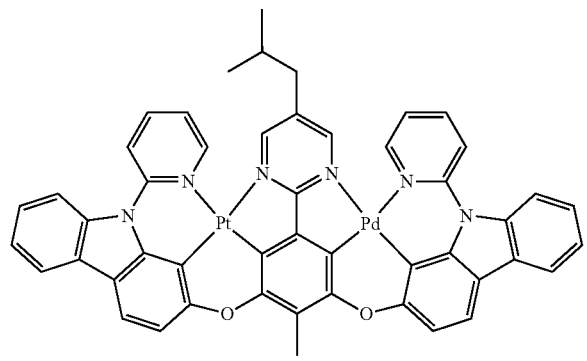
Compound PtPd94
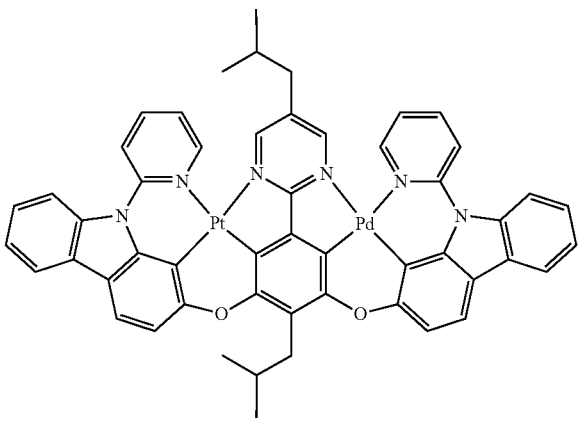
Compound PtPd95
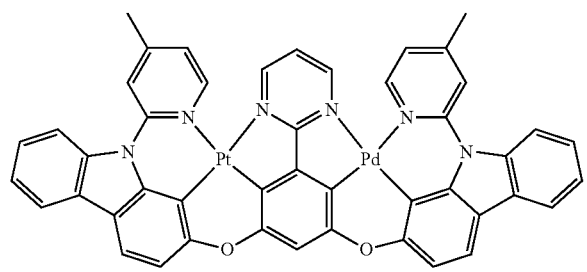
Compound PtPd96
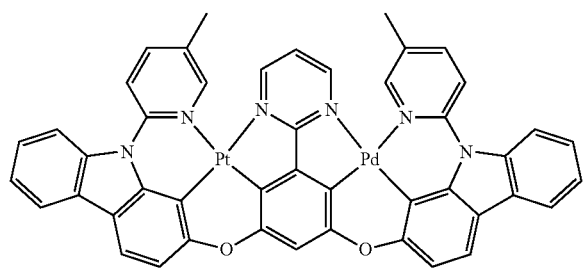
Compound PtPd97
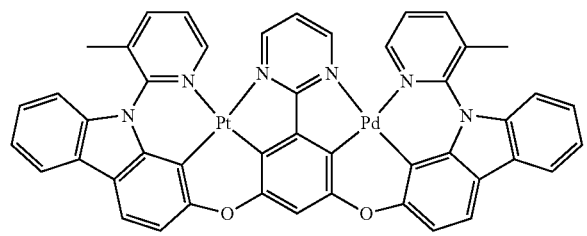
Compound PtPd98
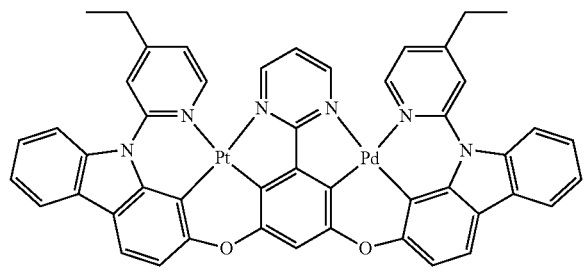
Compound PtPd99
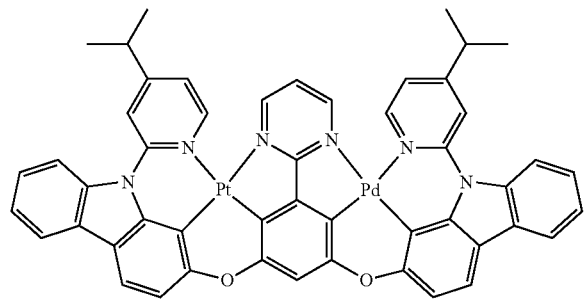
Compound PtPd100
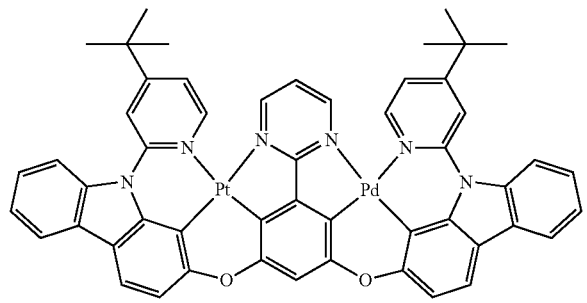

-continued
Compound PtPd101
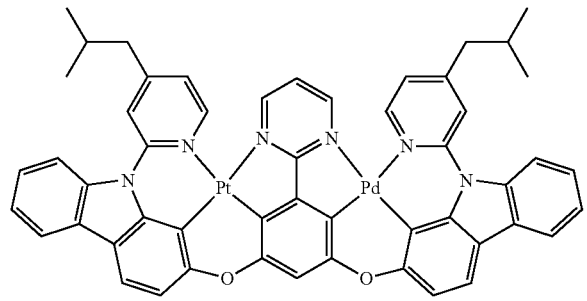
Compound PtPd102
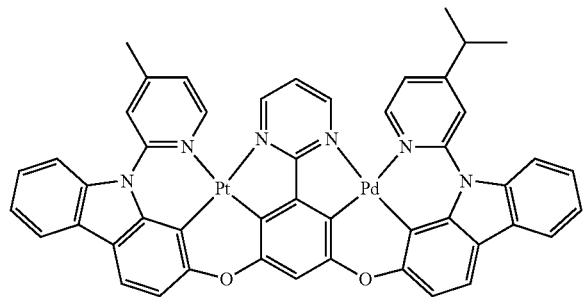
Compound PtPd103
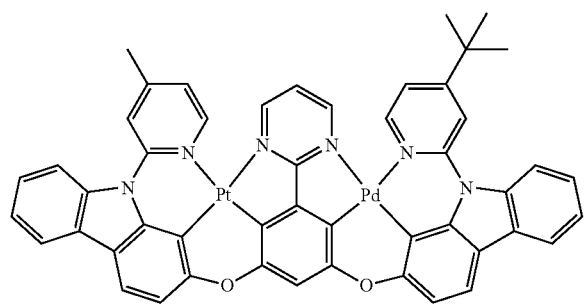
Compound PtPd104
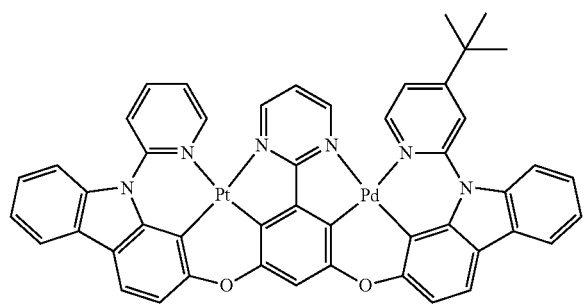
Compound PtPd105
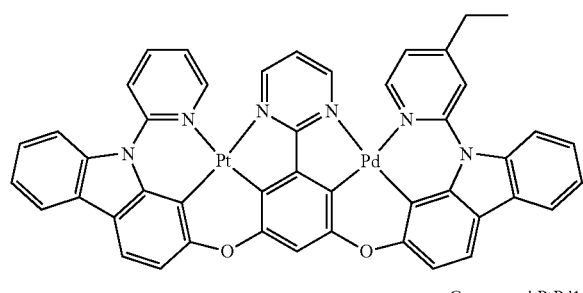
Compound PtPd106
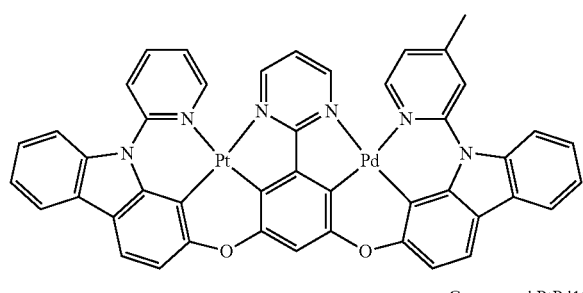
Compound PtPd107
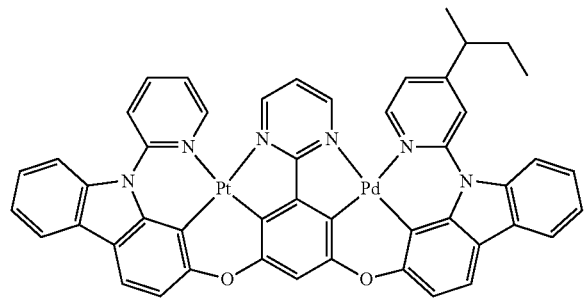
Compound PtPd108
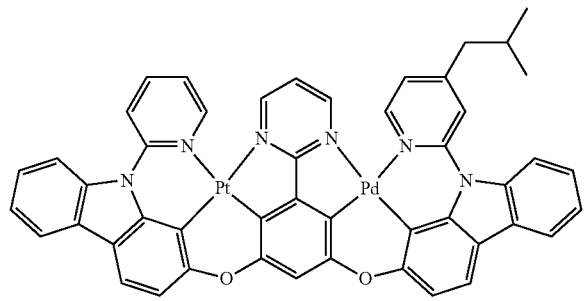
Compound PtPd109
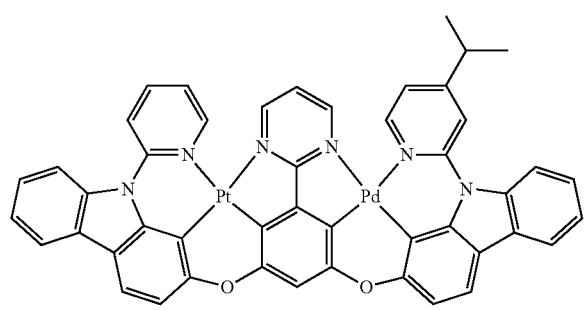
Compound PtPd110
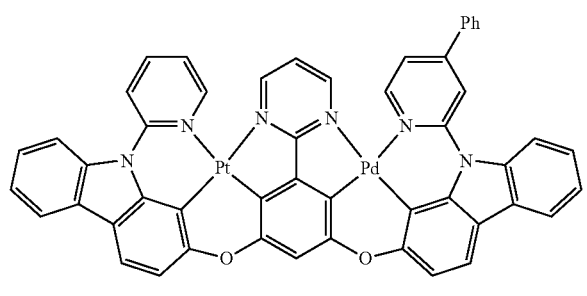

Compound PtPd111
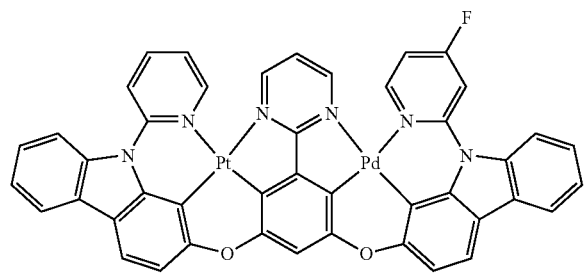
Compound PtPd112
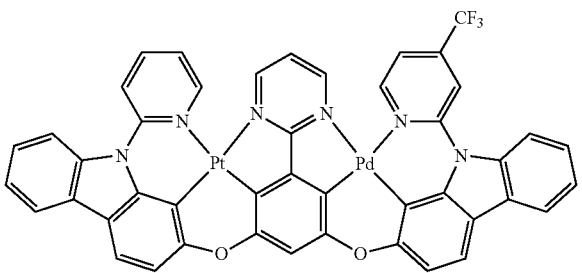
Compound PtPd113
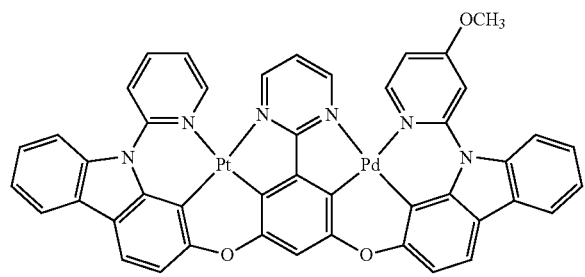
Compound PtPd114
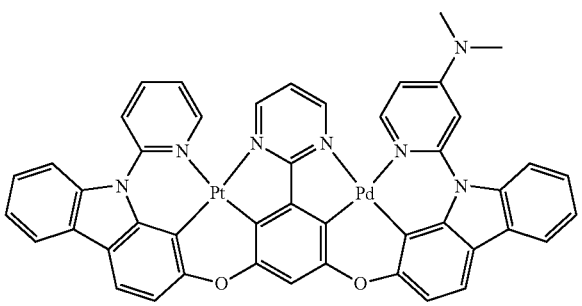
Compound PtPd115
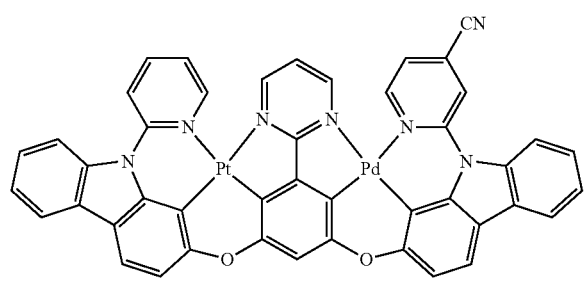
Compound PtPd116
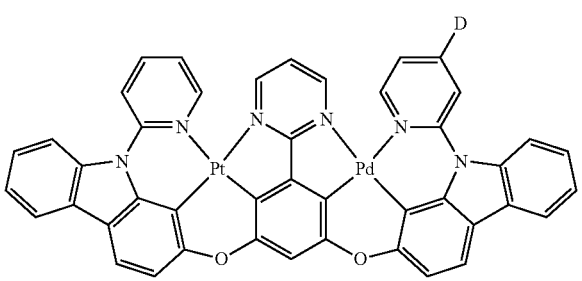
Compound PtPd117
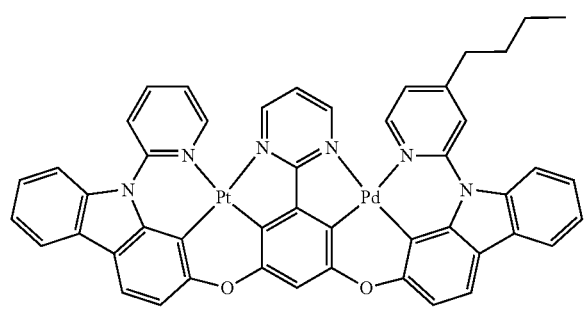
Compound PtPd118
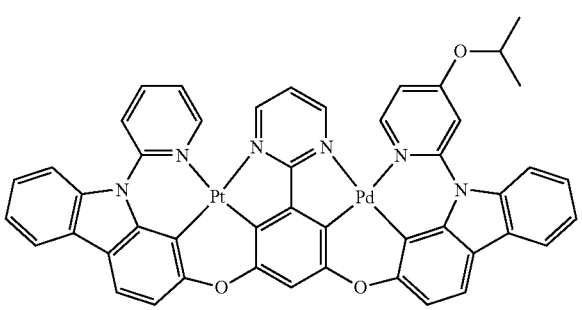
Compound PdPt119
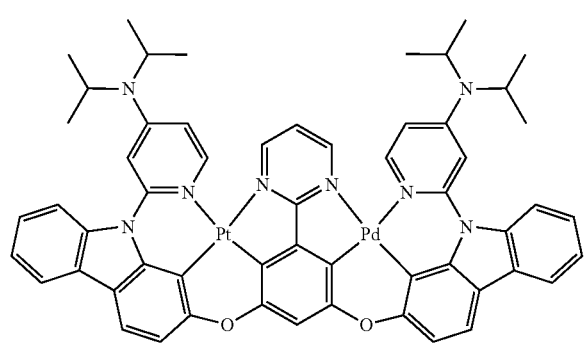
Compound PdPt120
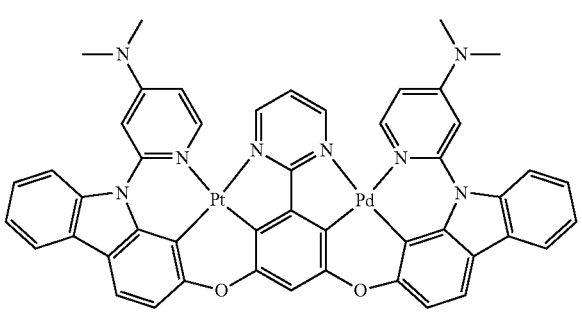

-continued
Compound PtPd121
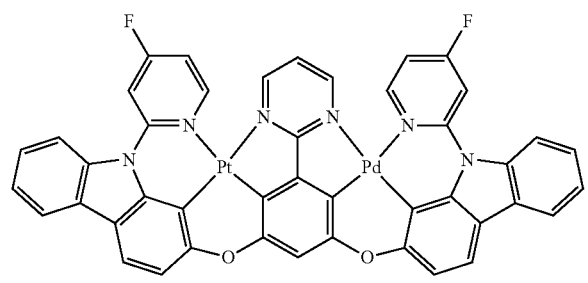
Compound PtPd123
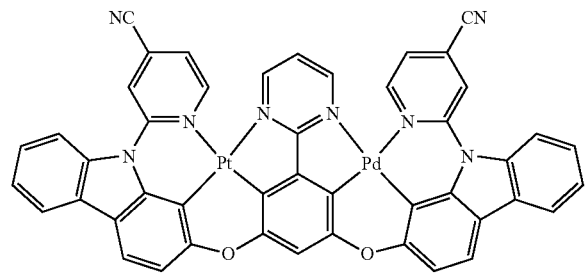
Compound PdPt25
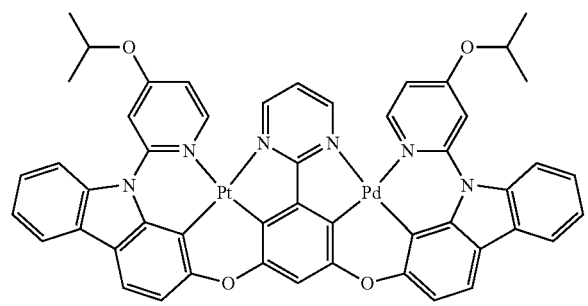
Compound PtPd127
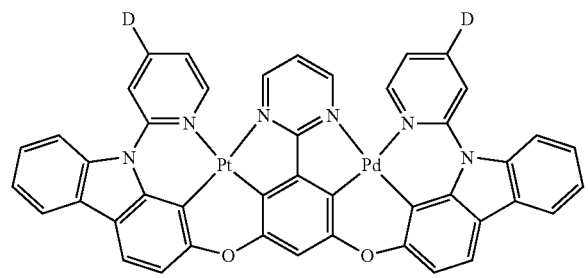
Compound PtPd129
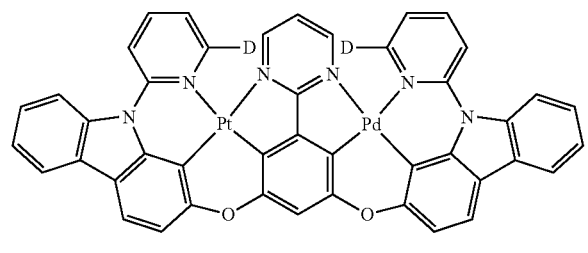
Compound PtPd122
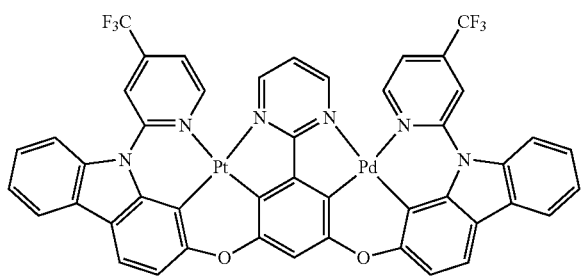
Compound PtPd124
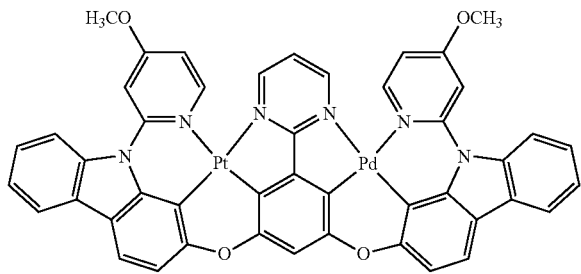
Compound PtPd126
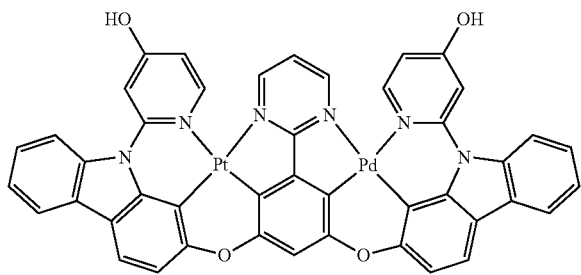
Compound PtPd128
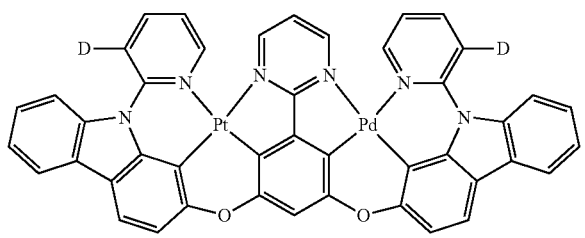
Compound PtPd130
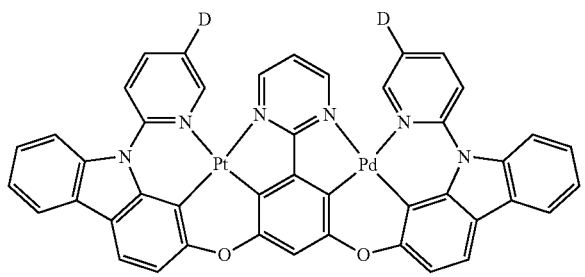

-continued
Compound PtPd131
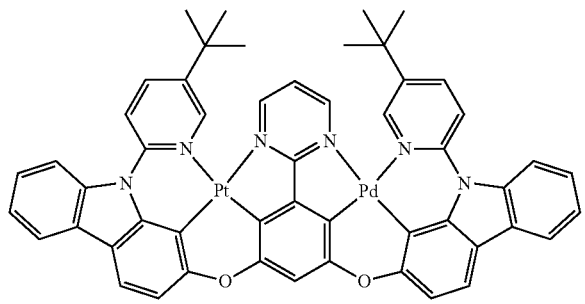
Compound PtPd132
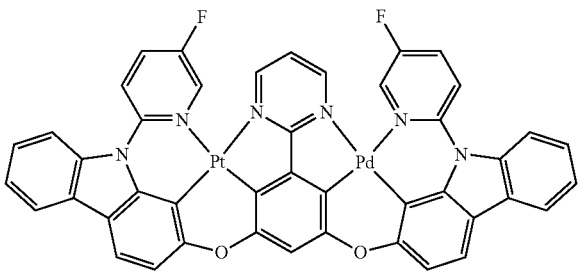
Compound PtPd133
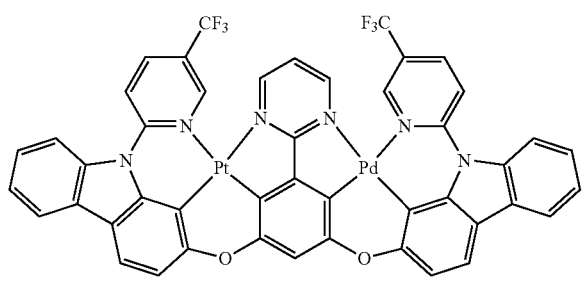
Compound PtPd134
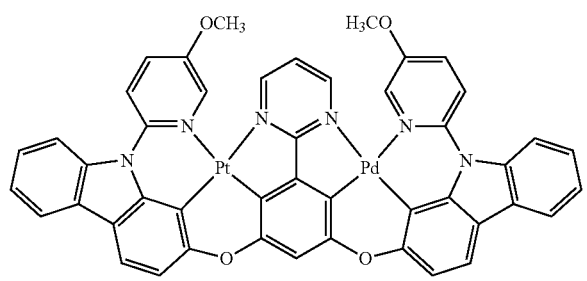
Compound PtPd135
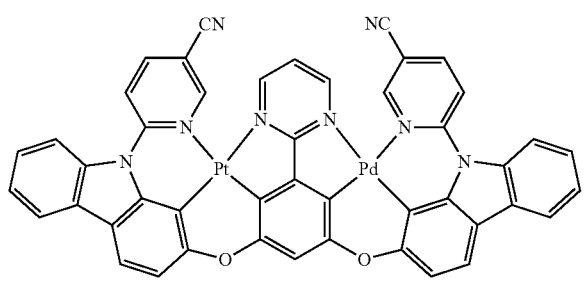
Compound PtPd136
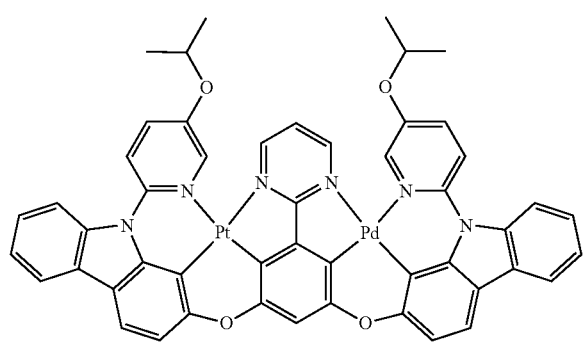
Compound PtPd137
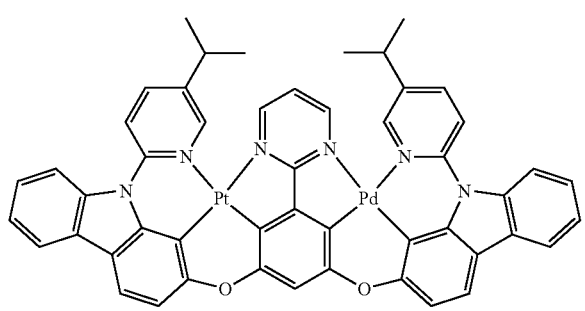
Compound PtPd138
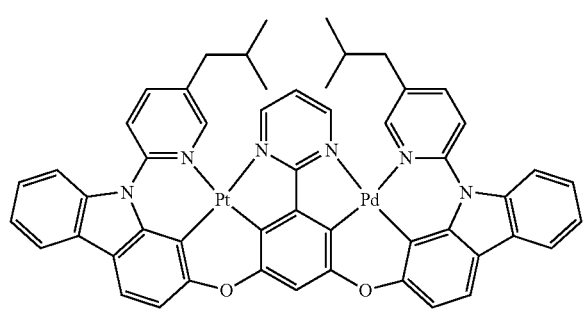
Compound PtPd139
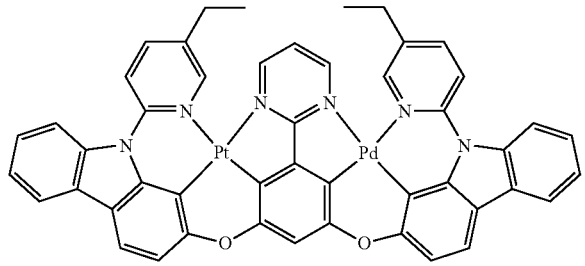

-continued
Compound PtPd140
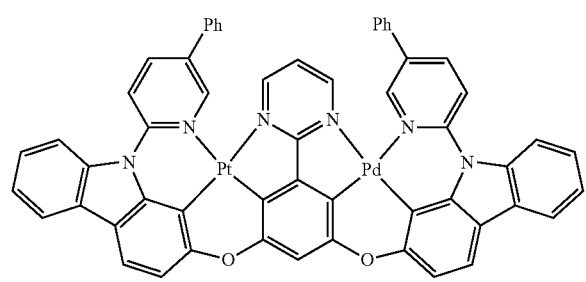
Compound PtPd141
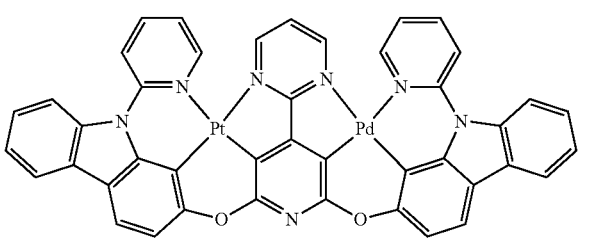
Compound PtPd142
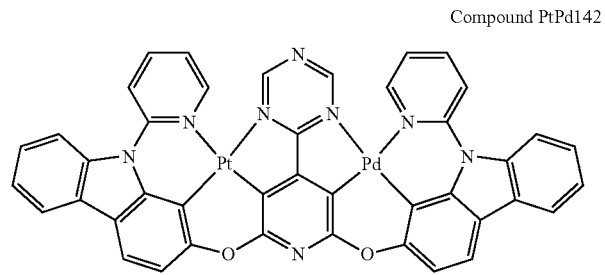
Compound PtPd143
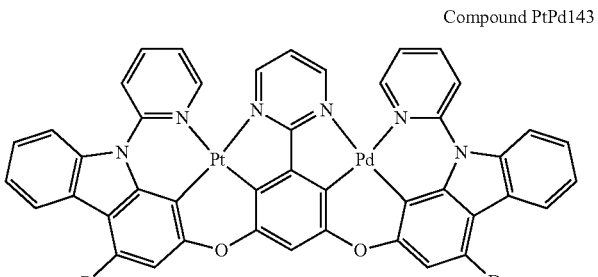
Compound PtPd144
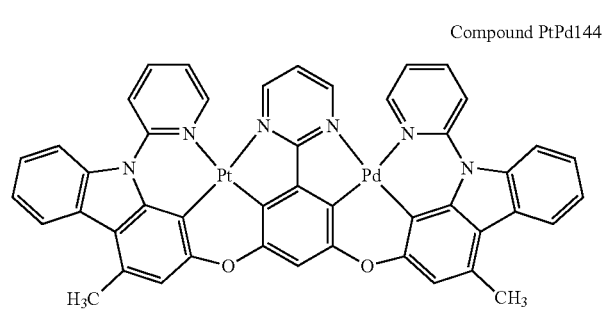
Compound PtPd145
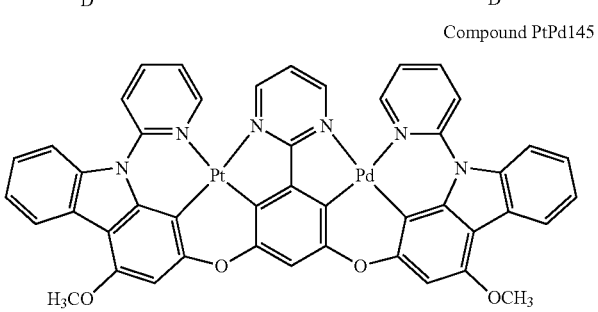
Compound PtPd146
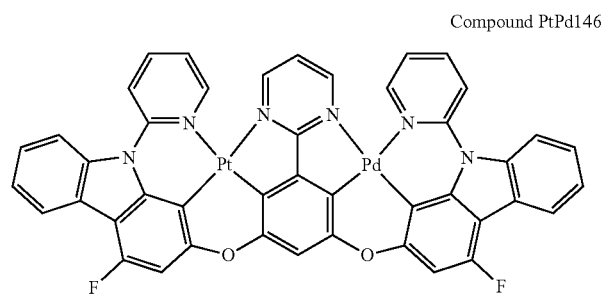
Compound PtPd147
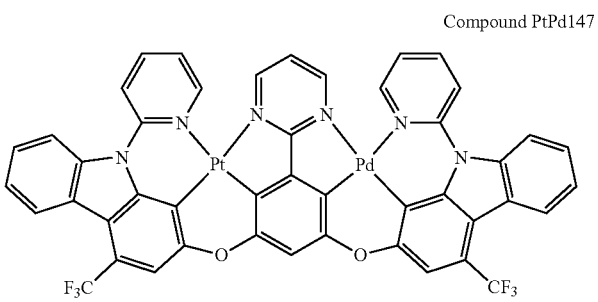
Compound PtPd148
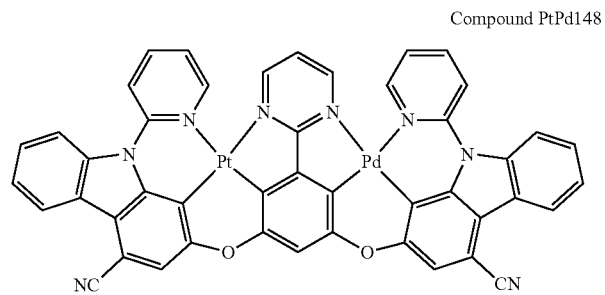
Compound PtPd149
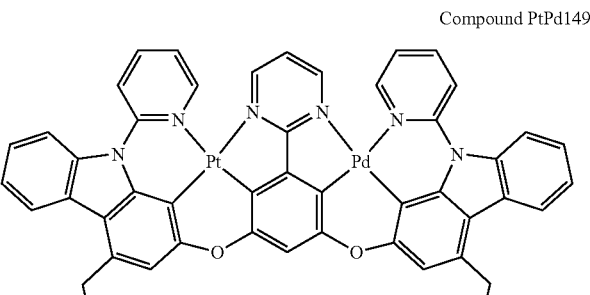

-continued
Compound PtPd150
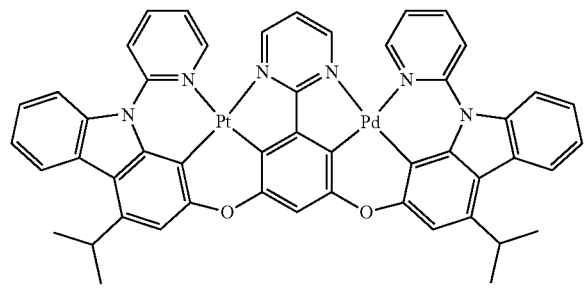
Compound PtPd152
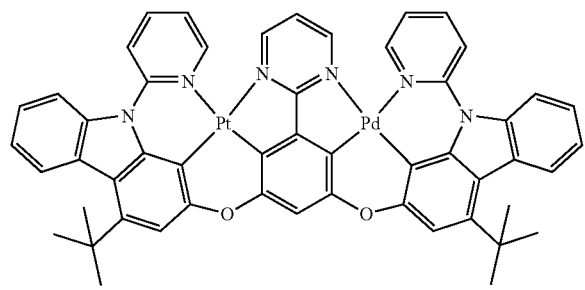
Compound PtPd154
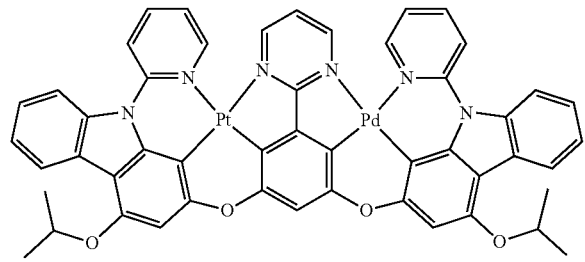
Compound PtPd156
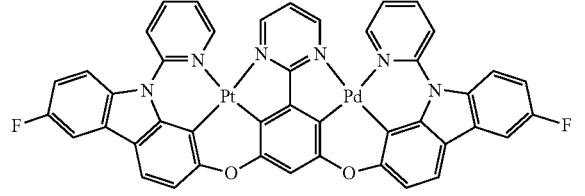
Compound PtPd158
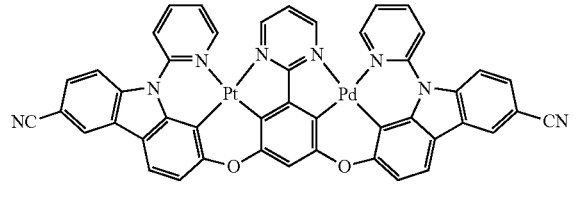
Compound PtPd160
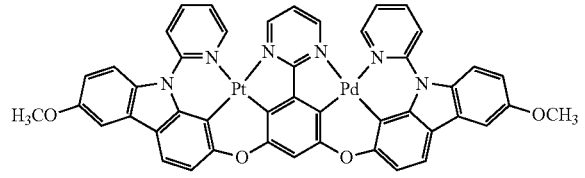
Compound PtPd151
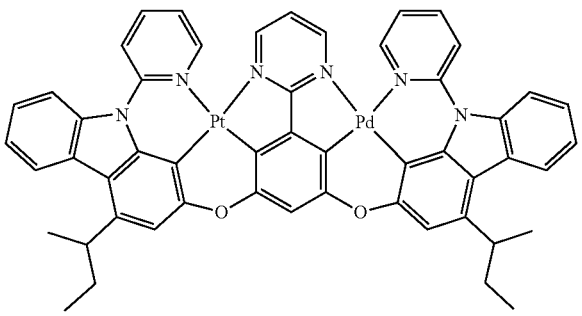
Compound PtPd153
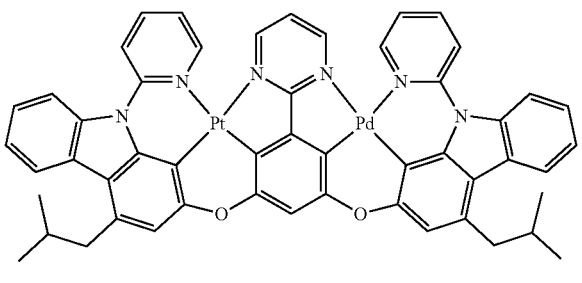
Compound PtPd155
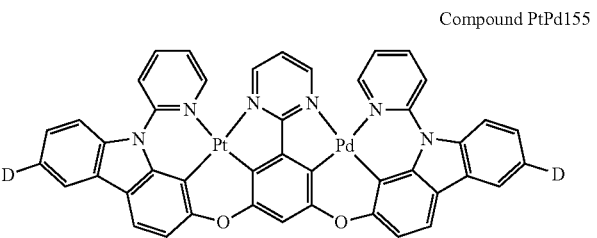
Compound PtPd157
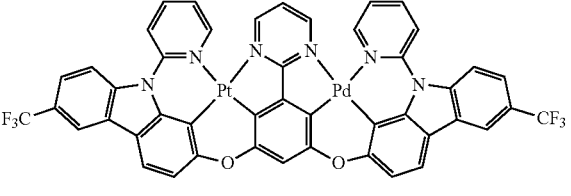
Compound PtPd159
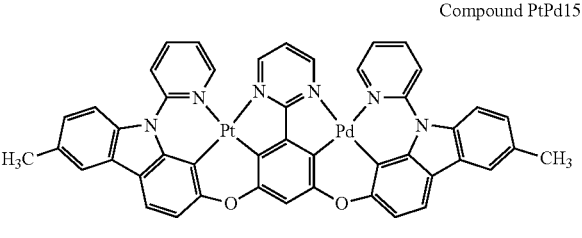
Compound PtPd161
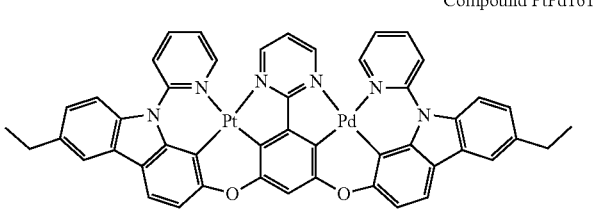

-continued
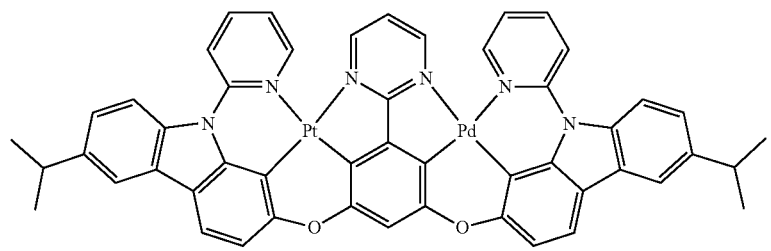
Compound PtPd162
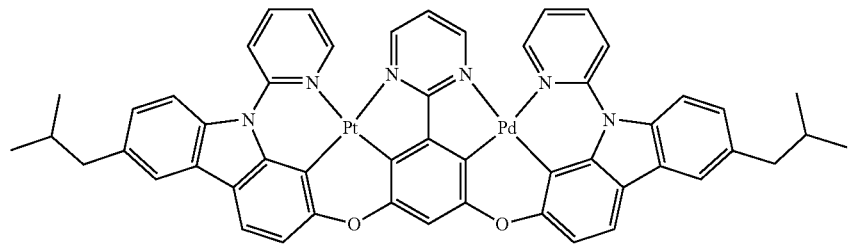
Compound PtPd163
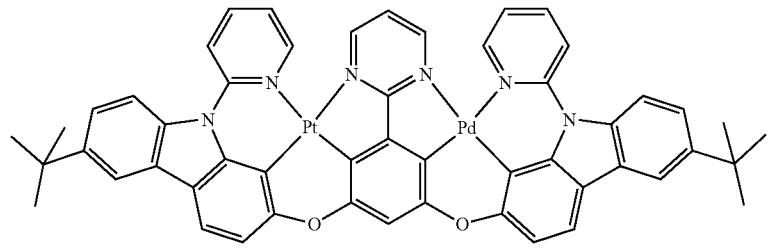
Compound PtPd164
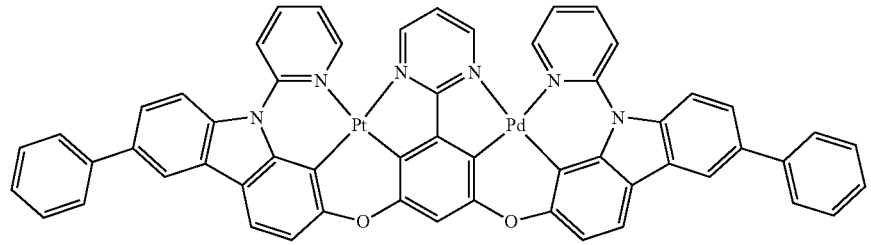
Compound PtPd165
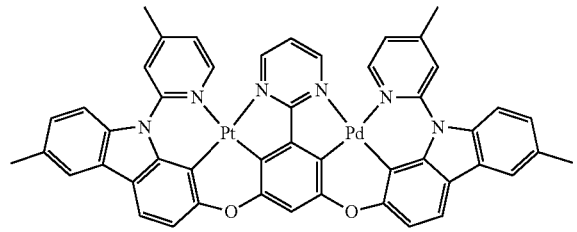
Compound PtPd166
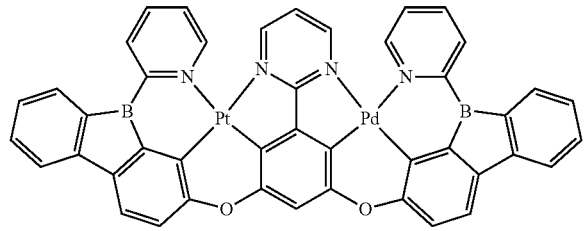
Compound PtPd167
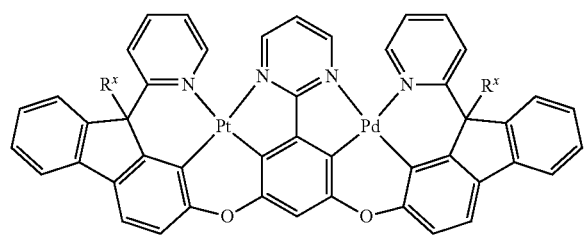
Compound PtPd168
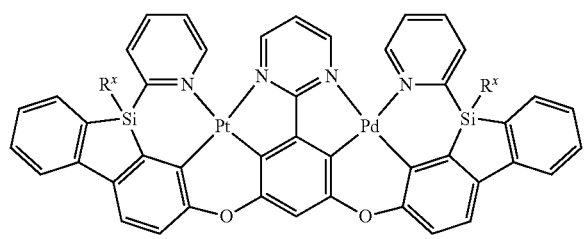
Compound PtPd169

-continued
Compound PtPd170
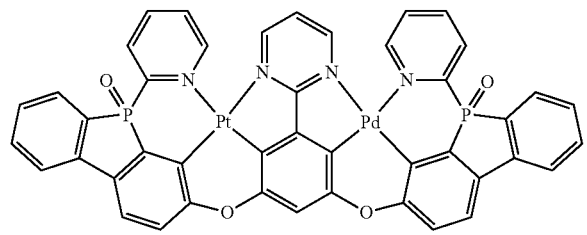
Compound PtPd171
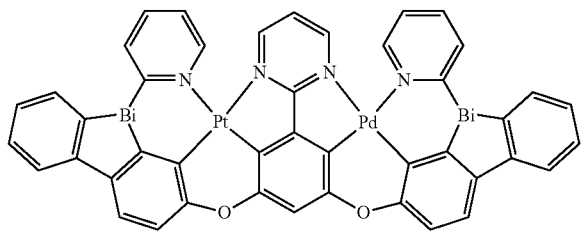
Compound PtPd172
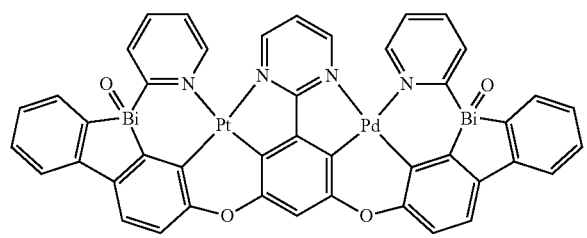
Compound PtPd173
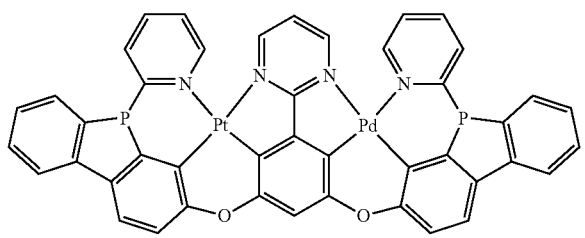
Compound PtPd174
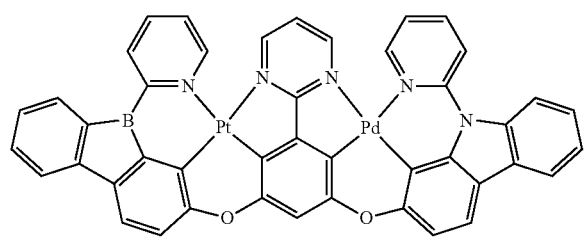
Compound PtPd175
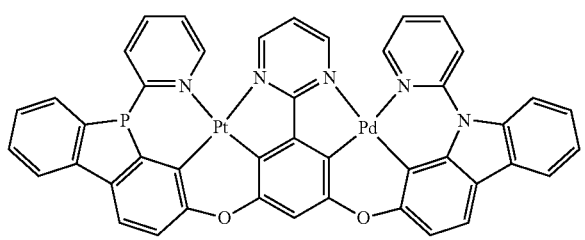
Compound PtPd176
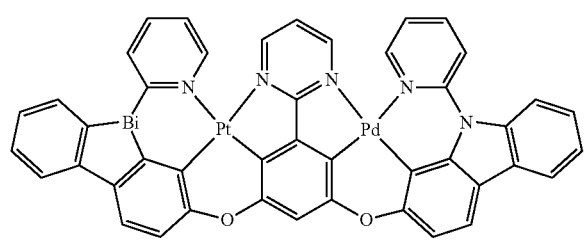
Compound PtPd177
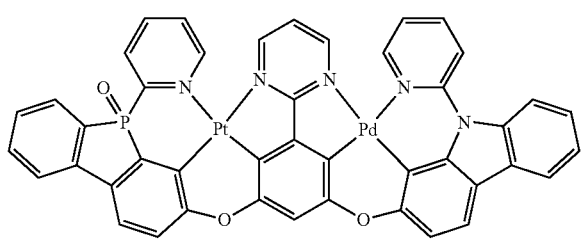
Compound PtPd178
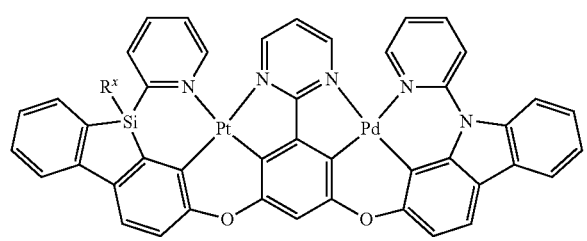
Compound PtPd179
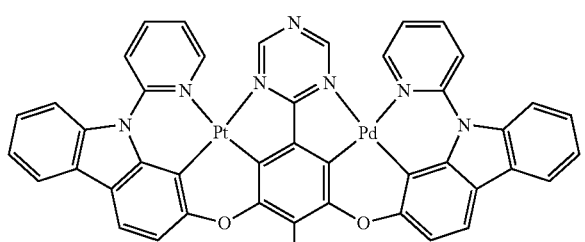
Compound PtPd180
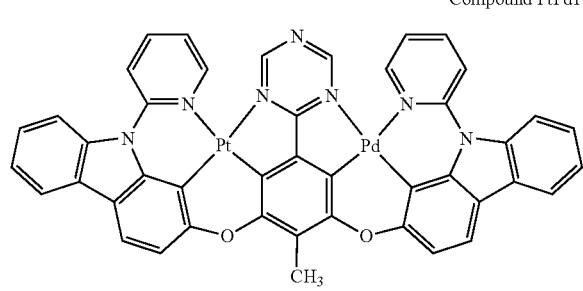
Compound PtPd181
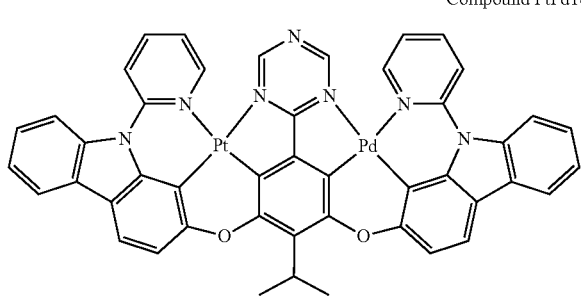

-continued
Compound PtPd182
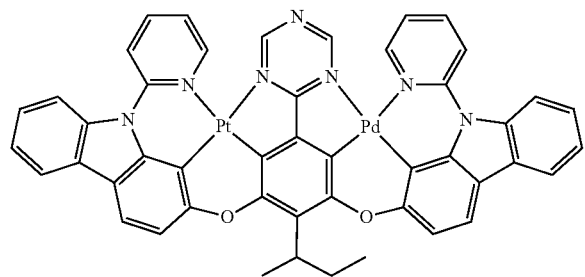
Compound PtPd183
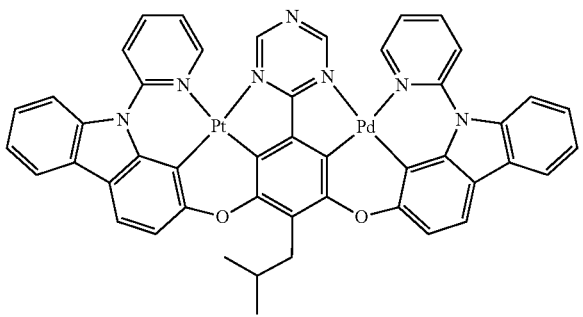
Compound PtPd184
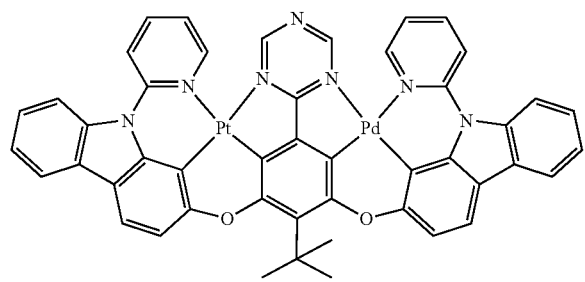
Compound PtPd185
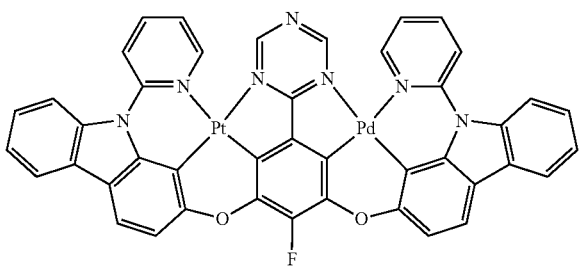
Compound PtPd186
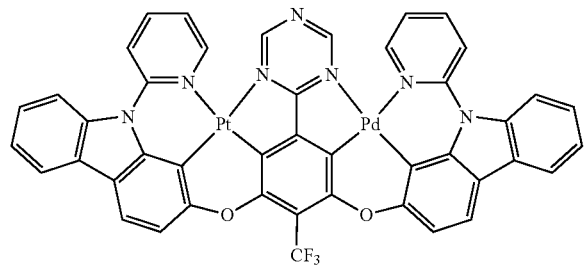
Compound PtPd187
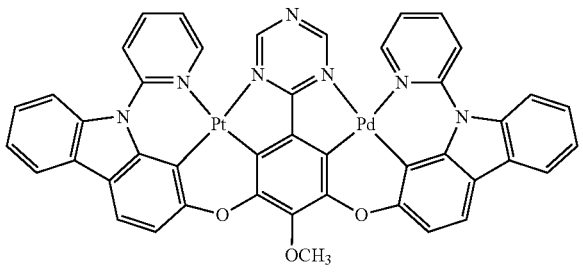
Compound PtPd188
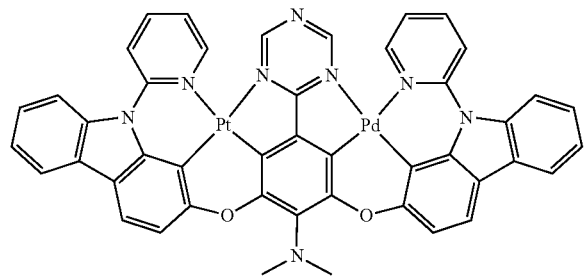
Compound PtPd189
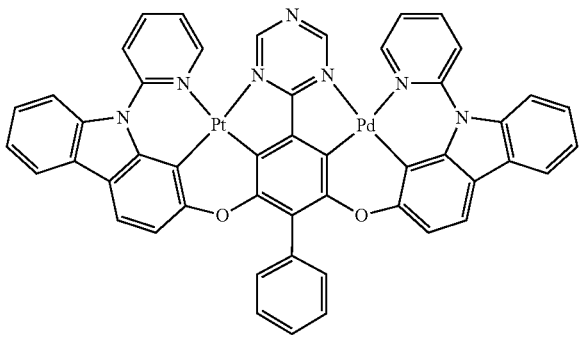
Compound PtPd190
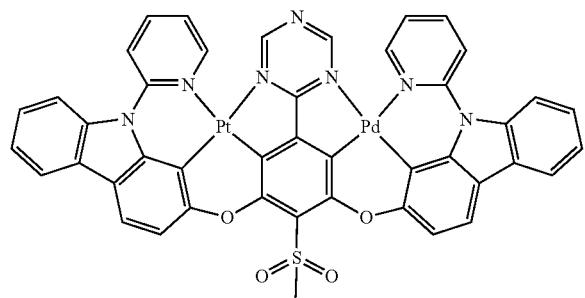

-continued
Compound PtPd192
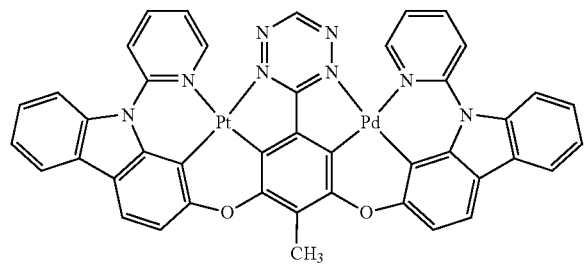
Compound PtPd193
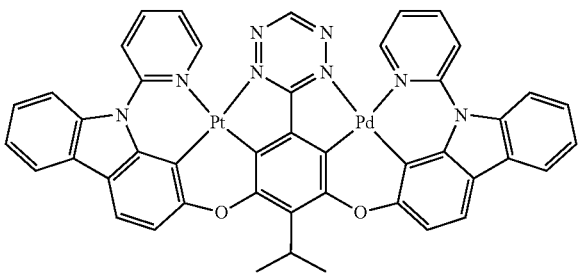
Compound PtPd194
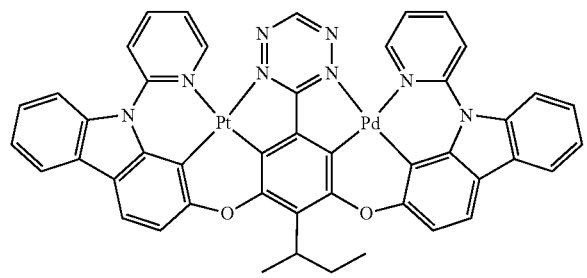
Compound PtPd195
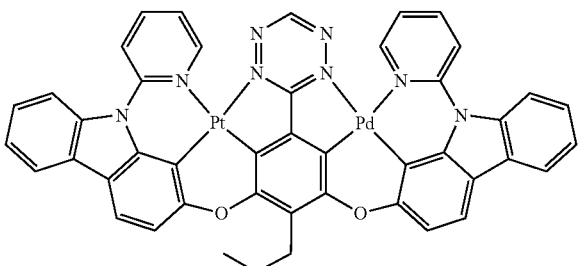
Compound PtPd196
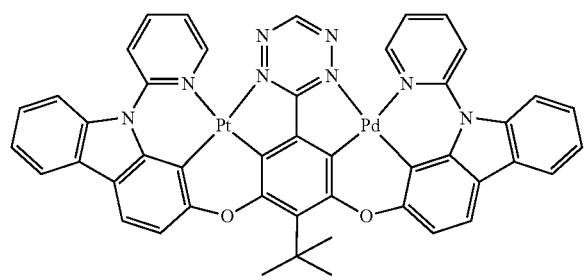
Compound PtPd197
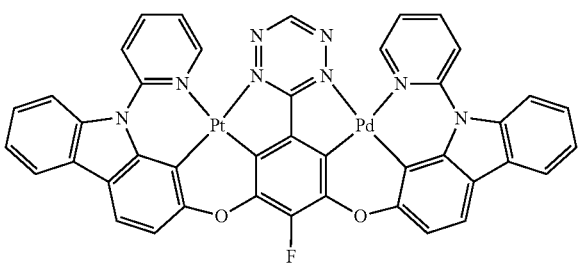
Compound PtPd198
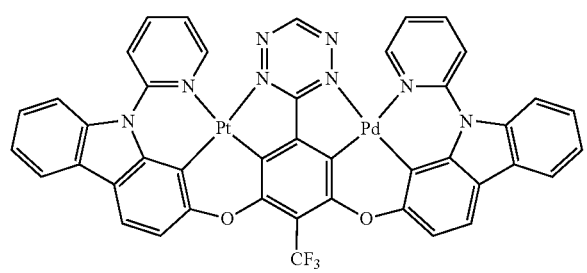
Compound PtPd199
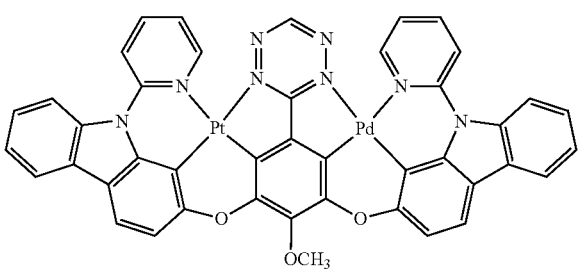
Compound PtPd200
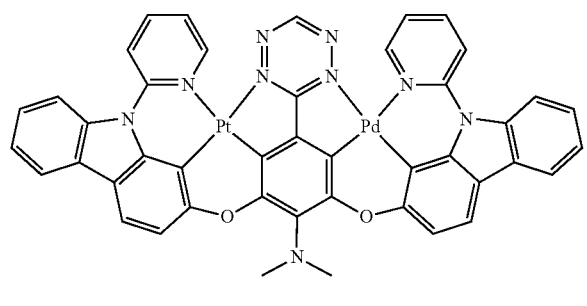
Compound PtPd201
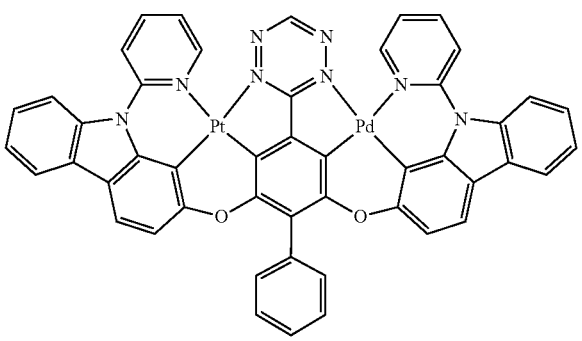

-continued
Compound PtPd202
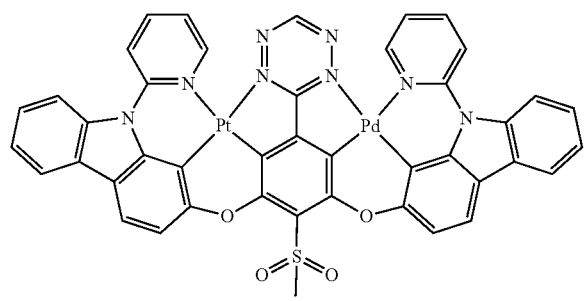
Compound PtPd203
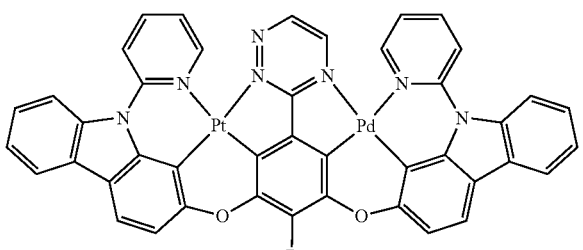
Compound PtPd204
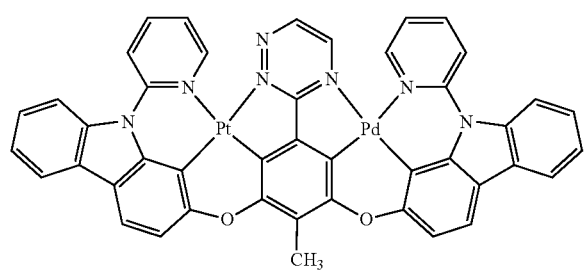
Compound PtPd205
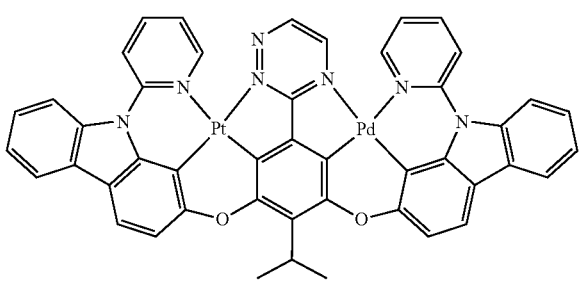
Compound PtPd206
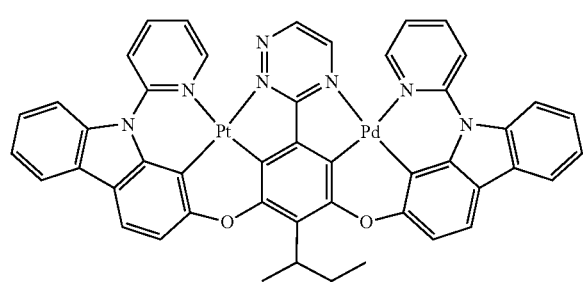
Compound PtPd207
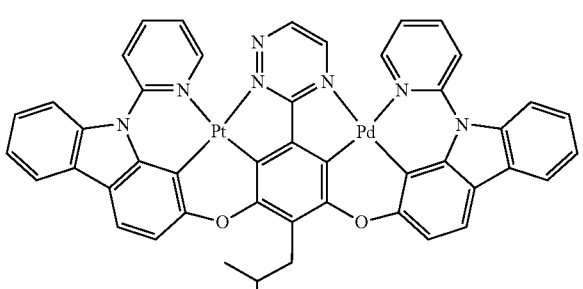
Compound PtPd208
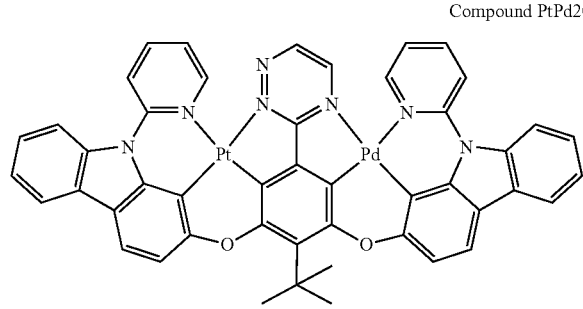
Compound PtPd209
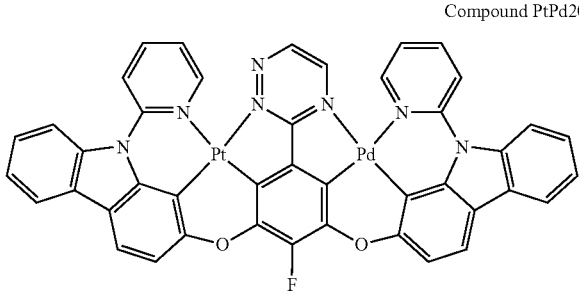
Compound PtPd210
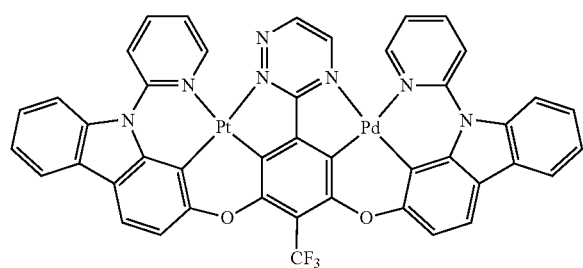
Compound PtPd211
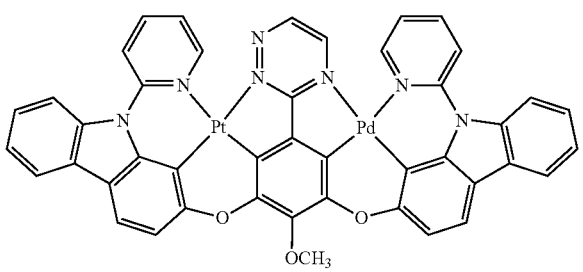

-continued
Compound PtPd212
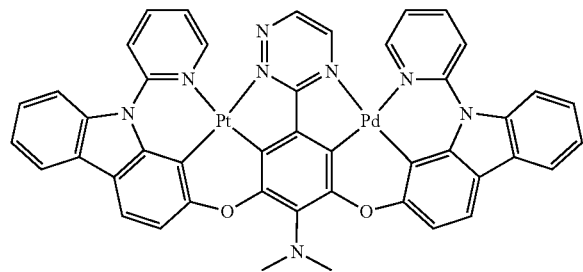
Compound PtPd213
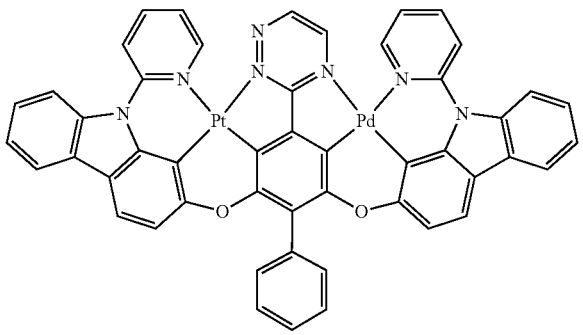
Compound PtPd214
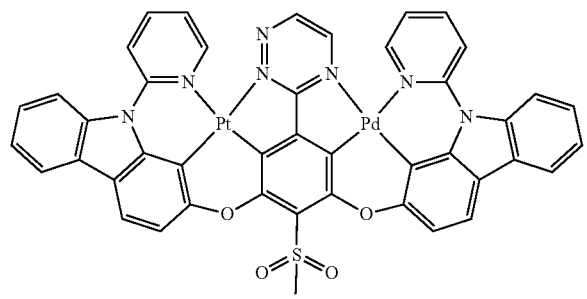
Compound PtPd215
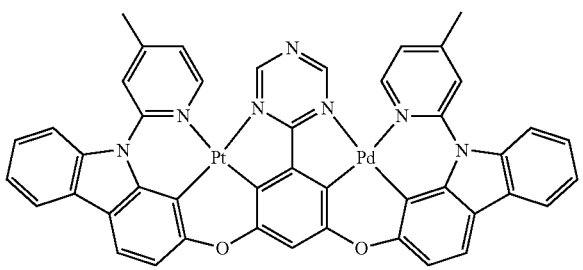
Compound PtPd216
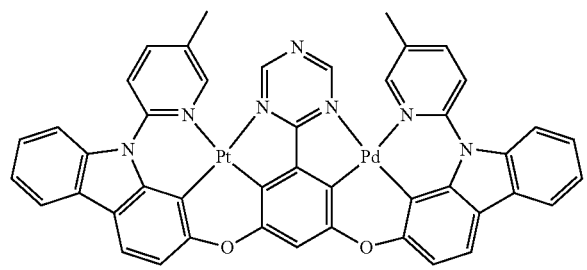
Compound PtPd217
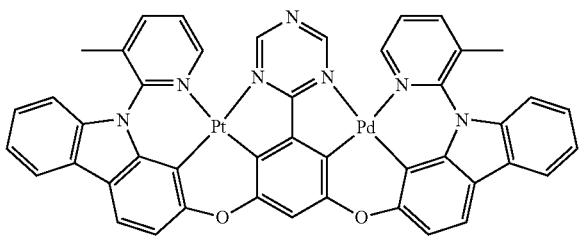
Compound PtPd218
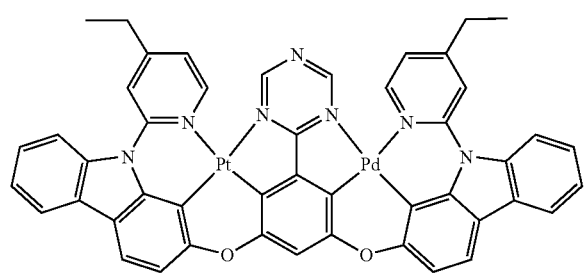
Compound PtPd219
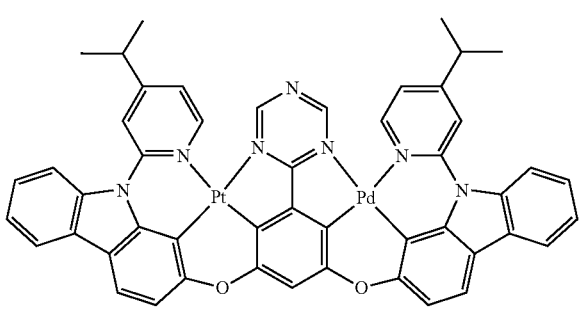
Compound PtPd220
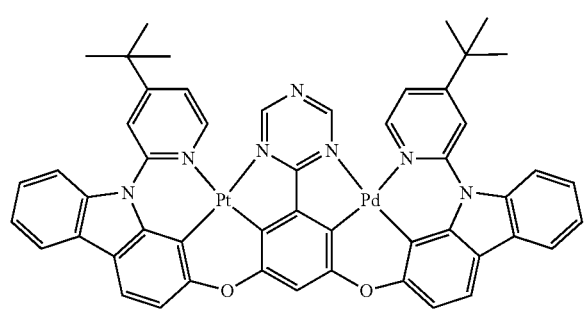
Compound PtPd221
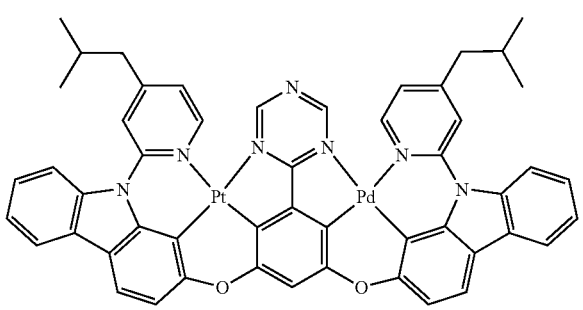

-continued
Compound PtPd222
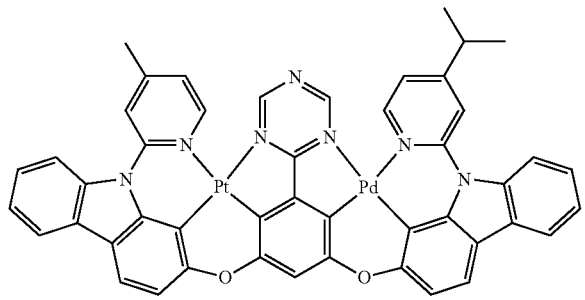
Compound PtPd223
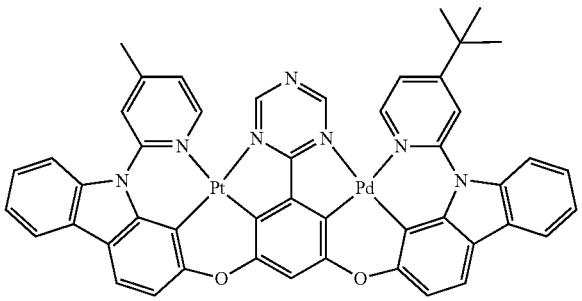
Compound PtPd224
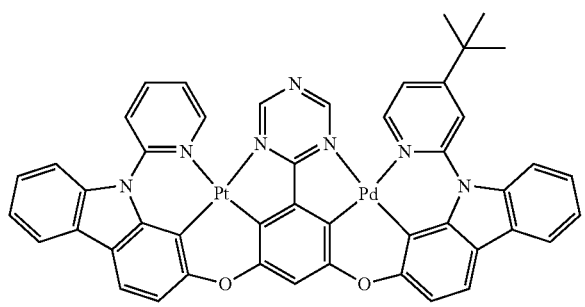
Compound PtPd225
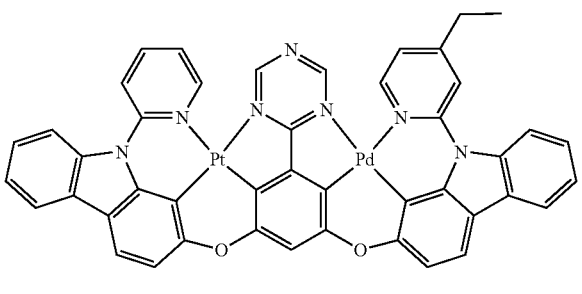
Compound PtPd226
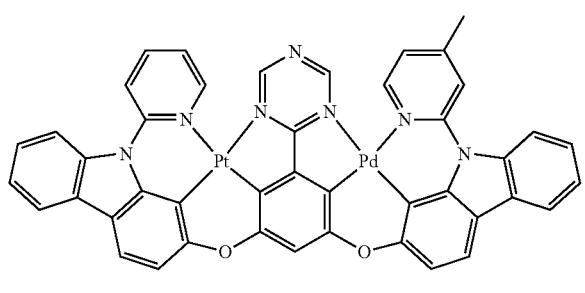
Compound PtPd227
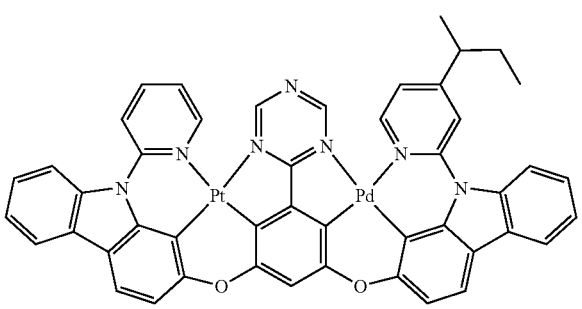
Compound PtPd228
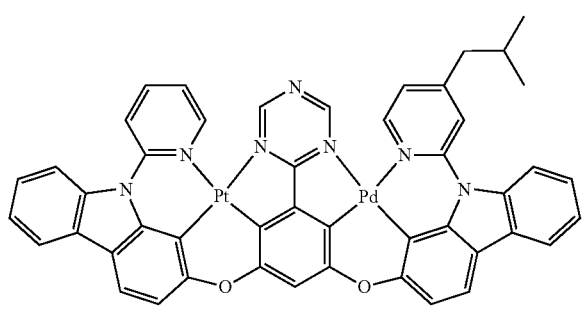
Compound PtPd229
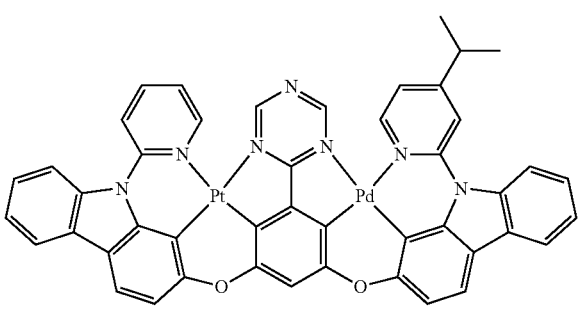
Compound PtPd230
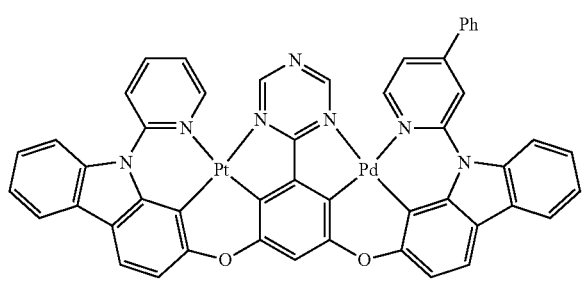
Compound PtPd231
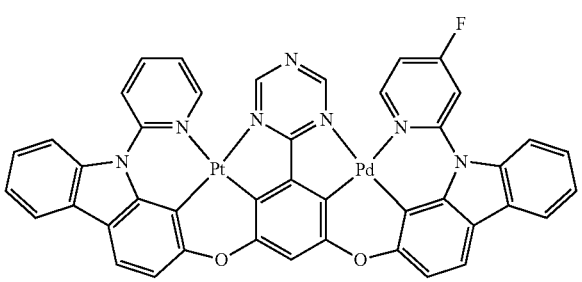

-continued
Compound PtPd232
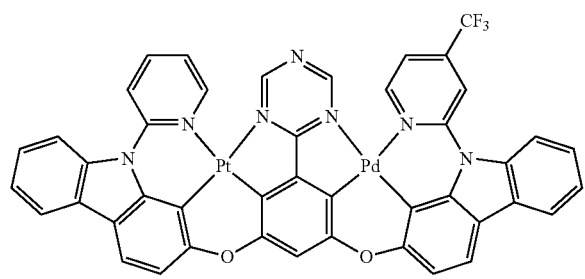
Compound PtPd233
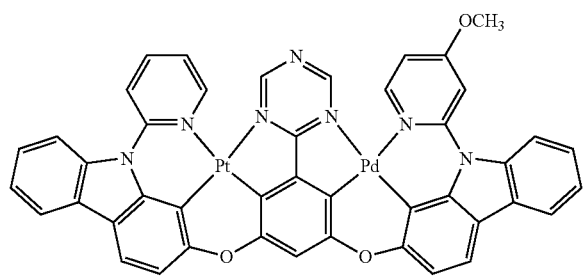
Compound PtPd234
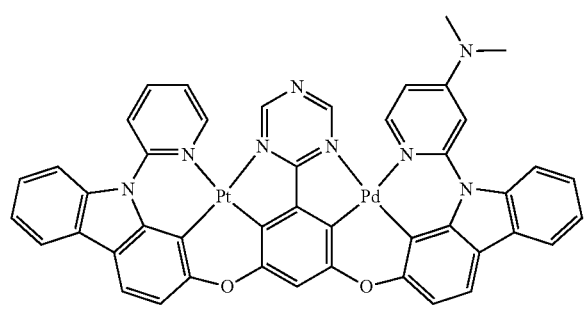
Compound PtPd235
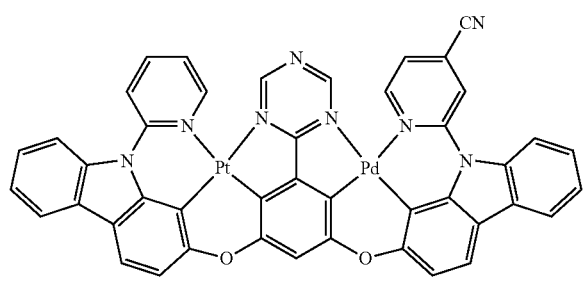
Compound PtPd236
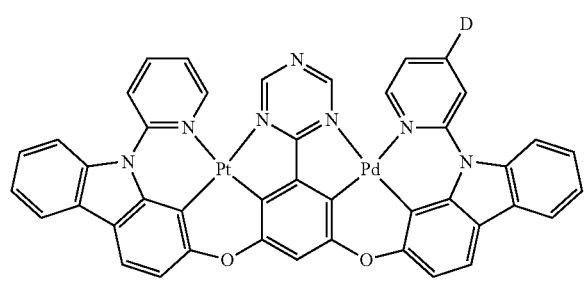
Compound PtPd237
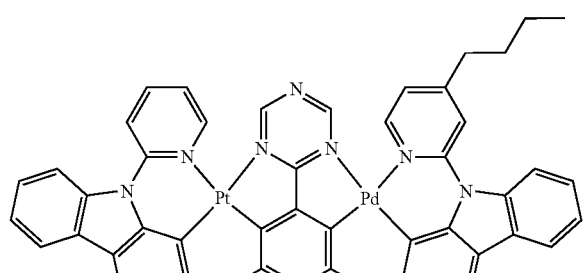
Compound PtPd238
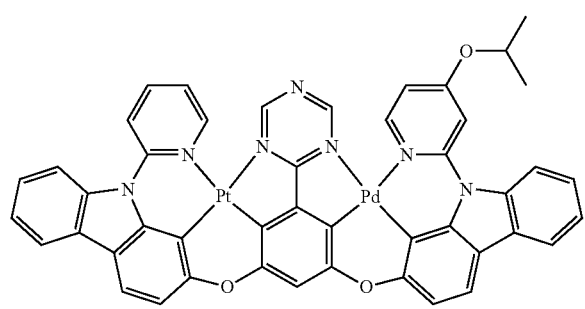
Compound PtPd239
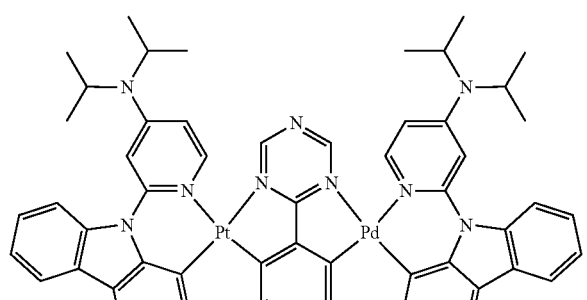
Compound PtPd240
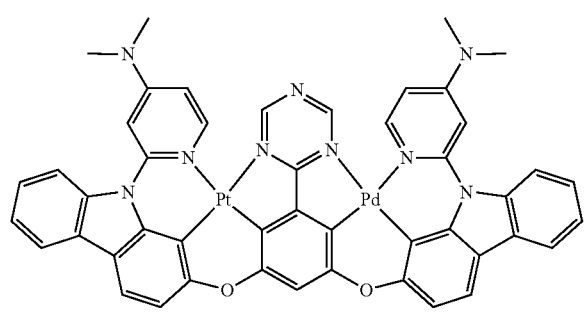
Compound PtPd241
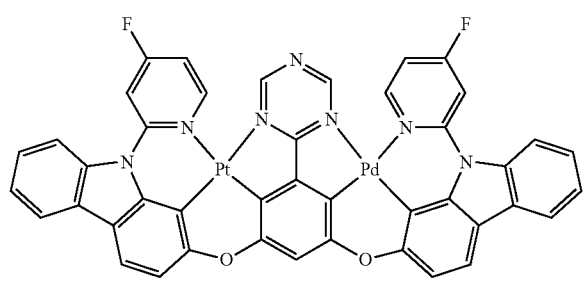

Compound PtPd242
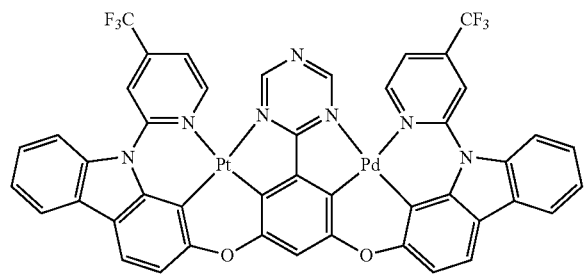
Compound PtPd243
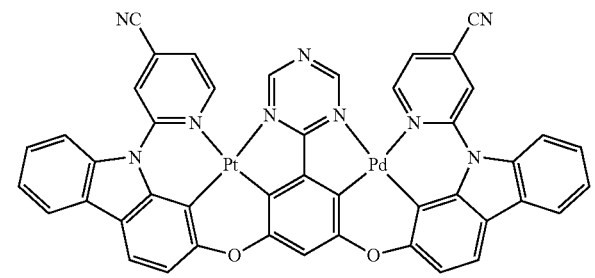
Compound PtPd244
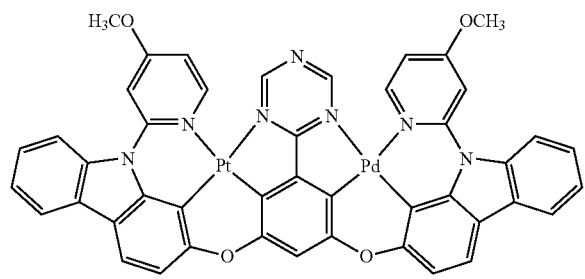
Compound PtPd245
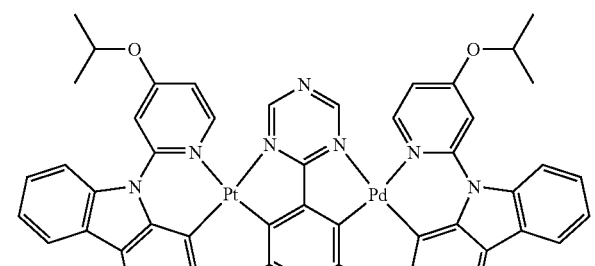
Compound PtPd246
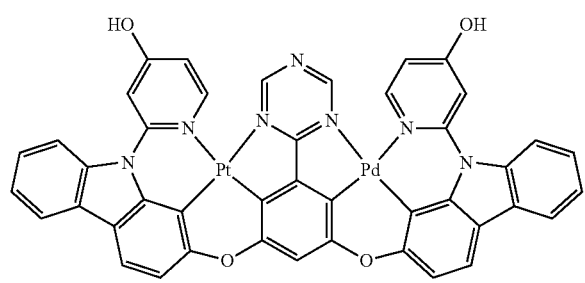
Compound PtPd247
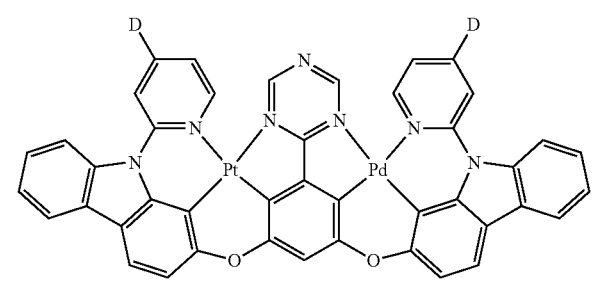
Compound PtPd248
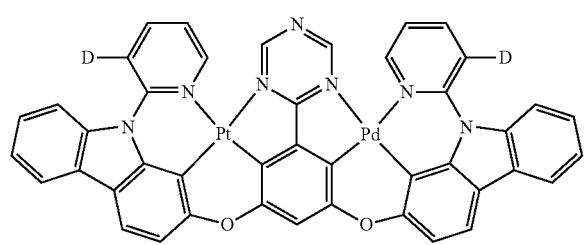
Compound PtPd249
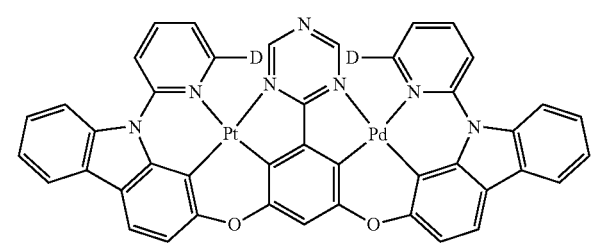
Compound PtPd250
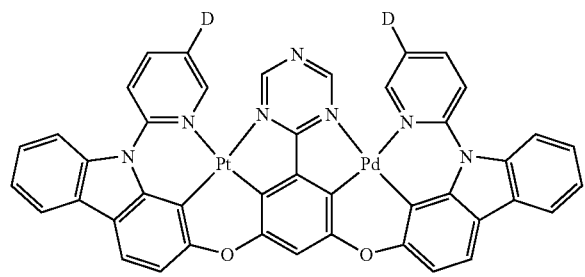
Compound PtPd251
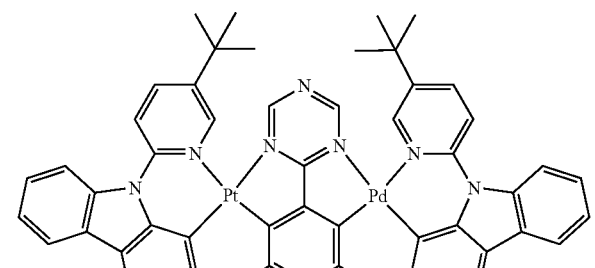

-continued
Compound PtPd252
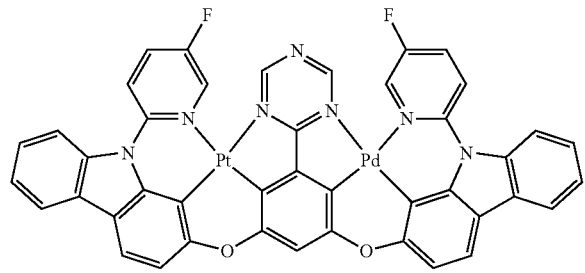
Compound PtPd253
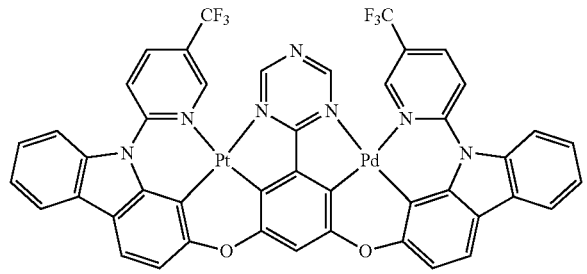
Compound PtPd254
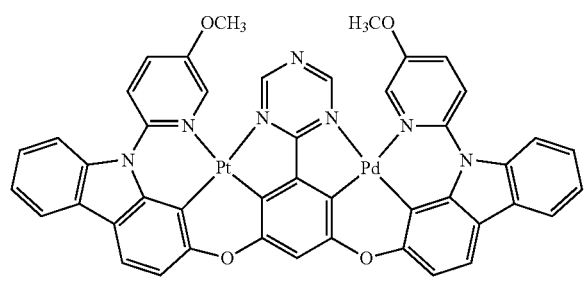
Compound PtPd255
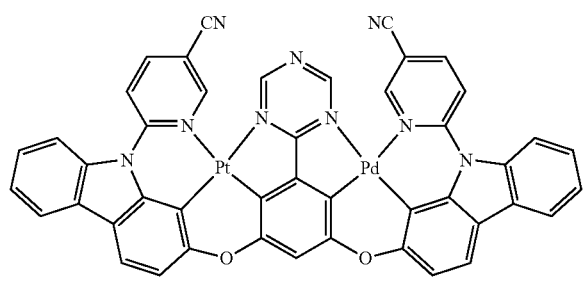
Compound PtPd256
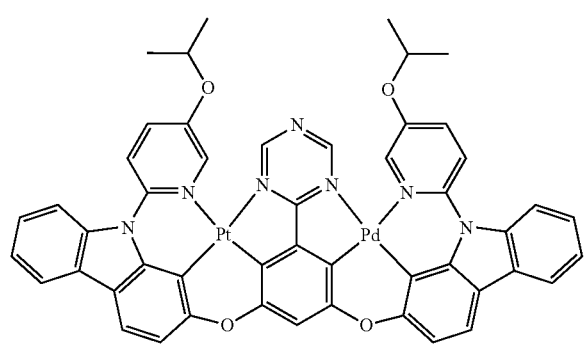
Compound PtPd257
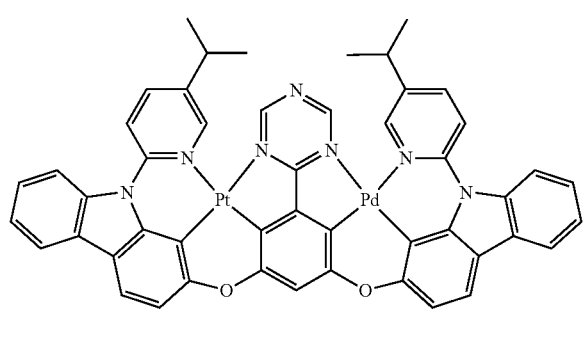
Compound PtPd258
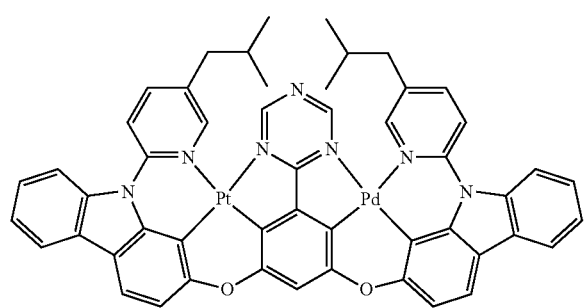
Compound PtPd259
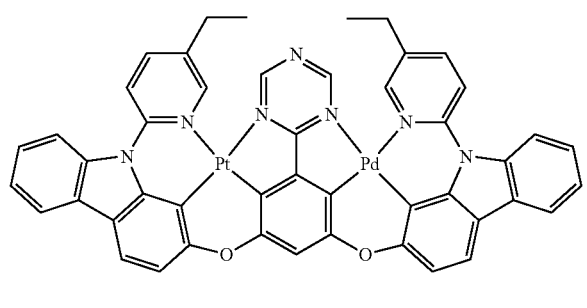
Compound PtPd260
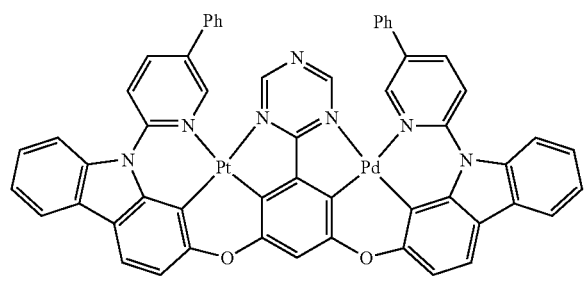
Compound PtPd261
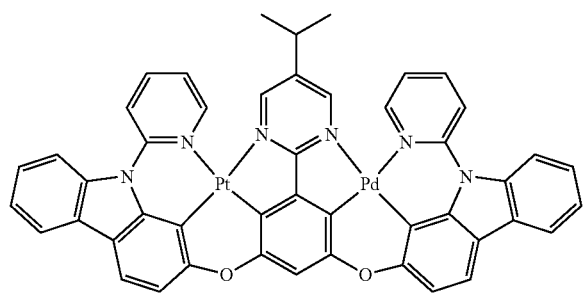

-continued
Compound PtPd262
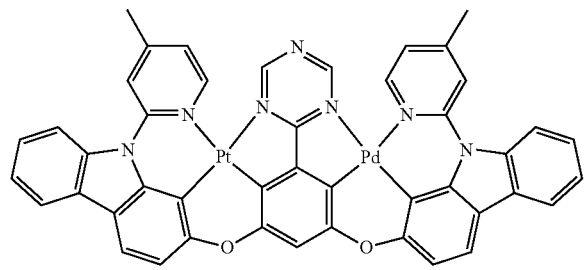
Compound PtPd263
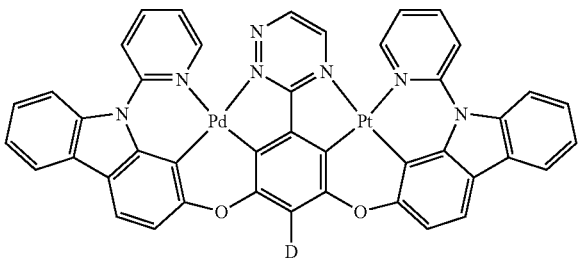
Compound PtPd264
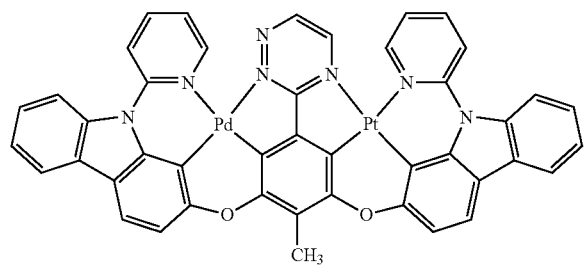
Compound PtPd265
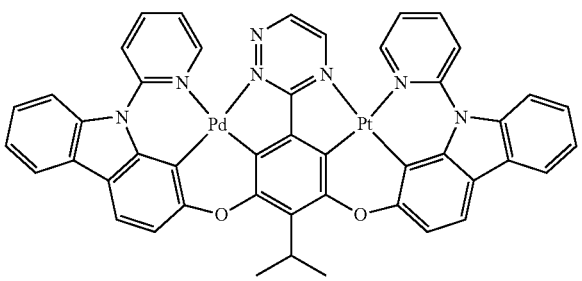
Compound PtPd266
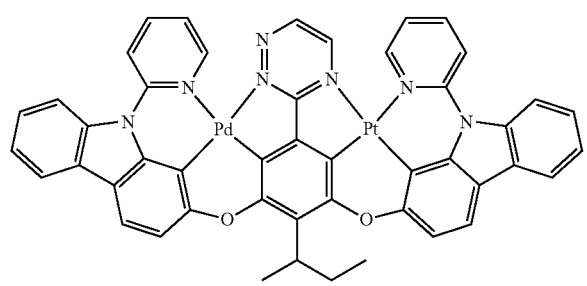
Compound PtPd267
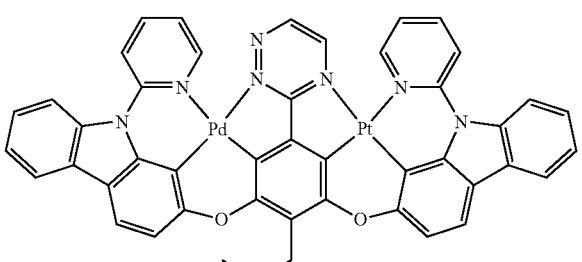
Compound PtPd268
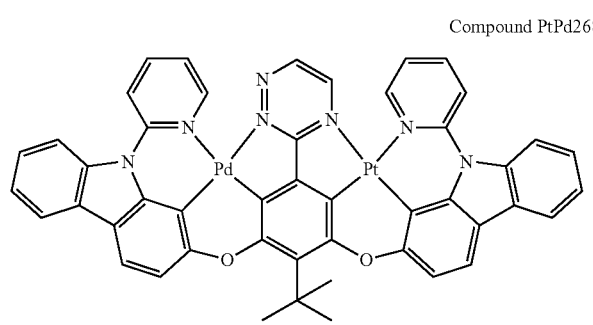
Compound PtPd269
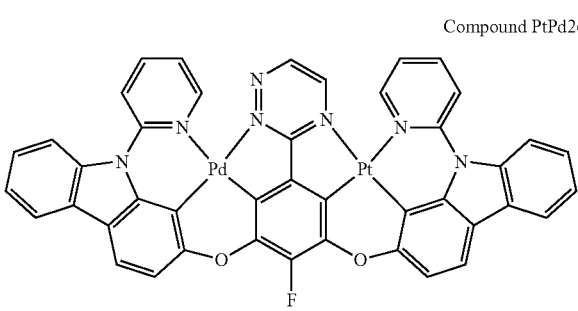
Compound PtPd270
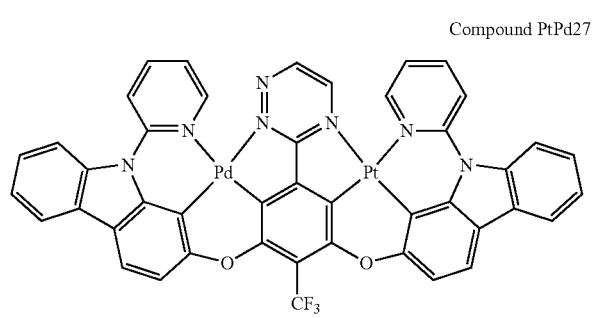
Compound PtPd271
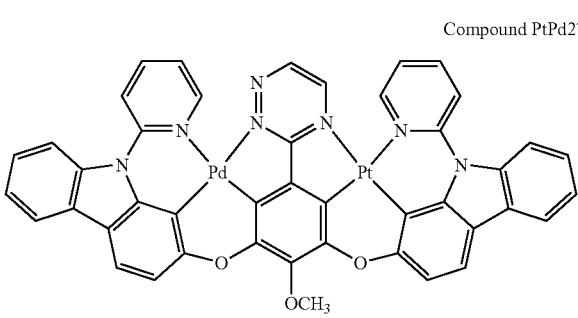

-continued
Compound PtPd272
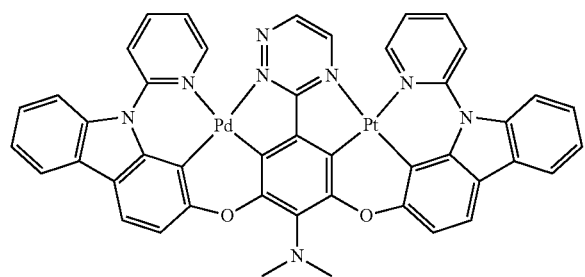
Compound PtPd273
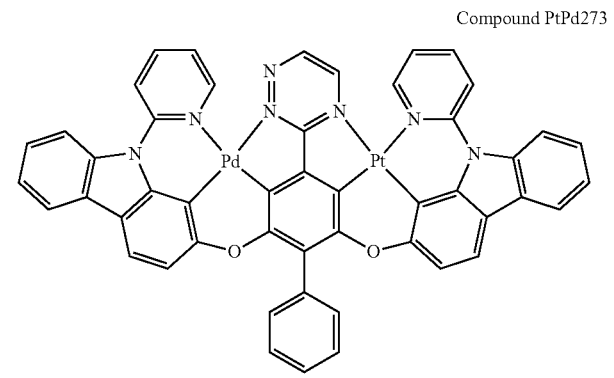
Compound PtPd274
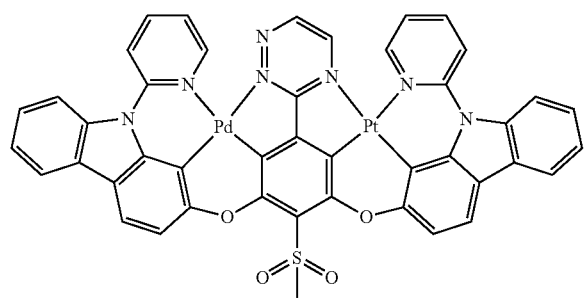
Compound PtPd275
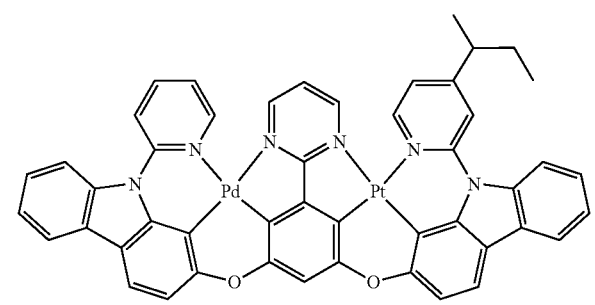
Compound PtPd276
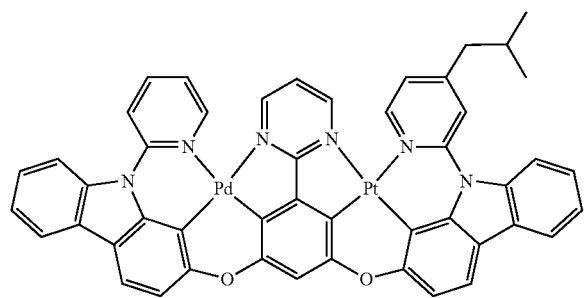
Compound PtPd277
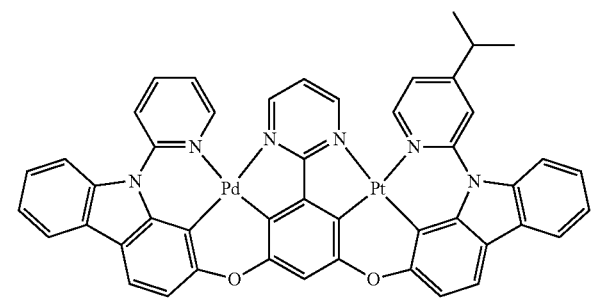
Compound PtPd278
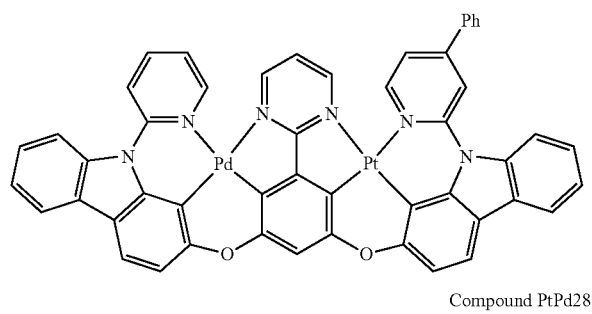
Compound PtPd279
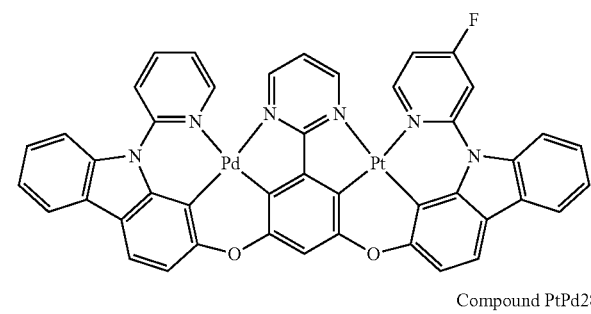
Compound PtPd280
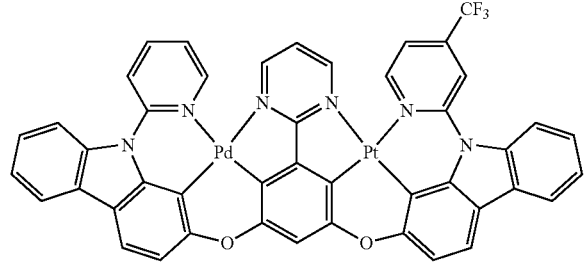
Compound PtPd281
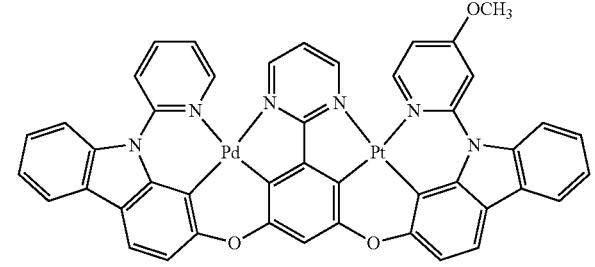

-continued
Compound PtPd282
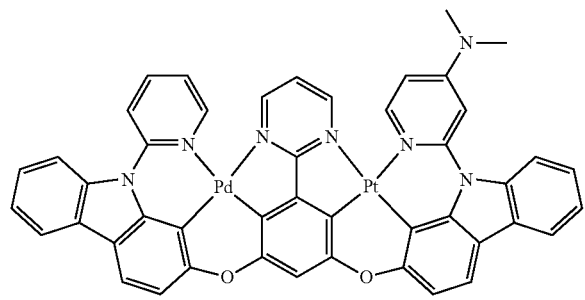
Compound PtPd283
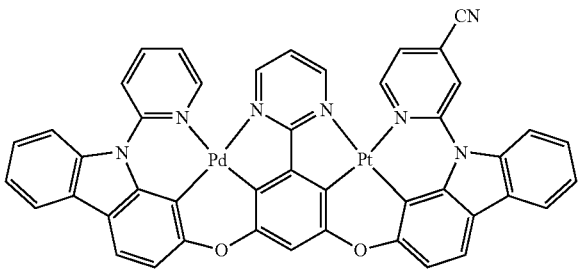
Compound PtPd284
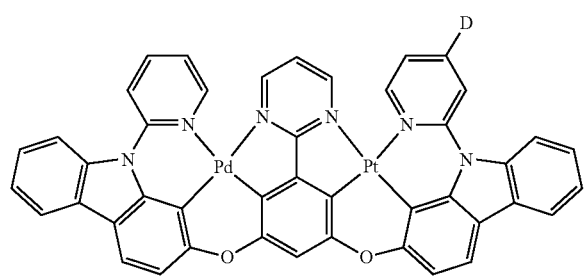
Compound PtPd285
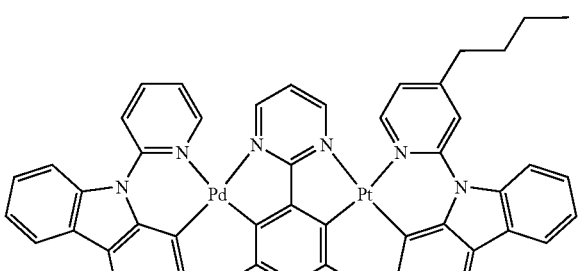
Compound PtPd286
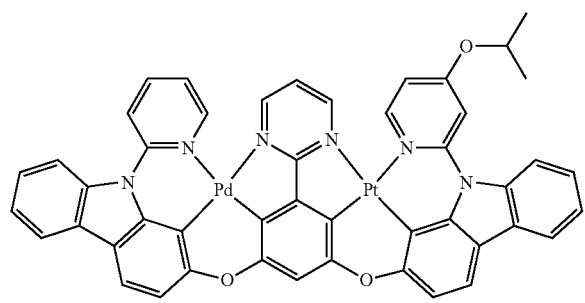
Compound PtPd287
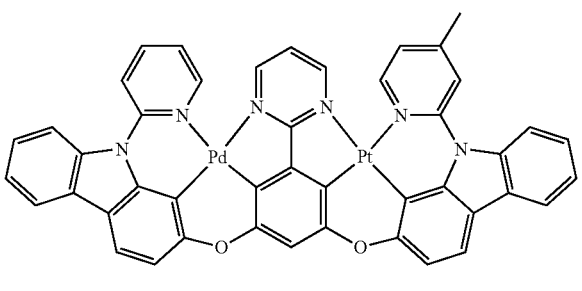
Compound PtPd288
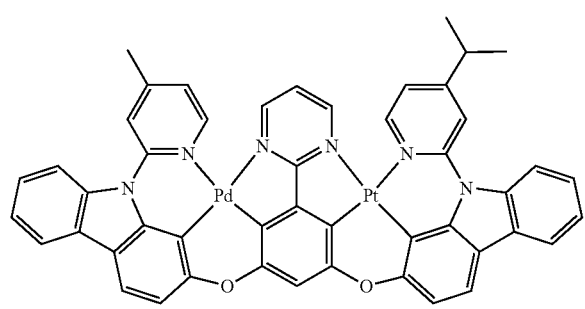
Compound PtPd289
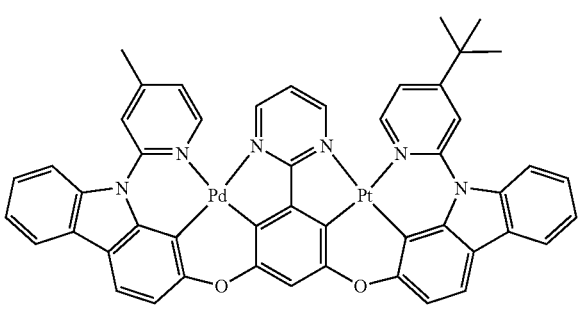
Compound PtPd290
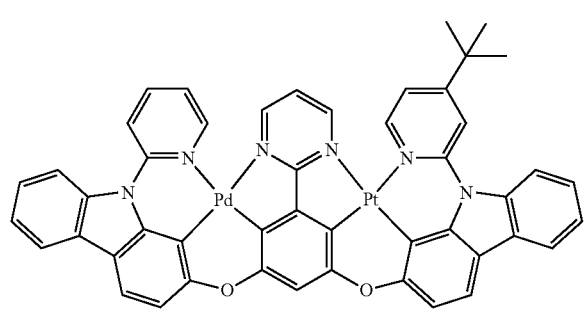
Compound PtPd291
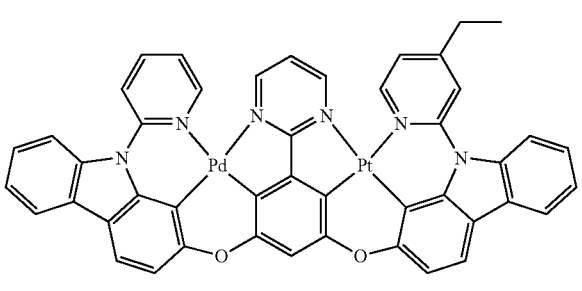

wherein $R^x$ is hydrogen, aryl, cycloalkyl, cycloalkenyl, heterocyclyl, heteroaryl, alkyl, alkenyl, alkynyl, deuterium, halogen, hydroxyl, thiol, nitro, cyano, amino, a mono- or di-alkylamino, a mono- or diaryl amino, alkoxy, aryloxy, haloalkyl, aralkyl, ester, nitrile, isonitrile, heteroaryl, alkoxycarbonyl, acylamino, alkoxycarbonylamino, aryloxycarbonylamino, sulfonylamino, sulfamoyl, carbamoyl, alkylthio, sulfinyl, ureido, phosphoramide, amercapto, sulfo, carboxyl, hydrzino, substituted silyl, or polymerizable, or any conjugate or combination thereof.

2. Devices

Also disclosed herein are devices comprising one or more of the compounds disclosed herein.

The compounds disclosed herein are suited for use in a wide variety of devices, including, for example, optical and electro-optical devices, including, for example, photo-absorbing devices such as solar- and photo-sensitive devices, organic light emitting diodes (OLEDs), photo-emitting devices, or devices capable of both photo-absorption and emission and as markers for bio-applications.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Various methods for the preparation method of the inventive compounds described herein are recited in the examples. These methods are provided to illustrate various methods of preparation, but the present invention is not intended to be limited to any of the methods recited herein. Accordingly, one of skill in the art in possession of this disclosure could readily modify a recited method or utilize a different method to prepare one or more of the inventive compounds. The following aspects are only exemplary and are not intended to limit the scope of the invention. Temperatures, catalysts, concentrations, reactant compositions, and other process conditions can vary, and one of skill in the art, in possession of this disclosure, could readily select appropriate reactants and conditions for a desired complex.

$^1$H spectra were recorded at 400 MHz, $^{13}$C NMR spectra were recorded at 100 MHz on Varian Liquid-State NMR instruments in CDCl$_3$ or DMSO-d$_6$ solutions and chemical shifts were referenced to residual protiated solvent. If CDCl$_3$ was used as solvent, $^1$H NMR spectra were recorded with tetramethylsilane ($\delta$=0.00 ppm) as internal reference; $^{13}$C NMR spectra were recorded with CDCl$_3$ ($\delta$=77.00 ppm) as internal reference. If DMSO-d$_6$ was used as solvent, $^1$H NMR spectra were recorded with residual H$_2$O ($\delta$=3.33 ppm) as internal reference; $^{13}$C NMR spectra were recorded with DMSO-d$_6$ ($\delta$=39.52 ppm) as internal reference. The following abbreviations (or combinations thereof) were used to explain $^1$H NMR multiplicities: s=singlet, d=doublet, t=triplet, q=quartet, p=quintet, m=multiplet, br=broad.

Prophetic Synthetic Routes

A general proposed synthetic route for the compounds disclosed herein includes:

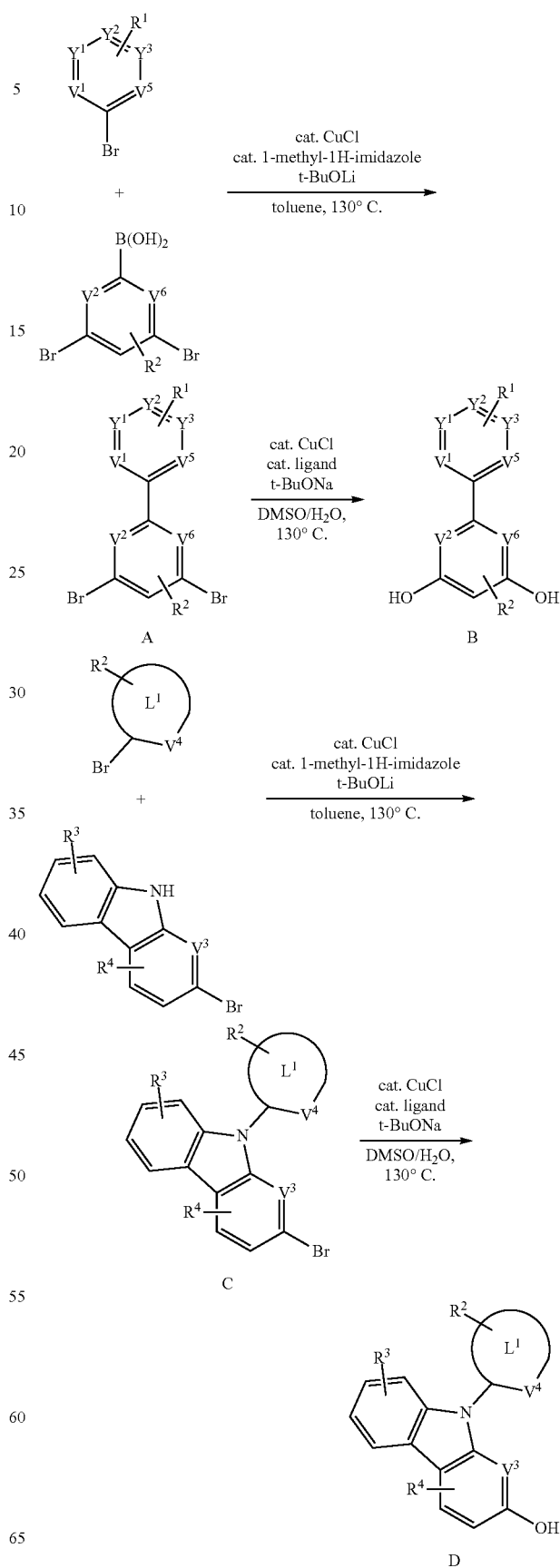

-continued

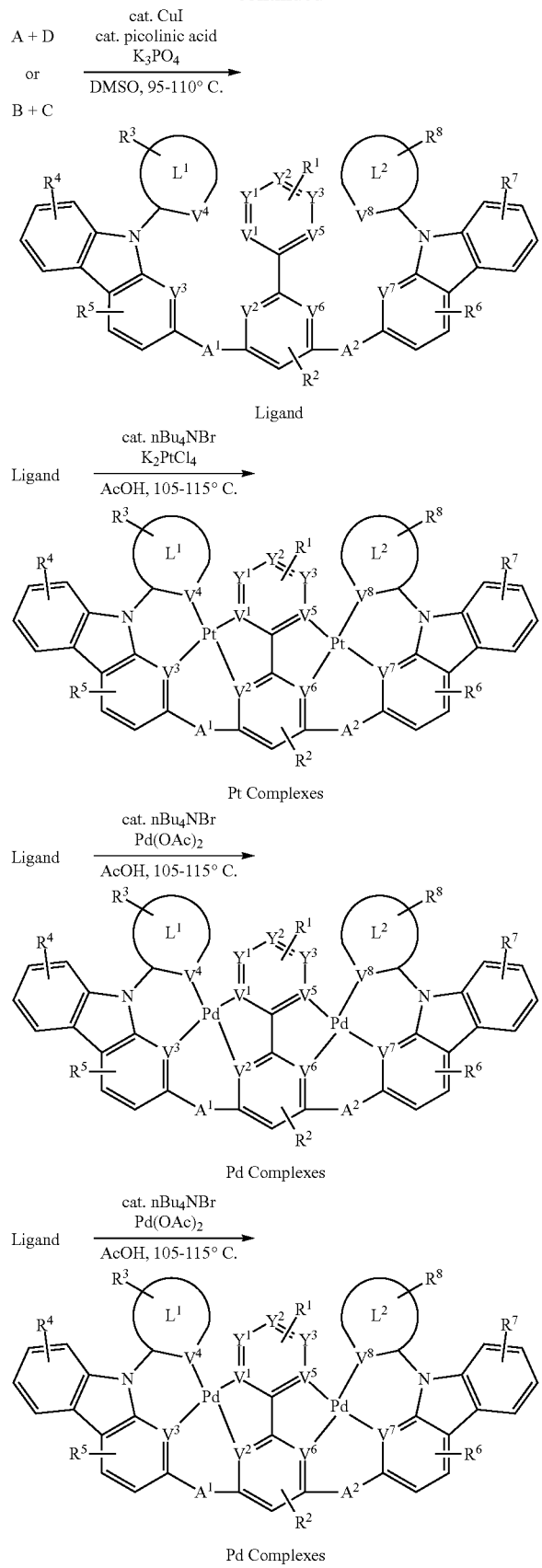

Platinum complex Compound 1 can be prepared according to the following scheme:

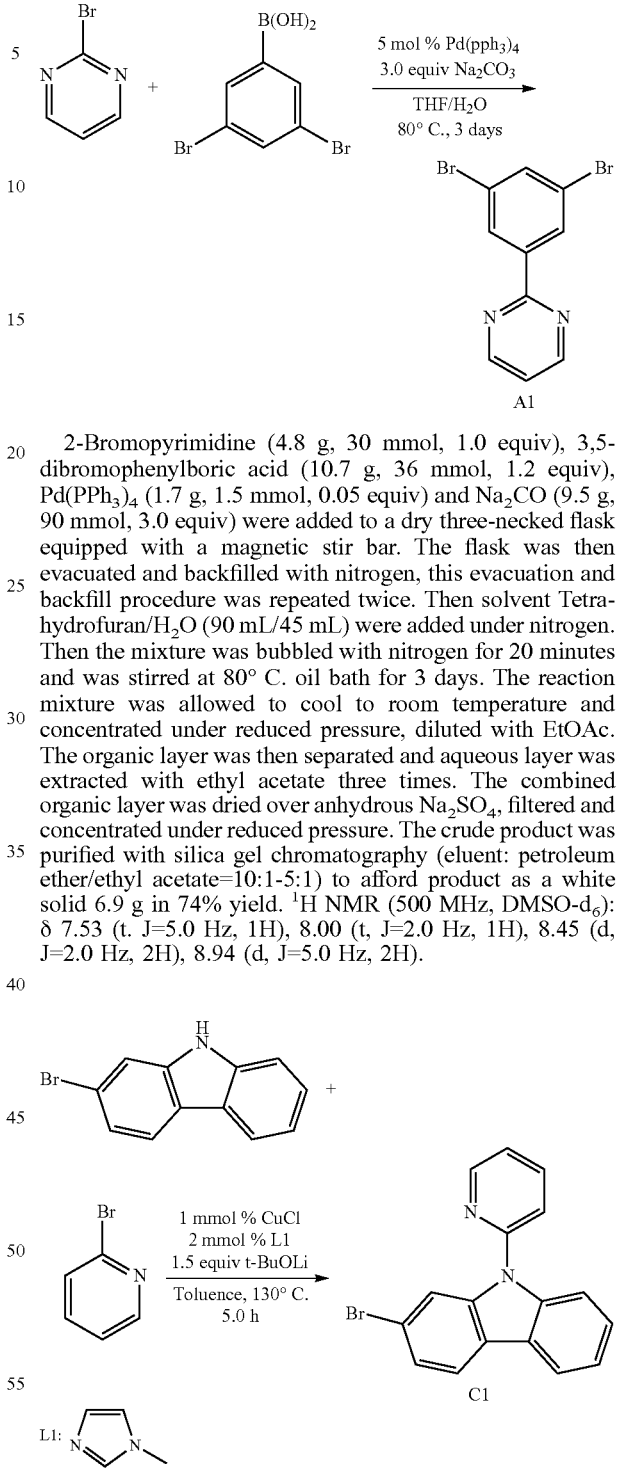

2-Bromopyrimidine (4.8 g, 30 mmol, 1.0 equiv), 3,5-dibromophenylboric acid (10.7 g, 36 mmol, 1.2 equiv), Pd(PPh$_3$)$_4$ (1.7 g, 1.5 mmol, 0.05 equiv) and Na$_2$CO (9.5 g, 90 mmol, 3.0 equiv) were added to a dry three-necked flask equipped with a magnetic stir bar. The flask was then evacuated and backfilled with nitrogen, this evacuation and backfill procedure was repeated twice. Then solvent Tetrahydrofuran/H$_2$O (90 mL/45 mL) were added under nitrogen. Then the mixture was bubbled with nitrogen for 20 minutes and was stirred at 80° C. oil bath for 3 days. The reaction mixture was allowed to cool to room temperature and concentrated under reduced pressure, diluted with EtOAc. The organic layer was then separated and aqueous layer was extracted with ethyl acetate three times. The combined organic layer was dried over anhydrous Na$_2$SO$_4$, filtered and concentrated under reduced pressure. The crude product was purified with silica gel chromatography (eluent: petroleum ether/ethyl acetate=10:1-5:1) to afford product as a white solid 6.9 g in 74% yield. $^1$H NMR (500 MHz, DMSO-d$_6$): δ 7.53 (t. J=5.0 Hz, 1H), 8.00 (t, J=2.0 Hz, 1H), 8.45 (d, J=2.0 Hz, 2H), 8.94 (d, J=5.0 Hz, 2H).

2-Bromo-9H-carbazole (14.77 g, 60.00 mmol, 1.0 eq), CuCl (60.0 mg, 0.60 mmol, 0.01 eq) and lithium t-butoxide (7.21 g, 90.00 mmol, 1.5 eq) were added to a 500 mL three-neck bottom flask with magnetic stir bar. Then the flask was evacuated and backfilled with nitrogen. This procedure was repeated for total of three times. Then 2-bromopyridine (8.58 mL, 90.00 mmol, 1.5 eq), 1-methylimidazole (95.1 uL, 1.20 mmol, 0.02 eq) and toluene (240.0 mL) were added into flask under nitrogen atmosphere. The flask was placed in 130° C. oil bath and stirred for 5.0 h. Cooled down, 100.0 mL solution of $Na_2SO_3$ was added. Then vacuum filtered and washed with ethyl acetate. The organic layer was separated, and the aqueous layer was extracted with EtOAc (100 mL×3). The mixture was washed with 50 mL water Then dried over $Na_2SO_4$ and filtered, and the filtrate was concentrated in vacuum. The residue was recrystallized in PE/DCM (40 mL/5 mL) to afford the desired product as a white solid 16.77 g in 87%. $^1$H NMR (500 MHz, $CDCl_3$): δ 7.31-7.34 (m, 2H), 7.42 (dd, J=8.0, 1.5 Hz, H), 7.44-7.47 (m, 1H), 7.61 (d, J=8.5 Hz, 1H), 7.77 (d, J=8.0 Hz, 1H), 7.93-7.96 (m, 2H), 8.01 (d, J=1.5 Hz, 1H), 8.08 (d, J=7.5 Hz, 1H), 8.73 (d, J=5.0, 1.5 Hz, 1H).

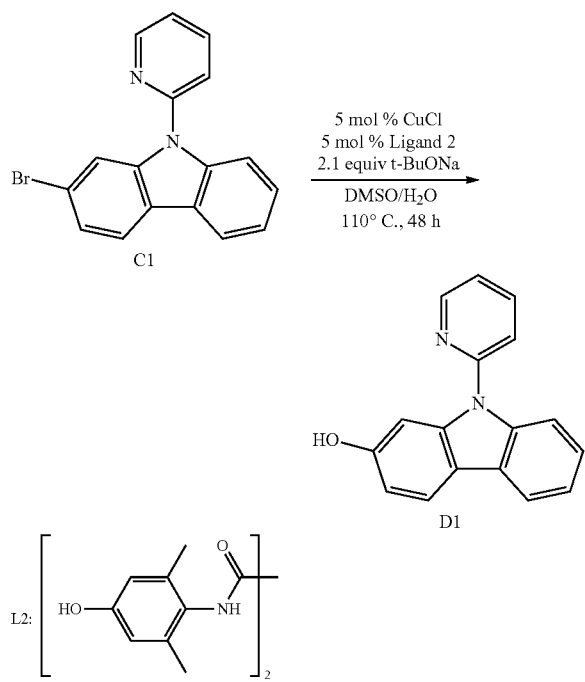

2-Bromo-9-(2-pyridinyl)-carbazole (9.70 g, 30.00 mmol, 1.0 eq), CuCl (148.5 mg, 1.50 mmol, 0.05 eq), L2 (493.0 mg, 1.50 mmol, 0.05 eq) and t-BuONa (6.05 g, 63.0 mmol, 2.1 eq) were added to a dry flask equipped with a magnetic stir bar. The flask was then evacuated and backfilled with nitrogen, this evacuation and backfill procedure was repeated twice. Then $DMSO/H_2O$ (37.5 mL/9.5 mL) were added into the tube under nitrogen atmosphere. The tube was placed in oil bath (110° C.) and stirred for 48 h until the starting material was consumed completely monitoring by TLC. Then the mixture was cooled to room temperature, $H_2O$ (100 mL) and EtOAc (100 mL) were added, filtered through a pad of celite, and washed with EtOAc three times. The organic layer was then separated, and the aqueous layer was extracted with EtOAc (100 mL×5). The combined organic layer was washed with water (50 mL) and then dried over $Na_2SO_4$ and filtered, and the filtrate was concentrated in vacuum. The residue was recrystallized in PE/EtOAc (10 mL×10 mL) to afford the desired product as a gray solid 5.77 g. The mother liquor was concentrated, and the residue was purified through column chromatography on silica gel using PE/DCM=5:1-3:1 as eluent to afford the product as a gray solid 1.5 g. The total yield was 93%. $^1$H NMR (500 MHz, DMSO-$d_6$): δ 6.79 (dd, J=8.5, 2.0 Hz, 1H), 7.18 (d, J=2.0 Hz, 1H), 7.23-7.26 (m, 1H), 7.32 (td, J=8.5, 1.0 Hz, 1H), 7.47 (ddd, J=7.5, 5.0, 1.0 Hz, 1H), 7.69 (d, J=8.0 Hz, 1H), 7.74 (d, J=8.0 Hz, 1H), 7.99 (d, J=8.5 Hz, 1H), 8.06 (d, J=7.5 Hz, 1H), 8.11 (td, J=8.0, 2.0 Hz, 1H), 8.72 (ddd, J=5.0, 2.0, 0.5 Hz, 1H), 9.61 (s, 1H). $^{13}$C NMR (126 MHz, DMSO-$d_6$): δ 97.10, 110.34, 110.77, 115.85, 119.01, 119.12, 120.78, 121.08, 121.80, 124.02, 124.48, 138.79, 139.29, 140.54, 149.45, 150.88, 157.02. HRMS (ESI): calcd for $C_{17}H_{13}N_2O$ $[M+H]^+$ 261.1022, found 261.1028.

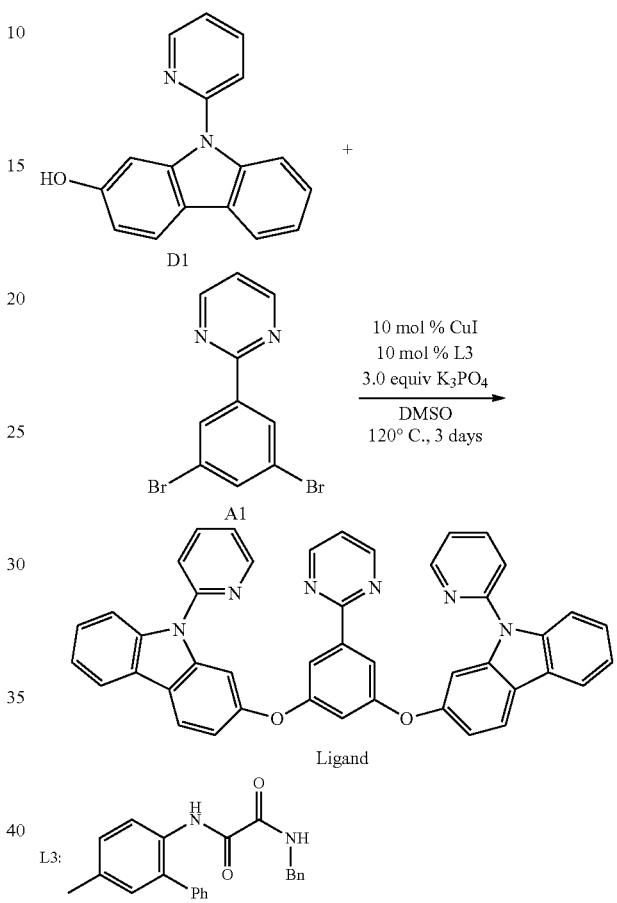

2-(3,5-Dibromophenyl)-pyrimidine (936 mg, 3.0 mmol, 1.0 equiv), 9-(pyridin-2-yl)-9H-carbazol-2-ol D1 (2.03 g, 7.8 mmol, 2.6 equiv), CuI (57 mg, 0.3 mmol, 0.1 equiv), L3 (103 mg, 0.3 mmol, 0.1 equiv) and $K_3PO_4$ (1.91 g, 9.0 mmol, 3.0 equiv) were added to a dry flask equipped with a magnetic stir bar. The flask was then evacuated and back-filled with nitrogen, this evacuation and backfill procedure was repeated twice. Then DMSO (12.0 mL) were added into the tube under nitrogen atmosphere. The flask was placed in oil bath (120° C.) and stirred for 3 days. Then the mixture was cooled to room temperature, $H_2O$ (50 mL) and EtOAc (50 mL) were added. The organic layer was then separated, and the aqueous layer was extracted with EtOAc (50 mL×3). The combined organic layer was dried over $Na_2SO_4$ and filtered, and the filtrate was concentrated in vacuum. The residue was purified through column chromatography on silica gel using petroleum ether/ethyl acetate (2:1-1:1) as eluent to afford the desired product as a gray solid 1.16 g in 57% yield. $^1$H NMR (500 MHz, DMSO-$d_6$): δ 6.97 (t, J=2.0 Hz, 1H), 7.14 (dd, J=8.5, 2.0 Hz, 2H), 7.34-7.37 (m, 2H), 7.39 (t, J=5.0 Hz, 1H), 7.45-7.48 (m, 4H), 7.61 (d, J=2.0 Hz, 2H), 7.65 (d, J=2.5 Hz, 2H), 7.80 (dt, J=8.0, 1.0 Hz, 4H), 8.07-8.11 (m, 2H), 8.25 (d, J=7.5 Hz, 2H), 8.30 (d, J=8.5 Hz, 2H), 8.69 (ddd, J=5.0, 2.0, 1.0 Hz, 2H), 8.77 (d, J=5.0 Hz, 2H).

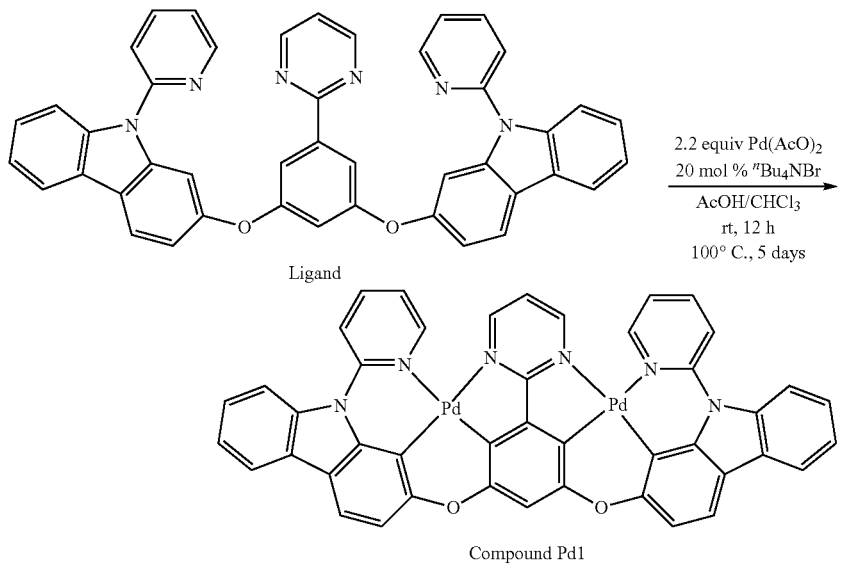

Compound Pd1

Figure 2:
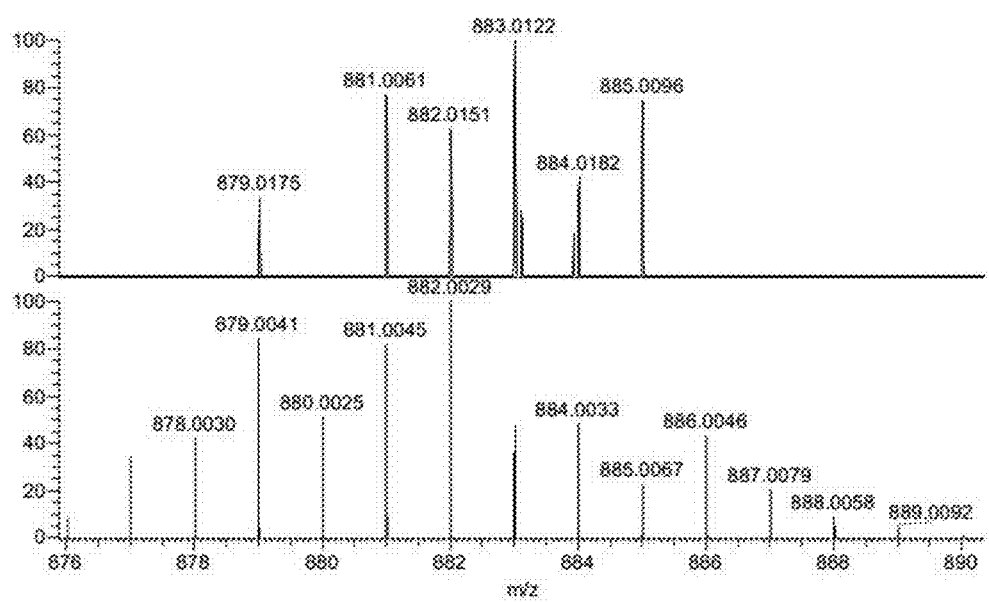
FIG. 2 shows the High Resolution MS of Compound Pd 1.
Figure 2:
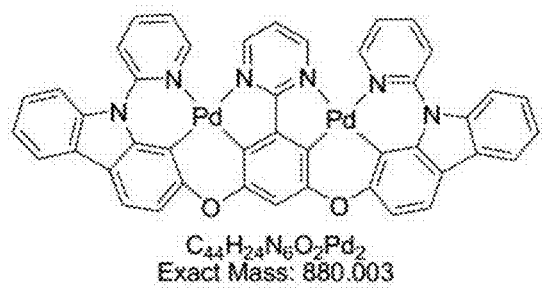

The ligand (300 mg, 0.45 mmol, 1.0 equiv). Pd(AcO)₂ (220 mg, 0.98 mmol, 2.2 equiv). "Bu₄NBr (29 mg, 0.09 mmol, 0.2 equiv) were added to a dry tube equipped with a magnetic stir bar. The flask was then evacuated and backfilled with nitrogen, this evacuation and backfill procedure was repeated twice. Then AcOH (54 mL) and CHCl₃ (5 mL) were added into the flask under nitrogen atmosphere. The mixture was placed in room temperature and stirred for 12 h. Then it was placed in oil bath (110° C.) and stirred for 5 days. Cooled down, and concentrated in vacuum. The residue was purified through column chromatography on silica gel using petroleum ether/dichloromethane (3:1-0:1) as eluent to afford the desired product as a yellow solid 320 mg in 81% yield. $^1$H NMR (500 MHz, DMSO-$d_6$): δ 6.94 (s, 1H), 7.26 (d, J=8.5 Hz, 2H), 7.39-7.42 (m, 2H), 7.45-7.50 (m, 4H), 7.70 (t, J=5.5 Hz, 1H), 7.95 (d, J=8.0 Hz, 2H), 8.06 (d, J=8.0 Hz, 2H), 8.15-8.20 (m, 6H), 9.02 (dd, J=5.5, 1.0 Hz, 2H), 9.13 (d, J=5.5 Hz, 2H). HRMS (MALDI-FT_DHB): calcd for $C_{44}H_{25}N_6O_2Pd_2$ [M+H]⁺ 881.0045, found 881.0061. The emission peak of Compound Pd1 in diclomethane is at 561 nm. The $^1$H NMR spectrum of in MDSO-$d_6$ and High Resolution MS of Compound Pd1 are shown in FIGS. 1 and 2 respectively.

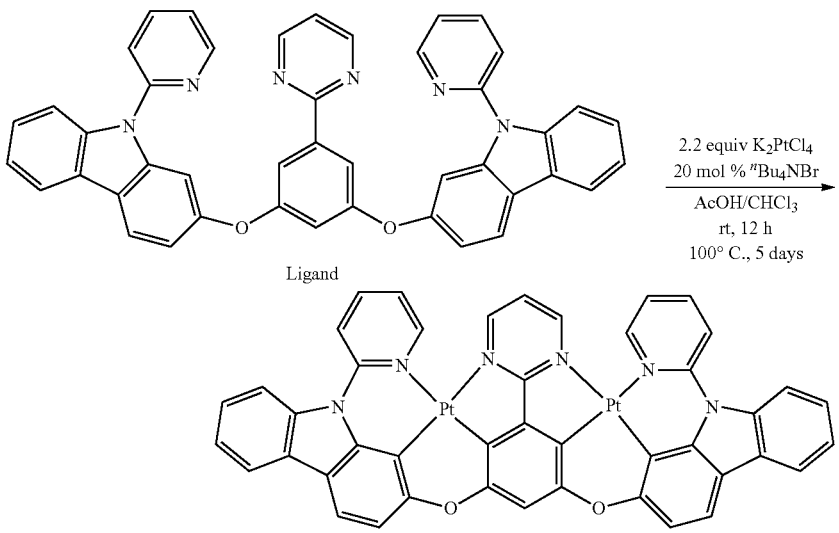

Figure 3:
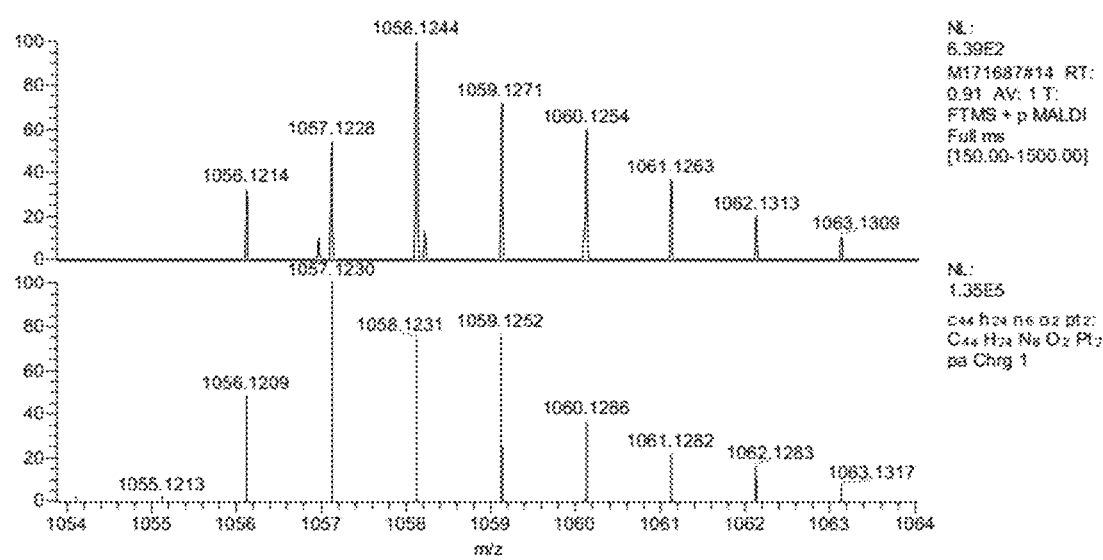
FIG. 3 shows the PL spectrum of Compound Pd 1 in dichloromethane at room temperature.
Figure 3:
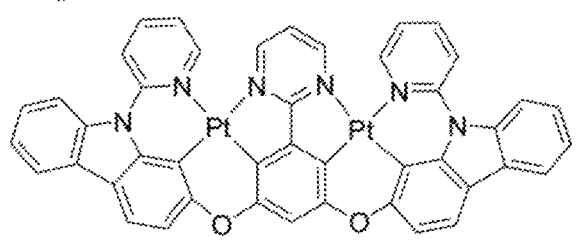

The ligand (300 mg, 0.45 mmol, 1.0 equiv), K₂PtCl₄ (407 mg, 0.98 mmol, 2.2 equiv), "Bu₄NBr (29 mg, 0.09 mmol, 0.2 equiv) were added to a dry flask equipped with a magnetic stir bar. The flask was then evacuated and backfilled with nitrogen, this evacuation and backfill procedure was repeated twice. Then AcOH (54 mL) and CHCl₃ (5 mL) were added into the flask under nitrogen atmosphere. The mixture was placed in room temperature and stirred for 12 h, then at 110° C. for 5 days. Cooled down, and concentrated in vacuum. The residue was purified through column chromatography on silica gel using petroleum ether/dichloromethane (3:1-0:1) as eluent to afford the desired product as a red solid 114.5 mg in 24% yield. The product was confirmed by HRMS (MALDI-FT_DHB): calcd for $C_{44}H_{24}N_6O_2Pt_2$ $[M+H]^+$ 1058.1231, found 1058.1244. The High Resolution MS of Compound Pt1 are shown in FIG. 3.

What is claimed is:

1. A compound of Formula I:

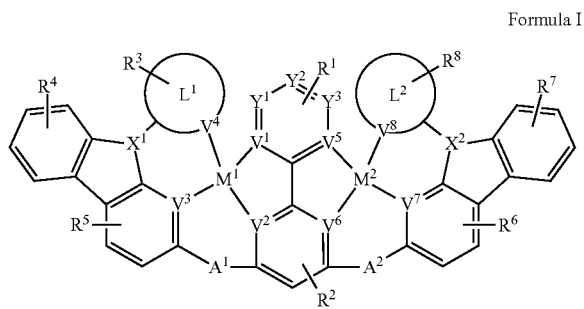

Formula I wherein each of $M^1$ and $M^2$ is independently a platinum or palladium;

wherein each of $L^1$ and $L^2$ is independently heteroaryl ring;

wherein $V^1, V^2, V^3, V^4, V^5, V^6, V^7$ and $V^8$ are coordinated with $M^1$ or $M^2$; wherein $V^1, V^4, V^5$ and $V^8$ are N; $V^2, V^3, V^6$ and $V^7$ are C;

wherein each of $A^1$ and $A^2$ is independently an O;

wherein each of $X^1$ and $X^2$ is independently a N;

wherein each of $Y^1, Y^2$ and $Y^3$ is independently a hydrogen;

wherein each of $R^1, R^2, R^3, R^4, R^5, R^6, R^7$ and $R^8$ is independently a hydrogen.

2. The compound of claim 1, wherein the compound has a neutral charge.

3. A device comprising the compound of claim 1.

4. The device of claim 3, wherein the device comprises a full color display.

5. The device of claim 3, wherein the device is a photovoltaic device.

6. The device of claim 3, wherein the device is a luminescent display device.

7. The device of claim 3, wherein the device comprises an organic light emitting diode (OLED).

8. The device of claim 3, wherein the device comprises a phosphorescent organic light emitting diode.

9. The device of claim 3, wherein the device is a phosphorescent organic light emitting diode.

10. A light emitting device comprising the compound of claim 1.

11. The device of claim 3, wherein the compound is selected to have 100% internal quantum efficiency in the device settings.

* * * * *